US012612379B2

(12) United States Patent
Dakin et al.

(10) Patent No.: US 12,612,379 B2
(45) Date of Patent: Apr. 28, 2026

(54) INHIBITORS OF APOL1 AND METHODS OF USING SAME

(71) Applicant: Vertex Pharmaceuticals Incorporated, Boston, MA (US)

(72) Inventors: Leslie A. Dakin, Framingham, MA (US); Michael A. Brodney, Newton, MA (US); Kevin B. Daniel, Boston, MA (US); Elena Dolgikh, Boston, MA (US); Pedro M. Garcia Barrantes, Melrose, MA (US); Ales Medek, Winchester, MA (US); Jessica H. Olsen, Jamaica Plain, MA (US); Timothy J. Senter, Arlington, MA (US); Akira J. Shimizu, Framingham, MA (US); Steven D. Stone, Quincy, MA (US); Charlene Tsay, Boston, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 557 days.

(21) Appl. No.: 18/071,153

(22) Filed: Nov. 29, 2022

(65) Prior Publication Data

US 2023/0203000 A1 Jun. 29, 2023

Related U.S. Application Data

(60) Provisional application No. 63/310,832, filed on Feb. 16, 2022, provisional application No. 63/286,165, (Continued)

(51) Int. Cl.

| | |
|---|---|
| ***C07D 401/04*** | (2006.01) |
| ***C07D 401/14*** | (2006.01) |
| ***C07D 405/14*** | (2006.01) |

(52) U.S. Cl.
CPC ......... *C07D 401/04* (2013.01); *C07D 401/14* (2013.01); *C07D 405/14* (2013.01)

(58) Field of Classification Search
CPC ... C07D 401/04; C07D 401/14; C07D 405/14
(Continued)

(56) References Cited

U.S. PATENT DOCUMENTS 4,140,781 A 2/1979 Huebner
6,605,633 B1 8/2003 Paquet et al.
(Continued)

FOREIGN PATENT DOCUMENTS

CN 106749330 A 5/2017
EP 0934941 A1 8/1999
(Continued)

OTHER PUBLICATIONS

Haller R, Ebersberg J. Kernresonanzspektroskopische Untersuchung einiger 2, 2âdimethylsubstituierter Piperidone und Piperidinole. Archiv der Pharmazie. 1969;302(3):197-203. (Year: 1969).*
(Continued)

*Primary Examiner* — Jeffrey S Lundgren
*Assistant Examiner* — Heather Dahlin
(74) *Attorney, Agent, or Firm* — Finnegan, Henderson, Farabow, Garrett & Dunner, LLP

(57) ABSTRACT

The disclosure provides at least one compound, tautomer, deuterated derivative, or pharmaceutically acceptable salt chosen from compounds of Formula I, tautomers thereof, deuterated derivatives of those compounds or tautomers, and pharmaceutically acceptable salts of any of the foregoing, compositions comprising the same, and methods of using the same, including uses in treating APOL1-mediated diseases, including pancreatic cancer, focal segmental glomerulosclerosis (FSGS), and/or non-diabetic kidney disease (NDKD).

(Continued)

Formula I

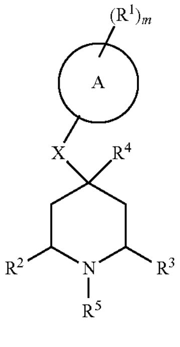

41 Claims, 4 Drawing Sheets

Related U.S. Application Data filed on Dec. 6, 2021, provisional application No. 63/284,166, filed on Nov. 30, 2021.

(58) Field of Classification Search
USPC .......................................................... 514/341
See application file for complete search history.

(56) References Cited

U.S. PATENT DOCUMENTS

| | | | |
|---|---|---|---|
| 11,618,746 | B2 | 4/2023 | Cao et al. |
| 11,801,234 | B2 | 10/2023 | Mallalieu et al. |
| 11,866,446 | B2 | 1/2024 | Ahn et al. |
| 2002/0042413 | A1 | 4/2002 | Rault et al. |
| 2004/0138287 | A1 | 7/2004 | Barth et al. |
| 2005/0100902 | A1 | 5/2005 | Barth et al. |
| 2008/0249128 | A1 | 10/2008 | Oberboersch et al. |
| 2013/0237532 | A1 | 9/2013 | Kim et al. |
| 2018/0118681 | A1 | 5/2018 | Ross et al. |
| 2021/0246121 | A1 | 8/2021 | Lai et al. |
| 2021/0275496 | A1 | 9/2021 | Mallalieu et al. |
| 2022/0106327 | A1 | 4/2022 | Ahn et al. |
| 2022/0340523 | A1 | 10/2022 | Dakin et al. |
| 2023/0011118 | A1 | 1/2023 | Dakin et al. |
| 2023/0014907 | A1 | 1/2023 | Dakin et al. |
| 2023/0119114 | A1 | 4/2023 | Daniel et al. |
| 2023/0201201 | A1 | 6/2023 | Skorecki et al. |
| 2023/0250087 | A1 | 8/2023 | Gagnon et al. |
| 2024/0277661 | A1 | 8/2024 | Mallalieu et al. |
| 2024/0368180 | A1 | 11/2024 | Ahn et al. |
| 2025/0084094 | A1 | 3/2025 | Senter et al. |
| 2025/0163021 | A1 | 5/2025 | Senter et al. |

FOREIGN PATENT DOCUMENTS

| | | | |
|---|---|---|---|
| EP | 2905278 | A1 | 8/2015 |
| FR | 2315272 | A1 | 1/1977 |
| WO | WO 01/17965 | A2 | 3/2001 |
| WO | WO 01/38305 | A2 | 5/2001 |
| WO | WO 02/28831 | A1 | 4/2002 |
| WO | WO 02/092568 | A1 | 11/2002 |
| WO | WO 2003/104180 | A1 | 12/2003 |
| WO | WO 2005/021505 | A1 | 3/2005 |
| WO | WO 2005/115983 | A1 | 4/2005 |
| WO | WO 2005/092854 | A1 | 10/2005 |
| WO | WO 2008/092231 | A1 | 8/2008 |
| WO | WO 2010/137351 | A1 | 12/2010 |
| WO | WO 2012/025155 | A1 | 3/2012 |
| WO | WO 2014/085154 | A1 | 6/2014 |
| WO | WO 2015/048301 | A1 | 4/2015 |
| WO | WO 2016/055517 | A1 | 4/2016 |
| WO | WO 2017/033093 | A1 | 3/2017 |
| WO | WO 2019/213148 | A1 | 11/2019 |
| WO | WO 2020/131807 | A1 | 6/2020 |
| WO | WO 2020/186220 | A1 | 9/2020 |
| WO | WO 2021/216665 | A1 | 4/2021 |
| WO | WO 2021/154997 | A1 | 8/2021 |
| WO | WO 2021/158666 | A1 | 8/2021 |
| WO | WO 2021/178768 | A1 | 9/2021 |
| WO | WO 2021/224927 | A1 | 9/2021 |
| WO | WO 2021/252849 | A1 | 12/2021 |
| WO | WO 2021/252859 | A1 | 12/2021 |
| WO | WO 2021/252863 | A1 | 12/2021 |
| WO | WO 2022/047031 | A1 | 3/2022 |
| WO | WO 2023/028237 | A1 | 3/2023 |
| WO | WO 2023/101981 | A1 | 6/2023 |
| WO | WO 2023/154309 | A1 | 8/2023 |
| WO | WO 2023/154310 | A1 | 8/2023 |
| WO | WO 2023/154314 | A1 | 8/2023 |
| WO | WO 2023/154344 | A1 | 8/2023 |

OTHER PUBLICATIONS

Harper NJ, Beckett AH, Balon AD. Science Papers: Potential Analgesics. the Stereochemistry of Some Isomeric Piperidinol Derivatives. Journal of Pharmacy and Pharmacology. Dec. 1959;11(S1):67T-9T. (Year: 1959).*

Balasubramanian, M. et al. (1970) "Studies on Conformation: Part X—Addition of Grignard Reagents to 4-Piperidones." *Indian J. Chem.*, vol. 8, May 1, 1970, pp. 420-422.

Bartolucci, S. et al. (2015), "Iridium-Catalyzed Direct Synthesis of Tryptamine Derivatives from Indoles: Exploiting N-Protected Amino Alcohols as Alkylating Agents," *J. Org. Chem*, 2015, 80, 3217-3222.

Casy, A.F. et. al. (1976), "Reversed ester analogues of pethidine: isomeric 4-acetoxy-1,2,6-trimethyl-4-phenyrpiperidi nes." *JPP*, vol. 28, No. 2, pp. 106-110.

Database Registry (2002), Chembridge Corporation: 4-Piperidinol, 4-(2-methoxyphenyl)-1-methyl-2,6-diphenyl-IIXP093022694, Database accession No. 471293-86-4 compound with Registry No. 471293-86-4.

Database Registry (2016), Aurora Fine Chemicals: "Piperidine, 4-[(I,3-diethyl-IH-pyrazol-5-yl)methyl]-2, 6-dimethyl", XP093022702, Database accession No. 1993174-76-7 compounds with Registry Nos. 1993174-76-7, 1993166-16-7 and1993166-02-1.

Database Registry (2018), Aurora Fine Chemicals: "4-Piperidinol, 1,2,6-trimethyl-4-(2-methylphenyl)," XP093022693, Database accession No. 2182802-01-1 compound with Registry No. 2182802-01-1.

Database Registry (2021), "2'-Cyclopropyl-7,8-dihydro-6'-methylspiro [I,6-naphthyridine-5(6H),4'-piperidine]," XP093024331, retrieved from STN Database accession No. 2645191-67-7 abstract.

Database Registry (2021), "2'-Cyclopropyl-6,7-dihydro-6,6'-dimethyls piro[I,7-naphthyridine-8(5H),4'-piperidine], " XP093024335, retrieved from STN Database accession No. 2644543-73-5 abstract.

Database Registry (2021), Anonymous: "Name not yet assigned", XP093024338, retrieved from STN Database accession No. 2642534-36-7 abstract.

Database Registry (2021), Anonymous: "2'-Cyclopropyl-3,4-dihydro-6'-methylspiro [isoquinoline-1 (2H), 4'-piperidin]-7-ol," XP093024340, retrieved from STN Database accession No. 2631256-91-0 abstract.

Database Registry (2021), Anonymous: "2-Cyclopropyl-7',8'-dihydro-2',6-dimethyl spiro[piperidine-4,5'(3'H)-pyrido[4,3-d]py rimidin]-4' (6 'H)-one", XP093024343, retrieved from STN Database accession No. 2631119-41-8 abstract.

Database Registry (2021), Anonymous: "Name not yet assigned", XP093024344, retrieved from STN Database accession No. 2630494-88-9 abstract.

Database Registry (2021), Anonymous: "2'-Cyclopropyl-6,7-dihydro-6'-methylspiro [I,7-naphthyridine-8(5H),4' piperidine]-6-methanol," XP093024346, retrieved from STN Database accession No. 2626788-69-8.

Database Registry (2021), Anonymous: "rel-(2'R,6'R)-3,4-Dihydro-7-methoxy-2',6'-dimethylspiro[2,6-naphthyridine1(2H),4'-p iperidine]," XP093024348, retrieved from STN Database accession No. 2625380-27-8 abstract.

(56) References Cited

OTHER PUBLICATIONS

Database Registry (2021), Anonymous: "2'-Cyclopropyl-3,4-dihydro-3,6'-dimethyls piro[2,6-naphthyridine-1(2H),4'piperidine]," XP093024352, retrieved from STN Database accession No. 2620609-98-3 abstract.
Database Registry (2021), Anonymous: "2'-Cyclopropyl-6,7-dihydro-6'-methylspiro [I,7-naphthyridine-8(5H),4' piperidine]-5-methanol," XP093024350, retrieved from STN Database accession No. 2617381-98-1 abstract.
Dummer, P.D. et al. (2015), "APOL1 kidney disease risk variants—an evolving landscape," *Semin Nephrol.* 35(3):222-236. HHS Public Access Author Manuscript; available in PMC May 1, 2016 (25 pages).
Harish, B. et al. (2017) "N-Heterocyclic carbene (NHC)-catalysed atom economical construction of 2,3-disubstituted indoles," *Chem. Commun*, 2017, 53, 3338-3341.
Harper N.J. et al. (1960) "Some isomeric hydroxypiperidines." *J. Am. Chem. Soc.*, Jan. 1, 1960, pp. 2704-2711.
International Search Report and Written Opinion for International Application No. PCT/US2022/051364, mailed Feb. 20, 2023 (14 pages).
Jones, A.J. et al. (1973), "Carbon-13 Magnetic Resonance: the Stereochemistry of 1,2- and 1,3-Dimethyl-4-phenylpiperidine Derivatives." *Can. J. Chem.*, vol. 41, No. 11, pp. 1782-1789.
Kagabu, S. et al. (2009), "N-Thiophenylethyl-2,2-dichloro-1-cyclopropanecarboxamides: modification of the amide part of carpropamid and examination of fungicidal activity," J. Pestic. Sci. 34(3) 161-172.
Kozikowski, A.P. et al. (1993), "Chemistry, binding affinities, and behavioral properties of a new class of "antineophobic" mitochondrial DBI receptor complex (mDRC) ligands," *J. Med. Chem.* 36(20):2908-2920.
Lin, J. et al. (2021), "Oncogene APOL1 promotes proliferation and inhibits apoptosis via activating NOTCH1 signaling pathway in pancreatic cancer," *Cell Death and Disease* 12:760 (11 pages).
Manimekalai, A. et al. (2007), "Benzyl group conformation in 4-benzyl-4-hydroxypiperidines," *J. Struct. Chem.*, vol. 48, No. 6, pp. 1036-1045.
Meyers, A.L. et al. (1985), ".alpha.-Amino carbanions. Preparation, metalation, and alkylation of enamidines. Synthesis of piperidine and pyrrolidine natural products and homologation of carbonyl compounds," *J. Org. Chem.*, vol. 50, No. 7, pp. 1019-1026.
Notice of Allowance and Fee(s) Due for U.S. Appl. No. 16/717,099, mailed Nov. 7, 2022, Examiner Deepak R. Rao.
Prostakov, N.S. et al. (1975) "Synthesis of 3-Alkyl-2, 4, 6-Triphenylpyridines and 1, 3-Diphenyl-4- and -2-Azafluorenes." Chem Heterocycl Compd, vol. 11, pp. 971-975.
Takasawa, R. et al. (2011), "Discovery of a new type inhibitor of human glyoxalase I by myricetin-based 4-point pharmacophore," *Bioorganic Med. Chem. Lett.* 21:4337-4342.
Trotter, B.W. et al. (2001) "2-Arylindole-3-acetamides: FPP-Competitive Inhibitors of Farnesyl Protein Transferase," Bioorg. Med. Chem. Lett. 11(2001) 865-869.
Turnu, F. et al. (2019) "Catalytic Tandem Friedel-Crafts Alkylation/C4—C3 Ring-Contraction Reaction: An Efficient Route for the Synthesis of Indolyl Cyclopropanecarbaldehydes and Ketones," *Org. Lett.* 21:7329-7332, (4 pages).
U.S. Appl. No. 17/895,582, filed Aug. 25, 2022, by Daniel et al.
U.S. Appl. No. 17/923,508, filed Nov. 11, 2022 by Skorecki, et al.
U.S. Appl. No. 18/001,371, filed Dec. 9, 2022 by Gagnon, et al.
U.S. Appl. No. 18/071,153, filed Nov. 29, 2022, by Dakin et al.
Vajgel, G. et al. (2020), "A single APOL1 nephropathy variant increases risk of advanced lupus nephritis in Brazilians," *J Rheumatol.* 47(8):1209-1217. HHS Public Access Author Manuscript; available in PMC Aug. 1, 2021 (18 pages).
Valles, D.A. et al. (2021), "[alpha], [alpha]'-C—H Bond Difunctionalization of Unprotected Alicyclic Amines," Org. Lett., vol. 23, No. 16, pp. 6367-6371.
*Vertex Announces Positive Results From Phase 2 Study of VX-147 in APOL1-Mediated Focal Segmental Glomerulosclerosis*, Vertex (Dec. 1, 2021), https://news.vrtx.com/press-release/vertex-announces-positive-results-phase-2-study-vx-147-apol1-mediated-focal-segmental (6 pages).
Winters, M.P. et al. (2008), "Carboxylic acid bioisosteres acylsulfonamides, acylsulfamides, and sulfonylureas as novel antagonists of the CXCR2 receptor," *Bioorganic Med. Chem. Lett.* 18:1926-1930.
Brittain H. G. et al., (2001) "X-Ray Diffraction III: Pharmaceutical Applications of X-ray Powder Diffraction," Spectroscopy, 16(7), pp. 14-18.
Campbell K.N., et al. (1949) "Studies on γ-Pyrones. II. Synthesis of 4-Piperidinols from Pyrones," J. Org. Chem. 15(2), 337-342.
Casy, A.F., et al. (1972) "Diastereoisomeric esters of 1,2-dimethyl-4-phenylpiperidin-4-ol and related compounds," J. Chem. Soc., Perkin Trans. 1, 726-731.
"Chemical Encyclopedia," vol. 4, p. 499-501, Scientific Publishing House 'The Great Russian Encyclopedia', Moscow, 1995.
Harriman, G.C.B., et al. (2000) "Synthesis of 4-substituted 4-arylpiperidines," Tet. Lett. 41(46), 8853-8856.
Nitta, A. et al. (2008) "(3R)-3-Amino-4-(2,4,5-trifluorophenyl)-N-{4-[6-(2-methoxyethoxy)benzothiazol-2-yl]tetrahydropyran-4-yl}butanamide as a potent dipeptidylpeptidase IV inhibitor for the treatment of type 2 diabetes," Bioorg. Med. Chem. Lett. 18(2008), 5435-5438.
The United States Pharmacopeia, Jan. 1, 1995, 23rd Revision, USP 23/NF 18, General Chapter on X-ray diffraction, pp. 1843-1844.
Van Wijngaarden, I. et al. (1987) "2-Phenylpyrroles as conformationally restricted benzamide analogs. A new class of potential antipsychotics," J. Med. Chem. 30(11), 2099-2104.

* cited by examiner

INHIBITORS OF APOL1 AND METHODS OF USING SAME

This application claims the benefit of priority of U.S. Provisional Application No. 63/284,166, filed Nov. 30, 2021, U.S. Provisional Application No. 63/286,165, filed Dec. 6, 2021, and U.S. Provisional Application No. 63/310,832, filed Feb. 16, 2022, the contents of which are incorporated by reference herein in their entirety.

This disclosure provides compounds that may inhibit apolipoprotein L1 (APOL1) and methods of using those compounds to treat APOL1-mediated diseases, such as, e.g., pancreatic cancer, focal segmental glomerulosclerosis (FSGS), and/or non-diabetic kidney disease (NDKD). In some embodiments, the FSGS and/or NDKD is associated with at least one of the 2 common APOL1 genetic variants (G1: S342G:1384M and G2: N388del:Y389del). In some embodiments, the pancreatic cancer is associated with elevated levels of APOL1 (such as, e.g., elevated levels of APOL1 in pancreatic cancer tissues).

FSGS is a rare kidney disease with an estimated global incidence of 0.2 to 1.1/100,000/year. FSGS is a disease of the podocyte (glomerular visceral epithelial cells) responsible for proteinuria and progressive decline in kidney function. NDKD is a kidney disease involving damage to the podocyte or glomerular vascular bed that is not attributable to diabetes. NDKD is a disease characterized by hypertension and progressive decline in kidney function. Human genetics support a causal role for the G1 and G2 APOL1 variants in inducing kidney disease. Individuals with 2 APOL1 alleles are at increased risk of developing end-stage kidney disease (ESKD), including primary (idiopathic) FSGS, human immunodeficiency virus (HIV)-associated FSGS, NDKD, arterionephrosclerosis, lupus nephritis, microalbuminuria, and chronic kidney disease. See, P. Dummer et al., *Semin Nephrol.* 35(3): 222-236 (2015).

FSGS and NDKD can be divided into different subgroups based on the underlying etiology. One homogeneous subgroup of FSGS is characterized by the presence of independent common sequence variants in the apolipoprotein L1 (APOL1) gene termed G1 and G2, which are referred to as the "APOL1 risk alleles." G1 encodes a correlated pair of non-synonymous amino acid changes (S342G and 1384M), G2 encodes a 2 amino acid deletion (N388del:Y389del) near the C terminus of the protein, and G0 is the ancestral (low risk) allele. A distinct phenotype of NDKD is found in patients with APOL1 genetic risk variants as well. In both APOL1-mediated FSGS and NDKD, higher levels of proteinuria and a more accelerated loss of kidney function occur in patients with two risk alleles compared to patients with the same disease who have no or just 1 APOL1 genetic risk variant. Alternatively in AMKD, higher levels of proteinuria and accelerated loss of kidney function can also occur in patients with one risk allele. See, G. Vajgel et al., J. Rheumatol., November 2019, jrheum.190684.

APOL1 is a 44 kDa protein that is only expressed in humans, gorillas, and baboons. The APOL1 gene is expressed in multiple organs in humans, including the liver and kidney. APOL1 is produced mainly by the liver and contains a signal peptide that allows for secretion into the bloodstream, where it circulates bound to a subset of high-density lipoproteins. APOL1 is responsible for protection against the invasive parasite, *Trypanosoma brucei brucei* (*T. b. brucei*). APOL1 is endocytosed by *T. b. brucei* and transported to lysosomes, where it inserts into the lysosomal membrane and forms pores that lead to parasite swelling and death.

While the ability to lyse *T. b. brucei* is shared by all 3 APOL1 variants (G0, G1, and G2), APOL1 G1 and G2 variants confer additional protection against parasite species that have evolved a serum resistant associated-protein (SRA) which inhibits APOL1 G0; APOL1 G1 and G2 variants confer additional protection against *trypanosoma* species that cause sleeping sickness. G1 and G2 variants evade inhibition by SRA; G1 confers additional protection against *T. b. gambiense* (which causes West African sleeping sickness) while G2 confers additional protection against *T. b. rhodesiense* (which causes East African sleeping sickness).

In the kidney, APOL1 is expressed in podocytes, endothelial cells (including glomerular endothelial cells), and some tubular cells. Podocyte-specific expression of APOL1 G1 or G2 (but not G0) in transgenic mice induces structural and functional changes, including albuminuria, decreased kidney function, podocyte abnormalities, and glomerulosclerosis. Consistent with these data, G1 and G2 variants of APOL1 play a causative role in inducing FSGS and accelerating its progression in humans. Individuals with APOL1 risk alleles (i.e., homozygous or compound heterozygous for the APOL1 G1 or APOL1 G2 alleles) have increased risk of developing FSGS and they are at risk for rapid decline in kidney function if they develop FSGS. Thus, inhibition of APOL1 could have a positive impact in individuals who harbor APOL1 risk alleles.

Although normal plasma concentrations of APOL1 are relatively high and can vary at least 20-fold in humans, circulating APOL1 is not causally associated with kidney disease. However, APOL1 in the kidney is thought to be responsible for the development of kidney diseases, including FSGS and NDKD. Under certain circumstances, APOL1 protein synthesis can be increased by approximately 200-fold by pro-inflammatory cytokines such as interferons or tumor necrosis factor-α. In addition, several studies have shown that APOL1 protein can form pH-gated $Na^+/K^+$ pores in the cell membrane, resulting in a net efflux of intracellular $K^+$, ultimately resulting in activation of local and systemic inflammatory responses, cell swelling, and death.

The risk of ESKD is substantially higher in people of recent sub-Saharan African ancestry as compared to those of European ancestry. In the United States, ESKD is responsible for nearly as many lost years of life in women as from breast cancer and more lost years of life in men than from colorectal cancer.

FSGS and NDKD are caused by damage to podocytes, which are part of the glomerular filtration barrier, resulting in proteinuria. Patients with proteinuria are at a higher risk of developing end-stage kidney disease (ESKD) and developing proteinuria-related complications, such as infections or thromboembolic events. There is no standardized treatment regimen nor approved drugs for FSGS or NDKD. Currently, FSGS and NDKD are managed with symptomatic treatment (including blood pressure control using blockers of the renin angiotensin system), and patients with FSGS and heavy proteinuria may be offered high dose steroids. Current therapeutic options for NDKD are anchored on blood pressure control and blockade of the renin angiotensin system.

Corticosteroids, alone or in combination with other immunosuppressants, induce remission in a minority of patients (e.g., remission of proteinuria in a minority of patients) and are associated with numerous side effects. However, remission is frequently indurable even in patients initially responsive to corticosteroid and/or immunosuppressant treatment. As a result, patients, in particular individuals of recent sub-Saharan African ancestry with 2 APOL1 risk alleles, experience rapid disease progression leading to end-stage renal disease (ESRD). Thus, there is an unmet medical need for treatment for FSGS and NDKD. Illustratively, in view of evidence that APOL1 plays a causative role in inducing and accelerating the progression of kidney disease, inhibition of APOL1 should have a positive impact on patients with APOL1 mediated kidney disease, particularly those who carry two APO1 risk alleles (i.e., are homozygous or compound heterozygous for the G1 or G2 alleles).

Additionally, APO1 is an aberrantly expressed gene in multiple cancers (Lin et al., *Cell Death and Disease* (2021), 12:760). Recently, APOL1 was found to be abnormally elevated in human pancreatic cancer tissues compared with adjacent tissues and was associated with poor prognosis in pancreatic cancer patients. In in vivo and in vitro experiments, knockdown of APOL1 significantly inhibited cancer cell proliferation and promoted the apoptosis of pancreatic cancer cells.

One aspect of the disclosure provides at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, which can be employed in the treatment of diseases mediated by APOL1, such as FSGS and NDKD.

In some embodiments, at least one compound, tautomer, deuterated derivative, or pharmaceutically acceptable salt of the disclosure is a compound represented by the following structural formula:

Formula I

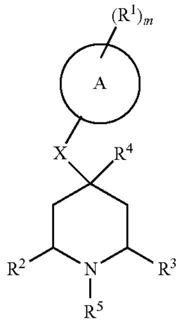

a tautomer thereof, a deuterated derivative of that compound or tautomer, or a pharmaceutically acceptable salt of any of the foregoing, wherein:

X is a bond (i.e., X is absent) or is chosen from $-(CH_2)-$, and $-(CH_2)SO_2-$;

Ring A is chosen from $C_6$ cycloalkyl, $C_6$ aryl and 5- and 6-membered heteroaryl groups;

$R^1$, for each occurrence, is independently chosen from halogen, $-OR^c$, $=O$, cyano, phenyl, $C_1$-$C_6$ alkyl, $C_1$-$C_6$ alkoxy, $C_3$-$C_6$ carbocyclyl, 4- to 6-membered heterocyclyl, $-C(=O)N(R^c)_2$, —S-(cyclopropyl), and $-SO_2(R^c)$ groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 6 groups independently chosen from halogen, cyano, —OH, $-NH_2$, $-NH(C_1$-$C_4$ alkyl), $-N(C_1$-$C_4$ alkyl$)_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, $-NH_2$, $-NH(C_1$-$C_4$ alkyl), $-N(C_1$-$C_4$ alkyl$)_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl$)_2$ groups; and the phenyl of $R^1$ is optionally substituted with 1 to 3 groups independently chosen from halogen, cyano, —OH, $-NH_2$, $-NH(C_1$-$C_4$ alkyl), $-N(C_1$-$C_4$ alkyl$)_2$, $C_1$-$C_4$ alkyl, $C_1$-$C_4$ alkoxy, $-C(=O)NH_2$, $-C(=O)NH(C_1$-$C_4$ alkyl), and $-C(=O)N(C_1$-$C_4$ alkyl$)_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, 5- to 6-membered heteroaryl are each optionally substituted with 1 to 4 groups selected from halogen, —OH, and $C_1$-$C_4$ alkyl;

$R^2$ is chosen from cyano, $C_1$-$C_6$ alkyl, $-C(=O)O(C_1$-$C_4$ alkyl), $C_2$-$C_6$ alkynyl, and

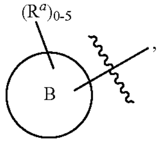

wherein:

the $C_1$-$C_6$ alkyl of $R^2$ is optionally substituted with 1 to 3 groups independently chosen from halogen, cyano, —OH, $-NH_2$, $-NH(C_1$-$C_4$ alkyl), $-N(C_1$-$C_4$ alkyl$)_2$, $C_1$-$C_4$ alkoxy, $-C(=O)NH_2$, $-C(=O)NH(C_1$-$C_4$ alkyl), $-C(=O)N(C_1$-$C_4$ alkyl$)_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, $-C(=O)NR^hR^i$, $-NR^hR^i$, $-NR^hC(=O)R^k$, $-NR^hC(=O)OR^k$, $-NR^hC(=O)NR^iR^j$, $-NR^hS(=O)_pR^k$, $-OR^k$, $-OC(=O)R^k$, $-OC(=O)OR^k$, $-OC(=O)NR^hR^i$, $-[O(CH_2)_q]_rO(C_1$-$C_6$ alkyl), $-S(=O)_pR^k$, $-S(=O)_pNR^hR^i$, $-C(=O)OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$ groups), cyano, —C(═O)$R^k$, —C(═O)O$R^k$, —C(═O)N$R^hR^i$, —N$R^hR^i$, —N$R^h$C(═O)$R^k$, —N$R^h$C(═O)O$R^k$, —N$R^h$C(═O)N$R^iR^j$, —N$R^h$S(═O)$R^k$, —O$R^k$, —OC(═O)$R^k$, —OC(═O)O$R^k$, —OC(═O)N$R^hR^i$, —S(═O)$_pR^k$, —S(═O)$_p$N$R^hR^i$, —O($C_6$ aryl) (optionally substituted with 1 to 3 $R^m$ groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —N$R^hR^i$, and —O$R^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_pR^k$, and —O$R^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from hydrogen, halogen, cyano, $C_1$-$C_6$ alkyl, $C_1$-$C_6$ haloalkyl, —$(CH_2)_n$C(═O)N$R^nR^o$, —N$R^nR^o$, —N$R^o$C(═O)$R^p$, —N$R^n$S(═O)$_pR^p$, —$(CH_2)_n$O$R^p$, —S(═O)$_pR^p$, —S(═O)$_p$N$R^nR^o$, —OS(═O)$_p$N$R^nR^o$, and —($CH_2$)~C(═O)O$R^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

$R^5$ is chosen from hydrogen and $C_1$-$C_6$ alkyl;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, the variable X in the compounds of Formula I is a bond (i.e., X is absent).

In some embodiments, Compound I296 and Compound 43a are excluded from Formula I.

In some embodiments, the compound of Formula I is a compound represented by the following structural formula:

Formula Ia

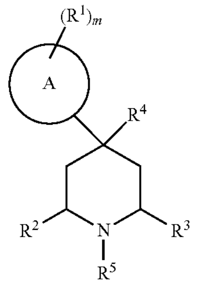

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, ═O, cyano, phenyl, $C_1$-$C_6$ alkyl, $C_1$-$C_6$ alkoxy, $C_3$-$C_6$ carbocyclyl, 4- to 6-membered heterocyclyl, —C(═O)N$(R^c)_2$, and —$SO_2$($R^c$) groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, 5- to 6-membered heteroaryl are each optionally substituted with 1 to 4 groups selected from halogen, —OH, and $C_1$-$C_4$ alkyl;

$R^2$ is chosen from cyano, $C_1$-$C_6$ alkyl, —C(=O)O($C_1$-$C_4$ alkyl), $C_2$-$C_6$ alkynyl, and

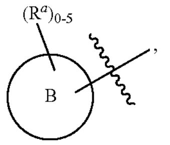

wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^h$C(=O)$R^k$, —$NR^h$C(=O)$OR^k$, —$NR^h$C(=O)$NR^iR^j$, —$NR^h$S(=O)$_pR^k$, —$OR^k$, —OC(=O)$R^k$, —OC(=O)$OR^k$, —OC(=O)$NR^hR^i$, —$[O(CH_2)_q]_r$O($C_1$-$C_6$ alkyl), —S(=O)$_pR^k$, —S(=O)$_p$$NR^hR^i$, —C(=O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(=O)$R^k$, —C(=O)$OR^k$, —C(=O)$NR^hR^i$, —$NR^hR^i$, —$NR^h$C(=O)$R^k$, —$NR^h$C(=O)$OR^k$, —$NR^h$C(=O)$NR^iR^j$, —$NR^h$S(=O)$_pR^k$, —$OR^k$, —OC(=O)$R^k$, —OC(=O)$OR^k$, —OC(=O)$NR^hR^i$, —S(=O)$_pR^k$, —S(=O)$_p$$NR^hR^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(=O)$_pR^k$, and —$OR^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(=O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), and —C(=O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(=O)$_2$($C_1$-$C_4$ alkyl)), $C_1$-$C_4$ alkoxy, —C(=O)$NH_2$, —C(=O)NH($C_1$-$C_4$ alkyl), —NHC(=O)($C_1$-$C_4$ alkyl), —C(=O)($C_1$-$C_4$ alkoxy), and —C(=O)N($C_1$-$C_4$ alkyl)$_2$ groups;

$R^4$ is chosen from halogen, cyano, $C_1$-$C_6$ alkyl, $C_1$-$C_6$ haloalkyl, —$(CH_2)_n$C(=O)$NR^nR^o$, —$NR^nR^o$, —$NR^o$C(=O)$R^p$, —$NR^n$S(=O)$_pR^p$, —$(CH_2)_n$$OR^p$, —S(=O)$_pR^p$, —S(=O)$_p$$NR^nR^o$, —OS(=O)$_p$$NR^nR^o$, and —$(CH_2)_n$C(=O)$OR^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

$R^5$ is chosen from hydrogen and $C_1$-$C_6$ alkyl;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, Compound I296 and Compound 43a are excluded from Formula Ia.

Formula I also encompasses compounds of Formula Ib having the following structure:

Formula Ib

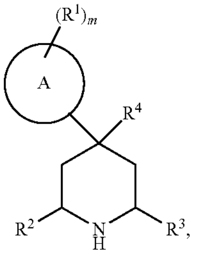

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, =O, cyano, phenyl, $C_1$-$C_6$ alkyl, $C_1$-$C_6$ alkoxy, $C_3$-$C_6$ carbocyclyl, 4- to 6-membered heterocyclyl, —C(=O)N($R^c$)$_2$, and —SO$_2$($R^c$) groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$ groups; and the phenyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, 5- to 6-membered heteroaryl are each optionally substituted with 1 to 4 groups selected from halogen, —OH, and $C_1$-$C_4$ alkyl;

$R^2$ is chosen from cyano, $C_1$-$C_6$ alkyl, —C(=O)O($C_1$-$C_4$ alkyl), $C_2$-$C_6$ alkynyl, and

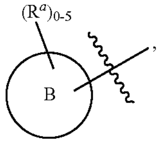

wherein:

the $C_1$-$C_6$ alkyl of $R^2$ is optionally substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)NR$^h$R$^i$, —NR$^h$R$^i$, —NR$^h$ C(=O)R$^k$, —NR$^h$ C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —[O(CH$_2$)$_q$]$_r$O($C_1$-$C_6$ alkyl), —S(=O)$_p$R$^k$, —S(=O)$_p$NR$^h$R$^i$, —C(=O)OR$^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(=O)R$^k$, —C(=O)OR$^k$, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —S(=O)$_p$R$^k$, —S(=O)$_p$NR$^h$R$^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —NR$^h$R$^i$, and —OR$^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^1$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$R$^k$, and —OR$^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from halogen, cyano, $C_1$-$C_6$ alkyl, $C_1$-$C_6$ haloalkyl, —(CH$_2$)$_n$C(═O)NR$^n$R$^o$, —NR$^n$R$^o$, —NR$^o$C(═O)R$^p$, —NR$^n$S(═O)$_p$R$^p$, —(CH$_2$)$_n$OR$^p$, —S(═O)$_p$R$^p$, —S(═O)$_p$NR$^n$R$^o$, —OS(═O)$_p$NR$^n$R$^o$, and —(CH$_2$)$_n$C(═O)OR$^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, Compound I296 and Compound 43a are excluded from Formula 1b.

Formula I also encompasses compounds of Formula Ic having the following structure:

Formula Ic

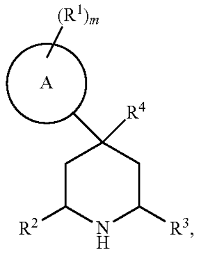

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, ═O, cyano, phenyl, $C_1$-$C_6$ alkyl, $C_1$-$C_6$ alkoxy, $C_3$-$C_6$ carbocyclyl, 4- to 6-membered heterocyclyl, and —C(═O)N($R^c$)$_2$ groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

$R^2$ is chosen from cyano, $C_1$-$C_6$ alkyl, —C(═O)O($C_1$-$C_4$ alkyl), $C_2$-$C_6$ alkynyl, and

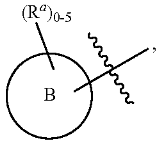

wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), —C(═O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)NR$^h$R$^i$, —NR$^h$R$^i$, —NR$^h$ C(═O)R$^k$, —NR$^h$ C(O)OR$^k$, —NR$^h$C(═O)NR$^i$R$^j$, —NR$^h$S(═O)$_p$R$^k$, —OR$^k$, —OC(═O)R$^k$, —OC(═O)OR$^k$, —OC(═O)NR$^h$R$^i$, —[O(CH$_2$)$_q$]$_r$O($C_1$-$C_6$ alkyl), —S(═O)$_p$R$^k$, —S(═O)$_p$NR$^h$R$^i$, —C(═O)OR$^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(═O)$R^k$, —C(═O)O$R^k$, —C(═O)N$R^h$$R^i$, —N$R^h$$R^i$, —N$R^h$C(═O)$R^k$, —N$R^h$C(═O)O$R^k$, —N$R^h$C(═O)N$R^i$$R^j$, —N$R^h$S(═O)$R^k$, —O$R^k$, —OC(═O)$R^k$, —OC(═O)O$R^k$, —OC(═O)N$R^h$$R^i$, —S(═O)$_p$$R^k$, —S(═O)$_p$N$R^h$$R^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —N$R^h$$R^i$, and —O$R^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$$R^k$, and —O$R^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from halogen, cyano, $C_1$-$C_6$ alkyl, $C_1$-$C_6$ haloalkyl, —$(CH_2)_n$C(═O)N$R^n$$R^o$, —N$R^n$$R^o$, —N$R^o$C(═O)$R^p$, —N$R^n$S(═O)$_p$$R^p$, —$(CH_2)_n$O$R^p$, —S(═O)$_p$$R^p$, —S(═O)$_p$N$R^n$$R^o$, —OS(═O)$_p$N$R^n$$R^o$, and —$(CH_2)_n$C(═O)O$R^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, Compound I296 and Compound 43a are excluded from Formula Ic.

In some embodiments, in a compound, tautomer, deuterated derivative, or pharmaceutically acceptable salt of Formula Ic, Ring A is chosen from $C_6$ aryl and 5- and 6-membered heteroaryl groups;

$R^1$, for each occurrence, is independently chosen from halogen, $C_1$-$C_6$ alkyl, $C_1$-$C_6$ alkoxy, $C_3$-$C_6$ carbocyclyl, 4- to 6-membered heterocyclyl, and —C(═O)N(R')$_2$ groups, wherein:

the 4- to 6-membered heterocyclyl of $R^1$ comprises one heteroatom chosen from nitrogen and oxygen;

the $C_1$-$C_6$ alkyl and $C_1$-$C_6$ alkoxy of $R^1$ are optionally substituted with 1-3 groups chosen from —OH, cyano, and halogen groups; and $R^c$, for each occurrence, is independently chosen from hydrogen and $C_1$-$C_4$ alkyl groups;

$R^2$ and $R^3$ are each independently chosen from $C_1$-$C_4$ alkyl, $C_3$-$C_6$ carbocyclic, and 5-membered heteroaryl groups, wherein:

the 5-membered heteroaryl groups are optionally substituted with 1-2 $C_1$-$C_4$ alkyl groups optionally substituted with —S(═O)$_2$$CH_3$; and the $C_1$-$C_4$ alkyl groups are optionally substituted with halogen and $C_3$-$C_6$ carbocyclic groups;

$R^4$ is —OH and —O($C_1$-$C_4$ alkyl) groups; and m is an integer chosen from 0, 1, 2, 3, 4, and 5.

In some embodiments, in a compound, tautomer, deuterated derivative, or pharmaceutically acceptable salt of Formula Ic, Ring A is chosen from $C_6$ aryl and 5- and 6-membered heteroaryl groups;

$R^1$, for each occurrence, is independently chosen from halogen, $C_1$-$C_4$ alkyl, $C_1$-$C_4$ alkoxy, $C_3$ cycloalkyl, and —C(═O)N(R)$_2$ groups, wherein:

the $C_1$-$C_4$ alkyl and $C_1$-$C_4$ alkoxy of $R^1$ are optionally substituted with 1-3 groups chosen from halogens; and $R^c$, for each occurrence, is independently chosen from hydrogen and $C_1$-$C_4$ alkyl groups;

$R^2$ and $R^3$ are each independently chosen from $C_1$-$C_4$ alkyl and 5-membered heteroaryl groups, wherein the 5-membered heteroaryl groups are optionally substituted with 1-2 $C_1$-$C_4$ alkyl groups optionally substituted with —S(═O)$_2$$CH_3$;

$R^4$ is —OH; and m is an integer chosen from 0, 1, and 2.

In some embodiments, Compound I296 and Compound 43a are excluded from Formula Ic.

In one aspect of the disclosure, the compounds of Formula I are chosen from Compounds 1 to 29, Compounds I5 to I295, Compounds 30 to 44, and Compounds 45 to 68, such that the at least one compound, pharmaceutically acceptable salt, solvate, or deuterated derivative is chosen from Compounds 1 to 29, Compounds I5 to I295, Compounds 30 to 44, and Compounds 45 to 68, pharmaceutically acceptable salts of any of those compounds, solvates of any of the foregoing, and deuterated derivatives of any of the foregoing.

In some embodiments, the disclosure provides a pharmaceutical composition comprising at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing. In some embodiments, the pharmaceutical composition may comprise at least one compound chosen from Compounds 1 to 29, Compounds I5 to I295, Compounds 30 to 44, and Compounds 45 to 68, pharmaceutically acceptable salts of any of those compounds, solvates of any of the foregoing, and deuterated derivatives of any of the foregoing. These compositions may further include at least one additional active pharmaceutical ingredient and/or at least one carrier.

Another aspect of the disclosure provides methods of treating an APOL1-mediated disease comprising administering to a subject in need thereof, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, or a pharmaceutical composition comprising the at least one compound, tautomer, deuterated derivative, or pharmaceutically acceptable salt. In some embodiments, the methods comprise administering at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing.

Another aspect of the disclosure provides methods of treating an APOL1-mediated cancer (such as, e.g., pancreatic cancer) comprising administering to a subject in need thereof, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, or a pharmaceutical composition comprising the at least one compound, tautomer, deuterated derivative, or pharmaceutically acceptable salt. In some embodiments, the methods comprise administering at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing.

Another aspect of the disclosure provides methods of treating APOL1-mediated kidney disease (such as, e.g., ESKD, FSGS and/or NDKD) comprising administering to a subject in need thereof, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, or a pharmaceutical composition comprising the at least one compound, tautomer, deuterated derivative, or pharmaceutically acceptable salt. In some embodiments, the methods comprise administering at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing.

In some embodiments, the methods of treatment include administration of at least one additional active agent to the subject in need thereof, either in the same pharmaceutical composition as the at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, or as separate compositions. In some embodiments, the methods comprise administering at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing with at least one additional active agent, either in the same pharmaceutical composition or in a separate composition.

Also provided are methods of inhibiting APOL1, comprising administering to a subject in need thereof, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, or a pharmaceutical composition comprising the at least one compound, tautomer, deuterated derivative, or pharmaceutically acceptable salt. In some embodiments, the methods of inhibiting APOL1 comprise administering at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing, or a pharmaceutical composition comprising the at least one compound, tautomer, deuterated derivative, or pharmaceutically acceptable salt.

DETAILED DESCRIPTION

Definitions

Figure 1:
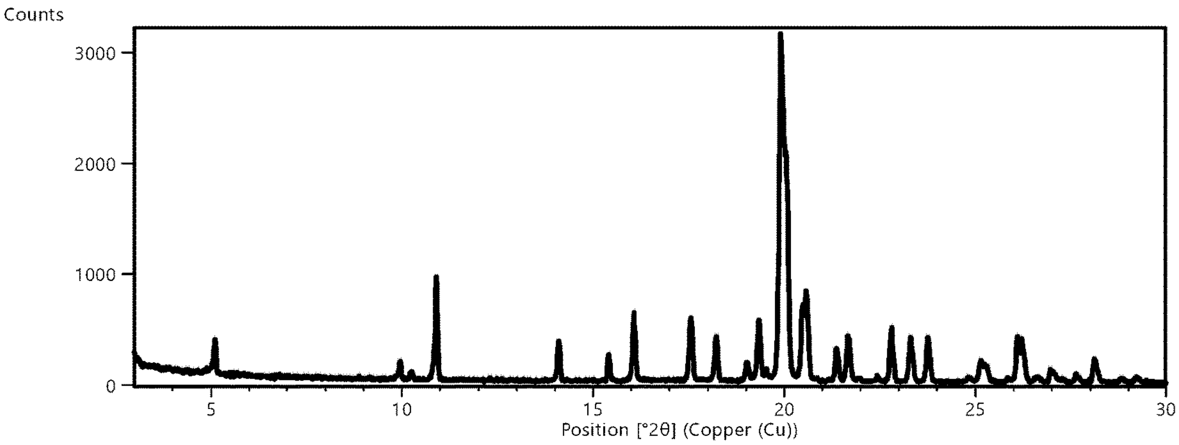
FIG. 1 depicts an XRPD diffractogram of Compound 16 Form A.

The term "APOL1," as used herein, means apolipoprotein L1 protein and the term "APOL1" means apolipoprotein L1 gene.

The term "APOL1 mediated disease" refers to a disease or condition associated with aberrant APOL1 (e.g., certain APOL1 genetic variants; elevated levels of APOL1). In some embodiments, an APOL1 mediated disease is an APOL1 mediated kidney disease. In some embodiments, an APOL1 mediated disease is associated with patients having two APOL1 risk alleles, e.g., patients who are homozygous or compound heterozygous for the G1 or G2 alleles. In some embodiments, an APOL1 mediated disease is associated with patients having one APOL1 risk allele.

The term "APOL1 mediated kidney disease" refers to a disease or condition that impairs kidney function and can be attributed to APOL1. In some embodiments, APOL1 mediated kidney disease is associated with patients having two APOL1 risk alleles, e.g., patients who are homozygous or compound heterozygous for the G1 or G2 alleles. In some embodiments, the APOL1 mediated kidney disease is chosen from ESKD, NDKD, FSGS, HIV-associated nephropathy, arterionephrosclerosis, lupus nephritis, microalbuminuria, and chronic kidney disease. In some embodiments, the APOL1 mediated kidney disease is chronic kidney disease or proteinuria.

The term "FSGS," as used herein, means focal segmental glomerulosclerosis, which is a disease of the podocyte (glomerular visceral epithelial cells) responsible for proteinuria and progressive decline in kidney function, and associated with 2 common APOL1 genetic variants (G1: S342G: I384M and G2: N388del:Y389del).

The term "NDKD," as used herein, means non-diabetic kidney disease, which is characterized by severe hypertension and progressive decline in kidney function, and associated with 2 commonAPOL1 genetic variants (G1: S342G: I384M and G2: N388del:Y389del).

The terms "ESKD" and "ESRD" are used interchangeably herein to refer to end stage kidney disease or end stage renal disease. ESKD/ESRD is the last stage of kidney disease, i.e., kidney failure, and means that the kidneys have stopped working well enough for the patient to survive without dialysis or a kidney transplant. In some embodiments, ESKD/ESRD is associated with two APOL1 risk alleles.

The term "compound," when referring to a compound of this disclosure, refers to a collection of molecules having an identical chemical structure unless otherwise indicated as a collection of stereoisomers (for example, a collection of racemates, a collection of cis/trans stereoisomers, or a collection of (E) and (Z) stereoisomers), except that there may be isotopic variation among the constituent atoms of the molecules. Thus, it will be clear to those of skill in the art that a compound represented by a particular chemical structure containing indicated deuterium atoms will also contain lesser amounts of isotopologues having hydrogen atoms at one or more of the designated deuterium positions in that structure. The relative amount of such isotopologues in a compound of this disclosure will depend upon a number of factors including the isotopic purity of reagents used to make the compound and the efficiency of incorporation of isotopes in the various synthesis steps used to prepare the compound. However, as set forth above, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

As used herein, "optionally substituted" is interchangeable with the phrase "substituted or unsubstituted." In general, the term "substituted," whether preceded by the term "optionally" or not, refers to the replacement of hydrogen radicals in a given structure with the radical of a specified substituent. Unless otherwise indicated, an "optionally substituted" group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

The term "isotopologue" refers to a species in which the chemical structure differs from a reference compound only in the isotopic composition thereof. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$ or $^{14}C$, are within the scope of this disclosure.

Unless otherwise indicated, structures depicted herein are also meant to include all isomeric forms of the structures, e.g., racemic mixtures, cis/trans isomers, geometric (or conformational) isomers, such as (Z) and (E) double bond isomers, and (Z) and (E) conformational isomers. Therefore, geometric and conformational mixtures of the present compounds are within the scope of the disclosure. Unless otherwise stated, all tautomeric forms of the compounds of the disclosure are within the scope of the disclosure.

The term "tautomer," as used herein, refers to one of two or more isomers of a compound that exist together in equilibrium, and are readily interchanged by migration of an atom, e.g., a hydrogen atom, or group within the molecule.

"Stereoisomer," as used herein, refers to enantiomers and diastereomers.

As used herein, "deuterated derivative" refers to a compound having the same chemical structure as a reference compound, but with one or more hydrogen atoms replaced by a deuterium atom ("D" or "$^{2}H$"). It will be recognized that some variation of natural isotopic abundance occurs in a synthesized compound depending on the origin of chemical materials used in the synthesis. The concentration of naturally abundant stable hydrogen isotopes, notwithstanding this variation, is small and immaterial as compared to the degree of stable isotopic substitution of deuterated derivatives described herein. Thus, unless otherwise stated, when a reference is made to a "deuterated derivative" of a compound of the disclosure, at least one hydrogen is replaced with deuterium at well above its natural isotopic abundance (which is typically about 0.015%). In some embodiments, the deuterated derivatives of the disclosure have an isotopic enrichment factor for each deuterium atom, of at least 3500 (52.5% deuterium incorporation at each designated deuterium), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), or at least 6600 (99% deuterium incorporation).

The term "isotopic enrichment factor," as used herein, means the ratio between the isotopic abundance and the natural abundance of a specified isotope.

The term "alkyl" or "aliphatic," as used herein, means a straight-chain (i.e., linear or unbranched) or branched, substituted or unsubstituted hydrocarbon chain that is completely saturated. Unless otherwise specified, alkyl groups contain 1 to 20 alkyl carbon atoms. In some embodiments, alkyl groups contain 1 to 10 aliphatic carbon atoms. In some embodiments, alkyl groups contain 1 to 8 aliphatic carbon atoms. In some embodiments, alkyl groups contain 1 to 6 alkyl carbon atoms. In some embodiments, alkyl groups contain 1 to 4 alkyl carbon atoms, in other embodiments, alkyl groups contain 1 to 3 alkyl carbon atoms, and in yet other embodiments, alkyl groups contain 1 or 2 alkyl carbon atoms. In some embodiments, alkyl groups are linear or straight-chain or unbranched. In some embodiments, alkyl groups are branched.

The terms “cycloalkyl” and “cyclic alkyl,” as used herein, refer to a monocyclic $C_{3-8}$ hydrocarbon or a spirocyclic, fused, or bridged bicyclic or tricyclic $C_{8-14}$ hydrocarbon that is completely saturated, wherein any individual ring in said bicyclic ring system has 3 to 7 members. In some embodiments, the cycloalkyl is a $C_3$ to Cu cycloalkyl. In some embodiments, the cycloalkyl is a $C_3$ to $C_8$ cycloalkyl. In some embodiments, the cycloalkyl is a $C_3$ to $C_6$ cycloalkyl. Non-limiting examples of monocyclic cycloalkyls include cyclopropyl, cyclobutyl, cyclopentanyl, and cyclohexyl.

The terms “carbocyclyl” or “cycloaliphatic,” as used herein, encompass the terms “cycloalkyl” or “cyclic alkyl,” and refer to a monocyclic $C_{3-8}$ hydrocarbon or a spirocyclic, fused, or bridged bicyclic or tricyclic $C_{8-14}$ hydrocarbon that is completely saturated, or is partially saturated as in it contains one or more units of unsaturation but is not aromatic, wherein any individual ring in said bicyclic ring system has 3 to 7 members. Bicyclic carbocyclyls include combinations of a monocyclic carbocyclic ring fused to a phenyl. In some embodiments, the carbocyclyl is a $C_3$ to $C_{12}$ carbocyclyl. In some embodiments, the carbocyclyl is a $C_3$ to $C_{10}$ carbocyclyl. In some embodiments, the carbocyclyl is a $C_3$ to $C_8$ carbocyclyl.

The term “heteroalkyl,” or “heteroaliphatic,” as used herein, means an alkyl or aliphatic group as defined above, wherein one or two carbon atoms are independently replaced by one or more of oxygen, sulfur, nitrogen, phosphorus, or silicon.

The term “alkenyl,” as used herein, means a straight-chain (i.e., linear or unbranched) or branched hydrocarbon chain that contains one or more double bonds. In some embodiments, alkenyl groups are straight-chain. In some embodiments, alkenyl groups are branched.

The term “heterocycle,” “heterocyclyl,” “heterocycloaliphatic,” or “heterocyclic,” as used herein, means non-aromatic (i.e., completely saturated or partially saturated as in it contains one or more units of unsaturation but is not aromatic), monocyclic, or spirocyclic, fused, or bridged bicyclic or tricyclic ring systems in which one or more ring members of the ring system is an independently chosen heteroatom. Bicyclic heterocyclyls include the following combinations of monocyclic rings: a monocyclic heteroaryl fused to a monocyclic heterocyclyl; a monocyclic heterocyclyl fused to another monocyclic heterocyclyl; a monocyclic heterocyclyl fused to phenyl; a monocyclic heterocyclyl fused to a monocyclic carbocyclyl/cycloalkyl; and a monocyclic heteroaryl fused to a monocyclic carbocyclyl/cycloalkyl.

In some embodiments, the heterocycle comprises a ring atom substituted with one or more oxo groups (such as, e.g., a C═O group, a S═O group, or a $SO_2$ group).

In some embodiments, the “heterocycle,” “heterocyclyl,” “heterocycloaliphatic,” or “heterocyclic” group has 3 to 14 ring members in which one or more ring members is a heteroatom independently chosen from oxygen, sulfur, nitrogen, and phosphorus. In some embodiments, each ring in a bicyclic or tricyclic ring system contains 3 to 7 ring members. In some embodiments, the heterocycle has at least one unsaturated carbon-carbon bond. In some embodiments, the heterocycle has at least one unsaturated carbon-nitrogen bond. In some embodiments, the heterocycle has one heteroatom independently chosen from oxygen, sulfur, nitrogen, and phosphorus. In some embodiments, the heterocycle has one heteroatom that is a nitrogen atom. In some embodiments, the heterocycle has one heteroatom that is an oxygen atom. In some embodiments, the heterocycle has two heteroatoms that are each independently chosen from nitrogen and oxygen. In some embodiments, the heterocycle has three heteroatoms that are each independently chosen from nitrogen and oxygen. In some embodiments, the heterocyclyl is a 3- to 12-membered heterocyclyl. In some embodiments, the heterocyclyl is a 3 to 10-membered heterocyclyl. In some embodiments, the heterocyclyl is a 3- to 8-membered heterocyclyl. In some embodiments, the heterocyclyl is a 5- to 10-membered heterocyclyl. In some embodiments, the heterocyclyl is a 5- to 8-membered heterocyclyl. In some embodiments, the heterocyclyl is a 5- or 6-membered heterocyclyl. Non-limiting examples of monocyclic heterocyclyls include piperidinyl, piperazinyl, tetrahydropyranyl, azetidinyl, tetrahydrothiophenyl 1,1-dioxide, etc.

The term “heteroatom” means one or more of oxygen, sulfur, nitrogen, phosphorus, or silicon (including, e.g., any oxidized form of nitrogen, sulfur, phosphorus, or silicon; the quaternized form of any basic nitrogen or; a substitutable nitrogen of a heterocyclic ring, for example, N (as in 3,4-dihydro-2H-pyrrolyl), NH (as in pyrrolidinyl) or $NR^+$ (as in N-substituted pyrrolidinyl)).

The term “unsaturated,” as used herein, means that a moiety has one or more units or degrees of unsaturation. Unsaturation is the state in which not all of the available valence bonds in a compound are satisfied by substituents and thus the compound contains double or triple bonds.

The term “alkoxy” or “thioalkyl,” as used herein, refers to an alkyl group, as previously defined, wherein one carbon of the alkyl group is replaced by an oxygen (“alkoxy”) or sulfur (“thioalkyl”) atom, respectively, provided that the oxygen and sulfur atoms are linked between two carbon atoms. A “cyclic alkoxy” refers to a monocyclic, spirocyclic, bicyclic, bridged bicyclic, tricyclic, or bridged tricyclic hydrocarbon that contains at least one alkoxy group, but is not aromatic. Non-limiting examples of cyclic alkoxy groups include tetrahydropyranyl, tetrahydrofuranyl, oxetanyl, 8-oxabicyclo[3.2.1]octanyl, and oxepanyl.

The terms “haloalkyl,” “haloalkenyl,” and “haloalkoxy,” as used herein, mean a linear or branched alkyl, alkenyl, or alkoxy, respectively, which is substituted with one or more halogen atoms. Non-limiting examples of haloalkyl groups include $—CHF_2$, $—CH_2F$, $—CF_3$, $—CF_2—$, and perhaloalkyls, such as $—CF_2CF_3$. Non-limiting examples of haloalkoxy groups include $—OCHF_2$, $—OCH_2F$, $—OCF_3$, and $—OCF_2$.

The term “halogen” includes F, Cl, Br, and I, i.e., fluoro, chloro, bromo, and iodo, respectively.

The term “aminoalkyl” means an alkyl group which is substituted with or contains an amino group.

As used herein, an “amino” refers to a group which is a primary, secondary, or tertiary amine.

As used herein, a “carbonyl” group refers to C═O.

As used herein, a “cyano” or “nitrile” group refer to —C≡N.

As used herein, a “hydroxy” group refers to —OH.

As used herein, a “thiol” group refers to —SH.

As used herein, “tert” and “t-” each refer to tertiary.

As used herein, “aromatic groups” or “aromatic rings” refer to chemical groups that contain conjugated, planar ring systems with delocalized pi electron orbitals comprised of [4n+2] p orbital electrons, wherein n is an integer ranging from 0 to 6. Non-limiting examples of aromatic groups include aryl and heteroaryl groups.

The term "aryl," used alone or as part of a larger moiety as in "arylalkyl," "arylalkoxy," or "aryloxyalkyl," refers to monocyclic or spirocyclic, fused, or bridged bicyclic or tricyclic ring systems having a total of five to fourteen ring members, wherein every ring in the system is an aromatic ring containing only carbon atoms and wherein each ring in a bicyclic or tricyclic ring system contains 3 to 7 ring members. Non-limiting examples of aryl groups include phenyl ($C_6$) and naphthyl ($C_{10}$) rings.

The term "heteroaryl," used alone or as part of a larger moiety as in "heteroarylalkyl" or "heteroarylalkoxy," refers to monocyclic or spirocyclic, fused, or bridged bicyclic or tricyclic ring systems having a total of five to fourteen ring members, wherein at least one ring in the system is aromatic, wherein at least one ring in the system contains one or more heteroatoms, and wherein each ring in a bicyclic or tricyclic ring system contains 3 to 7 ring members. Bicyclic heteroaryls include the following combinations of monocyclic rings: a monocyclic heteroaryl fused to another monocyclic heteroaryl; and a monocyclic heteroaryl fused to a phenyl. In some embodiments, heteroaryl groups have one or more heteroatoms chosen from nitrogen, oxygen, and sulfur. In some embodiments, heteroaryl groups have one heteroatom. In some embodiments, heteroaryl groups have two heteroatoms. In some embodiments, heteroaryl groups are monocyclic ring systems having five ring members. In some embodiments, heteroaryl groups are monocyclic ring systems having six ring members. In some embodiments, the heteroaryl is a 3- to 12-membered heteroaryl. In some embodiments, the heteroaryl is a 3- to 10-membered heteroaryl. In some embodiments, the heteroaryl is a 3- to 8-membered heteroaryl. In some embodiments, the heteroaryl is a 5- to 10-membered heteroaryl. In some embodiments, the heteroaryl is a 5- to 8-membered heteroaryl. In some embodiments, the heteroaryl is a 5- or 6-membered heteroaryl. Non-limiting examples of monocyclic heteroaryls are pyridinyl, pyrimidinyl, thiophenyl, thiazolyl, isoxazolyl, etc.

In some embodiments, the heteroaryl comprises a ring atom substituted with one or more oxo groups (such as, e.g., a C═O group, a S═O group, or a $SO_2$ group). Illustratively, a non-limiting example of a heteroaryl group is a benzo[d]oxazol-2(3H)-one group.

Non-limiting examples of useful protecting groups for nitrogen-containing groups, such as amine groups, include, for example, t-butyl carbamate (Boc), benzyl (Bn), tetrahydropyranyl (THP), 9-fluorenylmethyl carbamate (Fmoc) benzyl carbamate (Cbz), acetamide, trifluoroacetamide, triphenylmethylamine, benzylideneamine, and p-toluenesulfonamide. Methods of adding (a process generally referred to as "protecting") and removing (process generally referred to as "deprotecting") such amine protecting groups are well-known in the art and available, for example, in P. J. Kocienski, Protecting Groups, Thieme, 1994, which is hereby incorporated by reference in its entirety and in Greene and Wuts, *Protective Groups in Organic Synthesis, 3rd Edition* (John Wiley & Sons, New York, 1999) and 4th Edition (John Wiley & Sons, New Jersey, 2014).

Non-limiting examples of suitable solvents that may be used in this disclosure include, but are not limited to, water, methanol (MeOH), ethanol (EtOH), dichloromethane or "methylene chloride" ($CH_2Cl_2$), toluene, acetonitrile (MeCN), dimethylformamide (DMF), dimethyl sulfoxide (DMSO), methyl acetate (MeOAc), ethyl acetate (EtOAc), heptane, isopropyl acetate (IPAc), tert-butyl acetate (t-BuOAc), isopropyl alcohol (IPA), tetrahydrofuran (THF), 2-methyl tetrahydrofuran (2-Me THF), methyl ethyl ketone (MEK), tert-butanol, diethyl ether ($Et_2O$), methyl-tert-butyl ether (MTBE), 1,4-dioxane, and N-methyl pyrrolidone (NMP).

Non-limiting examples of suitable bases that may be used in this disclosure include, but are not limited to, 1,8-diazabicyclo[5.4.0]undec-7-ene (DBU), potassium tert-butoxide (KOtBu), potassium carbonate ($K_2CO_3$), N-methylmorpholine (NMM), triethylamine ($Et_3N$; TEA), diisopropyl-ethyl amine (i-$Pr_2EtN$; DIPEA), pyridine, potassium hydroxide (KOH), sodium hydroxide (NaOH), lithium hydroxide (LiOH) and sodium methoxide (NaOMe; $NaOCH_3$).

This disclosure includes certain substantially crystalline solid forms of the compounds of the invention. As used herein, the terms "crystalline form" and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, solid state nuclear magnetic resonance (SSNMR), differential scanning calorimetry (DSC), infrared radiation (IR), and/or thermogravimetric analysis (TGA). Accordingly, as used herein, the term "crystalline Form [X] of Compound [Y]" refers to a unique crystalline form that can be identified and distinguished from other crystalline forms of Compound [Y] by one or more characterization techniques including, for example, X-ray powder diffraction (XRPD), single crystal X-ray diffraction, SSNMR, differential scanning calorimetry (DSC), infrared radiation (IR), and/or thermogravimetric analysis (TGA). In some embodiments, the novel crystalline Form [X] of Compound [Y] is characterized by an X-ray powder diffractogram having one or more signals at one or more specified two-theta values (° 2θ).

As used herein, the term "SSNMR" refers to the analytical characterization method of solid state nuclear magnetic resonance. SSNMR spectra can be recorded at ambient or non-ambient (e.g., at 275 K) conditions on any magnetically active isotope present in the sample. Common examples of active isotopes for small molecule active pharmaceutical ingredients include $^1H$, $^2H$, $^{13}C$, $^{19}F$, $^{31}P$, $^{15}N$, $^{14}N$, $^{35}Cl$, $^{11}B$, $^7Li$, $^{17}O$, $^{23}Na$, $^{79}Br$, and $^{195}Pt$.

As used herein, the term "XRPD" refers to the analytical characterization method of X-ray powder diffraction. XRPD patterns can be recorded under ambient conditions in transmission or reflection geometry using a diffractometer.

As used herein, the terms "X-ray powder diffractogram," "X-ray powder diffraction pattern," and "XRPD pattern" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A "signal" or "peak," as used herein, refers to a point in an XRPD pattern or SSNMR spectrum where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at at . . . degrees two-theta," "a signal at [a] two-theta value[ ] of . . . ," and/or "a signal at at least . . . two-theta value(s) chosen from . . . " refer to X-ray reflection positions as measured and observed in X-ray powder diffraction experiments (° 2θ).

The repeatability of the angular values is in the range of ±0.2° 2θ, i.e., the angular value can be at the recited angular value+0.2 degrees two-theta, the angular value −0.2 degrees two-theta, or any value between those two end points (angular value+0.2 degrees two-theta and angular value −0.2 degrees two-theta).

As used herein, the terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

The terms "X-ray powder diffractogram having a signal at . . . two-theta values" and "X-ray powder diffractogram comprising a signal at . . . two-theta values" are used interchangeably herein and refer to an XRPD pattern that contains X-ray reflection positions as measured and observed in X-ray powder diffraction experiments (° 2θ).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal positions in XRPD diffractograms (in degrees two-theta (° 2θ) referred to herein) generally mean that value reported is +0.2 degrees 2θ of the reported value, an art-recognized variance.

As used herein, an SSNMR spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the signal positions in SSNMR spectra (in ppm) referred to herein generally mean that value reported is +0.2 ppm of the reported value, an art-recognized variance.

As used herein, the term "DSC" refers to the analytical method of Differential Scanning Calorimetry. A DSC curve is "substantially similar to that in [a particular] Figure" when at least 90%, such as at least 95%, at least 98%, or at least 99%, of the features in the two curves overlap. In determining "substantial similarity," one of ordinary skill in the art will understand that there may be variation in the intensities and/or peak (e.g., endotherm or exotherm) positions in DSC curves, even for the same solid form.

As used herein, the term "TGA" refers to the analytical method of Thermo Gravimetric (or thermogravimetric) Analysis. A TGA thermogram is "substantially similar to that in [a particular] Figure" when at least 90%, such as at least 95%, at least 98%, or at least 99%, of the features in the two thermograms overlap. In determining "substantial similarity," one of ordinary skill in the art will understand that there may be variation in the intensities and/or peak (e.g., degradation peak) positions in TGA thermograms even for the same solid form.

As used herein, the term "substantially crystalline" refers to a solid material having few or no amorphous molecules. For example, substantially crystalline materials have less than 15% amorphous molecules (e.g., less than 10% amorphous molecules, less than 5% amorphous molecules, or less than 2% amorphous molecules). It is also noted that the term "substantially crystalline" includes the descriptor "crystalline," which refers to materials that are 100% crystalline form.

As used herein, a crystalline form is "substantially pure" when it accounts for an amount by weight equal to or greater than 90% of the sum of all solid form(s) in a sample as determined by a method in accordance with the art, such as, e.g., quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

The disclosure includes pharmaceutically acceptable salts of the disclosed compounds. A salt of a compound is formed between an acid and a basic group of the compound, such as an amino functional group, or a base and an acidic group of the compound, such as a carboxyl functional group.

The term "pharmaceutically acceptable," as used herein, refers to a component that is, within the scope of sound medical judgment, suitable for use in contact with the tissues of humans and other mammals without undue toxicity, irritation, allergic response, and the like, and are commensurate with a reasonable benefit/risk ratio. A "pharmaceutically acceptable salt" means any non-toxic salt that, upon administration to a recipient, is capable of providing, either directly or indirectly, a compound of this disclosure. Suitable pharmaceutically acceptable salts are, for example, those disclosed in S. M. Berge, et al. *J Pharmaceutical Sciences,* 1977, 66, 1 to 19.

Acids commonly employed to form pharmaceutically acceptable salts include inorganic acids such as hydrogen bisulfide, hydrochloric acid, hydrobromic acid, hydroiodic acid, sulfuric acid, and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2- sulfonate, mandelate, and other salts. In some embodiments, pharmaceutically acceptable acid addition salts include those formed with mineral acids such as hydrochloric acid and hydrobromic acid, and those formed with organic acids such as maleic acid.

Pharmaceutically acceptable salts derived from appropriate bases include alkali metal, alkaline earth metal, ammonium, and $N^+(C_{1-4}\ alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

The terms "patient" and "subject" are used interchangeably herein and refer to an animal, including a human.

The terms "effective dose" and "effective amount" are used interchangeably herein and refer to that amount of compound that produces a desired effect for which it is administered (e.g., improvement in a symptom of FSGS and/or NDKD, lessening the severity of FSGS and/NDKD or a symptom of FSGS and/or NDKD, and/or reducing progression of FSGS and/or NDKD or a symptom of FSGS and/or NDKD). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the term "treatment" and its cognates refer to slowing or stopping disease progression. "Treatment" and its cognates as used herein, include, but are not limited to, the following: complete or partial remission, lower risk of kidney failure (e.g., ESRD), and disease-related complications (e.g., edema, susceptibility to infections, or thrombo-embolic events). Improvements in or lessening the severity of any of these symptoms can be readily assessed according to methods and techniques known in the art or subsequently developed.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range. As used herein, the symbol "~" appearing immediately before a numerical value has the same meaning as the terms "about" and "approximately."

The at least one compound, tautomer, deuterated derivative, or pharmaceutically acceptable salt chosen from compounds of Formulae I, Ia, Ib, Ic, Ic-1, Tc-2, Tc-3, Tc-4, Ic-5, Ic-6, II, II-1, II-2, 11-3, 11-4, 11-5, 11-6, II-6a and II-6b, a tautomer thereof, a deuterated derivative of that compound or tautomer, or a pharmaceutically acceptable salt of any of the foregoing may be administered once daily, twice daily, or three times daily, for example, for the treatment of FSGS.

In some embodiments, the compounds of Formulae I, Ia, Ib, Ic, Ic-1, Tc-2, Tc-3, Tc-4, Ic-5, Tc-6, II, II-1, 11-2, 11-3, 11-4, 11-5, 11-6, TT-6a and II-6b, are chosen from Compounds 1 to 29, Compounds I15 to I295, Compounds 30 to 44, and Compounds 45 to 68, a tautomer thereof, a deuterated derivative of that compound or tautomer, or a pharmaceutically acceptable salt of any of the foregoing. In some embodiments, at least one compound, tautomer, deuterated derivative, or pharmaceutically acceptable salt chosen from compounds of Formulae I, Ia, Ib, Ic, Ic-1, Tc-2, Ic-3, Ic-4, Ic-5, Ic-6, II, II-1, II-2, II-3, II-4, II-5, II-6, II-6a and II-6b, a tautomer thereof, a deuterated derivative of that compound or tautomer, or a pharmaceutically acceptable salt of any of the foregoing is administered once daily. In some embodiments, at least one compound, tautomer, deuterated derivative, or pharmaceutically acceptable salt chosen from Compounds 1 to 29, Compounds I5 to I295, Compounds 30 to 44, and Compounds 45 to 68, a tautomer thereof, a deuterated derivative of that compound or tautomer, or a pharmaceutically acceptable salt of any of the foregoing is administered once daily. In some embodiments, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, a tautomer thereof, a deuterated derivative of that compound or tautomer, or a pharmaceutically acceptable salt of any of the foregoing is administered twice daily. In some embodiments, at least one compound, tautomer, deuterated derivative, or pharmaceutically acceptable salt chosen from Compounds 1 to 29, Compounds I5 to I295, Compounds 30 to 44, and Compounds 45 to 68, a tautomer thereof, a deuterated derivative of that compound or tautomer, or a pharmaceutically acceptable salt of any of the foregoing is administered twice daily. In some embodiments, at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, 11-5, 11-6, II-6a and II-6b, a tautomer thereof, a deuterated derivative of that compound or tautomer, or a pharmaceutically acceptable salt of any of the foregoing are administered three times daily. In some embodiments, at least one compound, tautomer, deuterated derivative, or pharmaceutically acceptable salt chosen from Compounds 1 to 29, Compounds I5 to I295, Compounds 30 to 44, and Compounds 45 to 68, a tautomer thereof, a deuterated derivative of that compound or tautomer, or a pharmaceutically acceptable salt of any of the foregoing is administered three times daily.

In some embodiments, 2 mg to 1500 mg or 5 mg to 1000 mg of at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, a tautomer thereof, a deuterated derivative of that compound or tautomer, or a pharmaceutically acceptable salt of any of the foregoing are administered once daily, twice daily, or three times daily. In some embodiments, 2 mg to 1500 mg or 5 mg to 1000 mg of at least one compound, tautomer, deuterated derivative, or pharmaceutically acceptable salt chosen from Compounds 1 to 29, Compounds I5 to I295, Compounds 30 to 44, and Compounds 45 to 68, a tautomer thereof, a deuterated derivative of that compound or tautomer, or a pharmaceutically acceptable salt of any of the foregoing is administered once daily, twice daily, or three times daily.

One of ordinary skill in the art would recognize that, when an amount of compound is disclosed, the relevant amount of a pharmaceutically acceptable salt form of the compound is an amount equivalent to the concentration of the free base of the compound. The amounts of the compounds, pharmaceutically acceptable salts, solvates, and deuterated derivatives disclosed herein are based upon the free base form of the reference compound. For example, "1000 mg of at least one compound or pharmaceutically acceptable salt chosen from compounds of Formula I and pharmaceutically acceptable salts thereof" includes 1000 mg of a compound of Formula I and a concentration of a pharmaceutically acceptable salt of compounds of Formula I equivalent to 1000 mg of a compound of Formula I.

As used herein, the term "ambient conditions" means room temperature, open air condition, and uncontrolled humidity condition.

Compounds and Compositions

In some embodiments, at least one compound, tautomer, deuterated derivative, or pharmaceutically acceptable salt of the disclosure is a compound represented by the following structural formula:

Formula Ia

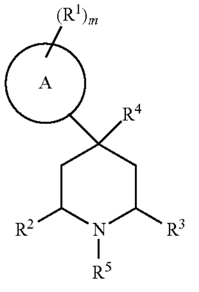

a tautomer thereof, a deuterated derivative of that compound or tautomer, or a pharmaceutically acceptable salt of any of the foregoing, wherein:

- Ring A is chosen from $C_6$ aryl and 5- and 6-membered heteroaryl groups;
- $R^1$, for each occurrence, is independently chosen from halogen, —OH, =O, cyano, phenyl, $C_1$-$C_6$ alkyl, $C_1$-$C_6$ alkoxy, $C_3$-$C_6$ carbocyclyl, 4- to 6-membered heterocyclyl, —C(=O)N($R^c$)$_2$, and —$SO_2R^c$ groups, wherein:
  - $R^c$, for each occurrence, is independently chosen from hydrogen and $C_1$-$C_4$ alkyl groups;
  - the 4- to 6-membered heterocyclyl of $R^1$ comprises one heteroatom chosen from nitrogen and oxygen;
  - the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;
  - the $C_1$-$C_6$ alkoxy of $R^1$ is optionally substituted with 1 to 3 groups independently chosen from —OH, cyano, and halogen groups;
  - the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; and
  - the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; or
  - wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring,
  - wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl;
- $R^2$ is chosen from cyano, $C_1$-$C_6$ alkyl, —C(=O)O($C_1$-$C_4$ alkyl), $C_2$-$C_6$ alkynyl, and

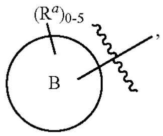

, wherein:

- the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;
- Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:
  - $R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^h$ C(=O)$R^k$, —$NR^h$ C(=O)$OR^k$, —$NR^h$C(=O)$NR^iR^j$, —$NR^h$S(=O)$_pR^k$, —$OR^k$, —OC(=O)$R^k$, —OC(=O)$OR^k$, —OC(=O)$NR^hR^i$, —[O(CH$_2$)$_q$]$_r$O($C_1$-$C_6$ alkyl), —S(=O)$_pR^k$, —S(=O)$_pNR^hR^i$, —C(=O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:
  - the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(=O)$R^k$, —C(=O)$OR^k$, —C(=O)$NR^hR^i$, —$NR^hR^i$, —$NR^h$C(=O)$R^k$, —$NR^h$C(=O)$OR^k$, —$NR^h$C(=O)$NR^iR^j$, —$NR^h$S(=O)$_pR^k$, —$OR^k$, —OC(=O)$R^k$, —OC(=O)$OR^k$, —OC(=O)$NR^hR^i$, —S(=O)$_pR^k$, —S(=O)$_pNR^hR^i$, —O($C_6$ aryl) (optionally substituted with 1 to 3 $R^m$groups), and $C_3$-$C_6$ carbocyclyl groups (optionally substituted with 1 to 3 $R^m$ groups);
  - the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^1$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$$R^k$, and —$OR^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from halogen, cyano, $C_1$-$C_6$ alkyl, $C_1$-$C_6$ haloalkyl, —$(CH_2)_n$C(═O)$NR^nR^o$, —$NR^nR^o$, —$NR^o$C(═O)$R^p$, —$NR^n$S(═O)$_p$$R^p$, —$(CH_2)_n$$OR^p$, —S(═O)$_p$$R^p$, —S(═O)$_p$$NR^nR^o$, —OS(═O)$_p$$NR^nR^o$, and —$(CH_2)_n$C(═O)$OR^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

$R^5$ is chosen from hydrogen and $C_1$-$C_6$ alkyl;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, in a compound of the disclosure (i.e., a compound of any one of Formulae I, Ia, Ib, and Ic), or a tautomer, deuterated derivative, or pharmaceutically acceptable salt thereof, $R^4$ is —OH; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof m is an integer chosen from 0, 1, and 2; and all other variables not specifically defined herein are as defined in any one of the foregoing embodiments. In some embodiments, in a compound of the disclosure (i.e., a compound of any one of Formulae I, Ia, Ib, and Ic), or a tautomer, deuterated derivative, or pharmaceutically acceptable salt thereof, tautomer, deuterated derivative, or pharmaceutically acceptable salt of the disclosure, m is 0; and all other variables not specifically defined herein are as defined in any one of the foregoing embodiments. In some embodiments, in a compound of the disclosure (i.e., a compound of any one of Formulae I, Ia, Ib, and Ic), or a tautomer, deuterated derivative, or pharmaceutically acceptable salt thereof, m is 1; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring A is phenyl, thiophenyl, or pyridinyl; and all other variables not specifically defined herein are as defined in any one of the foregoing embodiments. In some embodiments, in a compound of the disclosure (i.e., a compound of any one of Formulae I, Ia, Ib, and Ic), or a tautomer, deuterated derivative, or pharmaceutically acceptable salt thereof, Ring A is phenyl; and all other variables not specifically defined herein are as defined in any one of the foregoing embodiments. In some embodiments, in a compound of the disclosure (i.e., a compound of any one of Formulae I, Ia, Ib, and Ic), or a tautomer, deuterated derivative, or pharmaceutically acceptable salt thereof, Ring A is thiophenyl; and all other variables not specifically defined herein are as defined in any one of the foregoing embodiments. In some embodiments, in a compound of the disclosure (i.e., a compound of any one of Formulae I, Ia, Ib, and Ic), or a tautomer, deuterated derivative, or pharmaceutically acceptable salt thereof, Ring A is pyridinyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^2$ is chosen from $C_1$-$C_4$ alkyl and

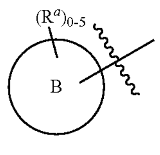

groups, wherein:

the $C_1$-$C_4$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_2$ alkoxy, $C_3$-$C_6$ cycloalkyl, 5- to 6-membered heterocyclyl, phenyl, and 5- to 6-membered heteroaryl groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^2$ is chosen from $C_1$-$C_2$ alkyl and

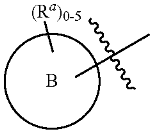

groups, wherein:

the $C_1$-$C_2$ alkyl of $R^2$ is optionally substituted with 1 to 3 groups independently chosen from halogen, cyano, —OH, and 5- to 6-membered heterocyclyl groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^2$ is chosen from —$CH_3$ and

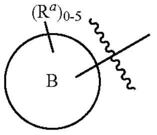

groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^2$ is chosen from —$CH_3$, —$CH_2OH$, and (tetrahydro-2H-pyran-4-yl)methyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring B is chosen from cyclopropyl, 5- to 10-membered heterocyclyl, phenyl, and 5 to 9-membered heteroaryl groups, each of which is optionally substituted with 1, 2, 3, 4, or 5 $R^a$ groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring B is chosen from cyclopropyl, 5- to 10-membered heterocyclyl comprising 1 to 3 heteroatoms chosen from N and O, phenyl, and 5- to 9-membered heteroaryl comprising 1 to 3 heteroatoms chosen from N and O; each of which is optionally substituted with 1, 2, 3, 4, or 5 $R^a$ groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring B is chosen from cyclopropyl, 5-membered heterocyclyl comprising 1 to 3 heteroatoms chosen from N and O, 6-membered heterocyclyl comprising 1 to 3 heteroatoms chosen from N and O, 9-membered heterocyclyl comprising 1 to 3 heteroatoms chosen from N and O, 10-membered heterocyclyl comprising 1 to 3 heteroatoms chosen from N and O, phenyl, 5-membered heteroaryl comprising 1 to 3 heteroatoms chosen from N and O, 6-membered heteroaryl comprising 1 to 3 heteroatoms chosen from N and O, and 9-membered heteroaryl comprising 1 to 3 heteroatoms chosen from N and O; each of which is optionally substituted with 1, 2, 3, 4, or 5 $R^a$ groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring B is chosen from

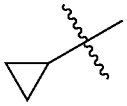, 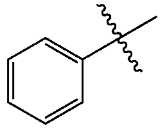, 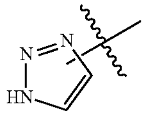,

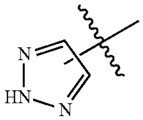, 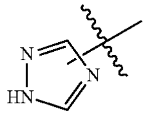, 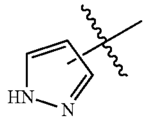,

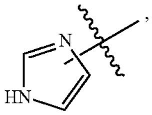, 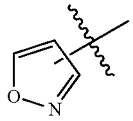, 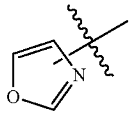,

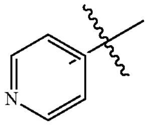, 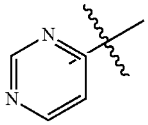, 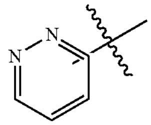,

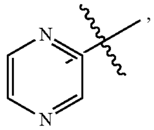, 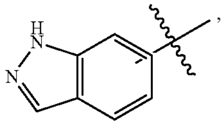,

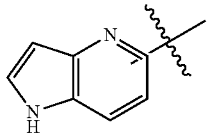, 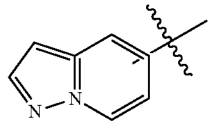,

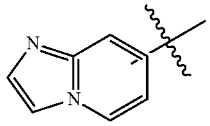, 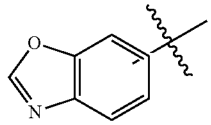,

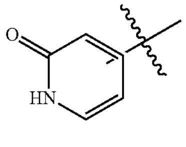, 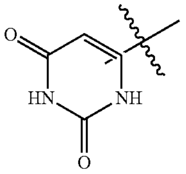,

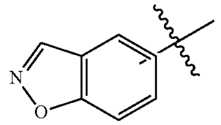, 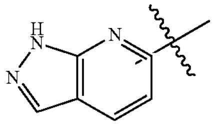,

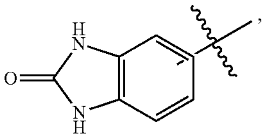, 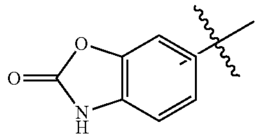,

-continued

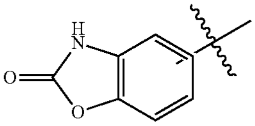,

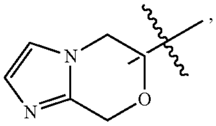,

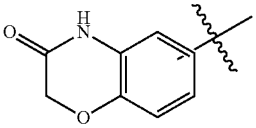, and

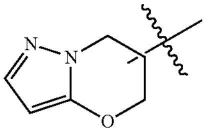;

each of which is optionally substituted with 1, 2, 3, 4, or 5 $R^a$ groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, Ring B is chosen from

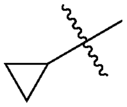, 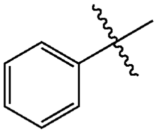, 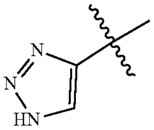,

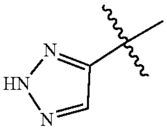, 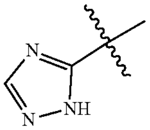, 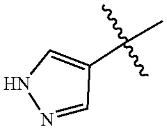,

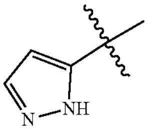, 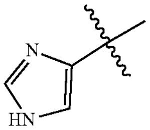, 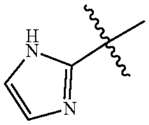,

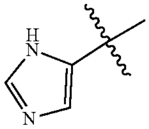, 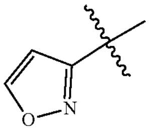, 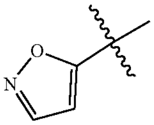,

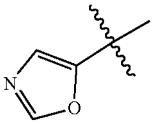, 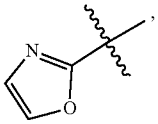, 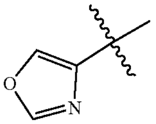,

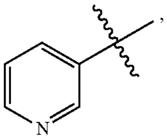, 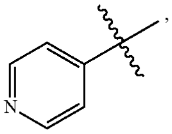, 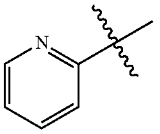,

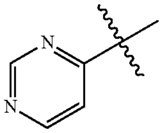, 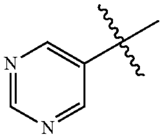, 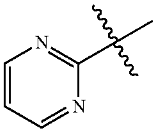,

-continued

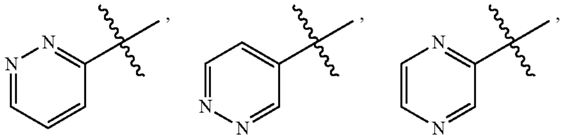

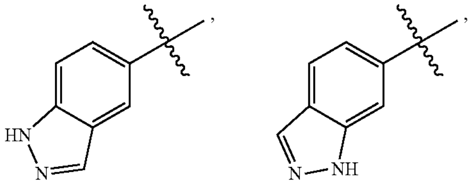

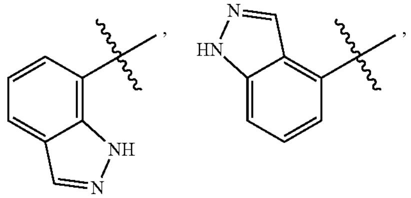

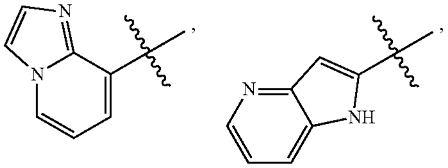

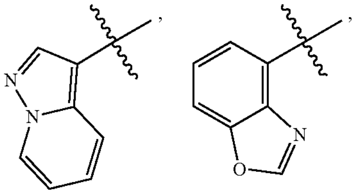

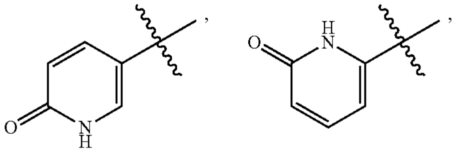

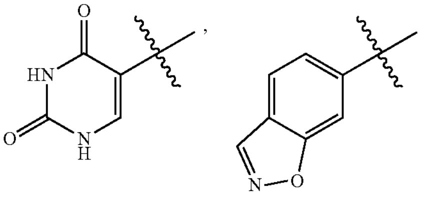

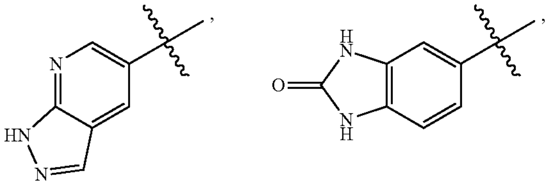

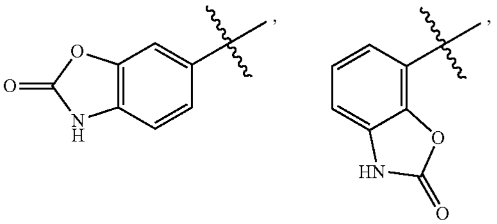

-continued

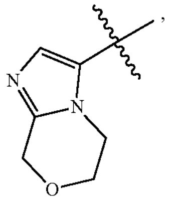,
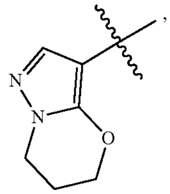,
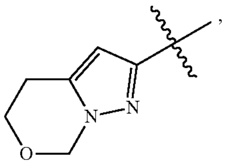,
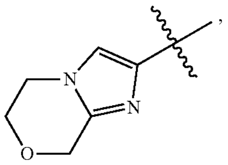,
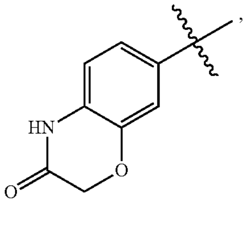,
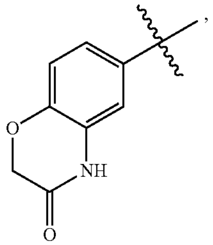,
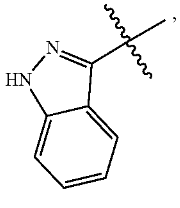, and
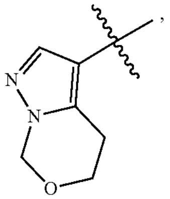, each of which is optionally substituted with 1, 2, 3, 4, or 5 $R^a$ groups; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^2$ is chosen from —$CH_3$ and Ring B, wherein Ring B is chosen from

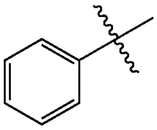,
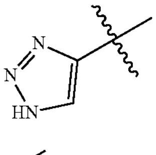,
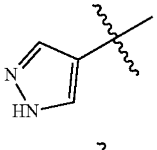,
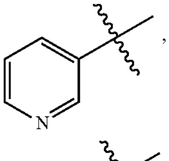,
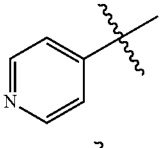,
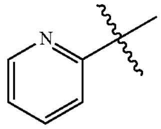,
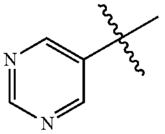,
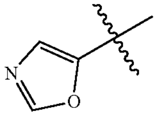,
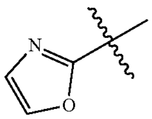,
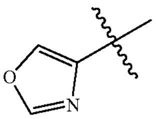, -continued

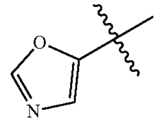, and
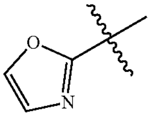, each of which is optionally substituted with 1, 2, 3, 4, or 5 $R^a$ groups; and all other variables not specifically defined herein are as defined in any one of the foregoing embodiments. In some embodiments, Ring B is

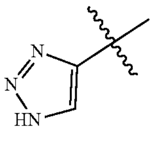 [SMILES: *c1c[nH]nn1]

which is optionally substituted with 1 $R^a$ group.

In some embodiments, in a compound of the disclosure (i.e., a compound of any one of Formulae I, Ia, Ib, and Ic), or a tautomer, deuterated derivative, or pharmaceutically acceptable salt thereof, $R^3$ is chosen from $C_1$-$C_4$ alkyl, —C(═O)O($C_1$-$C_2$ alkyl), $C_3$-$C_6$ cycloalkyl, and 5 to 10-membered heterocyclyl groups, wherein:

the $C_1$-$C_4$ alkyl of $R^3$ is optionally substituted with 1 to 3 groups independently chosen from halogen, cyano, —OH, and $C_1$-$C_2$ alkoxy groups; and the $C_3$-$C_6$ cycloalkyl and the 5- to 10-membered heterocyclyl of $R^3$ are each optionally substituted with 1 to 3 groups independently chosen from halogen, cyano, —OH, $C_1$-$C_2$ alkyl, and $C_1$-$C_2$ alkoxy groups;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^3$ is chosen from $C_1$-$C_2$ alkyl, —C(═O)O($C_1$-$C_2$ alkyl), cyclopropyl, cyclobutyl, and 5- to 6-membered heterocyclyl groups, wherein:

the $C_1$-$C_2$ alkyl of $R^3$ is optionally substituted with 1 to 3 groups independently chosen from F, Cl, Br, cyano, —OH, and $C_1$-$C_2$ alkoxy groups; and the cyclopropyl, the cyclobutyl, and the 5- to 6-membered heterocyclyl of $R^3$ are each optionally substituted with 1 to 3 groups independently chosen from F, Cl, Br, cyano, —OH, $C_1$-$C_2$ alkyl, and $C_1$-$C_2$ alkoxy groups;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^3$ is chosen from —$CH_3$, —$CH_2CH_3$, —$CH_2OH$, —C(═O)$OCH_3$, —$CH_2OCH_3$, —$CH(CH_3)_2$, cyclopropyl, difluorocyclopropyl, and tetrahydro-2H-pyranyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^3$ is —$CH_3$; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, wherein $R^1$, for each occurrence, is independently chosen from hydrogen, halogen, cyano, —OH, $C_1$-$C_4$ alkyl, $C_1$-$C_4$ alkoxy, —C(═O)N($R^c$)$_2$, and —$SO_2$($R^c$), and $C_3$-$C_6$ cycloalkyl groups, wherein:

$R^c$, for each occurrence, is independently chosen from hydrogen and $C_1$-$C_4$ alkyl groups;

the $C_1$-$C_4$ alkyl of $R^1$ is optionally substituted with 1 to 3 groups independently chosen from halogen, cyano, —OH, and $C_1$-$C_2$ alkoxy groups;

the $C_1$-$C_4$ alkoxy of $R^1$ is optionally substituted with 1 to 3 independently chosen from halogen groups; and the $C_3$-$C_6$ cycloalkyl of $R^1$ is optionally substituted with 1 to 3 groups independently chosen from halogen, cyano, —OH, and $C_1$-$C_2$ alkoxy groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from hydrogen, halogen, cyano, —OH, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen, cyano, —OH, and $C_1$-$C_2$ alkoxy groups;

the $C_1$-$C_4$ alkoxy of $R^1$ is optionally substituted with 1 to 3 independently chosen from halogen groups; and the $C_3$-$C_6$ cycloalkyl of $R^1$ is optionally substituted with 1 to 3 groups independently chosen from halogen, cyano, —OH, and $C_1$-$C_2$ alkoxy groups;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from hydrogen, halogen, cyano, —OH, $C_1$-$C_4$ alkyl, $C_1$-$C_4$ alkoxy, and $C_3$-$C_6$ cycloalkyl; wherein:

the $C_1$-$C_4$ alkyl of $R^1$ is optionally substituted with 1 to 3 groups independently chosen from halogen, cyano, —OH, and $C_1$-$C_2$ alkoxy;

the $C_1$-$C_4$ alkoxy of $R^1$ is optionally substituted with 1 to 3 independently chosen halogen groups; and the $C_3$-$C_6$ cycloalkyl of $R^1$ is optionally substituted with 1 to 3 groups independently chosen from halogen, cyano, —OH, and $C_1$-$C_2$ alkoxy;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, $C_1$-$C_4$ alkyl, and $C_3$-$C_6$ cycloalkyl, wherein:

the $C_1$-$C_4$ alkyl of $R^1$ is optionally substituted with 1 to 3 groups independently chosen from halogen and —OH; and the $C_3$-$C_6$ cycloalkyl of $R^1$ is optionally substituted with 1 to 3 groups independently chosen from halogen and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen and —OH;

the $C_1$-$C_4$ alkoxy of $R^1$ is optionally substituted with 1 to 3 independently chosen from halogen groups; and the $C_3$-$C_6$ cycloalkyl of $R^1$ is optionally substituted with 1 to 3 groups independently chosen from halogen and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, $C_1$-$C_4$ alkyl, and $C_3$-$C_6$ cycloalkyl; wherein:

the $C_1$-$C_4$ alkyl of $R^1$ is optionally substituted with 1 to 3 groups independently chosen from halogen and —OH; and the $C_3$-$C_6$ cycloalkyl of $R^1$ is optionally substituted with 1 to 3 groups independently chosen from halogen and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen and —OH; and the $C_1$-$C_4$ alkoxy of $R^1$ is optionally substituted with 1 to 3 independently chosen from halogen groups;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from Cl, Br, —$CH_3$, —$CF_3$, —$CH_2CH_3$, —$CH(CH_3)_2$, —$CH_2CHF_2$, —$CH_2CH(CH_3)_2$, difluorocyclobutyl, and cyclohexyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, —$CH_3$, —$CH(CH_3)_2$, —$CF_3$, —$OCH_3$, —$OCF_3$, —C(═O)N$(CH_3)_2$, and cyclopropyl; and all other variables not specifically defined herein are as defined in any one of the foregoing embodiments.

In some embodiments, in a compound, tautomer, deuterated derivative, or pharmaceutically acceptable salt of the disclosure, $R^1$, for each occurrence, is $C_1$; and all other variables not specifically defined herein are as defined in any one of the foregoing embodiments.

In some embodiments, in a compound, tautomer, deuterated derivative, or pharmaceutically acceptable salt of the disclosure, $R^1$, for each occurrence, is independently chosen from halogen, —OH, and $C_1$-$C_4$ alkyl; wherein:

the $C_1$-$C_4$ alkyl of $R^1$ is optionally substituted with 1 to 3 groups independently chosen from halogen and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, Cl, Br, —OH, and $C_1$-$C_2$ alkyl; wherein:

the $C_1$-$C_2$ alkyl of $R^1$ is optionally substituted with 1 to 3 groups independently chosen from F, $C_1$, and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from F, —OH, —$CH_3$, —$CHF_2$, and —$CH_2OH$; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^1$, for each occurrence, is independently chosen from —$SO_2(R^c)$, wherein $R^c$ is chosen from hydrogen and $C_1$-$C_2$ alkyl groups; and all other variables not specifically defined herein are as defined in any one of the foregoing embodiments. In some embodiments, $R^c$ is chosen from $C_1$-$C_2$ alkyl groups. In some embodiments, $R^c$ is chosen from $C_1$ alkyl groups. In some embodiments, $R^c$ is —$CH_3$.

In some embodiments, in a compound of the disclosure (i.e., a compound of any one of Formulae I, Ia, Ib, and Ic), or a tautomer, deuterated derivative, or pharmaceutically acceptable salt thereof, two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, two $R^1$ groups taken together form a group chosen from

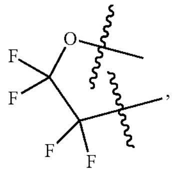, 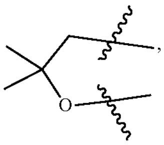, 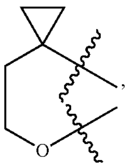, and 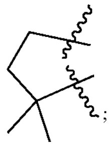;

and all other variables not specifically defined herein are as defined in any one of the foregoing embodiments.

In some embodiments, in a compound, tautomer, deuterated derivative, or pharmaceutically acceptable salt of the disclosure, two $R^1$ groups taken together with the Ring A atoms connecting them form a group chosen from

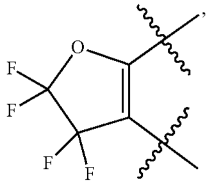, 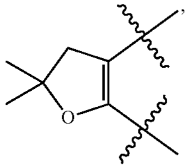, 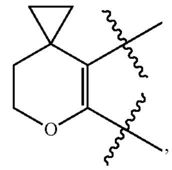, and 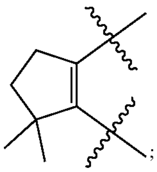;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^a$, for each occurrence, is independently chosen from halogen, cyano, $C_1$-$C_6$ alkyl, $C_1$-$C_4$ alkoxy, $C_1$-$C_6$ haloalkyl, $C_1$-$C_6$ haloalkoxy, —C(═O)N$R^hR^i$, —N$R^hR^i$, —N$R^h$C(═O)$R^k$, —O$R^k$, —$[O(CH_2)_q]_r$O($C_1$-$C_6$ alkyl), —S(═O)$_2R^k$, —S(═O)$_2$N$R^hR^i$, $C_3$-$C_6$ cycloalkyl, 5 to 10-membered heterocyclyl, phenyl, and 5- to 8-membered heteroaryl; wherein:

the $C_1$-$C_6$ alkyl of $R^a$ is optionally substituted with 1 to 3 groups independently chosen from cyano, —C(═O)N$R^hR^i$, —N$R^hR^i$, —N$R^h$C(═O)$R^k$, —N$R^h$C(═O)O$R^k$, —N$R^h$C(═O)N$R^iR^j$, —N$R^h$S(═O)$_pR^k$, —O$R^k$, —S(═O)$_2R^k$, —S(═O)$_p$N$R^hR^i$, and $C_3$-$C_6$ cycloalkyl;

the $C_3$-$C_6$ cycloalkyl, the 5 to 10-membered heterocyclyl, the phenyl, and the 5- to 8-membered heteroaryl of $R^a$ are each optionally substituted with 1 to 3 groups independently chosen from halogen, $C_1$-$C_2$ alkyl, and —O$R^k$, wherein:

$R^h$, $R^i$, and $R^j$, for each occurrence, are each independently chosen from hydrogen, $C_1$-$C_2$ alkyl, cyclopropyl, and cyclobutyl, wherein:

the $C_1$-$C_2$ alkyl of any one of $R^h$, $R^i$, and $R^j$ is optionally substituted with 1 to 3 groups independently chosen from halogen and —OH;

$R^k$, for each occurrence, is each independently chosen from hydrogen and $C_1$-$C_4$ alkyl, wherein:

the $C_1$-$C_4$ alkyl of $R^k$ is optionally substituted with 1 to 3 groups independently chosen from halogen and —OH; and q and r are each an integer chosen from 1, 2, and 3;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^a$, for each occurrence, is independently chosen from halogen, cyano, $C_1$-$C_6$ alkyl, $C_1$-$C_4$ alkoxy, $C_1$-$C_4$ haloalkyl, $C_1$-$C_4$ haloalkoxy, —C(═O)$NR^hR^i$, —$NR^hR^i$, —$NR^hC$(═O)$R^k$, —$OR^k$, —[O$(CH_2)_q]_r$O($C_1$-$C_4$ alkyl), —S(═O)$_2R^k$, —S(═O)$_2NR^hR^i$, cyclopropyl, cyclobutyl, 5- to 6-membered heterocyclyl, phenyl, and 5- to 6-membered heteroaryl, wherein:

the $C_1$-$C_6$ alkyl of $R^a$ is optionally substituted with 1 to 3 groups independently chosen from cyano, —C(═O)$NR^hR^i$, —$NR^hR^i$, —$OR^k$, cyclopropyl, and cyclobutyl;

the cyclopropyl, the cyclobutyl, the 5- to 6-membered heterocyclyl, the phenyl, and the 5 to 6-membered heteroaryl of $R^a$ are each optionally substituted with 1 to 3 groups independently chosen from halogen, —$CH_3$, —OH, and —$OCH_3$, wherein:

$R^h$ and $R^i$, for each occurrence, are each independently chosen from hydrogen, —$CH_3$, cyclopropyl, and cyclobutyl, wherein:

the —$CH_3$ of any one of $R^h$ and $R^i$ is optionally substituted with 1 to 3 groups independently chosen from F, $C_1$, and —OH;

$R^k$, for each occurrence, is each independently chosen from hydrogen and —$CH_3$; wherein:

the —$CH_3$ of $R^k$ is optionally substituted with 1 to 3 groups independently chosen from halogen and —OH;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^a$, for each occurrence, is independently chosen from F, Cl, Br, cyano, $C_1$-$C_6$ alkyl, $C_1$-$C_2$ alkoxy, $C_1$-$C_2$ haloalkyl, —C(═O)$NR^hR^i$, —$NR^hR^i$, —$NR^hC$(═O)$R^k$, —$OR^k$, —[O$(CH_2)_q]_r$O($C_1$-$C_2$ alkyl), —S(═O)$_2R^k$, —S(═O)$_2NR^hR^i$, cyclopropyl, cyclobutyl, 5-membered heterocyclyl, phenyl, and 6-membered heteroaryl, wherein:

the $C_1$-$C_6$ alkyl of $R^a$ is optionally substituted with 1 to 3 groups independently chosen from cyano, —C(═O)$NR^hR^i$, —$OR^k$, and cyclopropyl;

the cyclopropyl, the cyclobutyl, the 5 to 6-membered heterocyclyl, the phenyl, and the 5 to 6-membered heteroaryl of $R^a$ are each optionally substituted with 1 to 3 groups independently chosen from halogen, —$CH_3$, —OH, and —$OCH_3$, wherein:

$R^h$ and $R^i$, for each occurrence, are each independently chosen from hydrogen, —$CH_3$, and cyclopropyl; wherein:

the —$CH_3$ of any one of $R^h$ and $R^i$ is optionally substituted with 1 to 3 groups independently chosen from F, $C_1$, and —OH;

$R^k$, for each occurrence, is each independently chosen from hydrogen and —$CH_3$; and q and r are each an integer independently chosen from 1 and 2;

and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^a$, for each occurrence, is independently chosen from F, cyano, —OH, —$CH_3$, —$CF_3$, —CH$(CH_3)_2$, —$(CH_2)_2$OH, —$(CH_2)_2OCH_3$, —$CH_2$CH(OH)$C_2H_5$, —$CH_2C(CH_3)(CH_2OH)_2$, —$OCH_3$, —$OCH_2CH_3$, —[O$(CH_2)_2]_2OCH_3$, —$CH_2$C(═O)$NHCH_3$, —$(CH_2)_2SO_2CH_3$, —$CH_2$C(═O)N$(CH_3)_2$, —$CH_2$(cyclopropyl), —C(═O)$NH_2$, —C(═O)NH(cyclopropyl), —$NH_2$, —$NHCH_3$, —N$(CH_3)_2$, —NHC$(CH_3)_2CH_2$OH, —NHC(═O)$CH_3$, —$SO_2CH_3$, —$SO_2NH_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^a$, for each occurrence, is independently chosen from —$CH_3$ and —$(CH_2)_2SO_2CH_3$; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^5$ is chosen from hydrogen and $C_1$-$C_4$ alkyl; and all other variables not specifically defined herein are as defined in any one of the foregoing embodiments.

In some embodiments, of the disclosure (i.e., a compound of any one of Formulae I, Ia, Ib, and Ic), or a tautomer, deuterated derivative, or pharmaceutically acceptable salt thereof, $R^5$ is chosen from hydrogen, methyl, and propyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^5$ is hydrogen and $R^1$, for each occurrence, is independently chosen from —$SO_2(R^c)$, wherein $R^c$ is chosen from hydrogen and $C_1$-$C_2$ alkyl groups; and all other variables not specifically defined herein are as defined in any one of the foregoing embodiments. In some embodiments, $R^c$ is chosen from $C_1$-$C_2$ alkyl groups. In some embodiments, $R^1$ is chosen from $C_1$ alkyl groups. In some embodiments, $R^c$ is —$CH_3$.

In some embodiments, in a compound of the disclosure (i.e., a compound of any one of Formulae I, Ia, Ib, and Ic), or a tautomer, deuterated derivative, or pharmaceutically acceptable salt thereof, $R^5$ is hydrogen and two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl; and all other variables not specifically defined herein are as defined in any one of the foregoing embodiments.

In some embodiments, in a compound of the disclosure (i.e., a compound of any one of Formulae I, Ia, Ib, and Ic), or a tautomer, deuterated derivative, or pharmaceutically acceptable salt thereof, $R^5$ is hydrogen and two $R^1$ groups taken together form a group chosen from

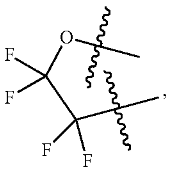
,
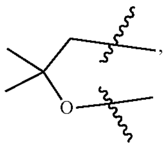
,
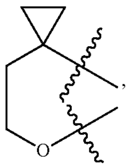
, and
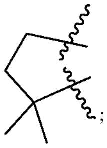
;

and all other variables not specifically defined herein are as defined in any one of the foregoing embodiments.

In some embodiments, of the disclosure (i.e., a compound of any one of Formulae I, Ia, Ib, and Ic), or a tautomer, deuterated derivative, or pharmaceutically acceptable salt thereof, $R^5$ is hydrogen and two $R^1$ groups taken together with the Ring A atoms connecting them form a group chosen from

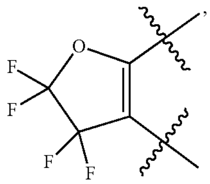
,
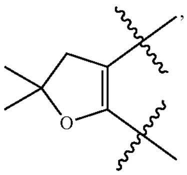
,
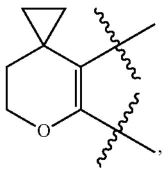
, and
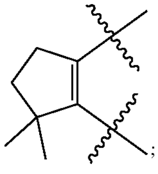
;

and all other variables not specifically defined herein are as defined in any one of the foregoing embodiments.

In some embodiments, a compound, tautomer, deuterated derivative, or pharmaceutically acceptable salt of the disclosure is represented by one of the following structural formulae:

Formula Ic-1

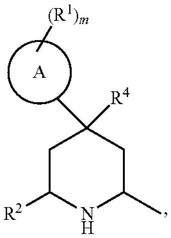
,

-continued

Formula Ic-2

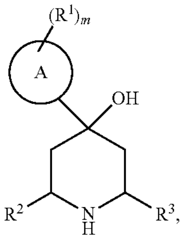
,

Formula Ic-3

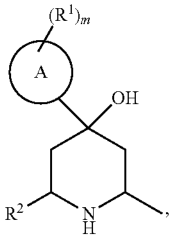
,

Formula Ic-4

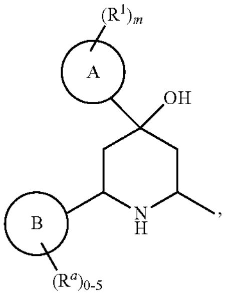
,

Formula Ic-5

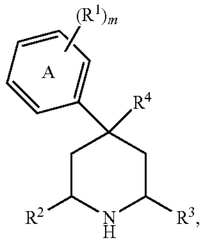
,

Formula Ic-6

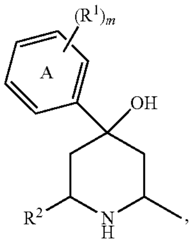
, a tautomer thereof, a deuterated derivative of that compound or tautomer, or a pharmaceutically acceptable salt of any of the foregoing; and all other variables not specifically defined herein are as defined in any one of the foregoing embodiments. In some embodiments of Formula Ic-1 through Ic-6, Compound I296 and Compound 43a are excluded.

In some embodiments, at least one compound, tautomer, deuterated derivative, or pharmaceutically acceptable salt of the disclosure is a compound represented by the following structural formula:

Formula II

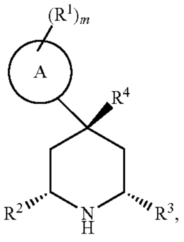

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, =O, cyano, phenyl, $C_1$-$C_6$ alkyl, $C_1$-$C_6$ alkoxy, $C_3$-$C_6$ carbocyclyl, 4- to 6-membered heterocyclyl, and —C(=O)N($R^c$)$_2$ groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups;

$R^2$ is chosen from cyano, $C_1$-$C_6$ alkyl, —C(=O)O($C_1$-$C_4$ alkyl), $C_2$-$C_6$ alkynyl, and

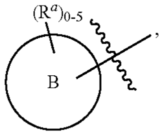

wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)N$R^h$$R^i$, —N$R^h$$R^i$, —N$R^h$ C(=O)$R^k$, —N$R^h$ C(O)O$R^k$, —N$R^h$C (=O)N$R^i$$R^j$, —N$R^h$S(=O)$_p$$R^k$, —O$R^k$, —OC (=O)$R^k$, —OC(=O)O$R^k$, —OC(=O)N$R^h$$R^i$, —[O(CH$_2$)$_q$]$_r$O($C_1$-$C_6$ alkyl), —S(=O)$_p$$R^k$, —S(=O)$_p$N$R^h$$R^i$, —C(=O)O$R^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(=O)$R^k$, —C(=O)O$R^k$, —C(=O)N$R^h$$R^i$, —N$R^h$$R^i$, —N$R^h$C(=O)$R^k$, —N$R^h$C(=O)O$R^k$, —N$R^h$C(=O)N$R^i$$R^j$, —N$R^h$S(=O)$R^k$, —O$R^k$, —OC(=O)$R^k$, —OC (=O)O$R^k$, —OC(=O)N$R^h$$R^i$, —S(=O)$_p$$R^k$, —S(=O)$_p$N$R^h$$R^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —N$R^h$$R^i$, and —O$R^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(=O)$_p$$R^k$, and —O$R^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(=O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), and —C(=O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(=O)$_2$($C_1$-$C_4$ alkyl)), $C_1$-$C_4$ alkoxy, —C(=O)$NH_2$, —C(=O)NH($C_1$-$C_4$ alkyl), —NHC(=O)($C_1$-$C_4$ alkyl), —C(=O)($C_1$-$C_4$ alkoxy), and —C(=O)N($C_1$-$C_4$ alkyl)$_2$ groups;

$R^4$ is chosen from halogen, cyano, $C_1$-$C_6$ alkyl, $C_1$-$C_6$ haloalkyl, —$(CH_2)_n$C(=O)NR$''$R$^o$, —NR$''$R$^o$, —NR$^o$C(=O)R$^p$, —NR$''$S(=O)$_p$R$^p$, —$(CH_2)_n$OR$^p$, —S(=O)$_p$R$^p$, —S(=O)$_p$NR$''$R$^o$, —OS(=O)$_p$NR$''$R$^o$, and —$(CH_2)_n$C(=O)OR$^p$ groups, wherein:

R$''$ and R$^o$, for each occurrence, are each independently chosen from hydrogen and $C_1$-$C_4$ alkyl groups; and R$^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

In some embodiments, Compound I296 and Compound 43a are excluded from Formula II.

In some embodiments, in a compound of Formula II or a tautomer, deuterated derivative, or pharmaceutically acceptable salt thereof, $R^4$ is —OH; and all other variables not specifically defined herein are as defined in any one of the foregoing embodiments.

In some embodiments, in a compound of Formula II or a tautomer, deuterated derivative, or pharmaceutically acceptable salt thereof, m is an integer chosen from 0, 1, and 2; and all other variables not specifically defined herein are as defined in any one of the foregoing embodiments.

In some embodiments, in a compound of Formula II or a tautomer, deuterated derivative, or pharmaceutically acceptable salt thereof, Ring A is phenyl, thiophenyl, or pyridinyl; and all other variables not specifically defined herein are as defined in any one of the foregoing embodiments.

In some embodiments, in a compound of Formula II or a tautomer, deuterated derivative, or pharmaceutically acceptable salt thereof, $R^3$ is chosen from Ci-4 alkyl groups; and all other variables not specifically defined herein are as defined in any one of the foregoing embodiments.

In some embodiments, in a compound of Formula II or a tautomer, deuterated derivative, or pharmaceutically acceptable salt thereof, $R^3$ is chosen from —$CH_3$ and Ring B, wherein Ring B is chosen from

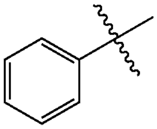 , 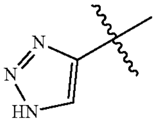 ,

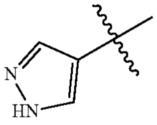 , 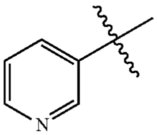 , 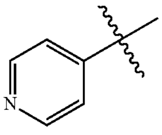 ,

-continued

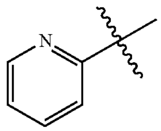 , 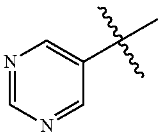 , 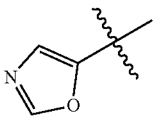 ,

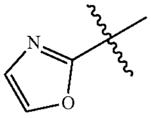 , 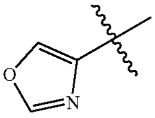 ,

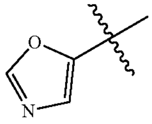 , and 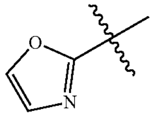 , each of which is optionally substituted with 1, 2, 3, 4, or 5 $R^a$ groups; and all other variables not specifically defined herein are as defined in any one of the foregoing embodiments.

In some embodiments, in a compound of Formula II or a tautomer, deuterated derivative, or pharmaceutically acceptable salt thereof, $R^3$ is —$CH_3$; and $R^2$ is chosen from —$CH_3$ and Ring B, wherein:

Ring B is chosen from

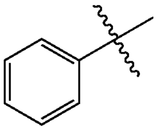 , 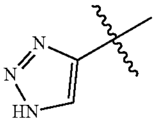 ,

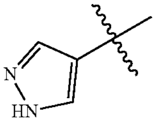 , 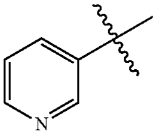 , 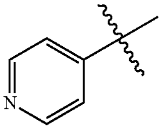 ,

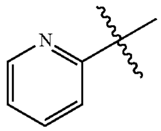 , 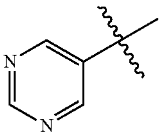 , 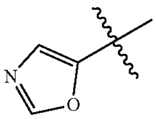 ,

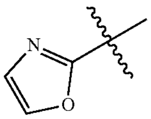 , 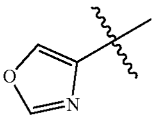 ,

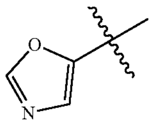 , and 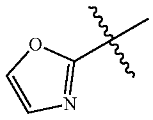 , each of which is optionally substituted with 1, 2, 3, 4, or 5 $R^a$ groups; and all other variables not specifically defined herein are as defined in any one of the foregoing embodiments.

In some embodiments, in a compound of Formula II or a tautomer, deuterated derivative, or pharmaceutically acceptable salt thereof, $R^3$ is —$CH_3$; and $R^2$ is chosen from —$CH_3$ and Ring B, wherein:

Ring B is

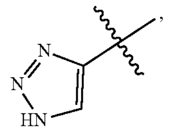 [SMILES: *c1c[nH]nn1]

which is optionally substituted with 1 or 2 $R^a$ groups; and all other variables not specifically defined herein are as defined in any one of the foregoing embodiments.

In some embodiments, in a compound of Formula II or a tautomer, deuterated derivative, or pharmaceutically acceptable salt thereof, Ring A is chosen from $C_6$ aryl and 5- and 6-membered heteroaryl groups;

$R^1$, for each occurrence, is independently chosen from halogen, $C_1$-4 alkyl, $C_1$-4 alkoxy, $C_3$ cycloalkyl, and —C(═O)N($R^c$)$_2$ groups, wherein:

the $C_1$-4 alkyl and $C_1$-4 alkoxy groups are optionally substituted with 1-3 groups chosen from halogens; and $R^c$, for each occurrence, is independently chosen from hydrogen and $C_1$-4 alkyl groups;

$R^2$ is chosen from $C_{1-4}$ alkyl and 5-membered heteroaryl groups, wherein the 5-membered heteroaryl groups are optionally substituted with 1-2 $C_1$-4 alkyl groups optionally substituted with —S(═O)$_2$CH$_3$; and $R^3$ is chosen from $C_1$-4 alkyl groups; and m is an integer chosen from 0, 1, and 2.

In some embodiments, a compound of Formula II or a tautomer, deuterated derivative, or pharmaceutically acceptable salt thereof is represented by one of the following structural formulae:

Formula II-1

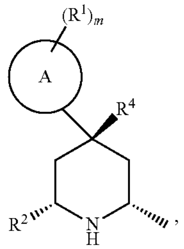

Formula II-2

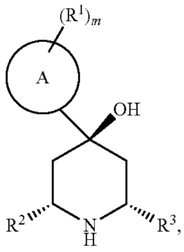

-continued

Formula II-3

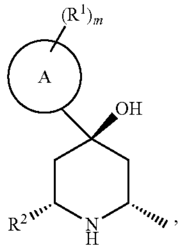

Formula II-4

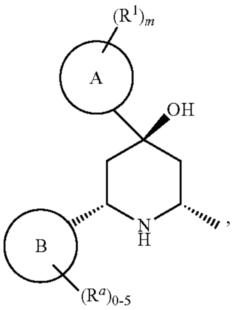

Formula II-5

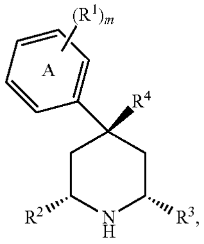

Formula II-6

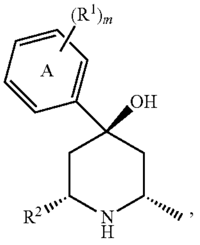

a tautomer thereof, a deuterated derivative of that compound or tautomer, or a pharmaceutically acceptable salt of any of the foregoing; and all other variables not specifically defined herein are as defined in any one of the foregoing embodiments. In some embodiments of Formula II-1 through 116, Compound I296 and Compound 43a are excluded.

In some embodiments, compounds of Formula II-6 are selected from Compounds of Formula II-6a and Formula II-6b:

II-6a

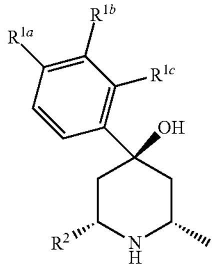

II-6b

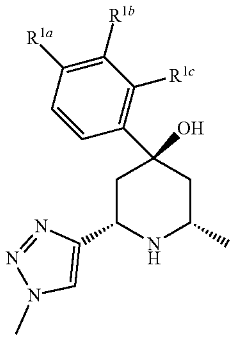

wherein $R^{1a}$ and $R^{1b}$ are independently chosen from halogen, H, $C_1$-$C_4$ alkyl, and $C_1$-$C_4$ haloalkyl groups;

$R^{1c}$ is chosen from halogen, H, CH3, —OH, and CH3OH; and wherein $R^2$ in Formula II-6a is defined for Formula II.

In some embodiments, the at least one compound, tautomer, deuterated derivative, or pharmaceutically acceptable salt of the disclosure is chosen from Compounds 1 to 29 depicted in Table 1, Compounds I5 to I295 depicted in Table 2, Compounds 30 to 44 and depicted in Table 3 and Compounds 45 to 68 depicted in Table 4, tautomers thereof, deuterated derivatives of those compounds and tautomers, and pharmaceutically acceptable salts of any of the foregoing. A wavy line in a compound depicted in any one of Tables 1-4 (i.e., ) represents a bond between two atoms and indicates a position of mixed stereochemistry for a collection of molecules, such as a racemic mixture, cis/trans isomers, or (E)/(Z) isomers. Similarly, a straight line (i.e., ) emanating from a chiral center (e.g.,

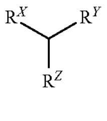 and 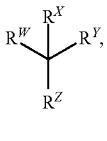, where $R^W$, $R^X$, $R^Y$, and $R^Z$ are different) in a compound depicted in Table 2 represents a position of mixed stereochemistry for a collection of molecules.

TABLE 1

| Compounds 1 to 29 | |
|---|---|
| 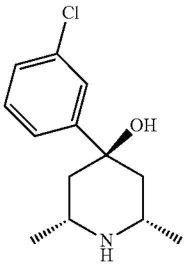 [SMILES: C[C@@H]1C[C@](O)(c2cccc(Cl)c2)C[C@H](C)N1] | 1 |
| 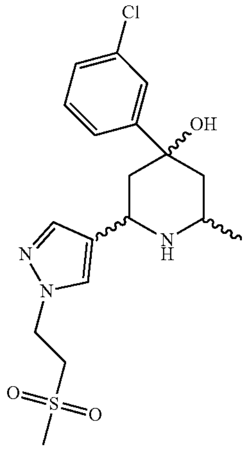 [SMILES: CC1CC(O)(c2cccc(Cl)c2)CC(c2cnn(CCS(C)(=O)=O)c2)N1] | 2 |
| 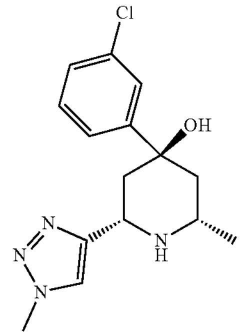 | 3 |
| 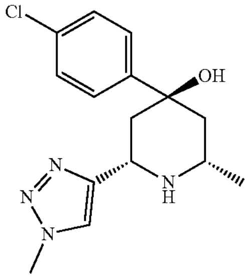 [SMILES: C[C@H]1C[C@@](O)(c2ccc(Cl)cc2)C[C@@H](c2cn(C)nn2)N1] | 4 |

TABLE 1-continued
Compounds 1 to 29
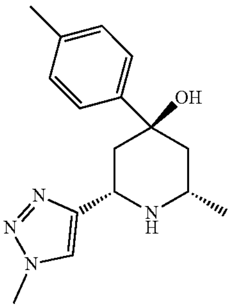 [SMILES: Cc1ccc([C@@]2(O)C[C@@H](c3cn(C)nn3)N[C@@H](C)C2)cc1]
5
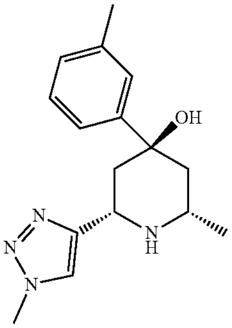 [SMILES: Cc1cccc([C@@]2(O)C[C@@H](c3cn(C)nn3)N[C@@H](C)C2)c1]
6
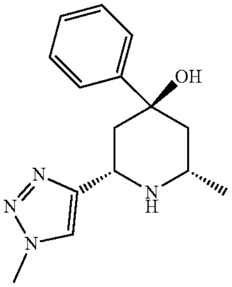 [SMILES: C[C@H]1C[C@@](O)(c2ccccc2)C[C@@H](c2cn(C)nn2)N1]
7
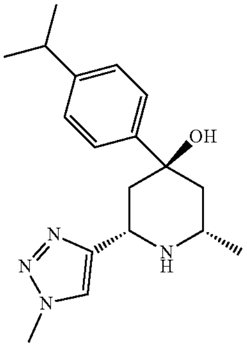 [SMILES: CC(C)c1ccc([C@@]2(O)C[C@@H](c3cn(C)nn3)N[C@@H](C)C2)cc1]
8
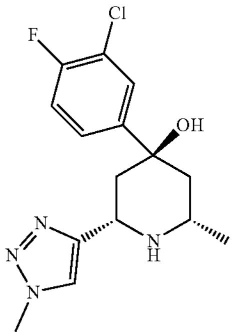 [SMILES: C[C@H]1C[C@@](O)(c2ccc(F)c(Cl)c2)C[C@@H](c2cn(C)nn2)N1]
9
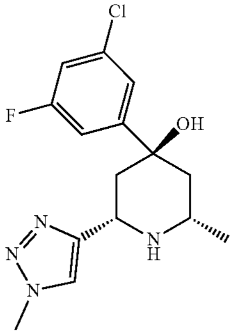 [SMILES: C[C@H]1C[C@@](O)(c2cc(F)cc(Cl)c2)C[C@@H](c2cn(C)nn2)N1]
10
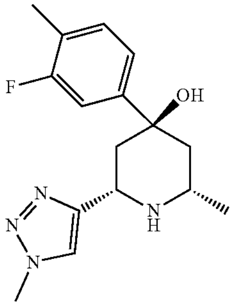 [SMILES: Cc1ccc([C@@]2(O)C[C@@H](c3cn(C)nn3)N[C@@H](C)C2)cc1F]
11
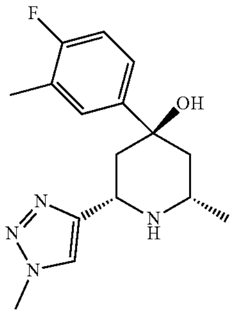
12

TABLE 1-continued
| Compounds 1 to 29 | |
|---|---|
| 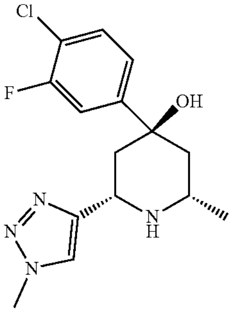 [SMILES: C[C@H]1C[C@@](O)(c2ccc(Cl)c(F)c2)C[C@@H](c2cn(C)nn2)N1] | 13 |
| 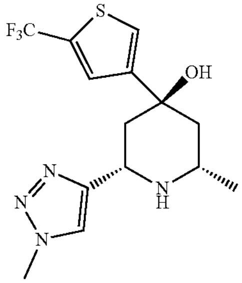 [SMILES: C[C@H]1C[C@@](O)(c2csc(C(F)(F)F)c2)C[C@@H](c2cn(C)nn2)N1] | 14 |
| 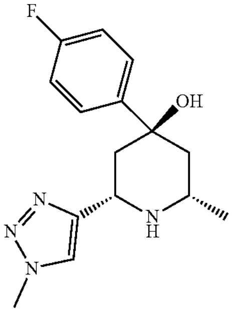 [SMILES: C[C@H]1C[C@@](O)(c2ccc(F)cc2)C[C@@H](c2cn(C)nn2)N1] | 15 |
| 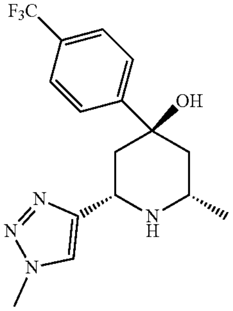 [SMILES: C[C@H]1C[C@@](O)(c2ccc(C(F)(F)F)cc2)C[C@@H](c2cn(C)nn2)N1] | 16 |
| 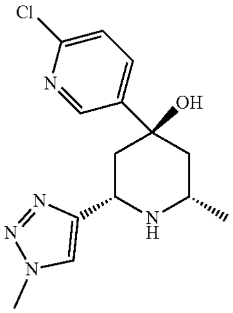 [SMILES: C[C@H]1C[C@@](O)(c2ccc(Cl)nc2)C[C@@H](c2cn(C)nn2)N1] | 17 |
TABLE 1-continued
| Compounds 1 to 29 | |
|---|---|
| 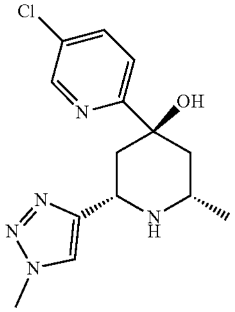 [SMILES: C[C@H]1C[C@@](O)(c2ccc(Cl)cn2)C[C@@H](c2cn(C)nn2)N1] | 18 |
| 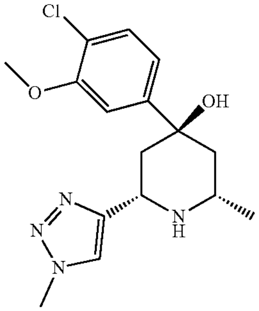 | 19 |
| 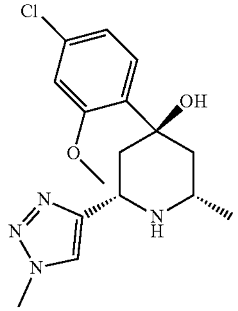 [SMILES: COc1cc(Cl)ccc1[C@@]1(O)C[C@@H](c2cn(C)nn2)N[C@@H](C)C1] | 20 |
| 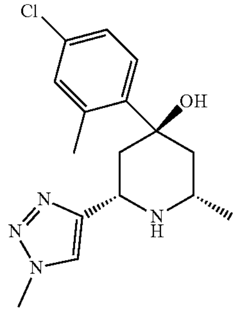 [SMILES: Cc1cc(Cl)ccc1[C@@]1(O)C[C@@H](c2cn(C)nn2)N[C@@H](C)C1] | 21 |
| 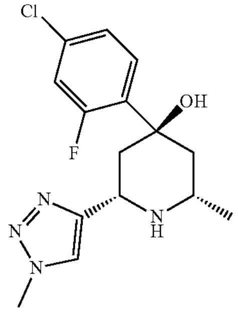 [SMILES: C[C@H]1C[C@@](O)(c2ccc(Cl)cc2F)C[C@@H](c2cn(C)nn2)N1] | 22 |

TABLE 1-continued
Compounds 1 to 29
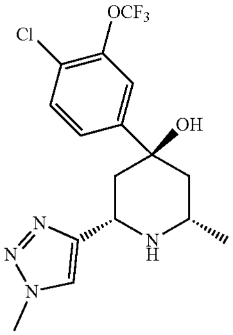 [SMILES: C[C@H]1C[C@@](O)(c2ccc(Cl)c(OC(F)(F)F)c2)C[C@@H](c2cn(C)nn2)N1]
23
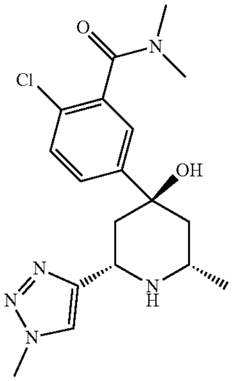 [SMILES: C[C@H]1C[C@@](O)(c2ccc(Cl)c(C(=O)N(C)C)c2)C[C@@H](c2cn(C)nn2)N1]
24
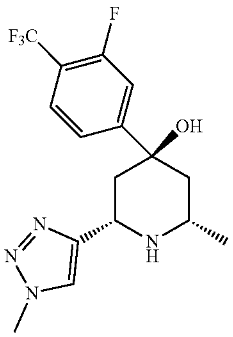 [SMILES: C[C@H]1C[C@@](O)(c2ccc(C(F)(F)F)c(F)c2)C[C@@H](c2cn(C)nn2)N1]
25
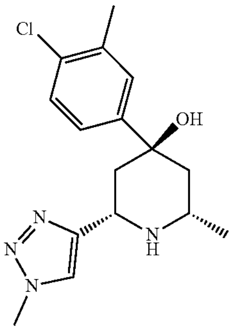 [SMILES: Cc1cc([C@@]2(O)C[C@@H](c3cn(C)nn3)N[C@@H](C)C2)ccc1Cl]
26
TABLE 1-continued
Compounds 1 to 29
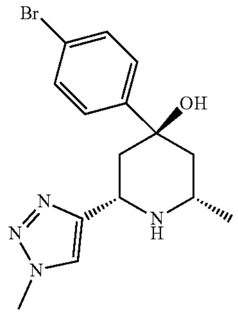 [SMILES: C[C@H]1C[C@@](O)(c2ccc(Br)cc2)C[C@@H](c2cn(C)nn2)N1]
27
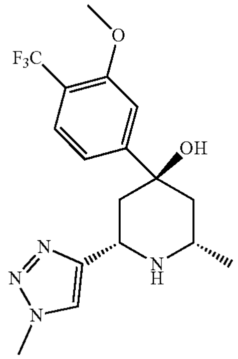 [SMILES: COc1cc([C@@]2(O)C[C@@H](c3cn(C)nn3)N[C@@H](C)C2)ccc1C(F)(F)F]
28
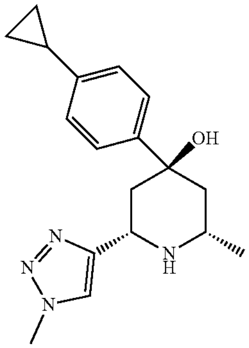 [SMILES: C[C@H]1C[C@@](O)(c2ccc(C3CC3)cc2)C[C@@H](c2cn(C)nn2)N1]
29
TABLE 2
Compounds I5 to I295
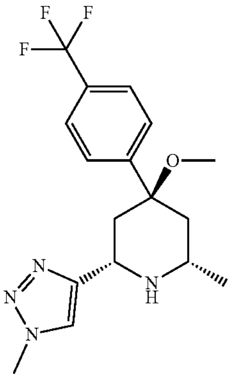 [SMILES: CO[C@]1(c2ccc(C(F)(F)F)cc2)C[C@@H](c2cn(C)nn2)N[C@@H](C)C1]
I5

TABLE 2-continued
Compounds I5 to I295
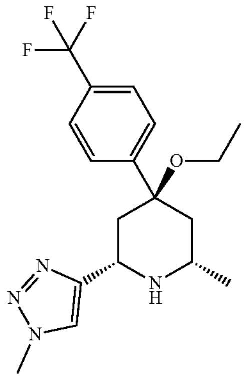 [SMILES: CCO[C@]1(c2ccc(C(F)(F)F)cc2)C[C@@H](c2cn(C)nn2)N[C@@H](C)C1]
I6
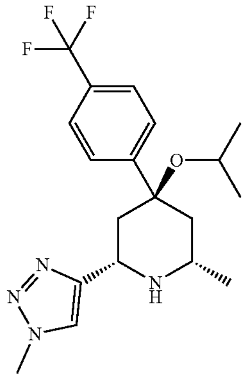 [SMILES: CC(C)O[C@]1(c2ccc(C(F)(F)F)cc2)C[C@@H](c2cn(C)nn2)N[C@@H](C)C1]
I7
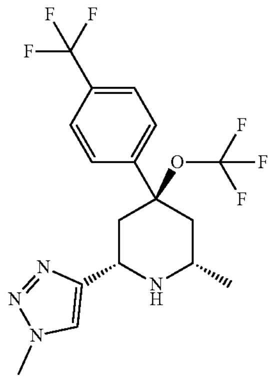 [SMILES: C[C@H]1C[C@@](OC(F)(F)F)(c2ccc(C(F)(F)F)cc2)C[C@@H](c2cn(C)nn2)N1]
I8
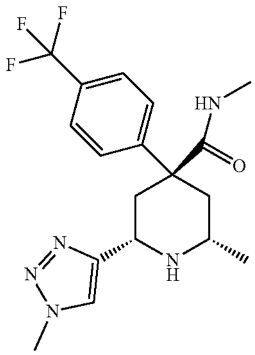 [SMILES: CNC(=O)[C@]1(c2ccc(C(F)(F)F)cc2)C[C@@H](c2cn(C)nn2)N[C@@H](C)C1]
I9
TABLE 2-continued
Compounds I5 to I295
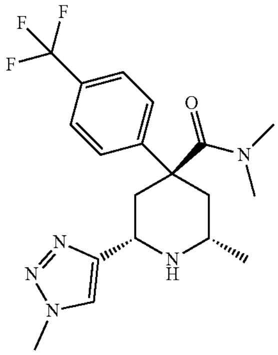 [SMILES: C[C@H]1C[C@@](C(=O)N(C)C)(c2ccc(C(F)(F)F)cc2)C[C@@H](c2cn(C)nn2)N1]
I10
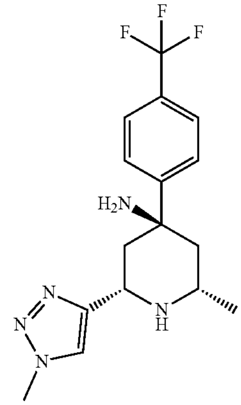 [SMILES: C[C@H]1C[C@@](N)(c2ccc(C(F)(F)F)cc2)C[C@@H](c2cn(C)nn2)N1]
I11
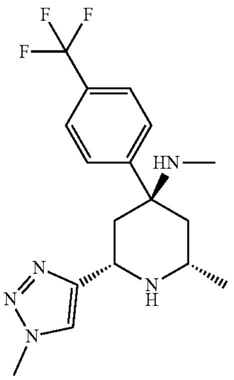 [SMILES: CN[C@]1(c2ccc(C(F)(F)F)cc2)C[C@@H](c2cn(C)nn2)N[C@@H](C)C1]
I12
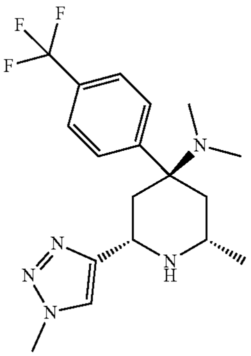
I13

TABLE 2-continued
| Compounds I5 to I295 | |
|---|---|
| 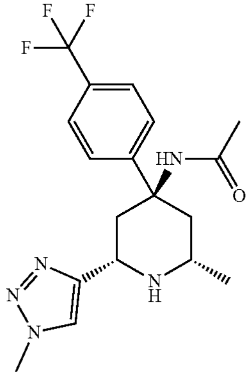 [SMILES: CC(=O)N[C@]1(c2ccc(C(F)(F)F)cc2)C[C@@H](c2cn(C)nn2)N[C@@H](C)C1] | I14 |
| 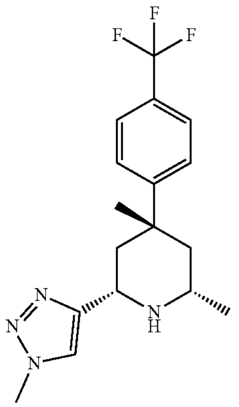 [SMILES: C[C@H]1C[C@@](C)(c2ccc(C(F)(F)F)cc2)C[C@@H](c2cn(C)nn2)N1] | I15 |
| 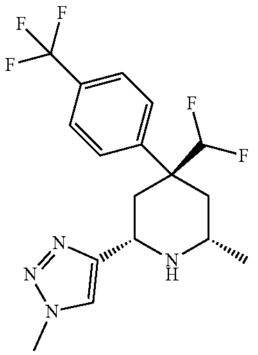 [SMILES: C[C@H]1C[C@](c2ccc(C(F)(F)F)cc2)(C(F)F)C[C@@H](c2cn(C)nn2)N1] | I16 |
| 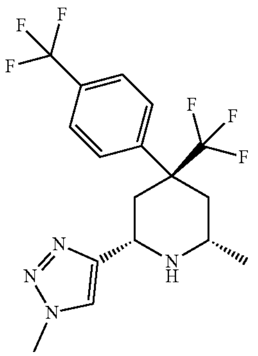 [SMILES: C[C@H]1C[C@](c2ccc(C(F)(F)F)cc2)(C(F)(F)F)C[C@@H](c2cn(C)nn2)N1] | I17 |
TABLE 2-continued
| Compounds I5 to I295 | |
|---|---|
| 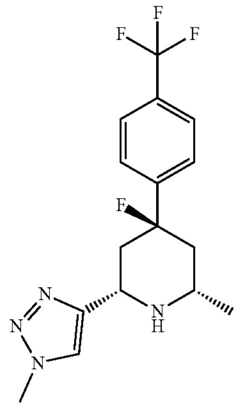 [SMILES: C[C@H]1C[C@@](F)(c2ccc(C(F)(F)F)cc2)C[C@@H](c2cn(C)nn2)N1] | I18 |
| 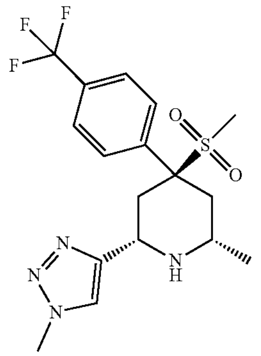 [SMILES: C[C@H]1C[C@](c2ccc(C(F)(F)F)cc2)(S(C)(=O)=O)C[C@@H](c2cn(C)nn2)N1] | I19 |
| 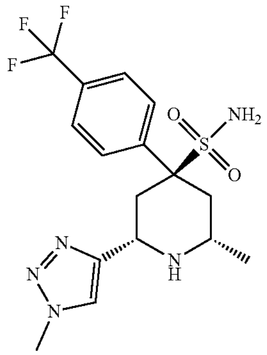 [SMILES: C[C@H]1C[C@](c2ccc(C(F)(F)F)cc2)(S(N)(=O)=O)C[C@@H](c2cn(C)nn2)N1] | I20 |
| 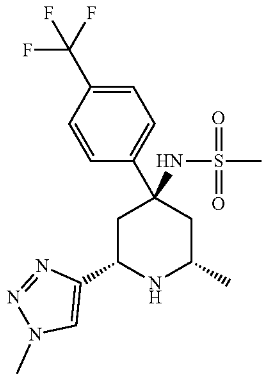 [SMILES: C[C@H]1C[C@@](NS(C)(=O)=O)(c2ccc(C(F)(F)F)cc2)C[C@@H](c2cn(C)nn2)N1] | I21 |

TABLE 2-continued
| Compounds I5 to I295 | |
|---|---|
| 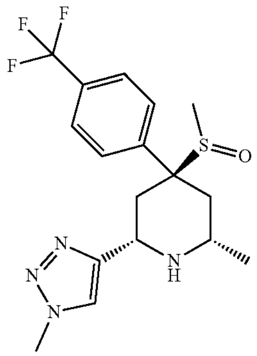 | I22 |
| 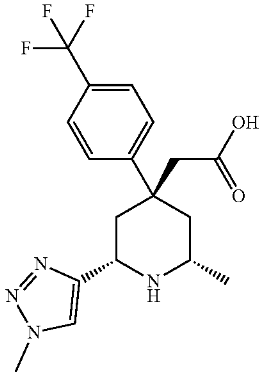 [SMILES: C[C@H]1C[C@@](CC(=O)O)(c2ccc(C(F)(F)F)cc2)C[C@@H](c2cn(C)nn2)N1] | I23 |
| 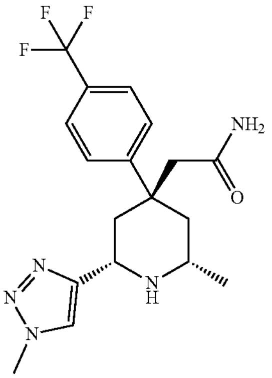 [SMILES: C[C@H]1C[C@@](CC(N)=O)(c2ccc(C(F)(F)F)cc2)C[C@@H](c2cn(C)nn2)N1] | I24 |
| 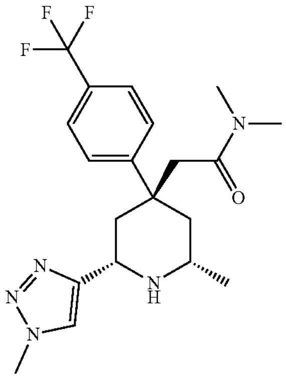 [SMILES: C[C@H]1C[C@@](CC(=O)N(C)C)(c2ccc(C(F)(F)F)cc2)C[C@@H](c2cn(C)nn2)N1] | I25 |
TABLE 2-continued
| Compounds I5 to I295 | |
|---|---|
| 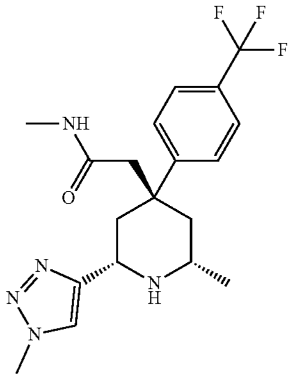 [SMILES: CNC(=O)C[C@]1(c2ccc(C(F)(F)F)cc2)C[C@@H](c2cn(C)nn2)N[C@@H](C)C1] | I26 |
| 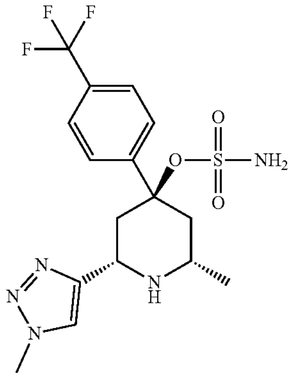 [SMILES: C[C@H]1C[C@@](OS(N)(=O)=O)(c2ccc(C(F)(F)F)cc2)C[C@@H](c2cn(C)nn2)N1] | I27 |
| 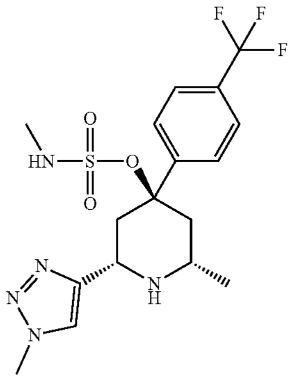 [SMILES: CNS(=O)(=O)O[C@]1(c2ccc(C(F)(F)F)cc2)C[C@@H](c2cn(C)nn2)N[C@@H](C)C1] | I28 |
| 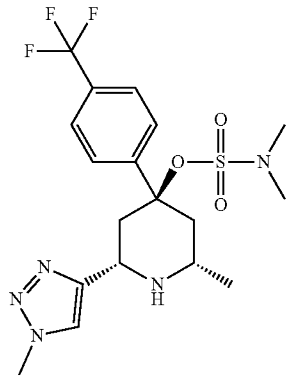 [SMILES: C[C@H]1C[C@@](OS(=O)(=O)N(C)C)(c2ccc(C(F)(F)F)cc2)C[C@@H](c2cn(C)nn2)N1] | I29 |

TABLE 2-continued
Compounds I5 to I295
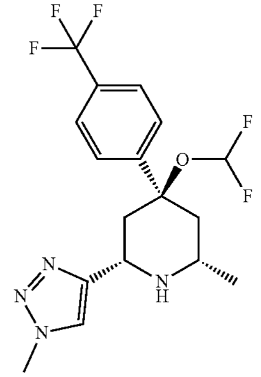 [SMILES: C[C@H]1C[C@@](OC(F)F)(c2ccc(C(F)(F)F)cc2)C[C@@H](c2cn(C)nn2)N1]
I30
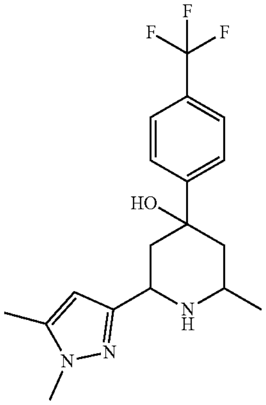
I31
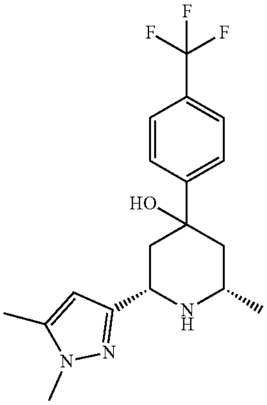
I32
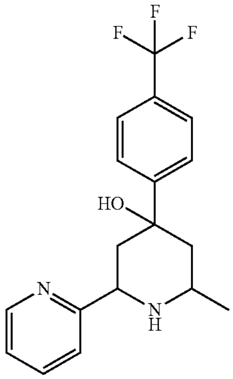 [SMILES: CC1CC(O)(c2ccc(C(F)(F)F)cc2)CC(c2ccccn2)N1]
I33
TABLE 2-continued
Compounds I5 to I295
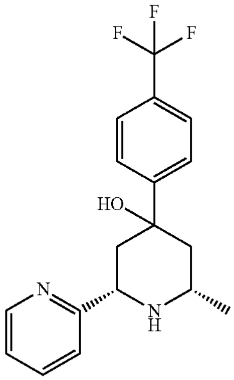 [SMILES: C[C@H]1CC(O)(c2ccc(C(F)(F)F)cc2)C[C@@H](c2ccccn2)N1]
I34
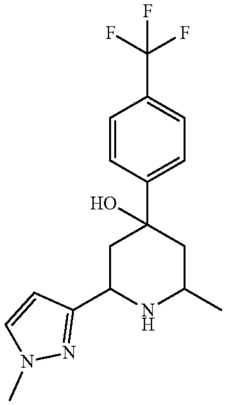 [SMILES: CC1CC(O)(c2ccc(C(F)(F)F)cc2)CC(c2ccn(C)n2)N1]
I35
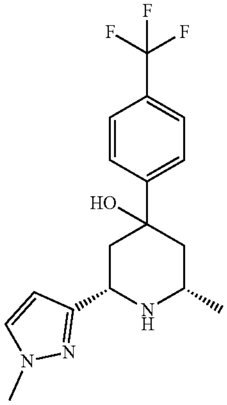 [SMILES: C[C@H]1CC(O)(c2ccc(C(F)(F)F)cc2)C[C@@H](c2ccn(C)n2)N1]
I36
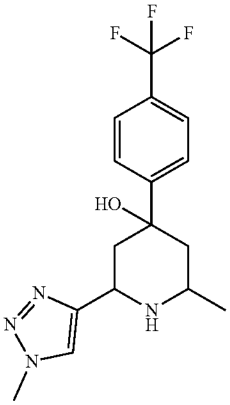 [SMILES: CC1CC(O)(c2ccc(C(F)(F)F)cc2)CC(c2cn(C)nn2)N1]
I37

TABLE 2-continued
Compounds I5 to I295
I38
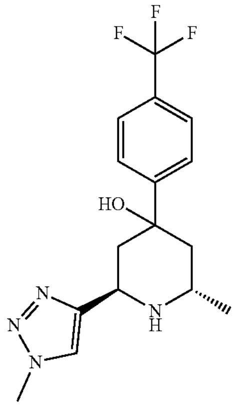 [SMILES: C[C@H]1CC(O)(c2ccc(C(F)(F)F)cc2)C[C@H](c2cn(C)nn2)N1]
I39
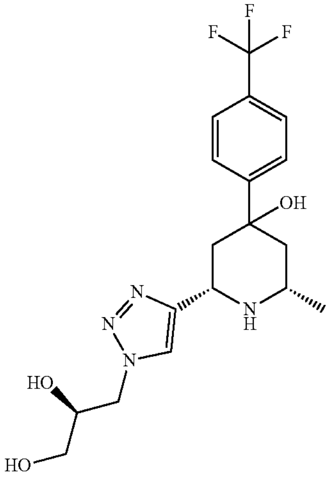 [SMILES: C[C@H]1CC(O)(c2ccc(C(F)(F)F)cc2)C[C@@H](c2cn(C[C@H](O)CO)nn2)N1]
I40
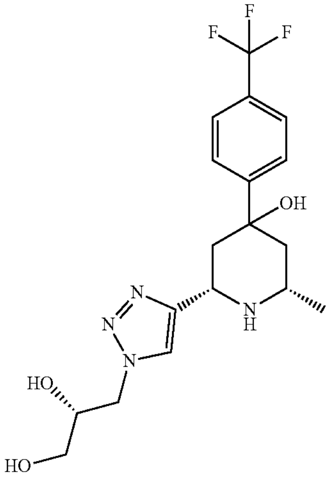 [SMILES: C[C@H]1CC(O)(c2ccc(C(F)(F)F)cc2)C[C@@H](c2cn(C[C@@H](O)CO)nn2)N1]
TABLE 2-continued
Compounds I5 to I295
I41
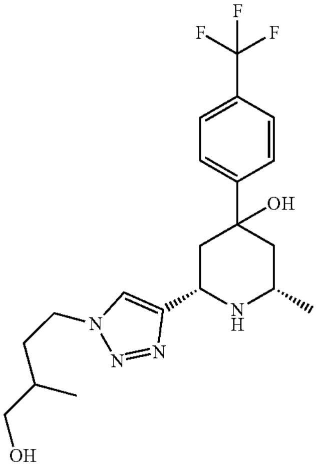 [SMILES: CC(CO)CCn1cc([C@@H]2CC(O)(c3ccc(C(F)(F)F)cc3)C[C@H](C)N2)nn1]
I42
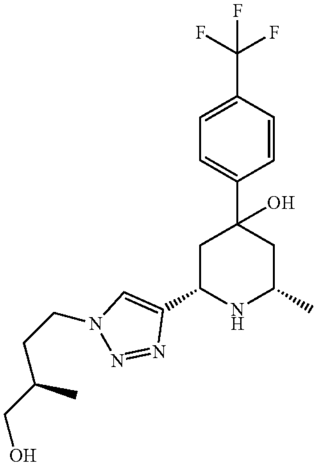 [SMILES: C[C@@H](CO)CCn1cc([C@@H]2CC(O)(c3ccc(C(F)(F)F)cc3)C[C@H](C)N2)nn1]
I43
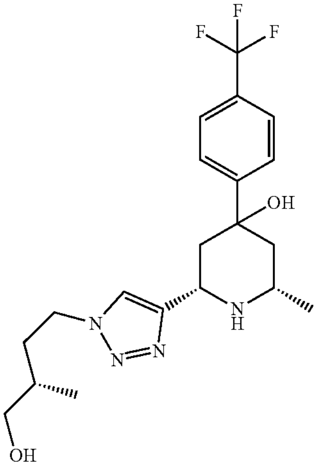 [SMILES: C[C@H](CO)CCn1cc([C@@H]2CC(O)(c3ccc(C(F)(F)F)cc3)C[C@H](C)N2)nn1]

TABLE 2-continued
Compounds I5 to I295
I44
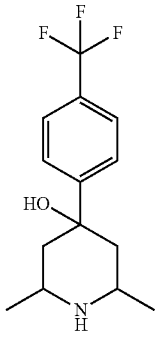
I45
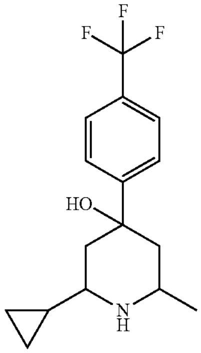 [SMILES: CC1CC(O)(c2ccc(C(F)(F)F)cc2)CC(C2CC2)N1]
I46
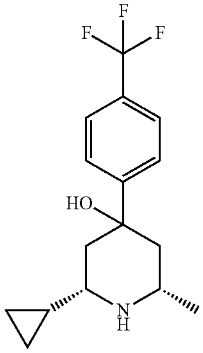 [SMILES: C[C@H]1CC(O)(c2ccc(C(F)(F)F)cc2)C[C@@H](C2CC2)N1]
I47
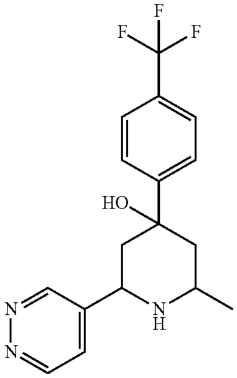 [SMILES: CC1CC(O)(c2ccc(C(F)(F)F)cc2)CC(c2ccnnc2)N1]
TABLE 2-continued
Compounds I5 to I295
I48
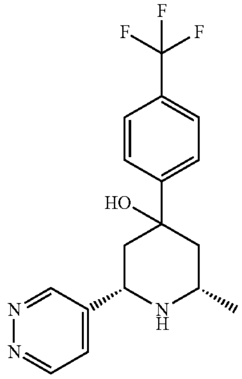 [SMILES: C[C@H]1CC(O)(c2ccc(C(F)(F)F)cc2)C[C@@H](c2ccnnc2)N1]
I49
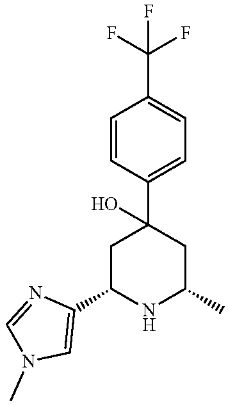 [SMILES: C[C@H]1CC(O)(c2ccc(C(F)(F)F)cc2)C[C@@H](c2cn(C)cn2)N1]
I50
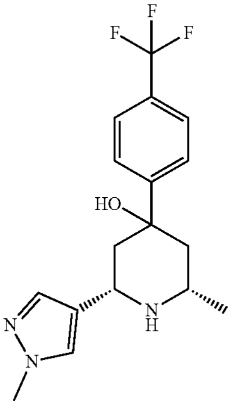 [SMILES: C[C@H]1CC(O)(c2ccc(C(F)(F)F)cc2)C[C@@H](c2cnn(C)c2)N1]
I51
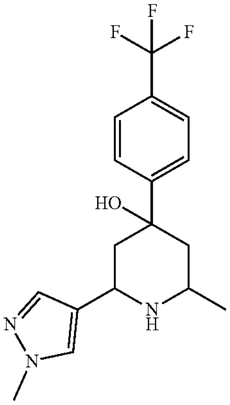 [SMILES: CC1CC(O)(c2ccc(C(F)(F)F)cc2)CC(c2cnn(C)c2)N1]

TABLE 2-continued
Compounds I5 to I295
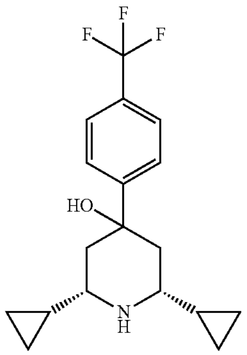 [SMILES: OC1(c2ccc(C(F)(F)F)cc2)C[C@@H](C2CC2)N[C@@H](C2CC2)C1]
I52
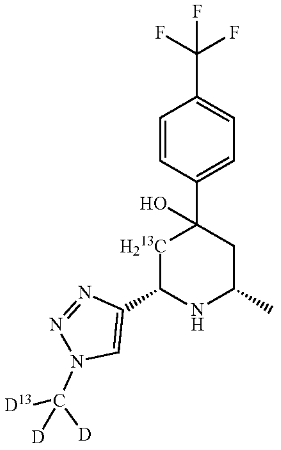
I53
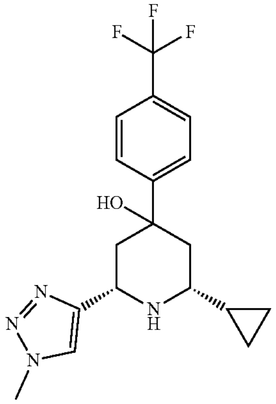 [SMILES: Cn1cc([C@@H]2CC(O)(c3ccc(C(F)(F)F)cc3)C[C@H](C3CC3)N2)nn1]
I54
TABLE 2-continued
Compounds I5 to I295
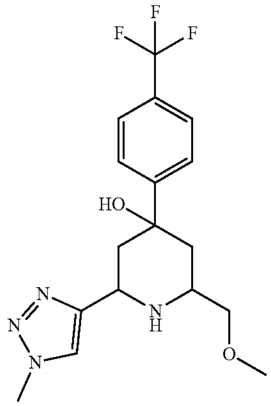 [SMILES: COCC1CC(O)(c2ccc(C(F)(F)F)cc2)CC(c2cn(C)nn2)N1]
I55
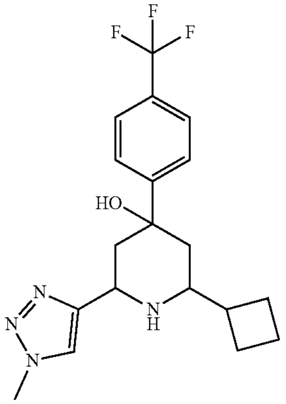 [SMILES: Cn1cc(C2CC(O)(c3ccc(C(F)(F)F)cc3)CC(C3CCC3)N2)nn1]
I56
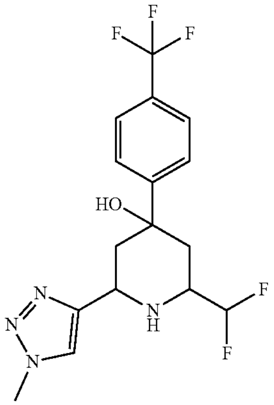 [SMILES: Cn1cc(C2CC(O)(c3ccc(C(F)(F)F)cc3)CC(C(F)F)N2)nn1]
I57

TABLE 2-continued
Compounds I5 to I295
I58
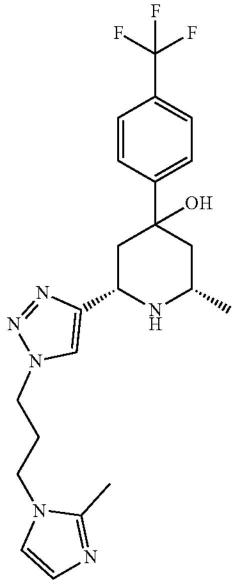 [SMILES: Cc1nccn1CCCn1cc([C@@H]2CC(O)(c3ccc(C(F)(F)F)cc3)C[C@H](C)N2)nn1]
I59
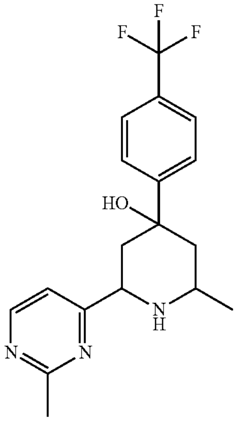 [SMILES: Cc1nccc(C2CC(O)(c3ccc(C(F)(F)F)cc3)CC(C)N2)n1]
I60
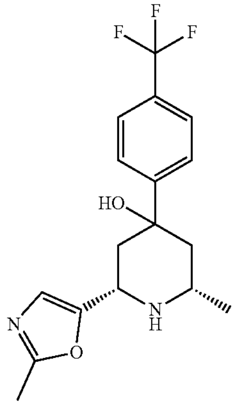 [SMILES: Cc1ncc([C@@H]2CC(O)(c3ccc(C(F)(F)F)cc3)C[C@H](C)N2)o1]
I61
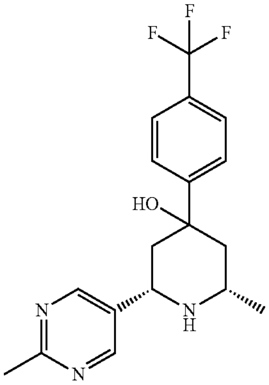
I62
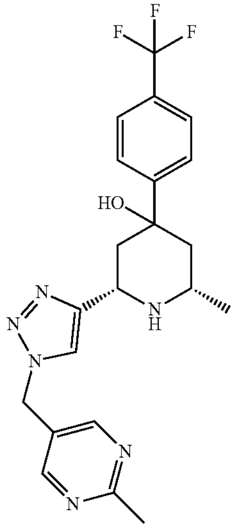 [SMILES: Cc1ncc(Cn2cc([C@@H]3CC(O)(c4ccc(C(F)(F)F)cc4)C[C@H](C)N3)nn2)cn1]
I63
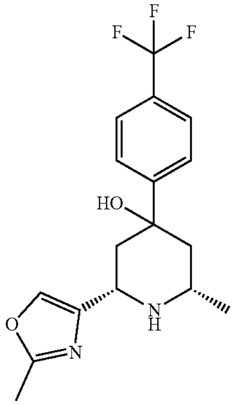 [SMILES: Cc1nc([C@@H]2CC(O)(c3ccc(C(F)(F)F)cc3)C[C@H](C)N2)co1]

TABLE 2-continued
Compounds I5 to I295
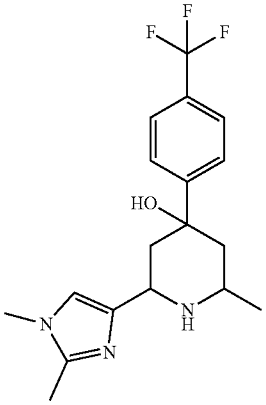
I64
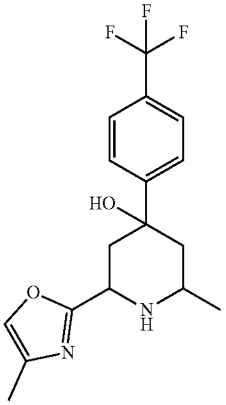 [SMILES: Cc1coc(C2CC(O)(c3ccc(C(F)(F)F)cc3)CC(C)N2)n1]
I65
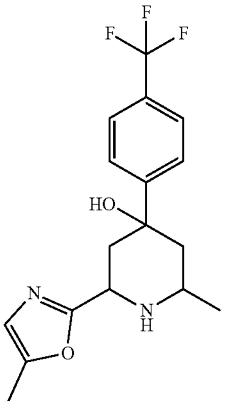 [SMILES: Cc1cnc(C2CC(O)(c3ccc(C(F)(F)F)cc3)CC(C)N2)o1]
I66
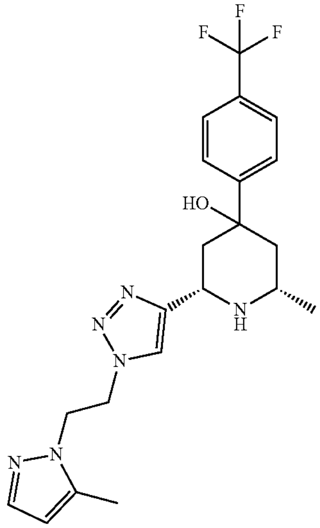 [SMILES: Cc1ccnn1CCn1cc([C@@H]2CC(O)(c3ccc(C(F)(F)F)cc3)C[C@H](C)N2)nn1]
I67
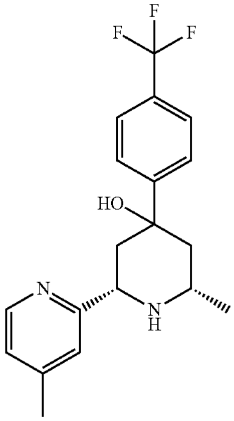 [SMILES: Cc1ccnc([C@@H]2CC(O)(c3ccc(C(F)(F)F)cc3)C[C@H](C)N2)c1]
I68
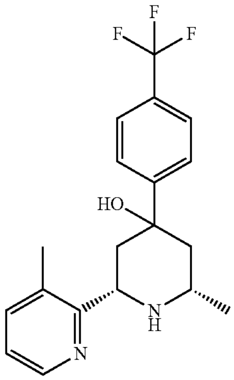 [SMILES: Cc1cccnc1[C@@H]1CC(O)(c2ccc(C(F)(F)F)cc2)C[C@H](C)N1]
I69

TABLE 2-continued
Compounds I5 to I295
I70
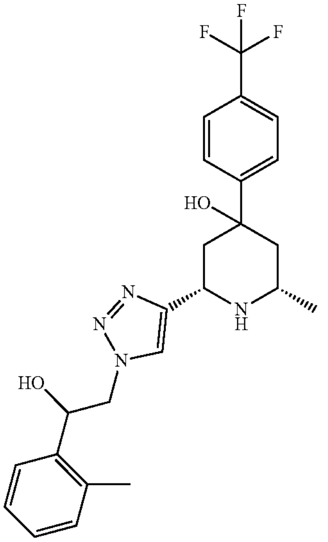 [SMILES: Cc1ccccc1C(O)Cn1cc([C@@H]2CC(O)(c3ccc(C(F)(F)F)cc3)C[C@H](C)N2)nn1]
I71
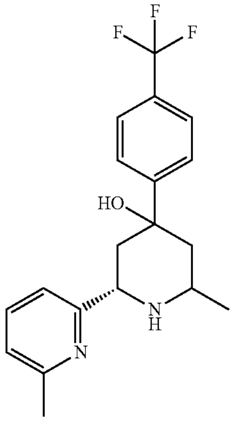 [SMILES: Cc1cccc([C@@H]2CC(O)(c3ccc(C(F)(F)F)cc3)CC(C)N2)n1]
I72
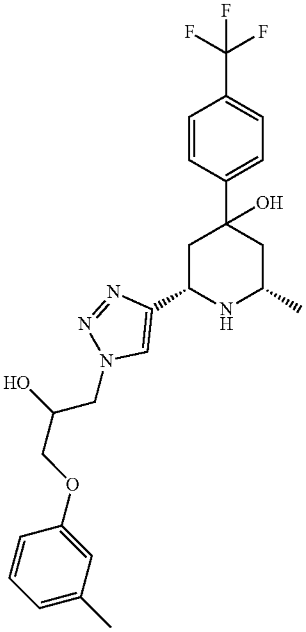 [SMILES: Cc1cccc(OCC(O)Cn2cc([C@@H]3CC(O)(c4ccc(C(F)(F)F)cc4)C[C@H](C)N3)nn2)c1]
TABLE 2-continued
Compounds I5 to I295
I73
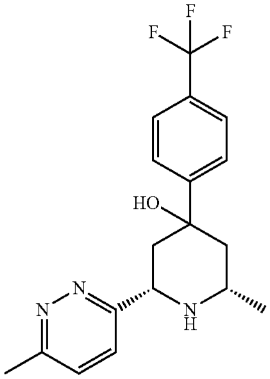
I74
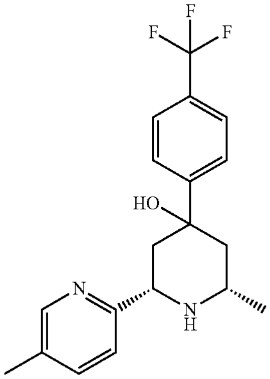
I75
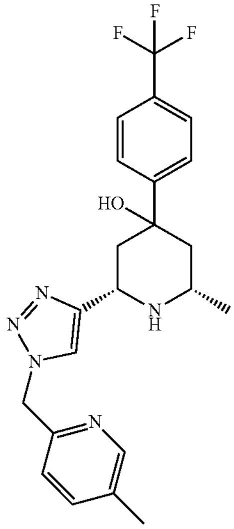 [SMILES: Cc1ccc(Cn2cc([C@@H]3CC(O)(c4ccc(C(F)(F)F)cc4)C[C@H](C)N3)nn2)nc1]

TABLE 2-continued
Compounds I5 to I295
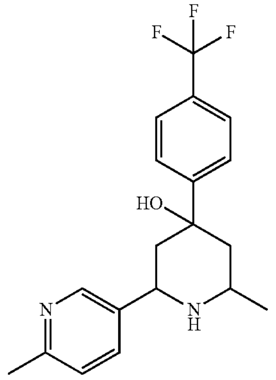
I76
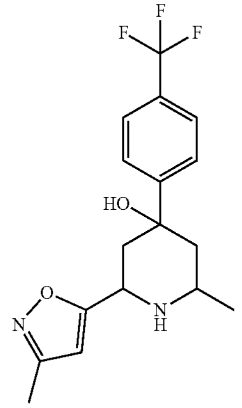 [SMILES: Cc1cc(C2CC(O)(c3ccc(C(F)(F)F)cc3)CC(C)N2)on1]
I77
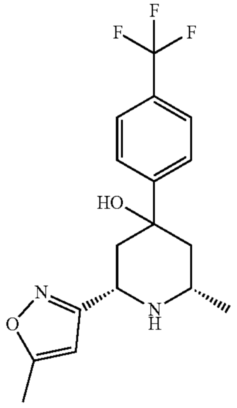 [SMILES: Cc1cc([C@@H]2CC(O)(c3ccc(C(F)(F)F)cc3)C[C@H](C)N2)no1]
I78
TABLE 2-continued
Compounds I5 to I295
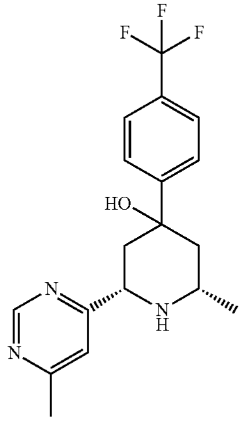 [SMILES: Cc1cc([C@@H]2CC(O)(c3ccc(C(F)(F)F)cc3)C[C@H](C)N2)ncn1]
I79
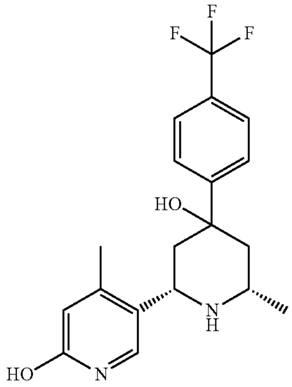 [SMILES: Cc1cc(O)ncc1[C@@H]1CC(O)(c2ccc(C(F)(F)F)cc2)C[C@H](C)N1]
I80
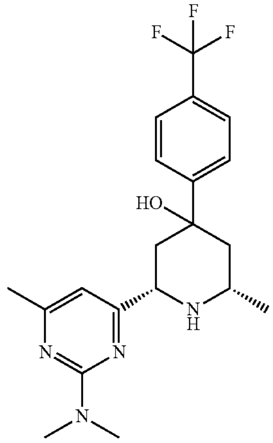
I81

TABLE 2-continued
Compounds I5 to I295
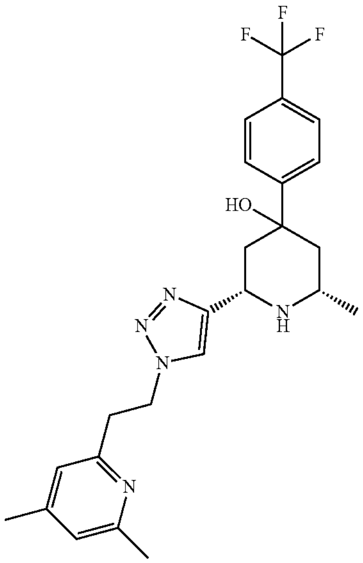
I82
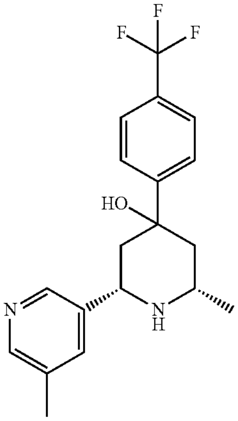 [SMILES: Cc1cncc([C@@H]2CC(O)(c3ccc(C(F)(F)F)cc3)C[C@H](C)N2)c1]
I83
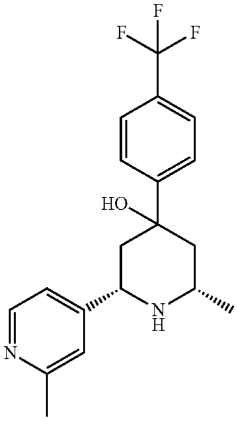 [SMILES: Cc1cc([C@@H]2CC(O)(c3ccc(C(F)(F)F)cc3)C[C@H](C)N2)ccn1]
I84
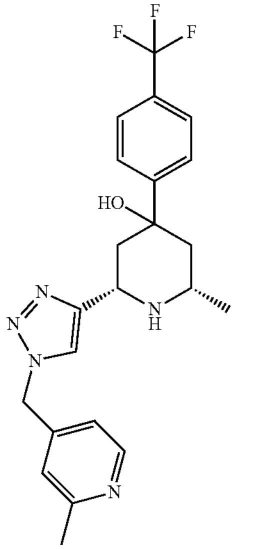 [SMILES: Cc1cc(Cn2cc([C@@H]3CC(O)(c4ccc(C(F)(F)F)cc4)C[C@H](C)N3)nn2)ccn1]
I85
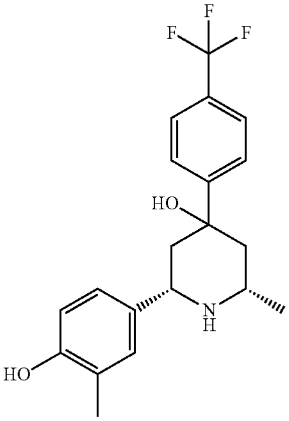 [SMILES: Cc1cc([C@@H]2CC(O)(c3ccc(C(F)(F)F)cc3)C[C@H](C)N2)ccc1O]
I86
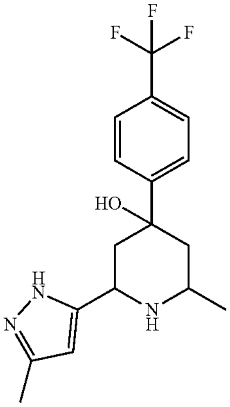 [SMILES: Cc1cc(C2CC(O)(c3ccc(C(F)(F)F)cc3)CC(C)N2)[nH]n1]
I87

TABLE 2-continued
Compounds I5 to I295
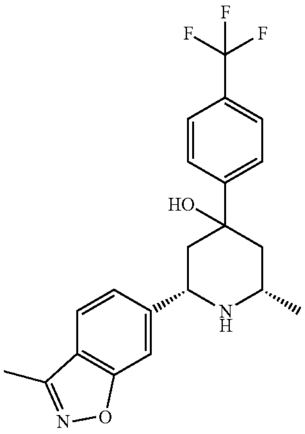
I88
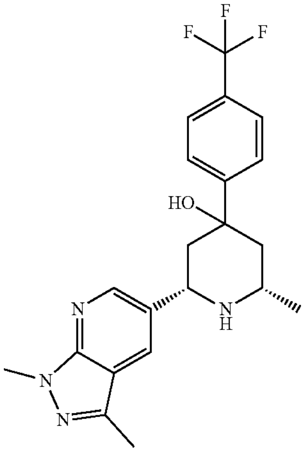
I89
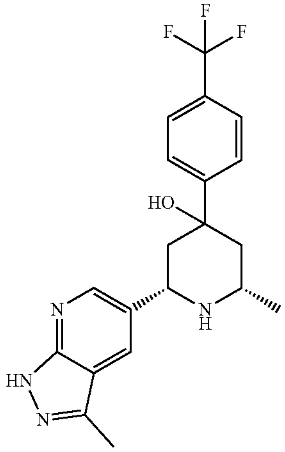 [SMILES: Cc1n[nH]c2ncc([C@@H]3CC(O)(c4ccc(C(F)(F)F)cc4)C[C@H](C)N3)cc12]
I90
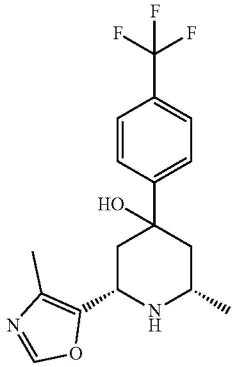 [SMILES: Cc1ncoc1[C@@H]1CC(O)(c2ccc(C(F)(F)F)cc2)C[C@H](C)N1]
I91
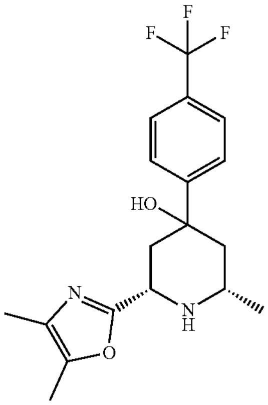
I92
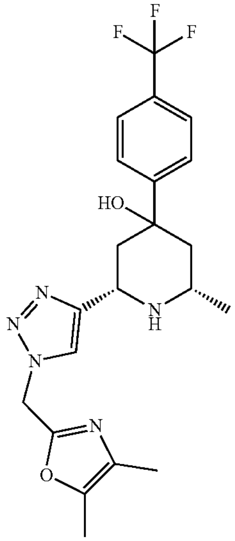 [SMILES: Cc1nc(Cn2cc([C@@H]3CC(O)(c4ccc(C(F)(F)F)cc4)C[C@H](C)N3)nn2)oc1C]
I93

TABLE 2-continued
| Compounds I5 to I295 |
| --- |
| 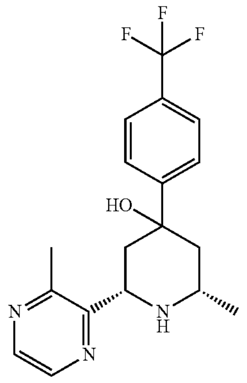 I94 |
| 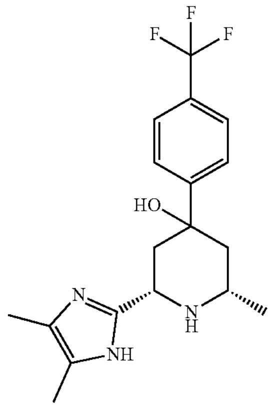 I95 |
| 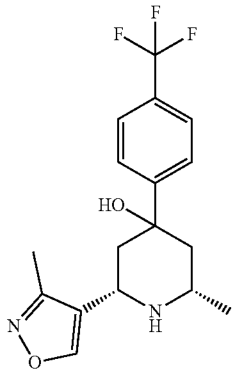 I96 |
| 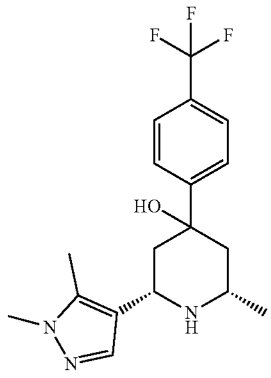 I97 |
TABLE 2-continued
| Compounds I5 to I295 |
| --- |
| 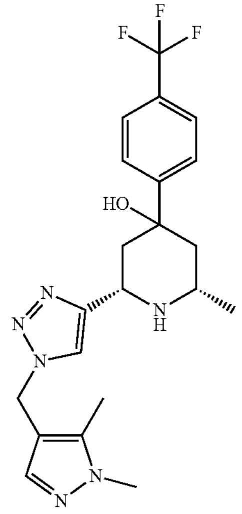 I98 |
| 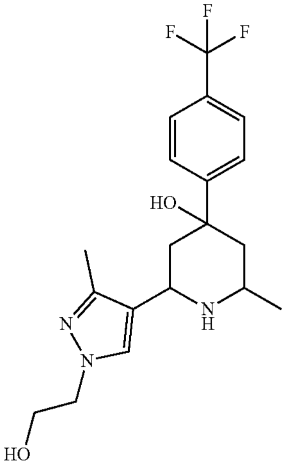 I99 |
| 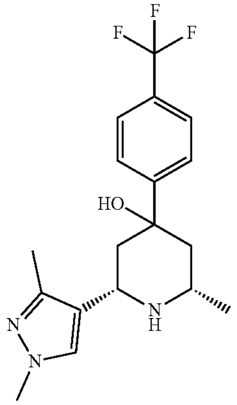 I100 |

TABLE 2-continued
Compounds I5 to I295
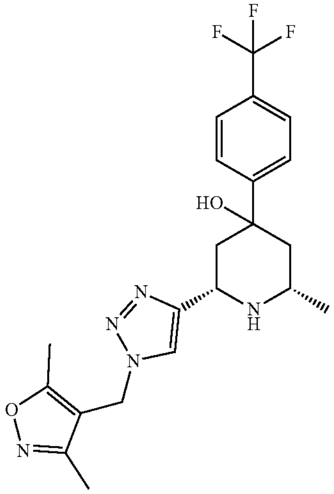 [SMILES: Cc1noc(C)c1Cn1cc([C@@H]2CC(O)(c3ccc(C(F)(F)F)cc3)C[C@H](C)N2)nn1]
I101
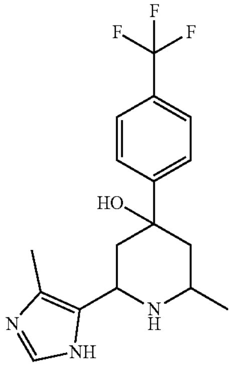 [SMILES: Cc1nc[nH]c1C1CC(O)(c2ccc(C(F)(F)F)cc2)CC(C)N1]
I102
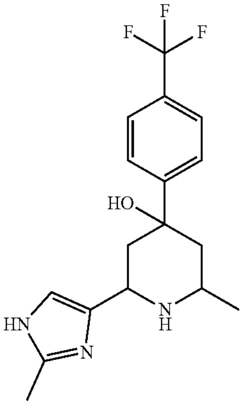 [SMILES: Cc1nc(C2CC(O)(c3ccc(C(F)(F)F)cc3)CC(C)N2)c[nH]1]
I103
TABLE 2-continued
Compounds I5 to I295
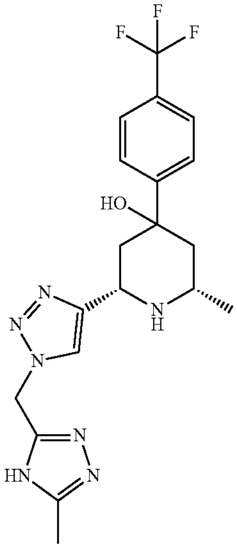 [SMILES: Cc1nnc(Cn2cc([C@@H]3CC(O)(c4ccc(C(F)(F)F)cc4)C[C@H](C)N3)nn2)[nH]1]
I104
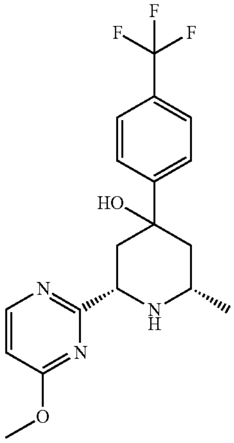 [SMILES: COc1ccnc([C@@H]2CC(O)(c3ccc(C(F)(F)F)cc3)C[C@H](C)N2)n1]
I105
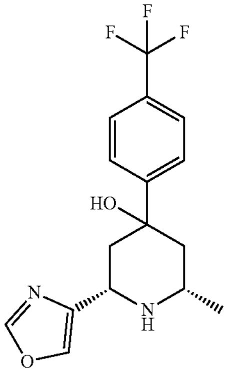 [SMILES: C[C@H]1CC(O)(c2ccc(C(F)(F)F)cc2)C[C@@H](c2cocn2)N1]
I106

TABLE 2-continued
Compounds I5 to I295
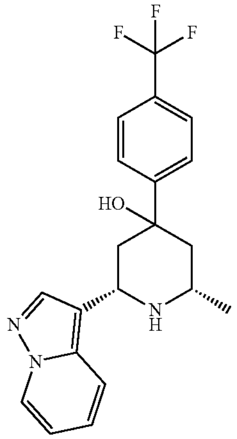 [SMILES: C[C@H]1CC(O)(c2ccc(C(F)(F)F)cc2)C[C@@H](c2cnn3ccccc23)N1]
I107
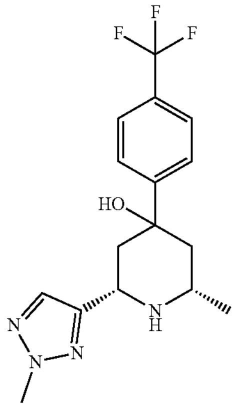 [SMILES: C[C@H]1CC(O)(c2ccc(C(F)(F)F)cc2)C[C@@H](c2cnn(C)n2)N1]
I108
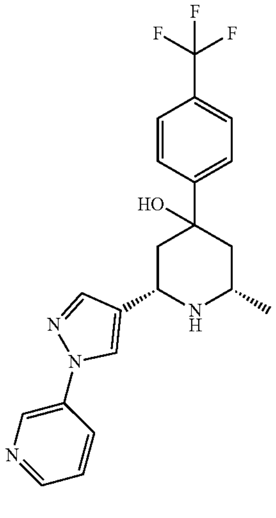 [SMILES: C[C@H]1CC(O)(c2ccc(C(F)(F)F)cc2)C[C@@H](c2cnn(-c3cccnc3)c2)N1]
I109
TABLE 2-continued
Compounds I5 to I295
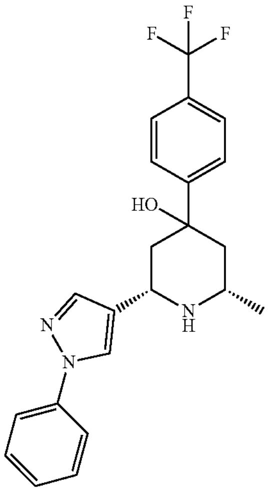 [SMILES: C[C@H]1CC(O)(c2ccc(C(F)(F)F)cc2)C[C@@H](c2cnn(-c3ccccc3)c2)N1]
I110
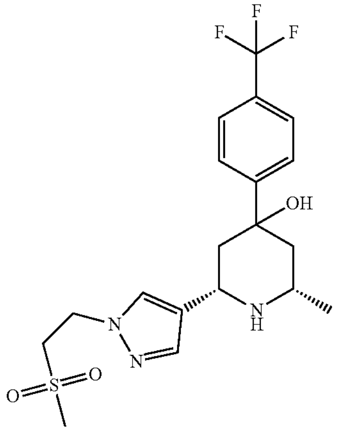 [SMILES: C[C@H]1CC(O)(c2ccc(C(F)(F)F)cc2)C[C@@H](c2cnn(CCS(C)(=O)=O)c2)N1]
I111
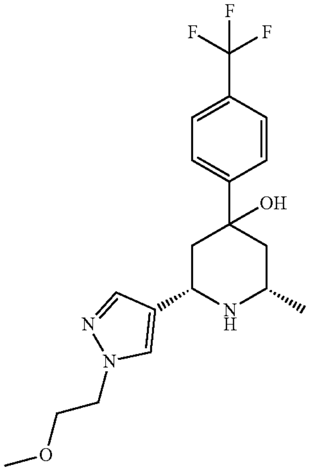
I112

TABLE 2-continued
| Compounds I5 to I295 |
| --- |
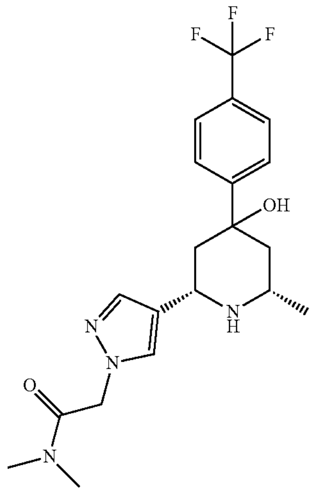
I113
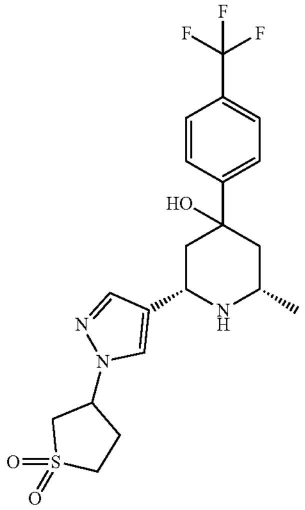 [SMILES: C[C@H]1CC(O)(c2ccc(C(F)(F)F)cc2)C[C@@H](c2cnn(C3CCS(=O)(=O)C3)c2)N1]
I114
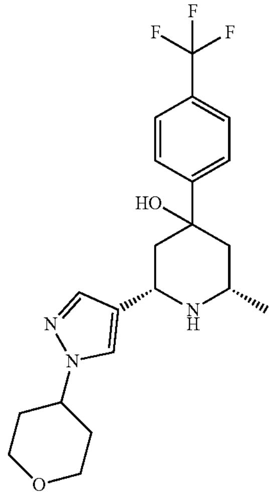 [SMILES: C[C@H]1CC(O)(c2ccc(C(F)(F)F)cc2)C[C@@H](c2cnn(C3CCOCC3)c2)N1]
I115
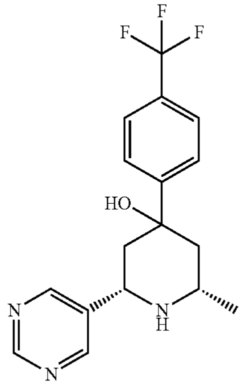 [SMILES: C[C@H]1CC(O)(c2ccc(C(F)(F)F)cc2)C[C@@H](c2cncnc2)N1]
I116
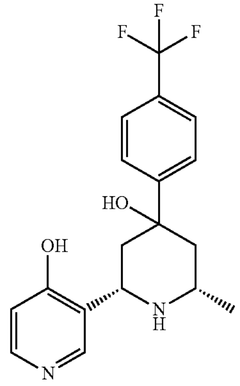 [SMILES: C[C@H]1CC(O)(c2ccc(C(F)(F)F)cc2)C[C@@H](c2cnccc2O)N1]
I117
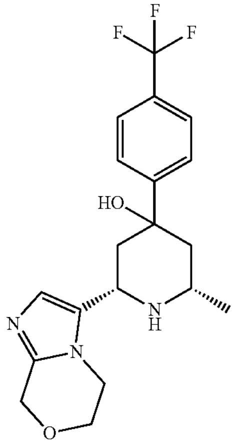 [SMILES: C[C@H]1CC(O)(c2ccc(C(F)(F)F)cc2)C[C@@H](c2cnc3n2CCOC3)N1]
I118

TABLE 2-continued
| Compounds I5 to I295 |
| --- |
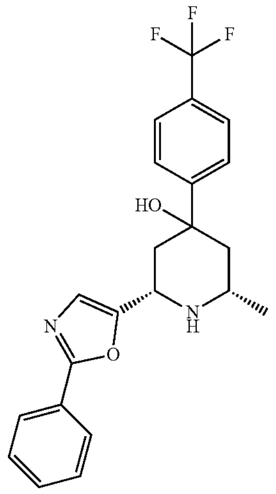 [SMILES: C[C@H]1CC(O)(c2ccc(C(F)(F)F)cc2)C[C@@H](c2cnc(-c3ccccc3)o2)N1]
I119
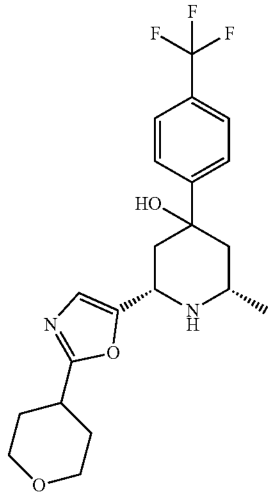 [SMILES: C[C@H]1CC(O)(c2ccc(C(F)(F)F)cc2)C[C@@H](c2cnc(C3CCOCC3)o2)N1]
I120
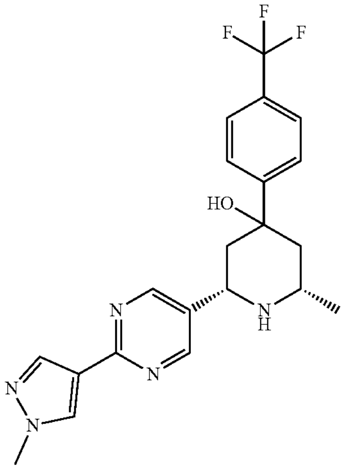 [SMILES: C[C@H]1CC(O)(c2ccc(C(F)(F)F)cc2)C[C@@H](c2cnc(-c3cnn(C)c3)nc2)N1]
I121
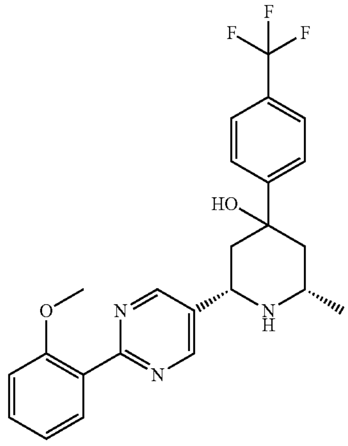 [SMILES: COc1ccccc1-c1ncc([C@@H]2CC(O)(c3ccc(C(F)(F)F)cc3)C[C@H](C)N2)cn1]
I122
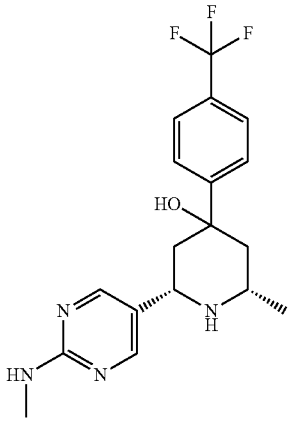 [SMILES: CNc1ncc([C@@H]2CC(O)(c3ccc(C(F)(F)F)cc3)C[C@H](C)N2)cn1]
I123
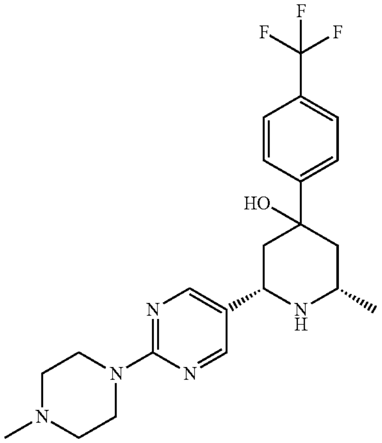
I124

TABLE 2-continued
| Compounds I5 to I295 |
| --- |
| 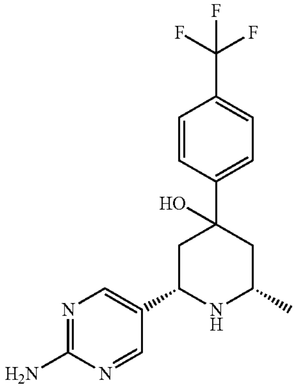 I125 |
| 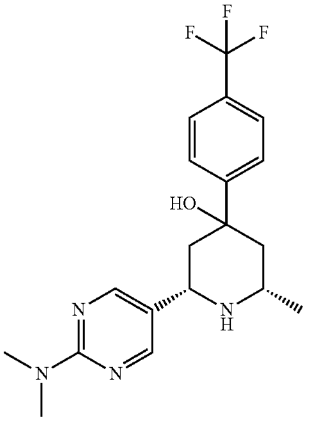 I126 |
| 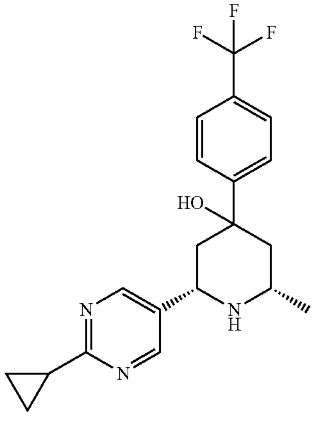 I127 |
TABLE 2-continued
| Compounds I5 to I295 |
| --- |
| 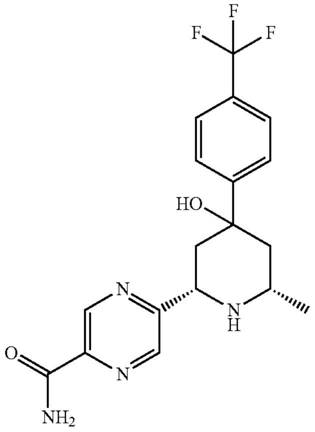 I128 |
| 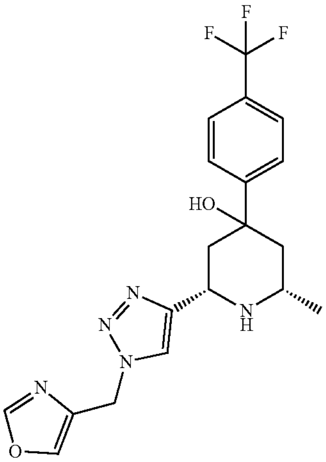 I129 |
| 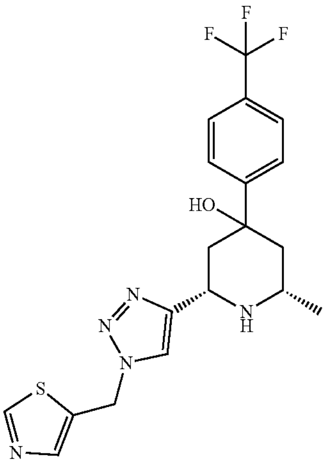 I130 |

TABLE 2-continued
Compounds I5 to I295
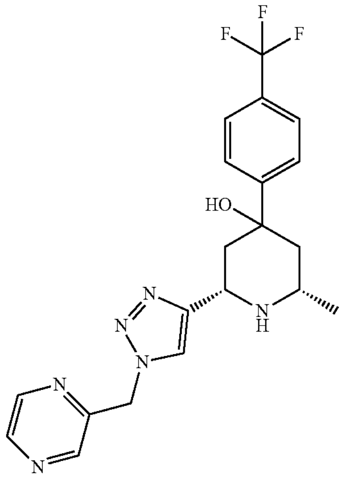 [SMILES: C[C@H]1CC(O)(c2ccc(C(F)(F)F)cc2)C[C@@H](c2cn(Cc3cnccn3)nn2)N1]
I131
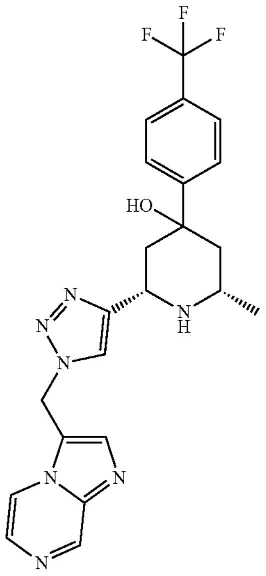 [SMILES: C[C@H]1CC(O)(c2ccc(C(F)(F)F)cc2)C[C@@H](c2cn(Cc3cnc4cnccn34)nn2)N1]
I132
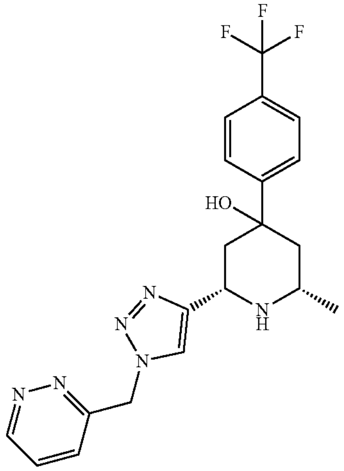 [SMILES: C[C@H]1CC(O)(c2ccc(C(F)(F)F)cc2)C[C@@H](c2cn(Cc3cccnn3)nn2)N1]
I133
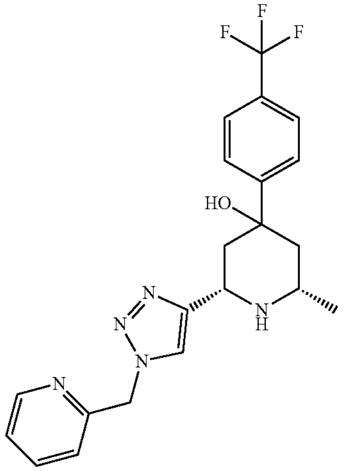 [SMILES: C[C@H]1CC(O)(c2ccc(C(F)(F)F)cc2)C[C@@H](c2cn(Cc3ccccn3)nn2)N1]
I134
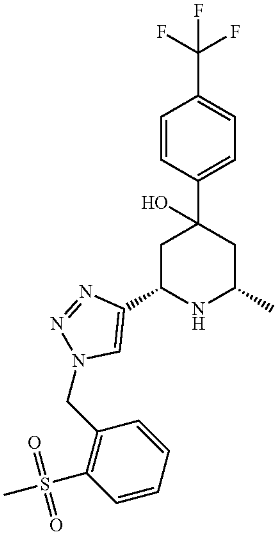
I135
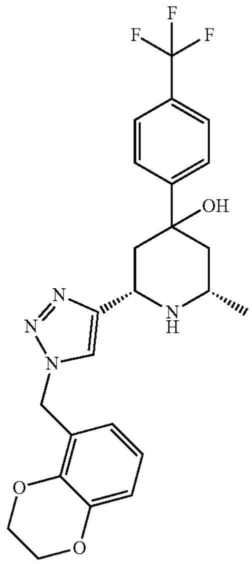 [SMILES: C[C@H]1CC(O)(c2ccc(C(F)(F)F)cc2)C[C@@H](c2cn(Cc3cccc4c3OCCO4)nn2)N1]
I136

TABLE 2-continued
Compounds I5 to I295
I137
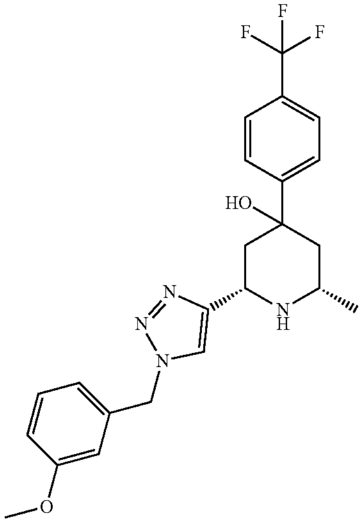
I138
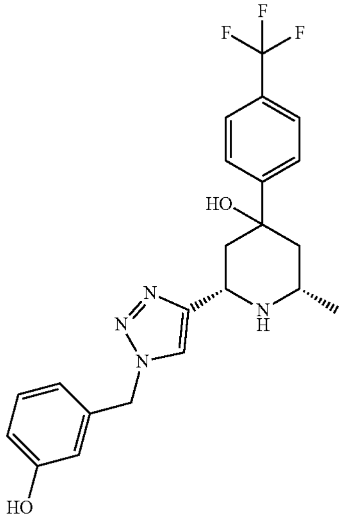 [SMILES: C[C@H]1CC(O)(c2ccc(C(F)(F)F)cc2)C[C@@H](c2cn(Cc3cccc(O)c3)nn2)N1]
I139
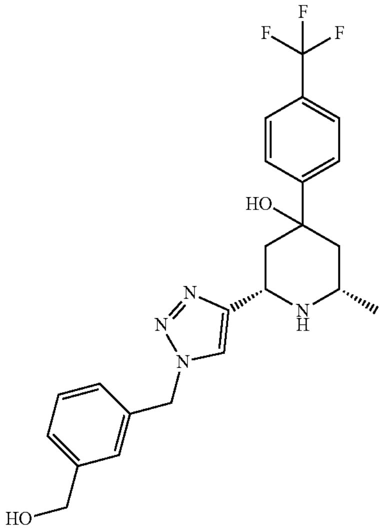 [SMILES: C[C@H]1CC(O)(c2ccc(C(F)(F)F)cc2)C[C@@H](c2cn(Cc3cccc(CO)c3)nn2)N1]
TABLE 2-continued
Compounds I5 to I295
I140
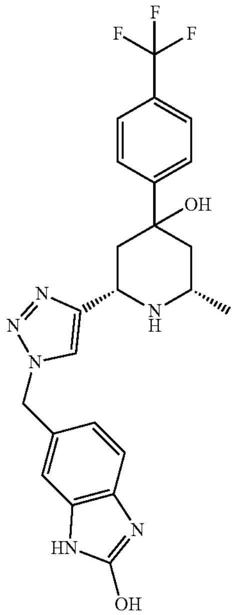 [SMILES: C[C@H]1CC(O)(c2ccc(C(F)(F)F)cc2)C[C@@H](c2cn(Cc3ccc4nc(O)[nH]c4c3)nn2)N1]
I141
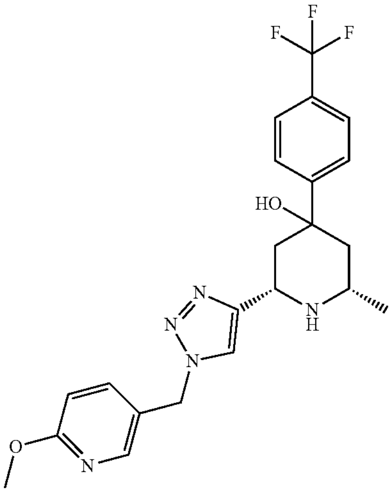

TABLE 2-continued
Compounds I5 to I295
I142
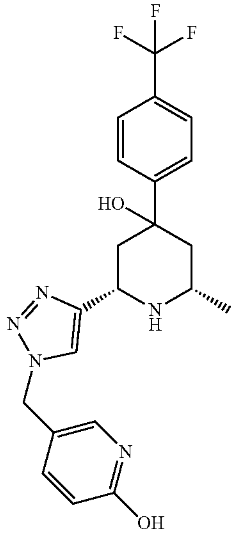 [SMILES: C[C@H]1CC(O)(c2ccc(C(F)(F)F)cc2)C[C@@H](c2cn(Cc3ccc(O)nc3)nn2)N1]
I143
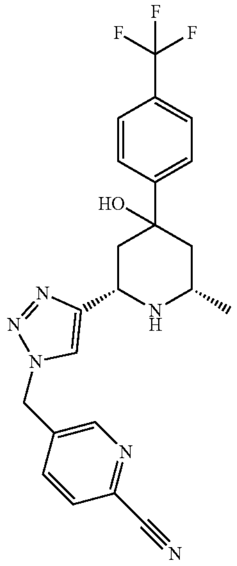 [SMILES: C[C@H]1CC(O)(c2ccc(C(F)(F)F)cc2)C[C@@H](c2cn(Cc3ccc(C#N)nc3)nn2)N1]
TABLE 2-continued
Compounds I5 to I295
I144
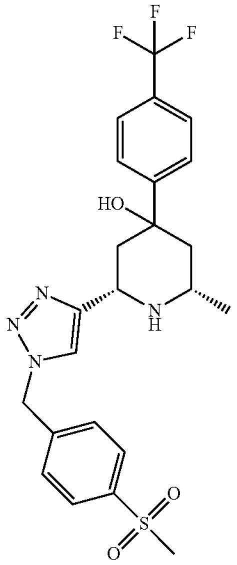 [SMILES: C[C@H]1CC(O)(c2ccc(C(F)(F)F)cc2)C[C@@H](c2cn(Cc3ccc(S(C)(=O)=O)cc3)nn2)N1]
I145
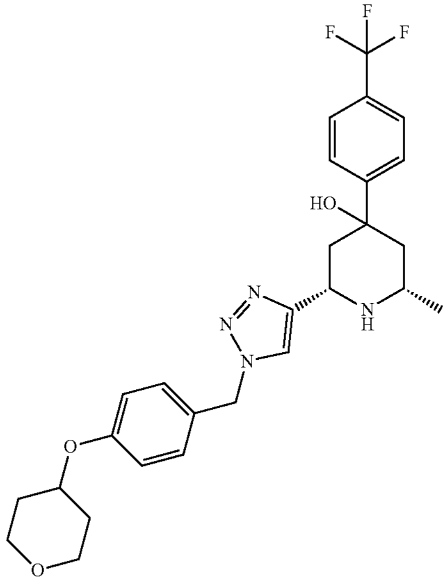 [SMILES: C[C@H]1CC(O)(c2ccc(C(F)(F)F)cc2)C[C@@H](c2cn(Cc3ccc(OC4CCOCC4)cc3)nn2)N1]

TABLE 2-continued
Compounds I5 to I295
I146
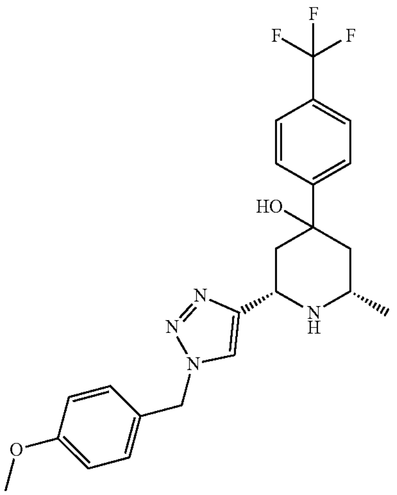
I147
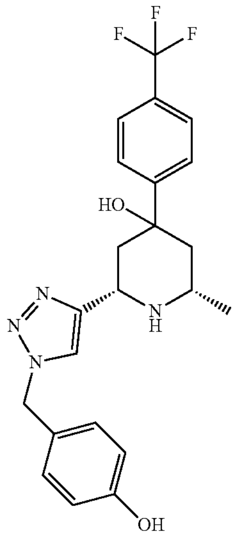 [SMILES: C[C@H]1CC(O)(c2ccc(C(F)(F)F)cc2)C[C@@H](c2cn(Cc3ccc(O)cc3)nn2)N1]
I148
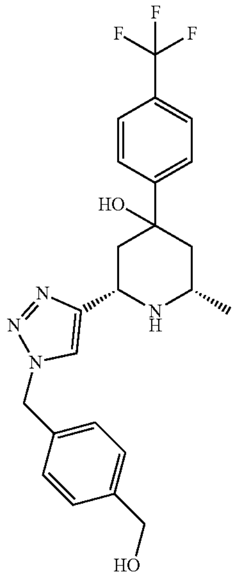 [SMILES: C[C@H]1CC(O)(c2ccc(C(F)(F)F)cc2)C[C@@H](c2cn(Cc3ccc(CO)cc3)nn2)N1]
TABLE 2-continued
Compounds I5 to I295
I149
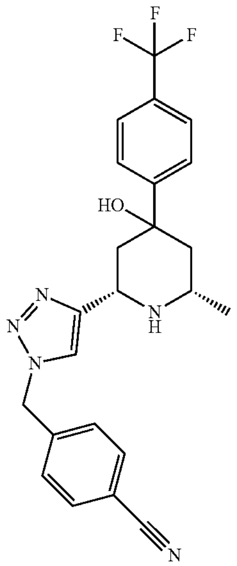 [SMILES: C[C@H]1CC(O)(c2ccc(C(F)(F)F)cc2)C[C@@H](c2cn(Cc3ccc(C#N)cc3)nn2)N1]
I150
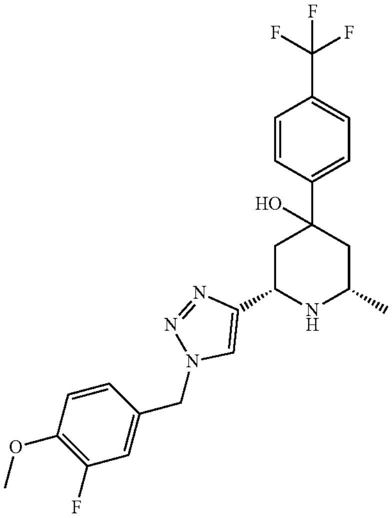
I151
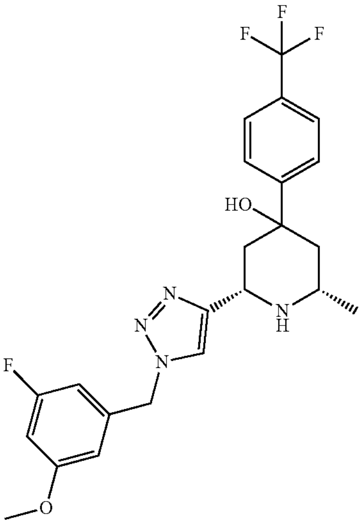

TABLE 2-continued
Compounds I5 to I295
I152
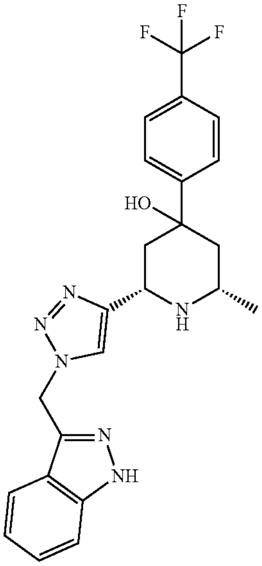 [SMILES: C[C@H]1CC(O)(c2ccc(C(F)(F)F)cc2)C[C@@H](c2cn(Cc3n[nH]c4ccccc34)nn2)N1]
I153
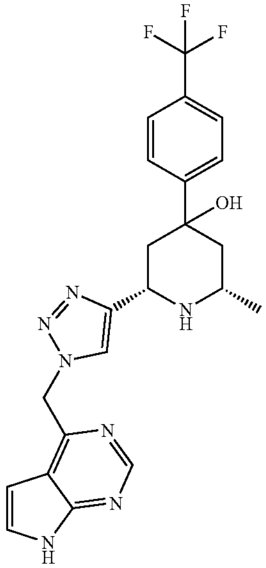 [SMILES: C[C@H]1CC(O)(c2ccc(C(F)(F)F)cc2)C[C@@H](c2cn(Cc3ncnc4[nH]ccc34)nn2)N1]
I154
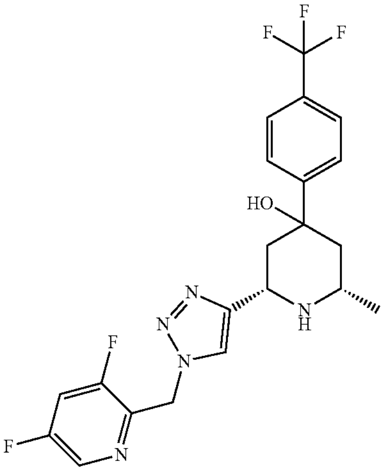 [SMILES: C[C@H]1CC(O)(c2ccc(C(F)(F)F)cc2)C[C@@H](c2cn(Cc3ncc(F)cc3F)nn2)N1]
TABLE 2-continued
Compounds I5 to I295
I155
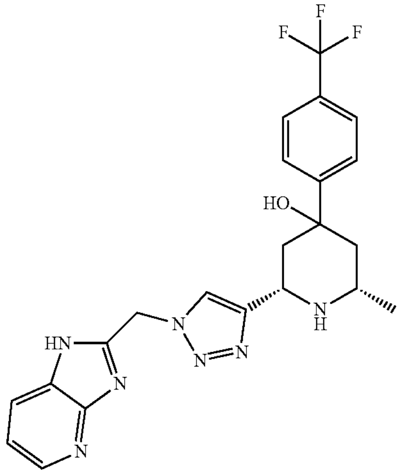 [SMILES: C[C@H]1CC(O)(c2ccc(C(F)(F)F)cc2)C[C@@H](c2cn(Cc3nc4ncccc4[nH]3)nn2)N1]
I156
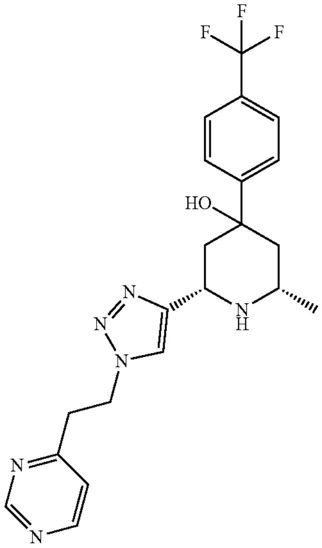 [SMILES: C[C@H]1CC(O)(c2ccc(C(F)(F)F)cc2)C[C@@H](c2cn(CCc3ccncn3)nn2)N1]
I157
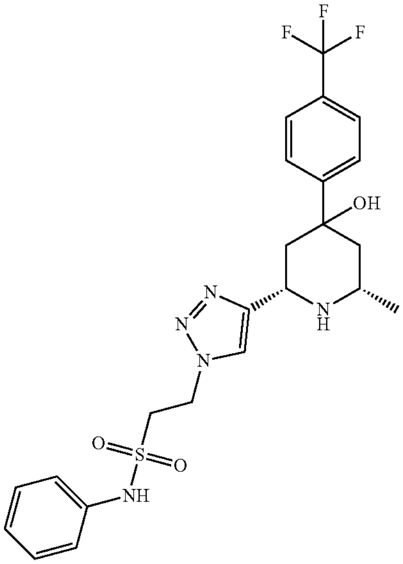 [SMILES: C[C@H]1CC(O)(c2ccc(C(F)(F)F)cc2)C[C@@H](c2cn(CCS(=O)(=O)Nc3ccccc3)nn2)N1]

TABLE 2-continued
| Compounds I5 to I295 |
|---|
| 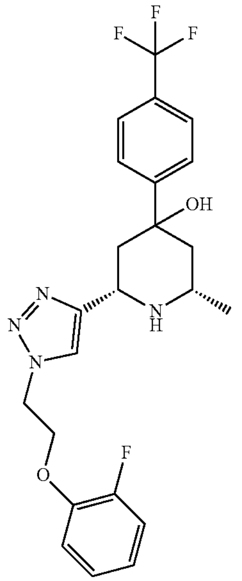 I158 |
| 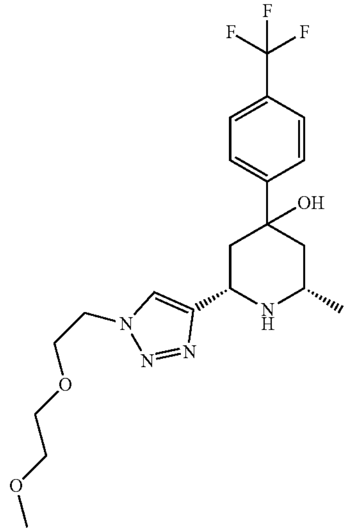 I159 |
| 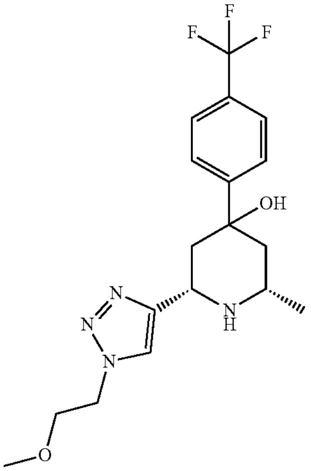 I160 |
TABLE 2-continued
| Compounds I5 to I295 |
|---|
| 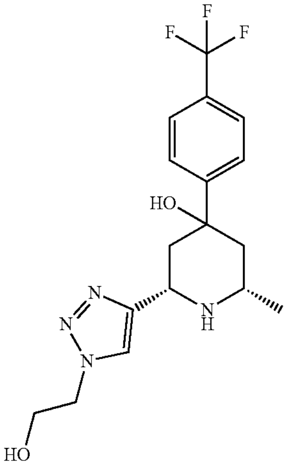 I161 |
| 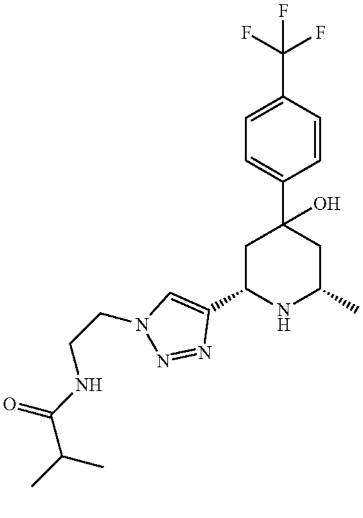 I162 |
| 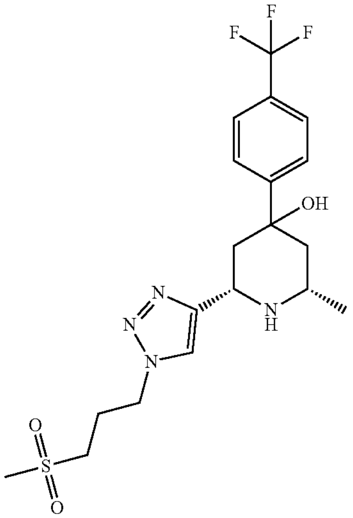 I163 |

TABLE 2-continued
Compounds I5 to I295
I164
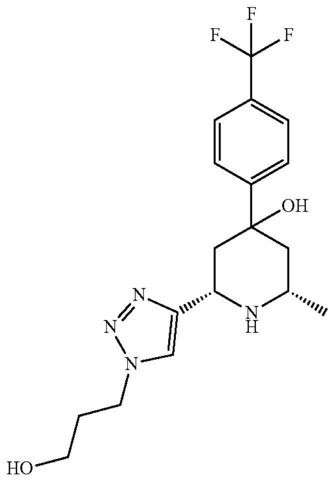 [SMILES: C[C@H]1CC(O)(c2ccc(C(F)(F)F)cc2)C[C@@H](c2cn(CCCO)nn2)N1]
I165
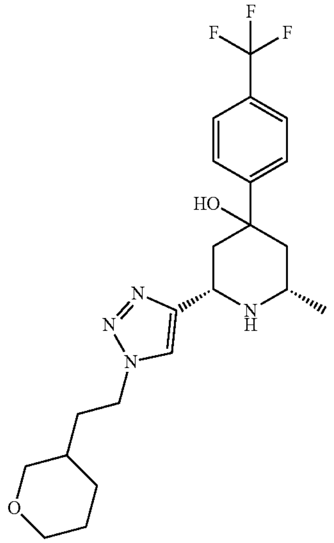 [SMILES: C[C@H]1CC(O)(c2ccc(C(F)(F)F)cc2)C[C@@H](c2cn(CCC3CCCOC3)nn2)N1]
I166
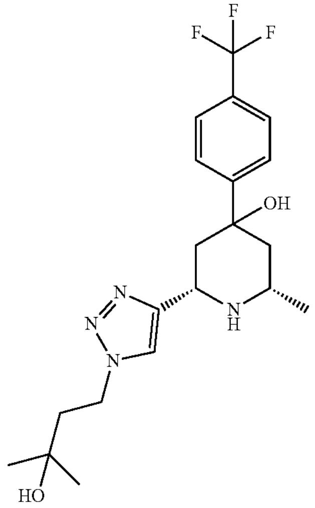 [SMILES: C[C@H]1CC(O)(c2ccc(C(F)(F)F)cc2)C[C@@H](c2cn(CCC(C)(C)O)nn2)N1]
TABLE 2-continued
Compounds I5 to I295
I167
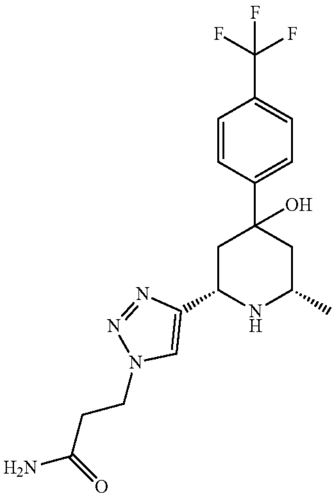 [SMILES: C[C@H]1CC(O)(c2ccc(C(F)(F)F)cc2)C[C@@H](c2cn(CCC(N)=O)nn2)N1]
I168
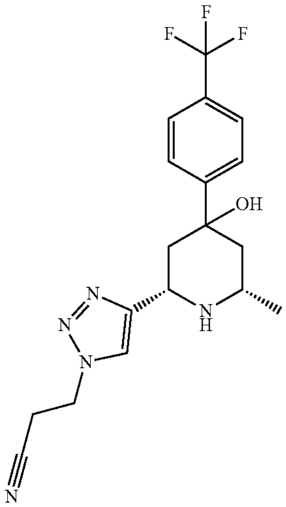 [SMILES: C[C@H]1CC(O)(c2ccc(C(F)(F)F)cc2)C[C@@H](c2cn(CCC#N)nn2)N1]
I169
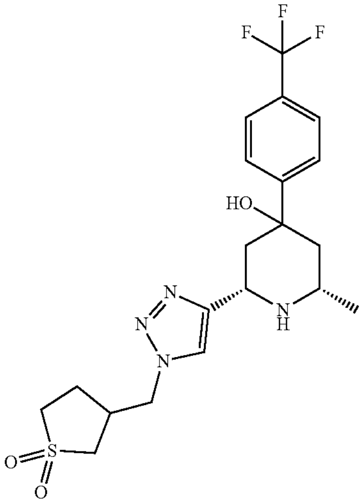 [SMILES: C[C@H]1CC(O)(c2ccc(C(F)(F)F)cc2)C[C@@H](c2cn(CC3CCS(=O)(=O)C3)nn2)N1]

TABLE 2-continued
| Compounds I5 to I295 |
|---|
I170
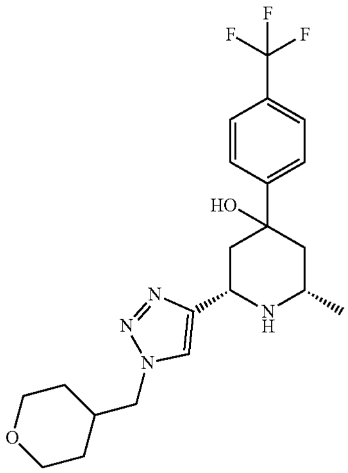 [SMILES: C[C@H]1CC(O)(c2ccc(C(F)(F)F)cc2)C[C@@H](c2cn(CC3CCOCC3)nn2)N1]
I171
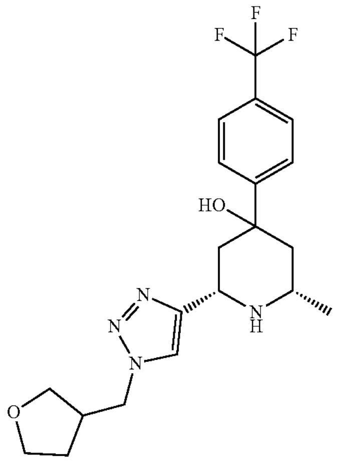 [SMILES: C[C@H]1CC(O)(c2ccc(C(F)(F)F)cc2)C[C@@H](c2cn(CC3CCOC3)nn2)N1]
I172
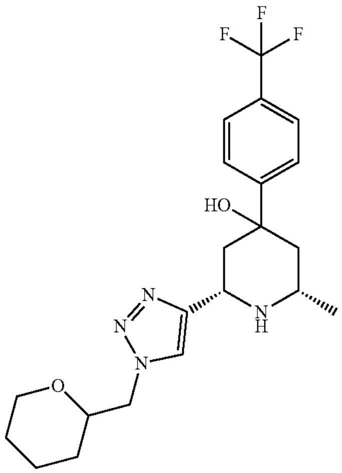 [SMILES: C[C@H]1CC(O)(c2ccc(C(F)(F)F)cc2)C[C@@H](c2cn(CC3CCCCO3)nn2)N1]
TABLE 2-continued
| Compounds I5 to I295 |
|---|
I173
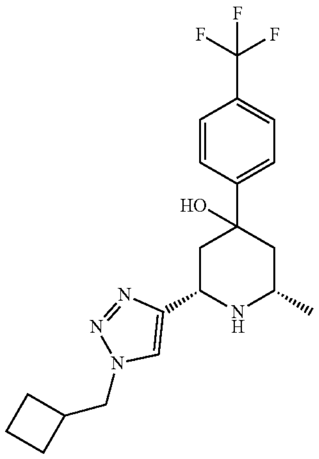 [SMILES: C[C@H]1CC(O)(c2ccc(C(F)(F)F)cc2)C[C@@H](c2cn(CC3CCC3)nn2)N1]
I174
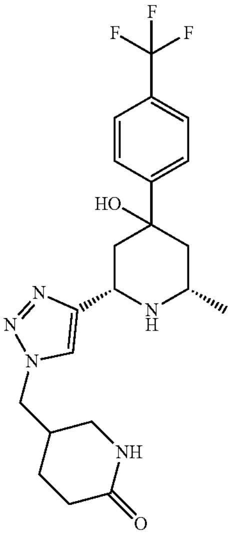 [SMILES: C[C@H]1CC(O)(c2ccc(C(F)(F)F)cc2)C[C@@H](c2cn(CC3CCC(=O)NC3)nn2)N1]
I175
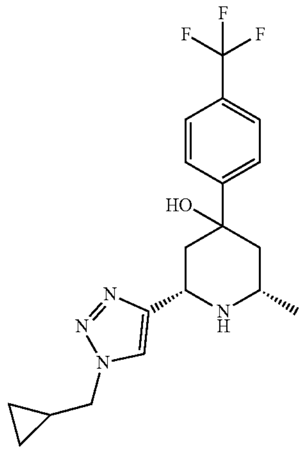 [SMILES: C[C@H]1CC(O)(c2ccc(C(F)(F)F)cc2)C[C@@H](c2cn(CC3CC3)nn2)N1]

TABLE 2-continued
Compounds I5 to I295
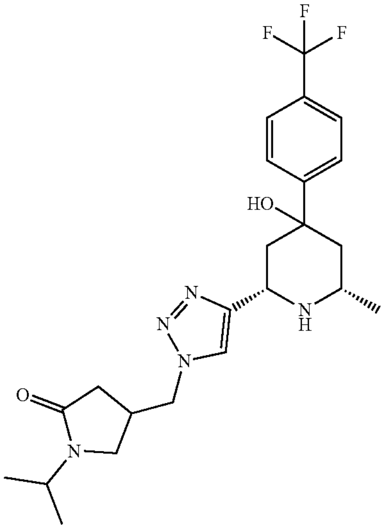 [SMILES: CC(C)N1CC(Cn2cc([C@@H]3CC(O)(c4ccc(C(F)(F)F)cc4)C[C@H](C)N3)nn2)CC1=O]
I176
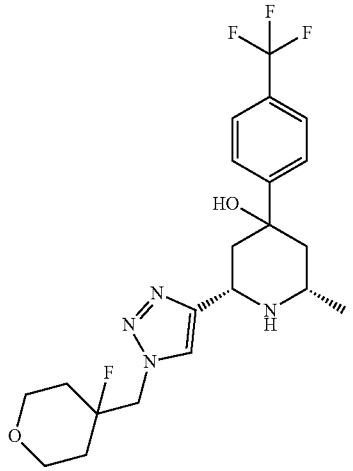 [SMILES: C[C@H]1CC(O)(c2ccc(C(F)(F)F)cc2)C[C@@H](c2cn(CC3(F)CCOCC3)nn2)N1]
I177
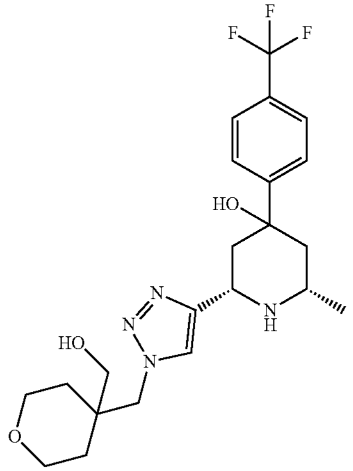 [SMILES: C[C@H]1CC(O)(c2ccc(C(F)(F)F)cc2)C[C@@H](c2cn(CC3(CO)CCOCC3)nn2)N1]
I178
TABLE 2-continued
Compounds I5 to I295
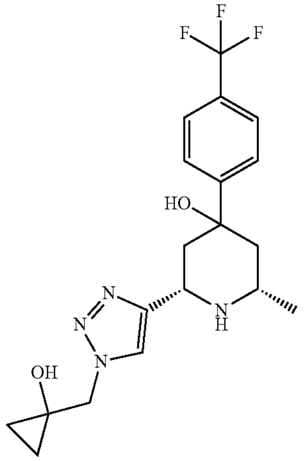 [SMILES: C[C@H]1CC(O)(c2ccc(C(F)(F)F)cc2)C[C@@H](c2cn(CC3(O)CC3)nn2)N1]
I179
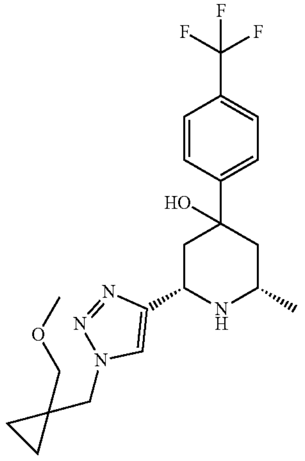 [SMILES: COCC1(Cn2cc([C@@H]3CC(O)(c4ccc(C(F)(F)F)cc4)C[C@H](C)N3)nn2)CC1]
I180
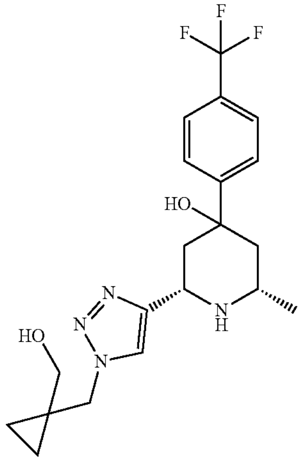 [SMILES: C[C@H]1CC(O)(c2ccc(C(F)(F)F)cc2)C[C@@H](c2cn(CC3(CO)CC3)nn2)N1]
I181

TABLE 2-continued
Compounds I5 to I295
I182
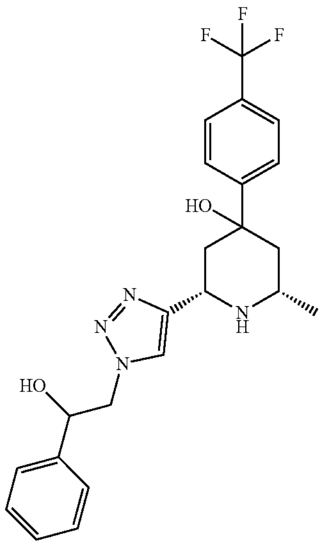 [SMILES: C[C@H]1CC(O)(c2ccc(C(F)(F)F)cc2)C[C@@H](c2cn(CC(O)c3ccccc3)nn2)N1]
I183
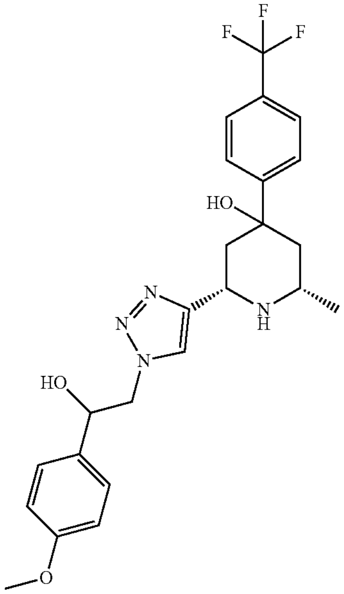
I184
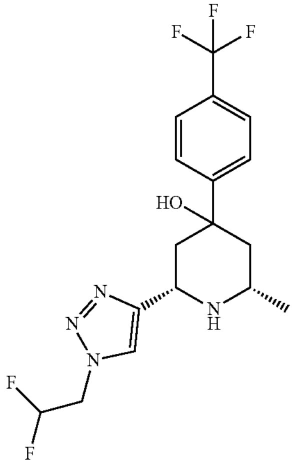 [SMILES: C[C@H]1CC(O)(c2ccc(C(F)(F)F)cc2)C[C@@H](c2cn(CC(F)F)nn2)N1]
TABLE 2-continued
Compounds I5 to I295
I185
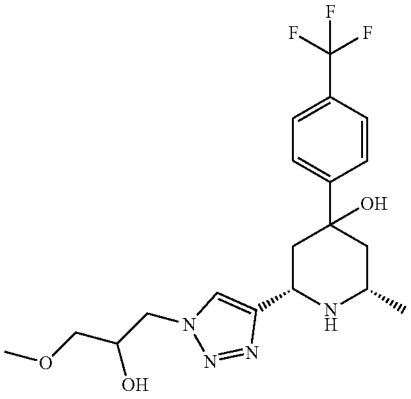
I186
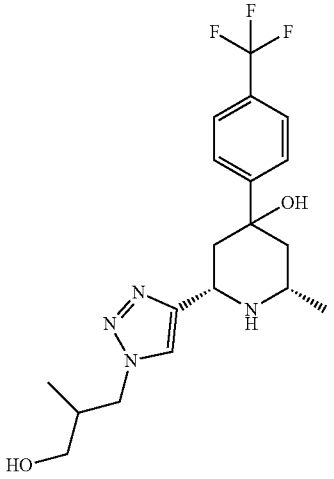 [SMILES: CC(CO)Cn1cc([C@@H]2CC(O)(c3ccc(C(F)(F)F)cc3)C[C@H](C)N2)nn1]
I187
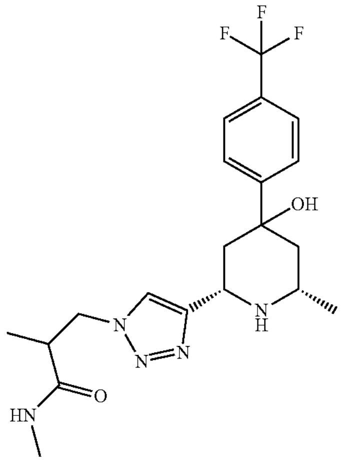 [SMILES: CNC(=O)C(C)Cn1cc([C@@H]2CC(O)(c3ccc(C(F)(F)F)cc3)C[C@H](C)N2)nn1]

TABLE 2-continued
| Compounds I5 to I295 |
| --- |
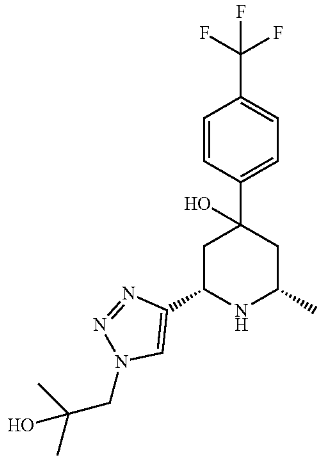 [SMILES: C[C@H]1CC(O)(c2ccc(C(F)(F)F)cc2)C[C@@H](c2cn(CC(C)(C)O)nn2)N1]
I188
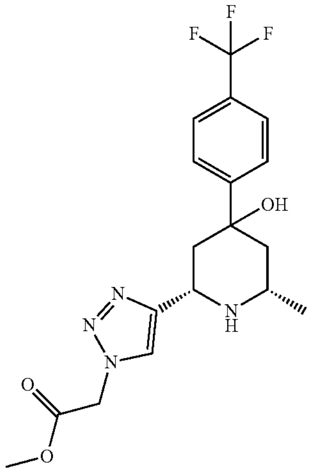
I189
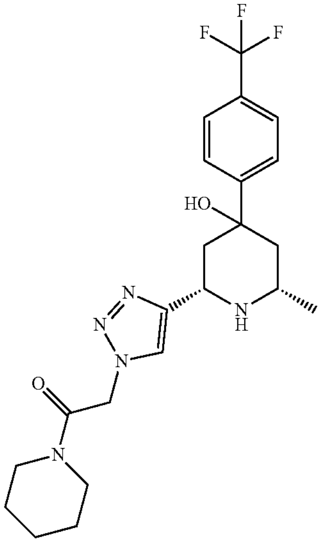 [SMILES: C[C@H]1CC(O)(c2ccc(C(F)(F)F)cc2)C[C@@H](c2cn(CC(=O)N3CCCCC3)nn2)N1]
I190
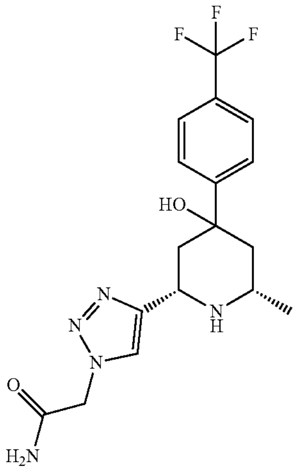 [SMILES: C[C@H]1CC(O)(c2ccc(C(F)(F)F)cc2)C[C@@H](c2cn(CC(N)=O)nn2)N1]
I191
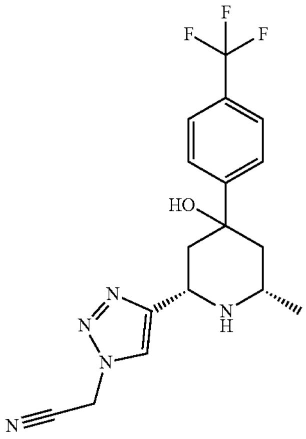 [SMILES: C[C@H]1CC(O)(c2ccc(C(F)(F)F)cc2)C[C@@H](c2cn(CC#N)nn2)N1]
I192
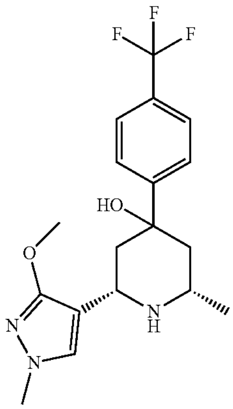 [SMILES: COc1nn(C)cc1[C@@H]1CC(O)(c2ccc(C(F)(F)F)cc2)C[C@H](C)N1]
I193

TABLE 2-continued
| Compounds I5 to I295 |
| --- |
| 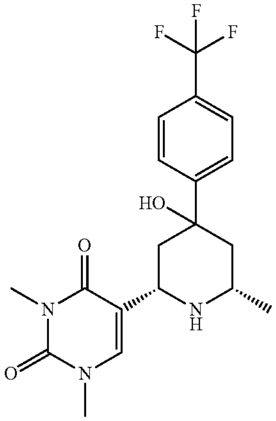 I194 |
| 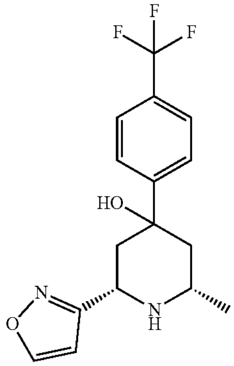 I195 |
| 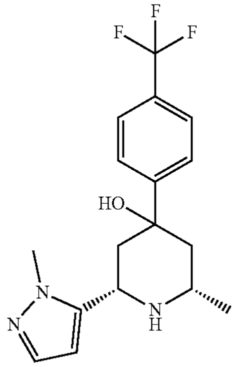 I196 |
| 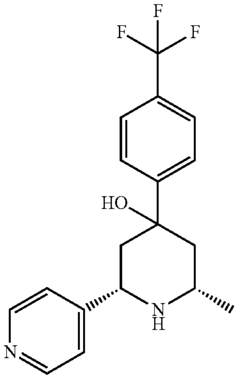 I197 |
TABLE 2-continued
| Compounds I5 to I295 |
| --- |
| 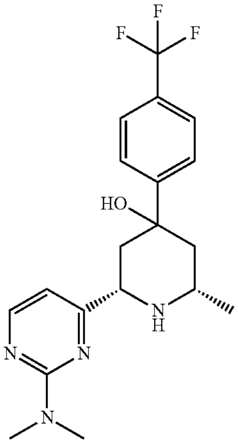 I198 |
| 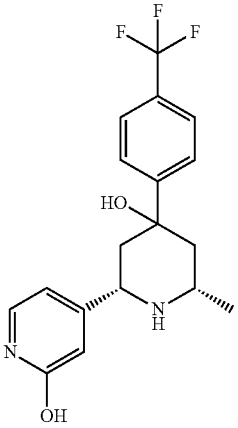 I199 |
| 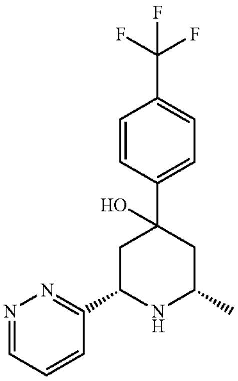 I200 |

TABLE 2-continued
Compounds I5 to I295
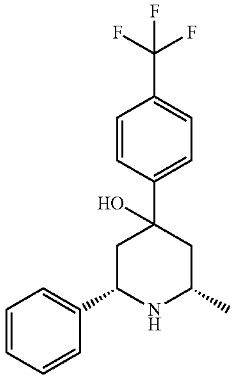 [SMILES: C[C@H]1CC(O)(c2ccc(C(F)(F)F)cc2)C[C@@H](c2ccccc2)N1]
I201
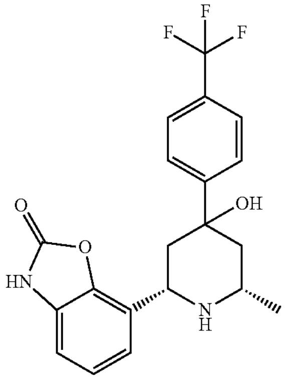 [SMILES: C[C@H]1CC(O)(c2ccc(C(F)(F)F)cc2)C[C@@H](c2cccc3[nH]c(=O)oc23)N1]
I202
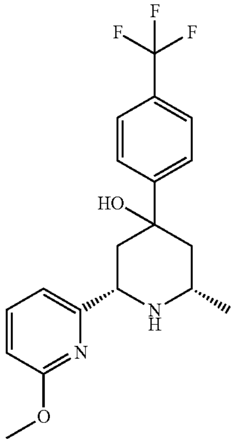 [SMILES: COc1cccc([C@@H]2CC(O)(c3ccc(C(F)(F)F)cc3)C[C@H](C)N2)n1]
I203
TABLE 2-continued
Compounds I5 to I295
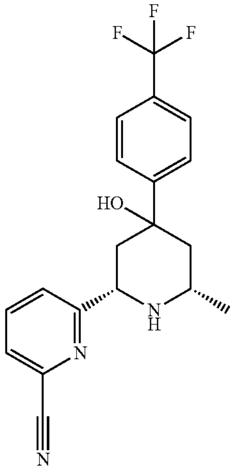 [SMILES: C[C@H]1CC(O)(c2ccc(C(F)(F)F)cc2)C[C@@H](c2cccc(C#N)n2)N1]
I204
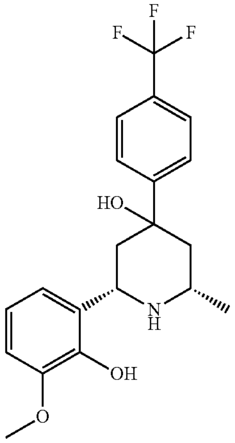 [SMILES: COc1cccc([C@@H]2CC(O)(c3ccc(C(F)(F)F)cc3)C[C@H](C)N2)c1O]
I205
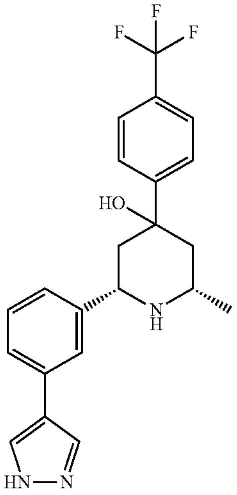 [SMILES: C[C@H]1CC(O)(c2ccc(C(F)(F)F)cc2)C[C@@H](c2cccc(-c3cn[nH]c3)c2)N1]
I206

| Compounds I5 to I295 |
| --- |
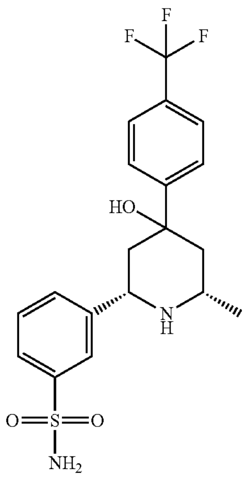 [SMILES: C[C@H]1CC(O)(c2ccc(C(F)(F)F)cc2)C[C@@H](c2cccc(S(N)(=O)=O)c2)N1]
I207
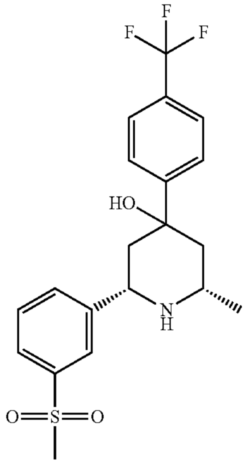 [SMILES: C[C@H]1CC(O)(c2ccc(C(F)(F)F)cc2)C[C@@H](c2cccc(S(C)(=O)=O)c2)N1]
I208
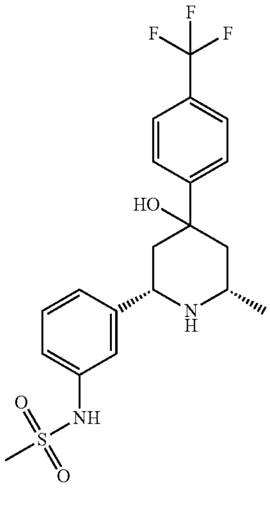
I209
| Compounds I5 to I295 |
| --- |
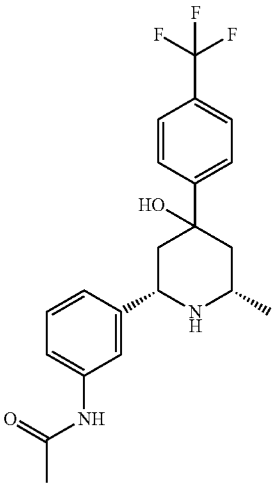 [SMILES: CC(=O)Nc1cccc([C@@H]2CC(O)(c3ccc(C(F)(F)F)cc3)C[C@H](C)N2)c1]
I210
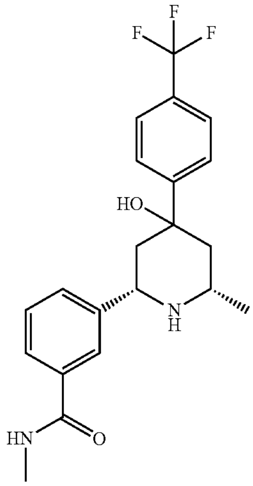 [SMILES: CNC(=O)c1cccc([C@@H]2CC(O)(c3ccc(C(F)(F)F)cc3)C[C@H](C)N2)c1]
I211
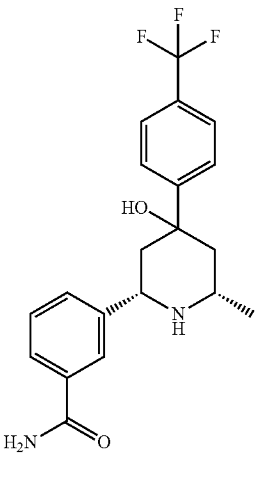 [SMILES: C[C@H]1CC(O)(c2ccc(C(F)(F)F)cc2)C[C@@H](c2cccc(C(N)=O)c2)N1]
I212

TABLE 2-continued
| Compounds I5 to I295 |
| --- |
| 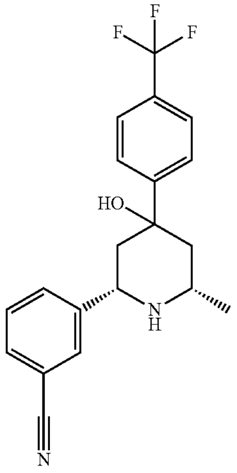 I213 |
| 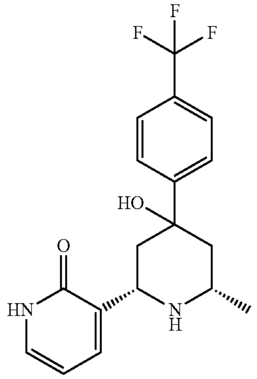 I214 |
| 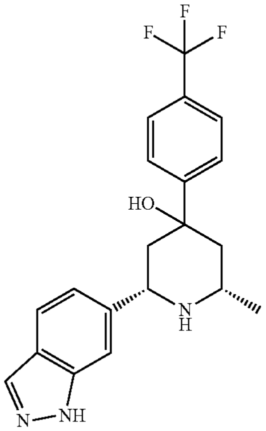 I215 |
TABLE 2-continued
| Compounds I5 to I295 |
| --- |
| 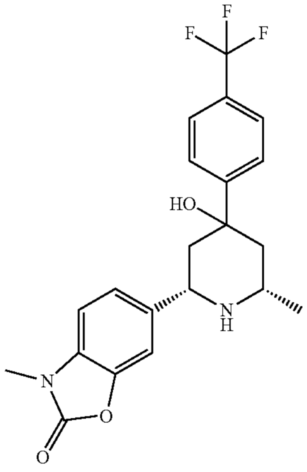 I216 |
| 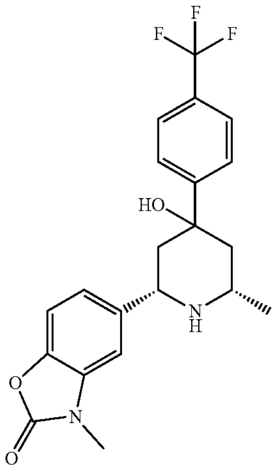 I217 |
| 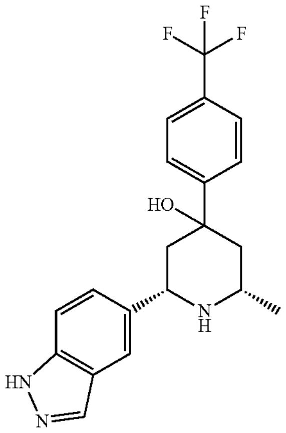 I218 |

TABLE 2-continued
| Compounds I5 to I295 |
| --- |
| 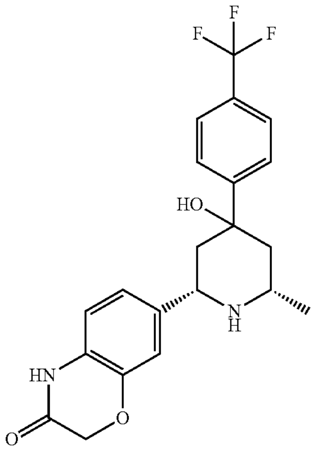 I219 |
| 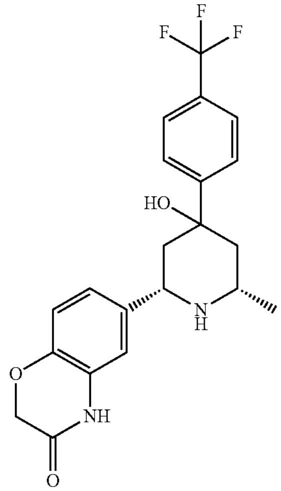 I220 |
| 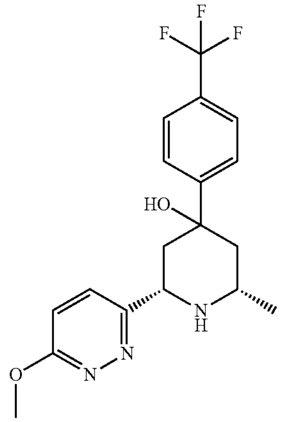 I221 |
TABLE 2-continued
| Compounds I5 to I295 |
| --- |
| 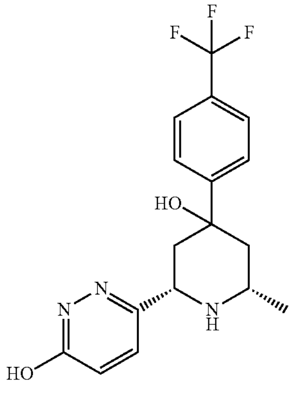 I222 |
| 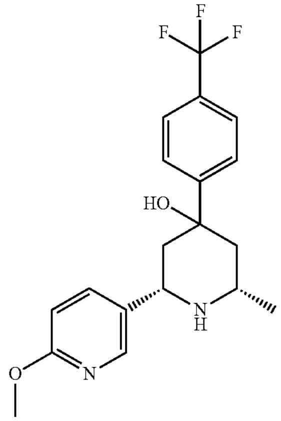 I223 |
| 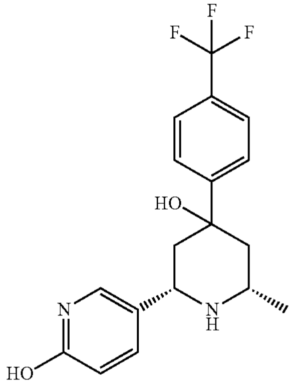 I224 |

TABLE 2-continued
Compounds I5 to I295
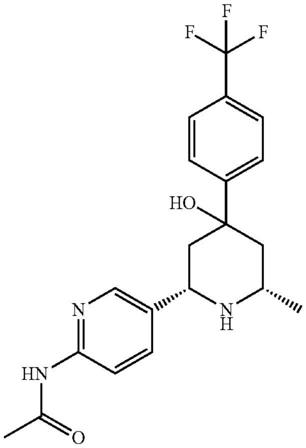 [SMILES: CC(=O)Nc1ccc([C@@H]2CC(O)(c3ccc(C(F)(F)F)cc3)C[C@H](C)N2)cn1]
I225
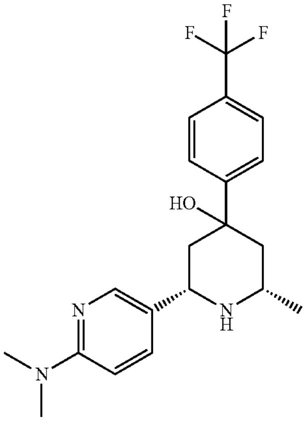
I226
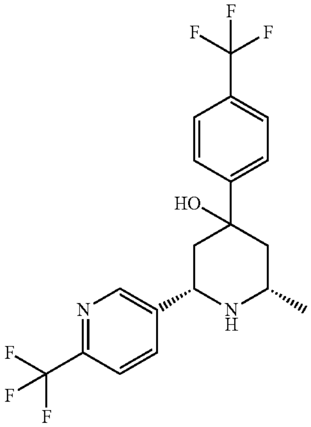 [SMILES: C[C@H]1CC(O)(c2ccc(C(F)(F)F)cc2)C[C@@H](c2ccc(C(F)(F)F)nc2)N1]
I227
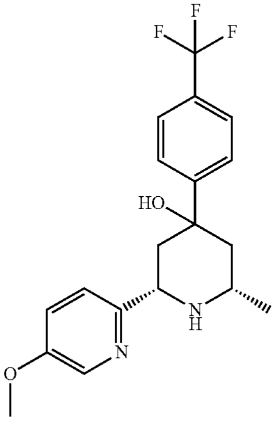 [SMILES: COc1ccc([C@@H]2CC(O)(c3ccc(C(F)(F)F)cc3)C[C@H](C)N2)nc1]
I228
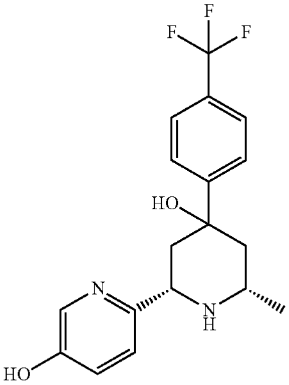 [SMILES: C[C@H]1CC(O)(c2ccc(C(F)(F)F)cc2)C[C@@H](c2ccc(O)cn2)N1]
I229
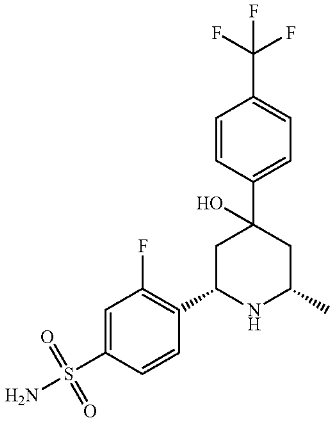 [SMILES: C[C@H]1CC(O)(c2ccc(C(F)(F)F)cc2)C[C@@H](c2ccc(S(N)(=O)=O)cc2F)N1]
I230

TABLE 2-continued
Compounds I5 to I295
I231
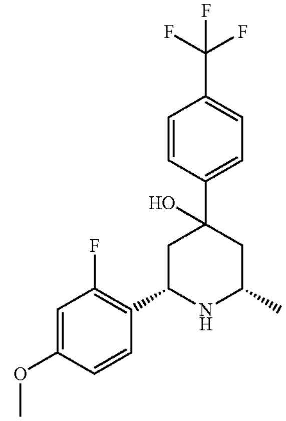 [SMILES: COc1ccc([C@@H]2CC(O)(c3ccc(C(F)(F)F)cc3)C[C@H](C)N2)c(F)c1]
I232
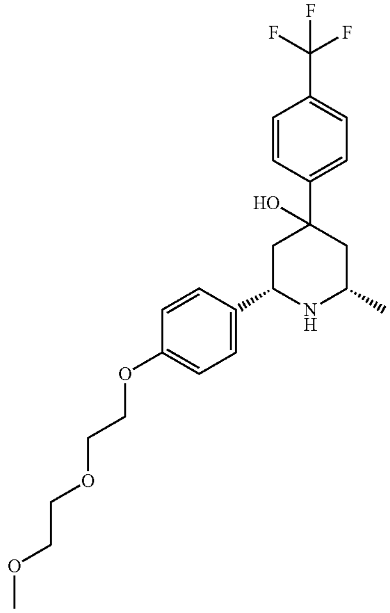 [SMILES: COCCOCCOc1ccc([C@@H]2CC(O)(c3ccc(C(F)(F)F)cc3)C[C@H](C)N2)cc1]
I233
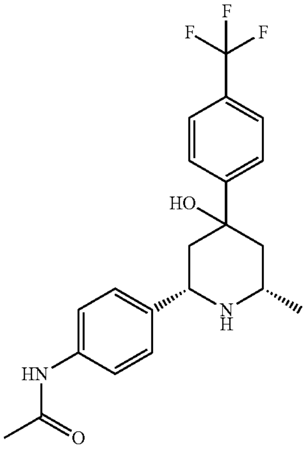 [SMILES: CC(=O)Nc1ccc([C@@H]2CC(O)(c3ccc(C(F)(F)F)cc3)C[C@H](C)N2)cc1]
TABLE 2-continued
Compounds I5 to I295
I234
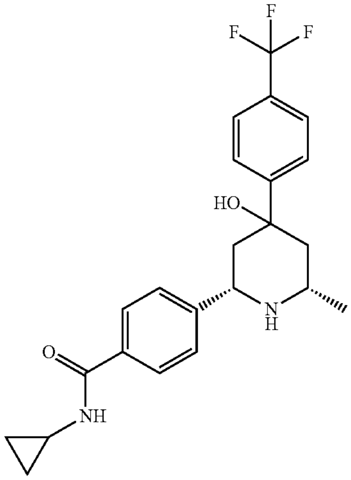 [SMILES: C[C@H]1CC(O)(c2ccc(C(F)(F)F)cc2)C[C@@H](c2ccc(C(=O)NC3CC3)cc2)N1]
I235
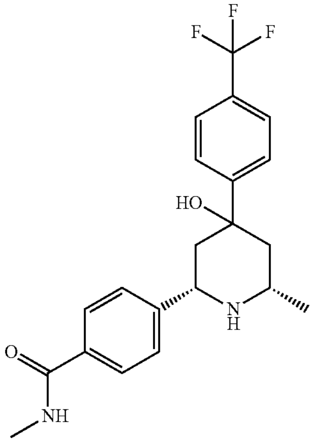 [SMILES: CNC(=O)c1ccc([C@@H]2CC(O)(c3ccc(C(F)(F)F)cc3)C[C@H](C)N2)cc1]
I236
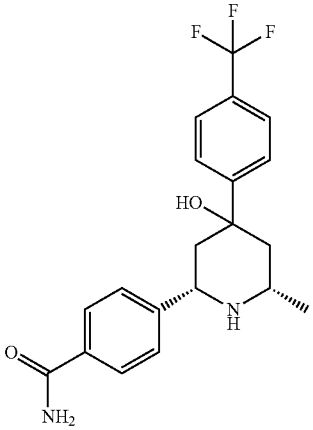 [SMILES: C[C@H]1CC(O)(c2ccc(C(F)(F)F)cc2)C[C@@H](c2ccc(C(N)=O)cc2)N1]

TABLE 2-continued
Compounds I5 to I295
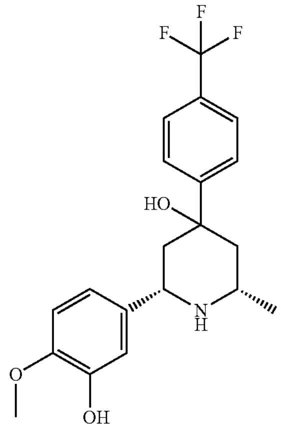 [SMILES: COc1ccc([C@@H]2CC(O)(c3ccc(C(F)(F)F)cc3)C[C@H](C)N2)cc1O]
I237
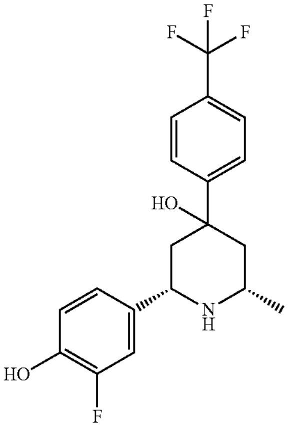 [SMILES: C[C@H]1CC(O)(c2ccc(C(F)(F)F)cc2)C[C@@H](c2ccc(O)c(F)c2)N1]
I238
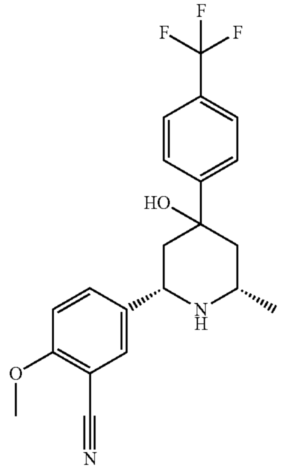 [SMILES: COc1ccc([C@@H]2CC(O)(c3ccc(C(F)(F)F)cc3)C[C@H](C)N2)cc1C#N]
I239
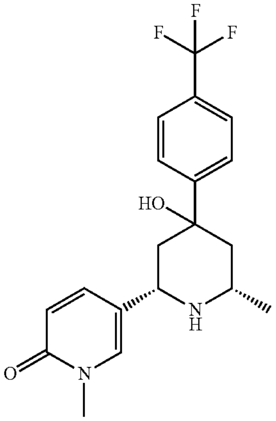 [SMILES: C[C@H]1CC(O)(c2ccc(C(F)(F)F)cc2)C[C@@H](c2ccc(=O)n(C)c2)N1]
I240
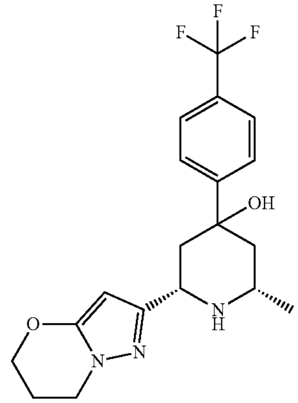 [SMILES: C[C@H]1CC(O)(c2ccc(C(F)(F)F)cc2)C[C@@H](c2cc3n(n2)CCCO3)N1]
I241
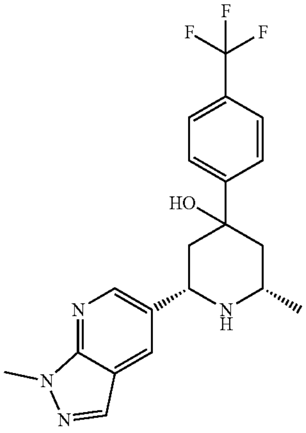
I242

TABLE 2-continued
Compounds I5 to I295
I243
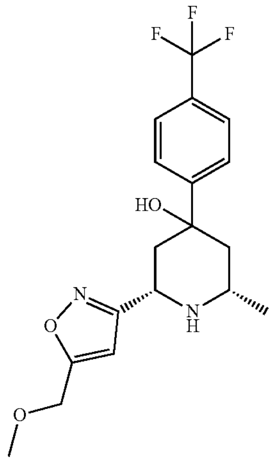
I244
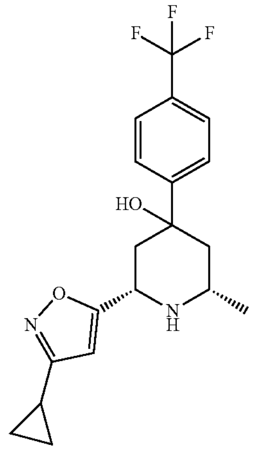 [SMILES: C[C@H]1CC(O)(c2ccc(C(F)(F)F)cc2)C[C@@H](c2cc(C3CC3)no2)N1]
I245
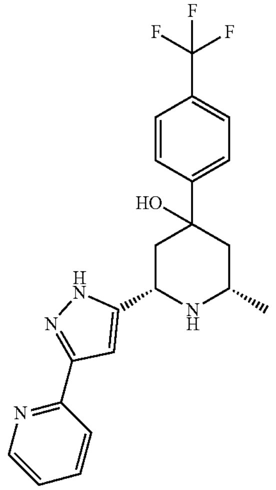 [SMILES: C[C@H]1CC(O)(c2ccc(C(F)(F)F)cc2)C[C@@H](c2cc(-c3ccccn3)n[nH]2)N1]
TABLE 2-continued
Compounds I5 to I295
I246
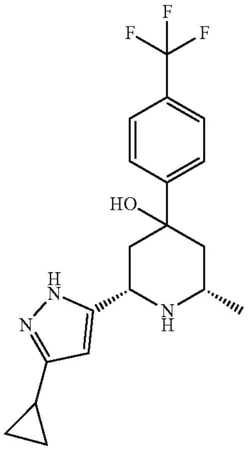 [SMILES: C[C@H]1CC(O)(c2ccc(C(F)(F)F)cc2)C[C@@H](c2cc(C3CC3)n[nH]2)N1]
I247
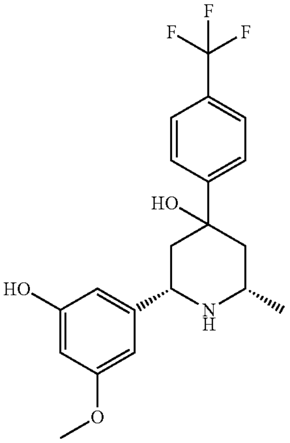 [SMILES: COc1cc(O)cc([C@@H]2CC(O)(c3ccc(C(F)(F)F)cc3)C[C@H](C)N2)c1]
I248
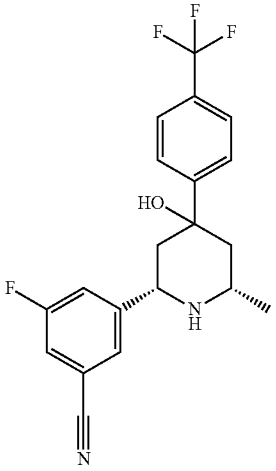 [SMILES: C[C@H]1CC(O)(c2ccc(C(F)(F)F)cc2)C[C@@H](c2cc(F)cc(C#N)c2)N1]

TABLE 2-continued
| Compounds I5 to I295 |
| --- |
| 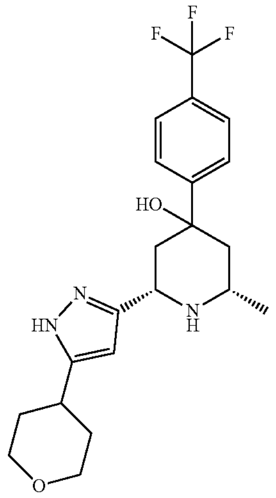 I249 |
| 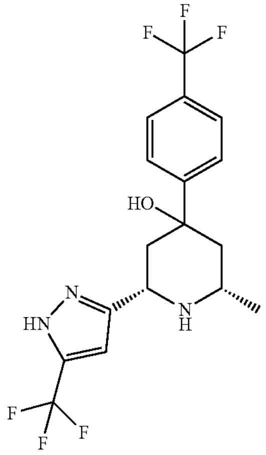 I250 |
| 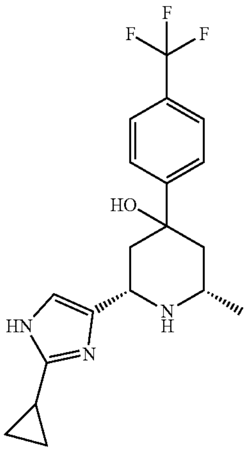 I251 |
TABLE 2-continued
| Compounds I5 to I295 |
| --- |
| 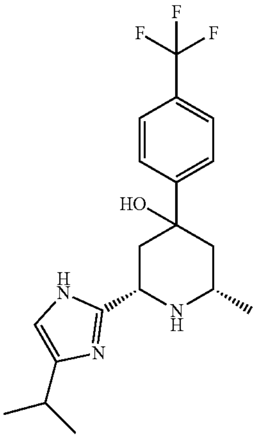 I252 |
| 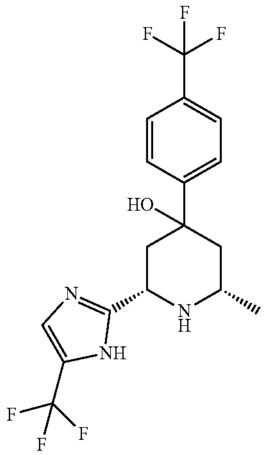 I253 |
| 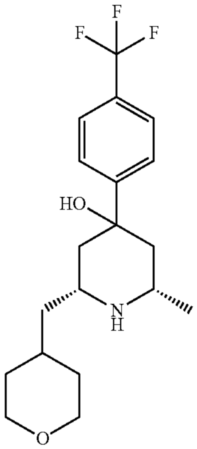 I254 |

TABLE 2-continued
Compounds I5 to I295
I255
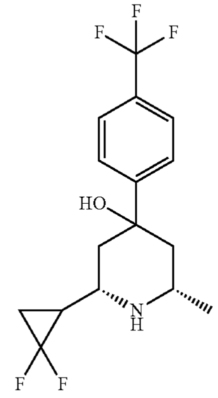
I256
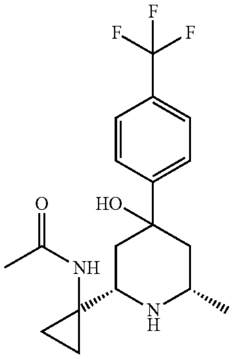 [SMILES: CC(=O)NC1([C@@H]2CC(O)(c3ccc(C(F)(F)F)cc3)C[C@H](C)N2)CC1]
I257
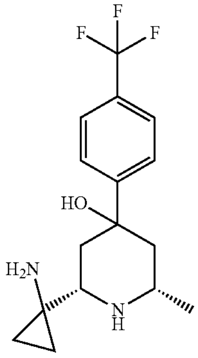 [SMILES: C[C@H]1CC(O)(c2ccc(C(F)(F)F)cc2)C[C@@H](C2(N)CC2)N1]
I258
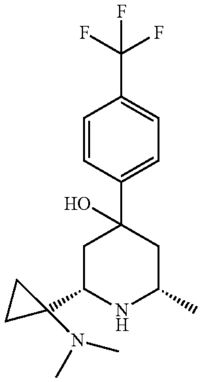 [SMILES: C[C@H]1CC(O)(c2ccc(C(F)(F)F)cc2)C[C@@H](C2(N(C)C)CC2)N1]
TABLE 2-continued
Compounds I5 to I295
I259
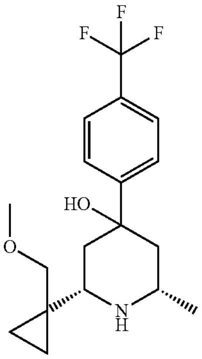 [SMILES: COCC1([C@@H]2CC(O)(c3ccc(C(F)(F)F)cc3)C[C@H](C)N2)CC1]
I260
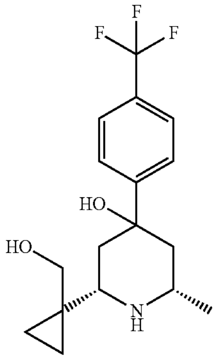 [SMILES: C[C@H]1CC(O)(c2ccc(C(F)(F)F)cc2)C[C@@H](C2(CO)CC2)N1]
I261
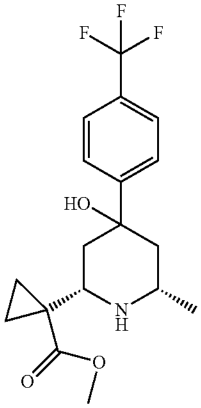 [SMILES: COC(=O)C1([C@@H]2CC(O)(c3ccc(C(F)(F)F)cc3)C[C@H](C)N2)CC1]
I262
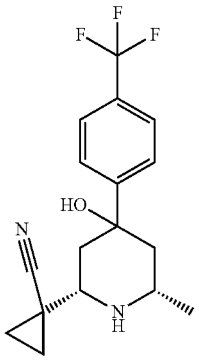 [SMILES: C[C@H]1CC(O)(c2ccc(C(F)(F)F)cc2)C[C@@H](C2(C#N)CC2)N1]

TABLE 2-continued
Compounds I5 to I295
I263
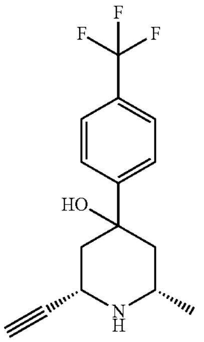 [SMILES: C#C[C@@H]1CC(O)(c2ccc(C(F)(F)F)cc2)C[C@H](C)N1]
I264
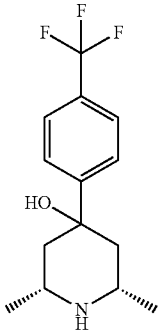
I265
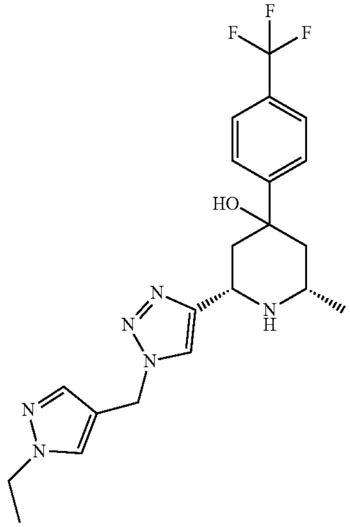 [SMILES: CCn1cc(Cn2cc([C@@H]3CC(O)(c4ccc(C(F)(F)F)cc4)C[C@H](C)N3)nn2)cn1]
TABLE 2-continued
Compounds I5 to I295
I266
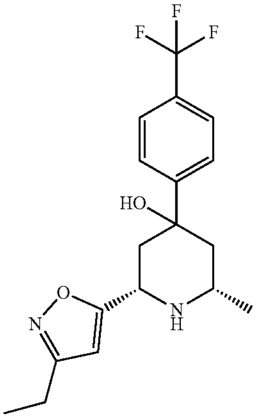 [SMILES: CCc1cc([C@@H]2CC(O)(c3ccc(C(F)(F)F)cc3)C[C@H](C)N2)on1]
I267
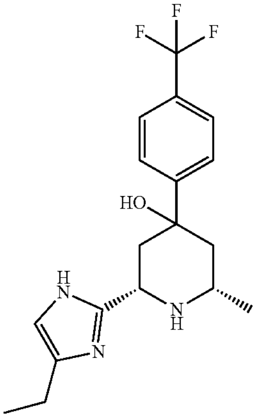 [SMILES: CCc1c[nH]c([C@@H]2CC(O)(c3ccc(C(F)(F)F)cc3)C[C@H](C)N2)n1]
I268
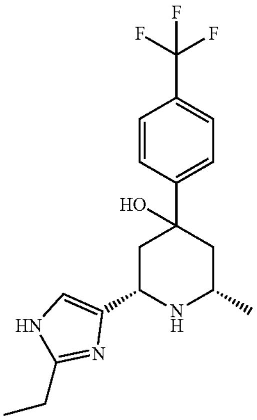 [SMILES: CCc1nc([C@@H]2CC(O)(c3ccc(C(F)(F)F)cc3)C[C@H](C)N2)c[nH]1]

TABLE 2-continued
Compounds I5 to I295
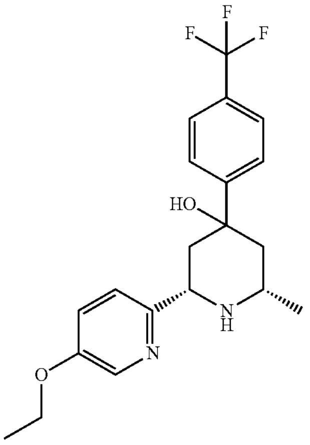 [SMILES: CCOc1ccc([C@@H]2CC(O)(c3ccc(C(F)(F)F)cc3)C[C@H](C)N2)nc1]
I269
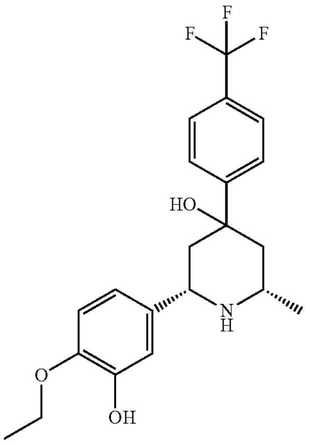 [SMILES: CCOc1ccc([C@@H]2CC(O)(c3ccc(C(F)(F)F)cc3)C[C@H](C)N2)cc1O]
I270
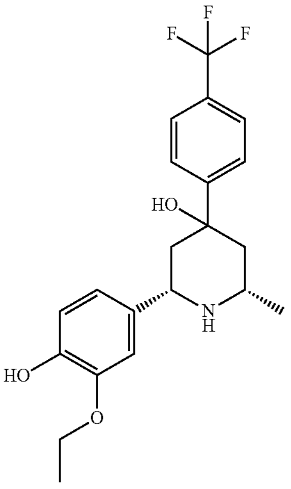 [SMILES: CCOc1cc([C@@H]2CC(O)(c3ccc(C(F)(F)F)cc3)C[C@H](C)N2)ccc1O]
I271
TABLE 2-continued
Compounds I5 to I295
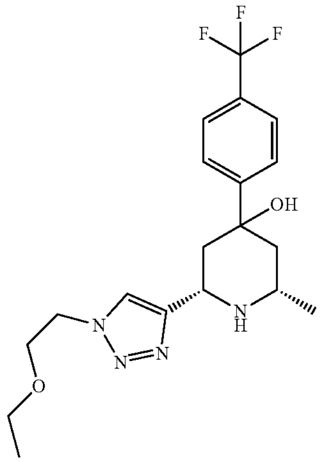 [SMILES: CCOCCn1cc([C@@H]2CC(O)(c3ccc(C(F)(F)F)cc3)C[C@H](C)N2)nn1]
I272
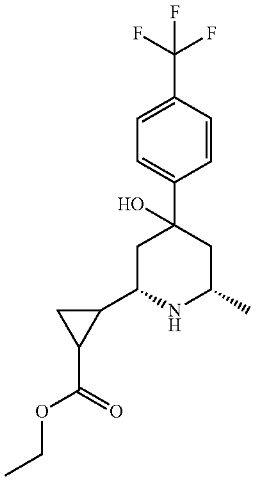
I273
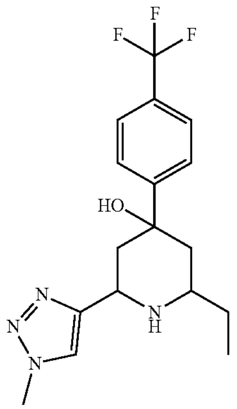 [SMILES: CCC1CC(O)(c2ccc(C(F)(F)F)cc2)CC(c2cn(C)nn2)N1]
I274

TABLE 2-continued
Compounds I5 to I295
I275
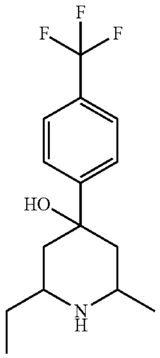 [SMILES: CCC1CC(O)(c2ccc(C(F)(F)F)cc2)CC(C)N1]
I276
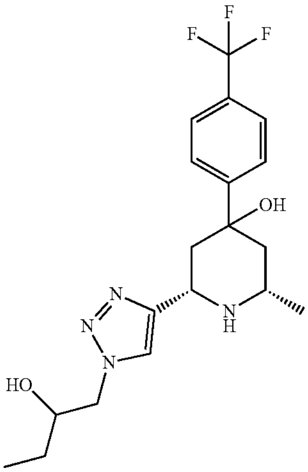 [SMILES: CCC(O)Cn1cc([C@@H]2CC(O)(c3ccc(C(F)(F)F)cc3)C[C@H](C)N2)nn1]
I277
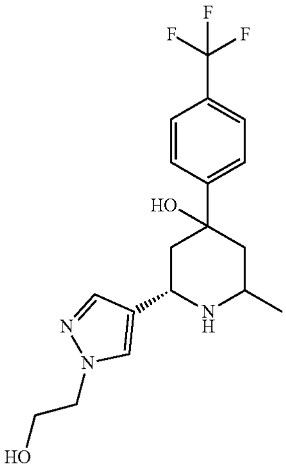 [SMILES: CC1CC(O)(c2ccc(C(F)(F)F)cc2)C[C@@H](c2cnn(CCO)c2)N1]
TABLE 2-continued
Compounds I5 to I295
I278
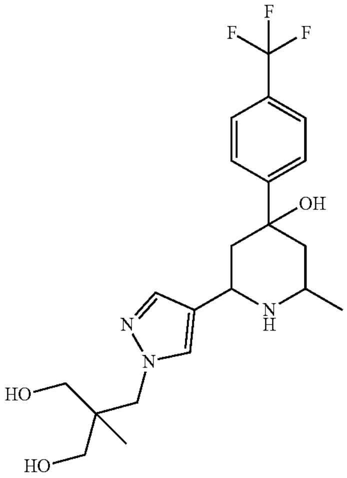 [SMILES: CC1CC(O)(c2ccc(C(F)(F)F)cc2)CC(c2cnn(CC(C)(CO)CO)c2)N1]
I279
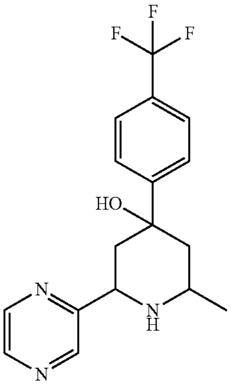 [SMILES: CC1CC(O)(c2ccc(C(F)(F)F)cc2)CC(c2cnccn2)N1]
I280
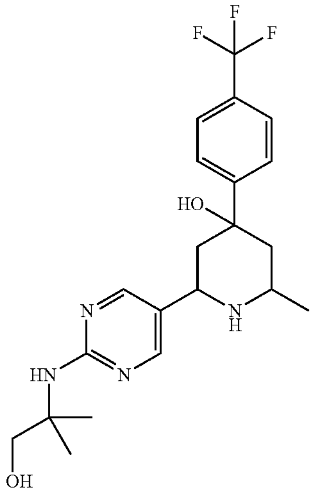 [SMILES: CC1CC(O)(c2ccc(C(F)(F)F)cc2)CC(c2cnc(NC(C)(C)CO)nc2)N1]

TABLE 2-continued
Compounds I5 to I295
I281
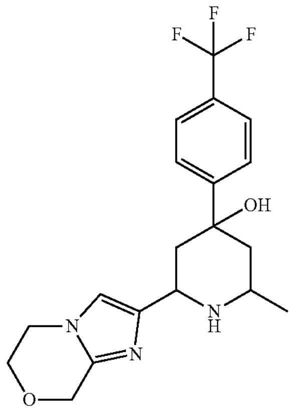 [SMILES: CC1CC(O)(c2ccc(C(F)(F)F)cc2)CC(c2cn3c(n2)COCC3)N1]
I282
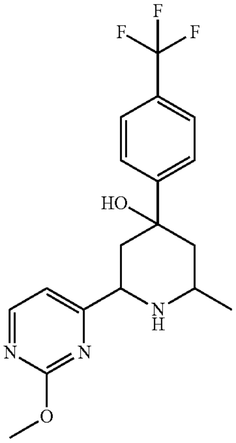 [SMILES: COc1nccc(C2CC(O)(c3ccc(C(F)(F)F)cc3)CC(C)N2)n1]
I283
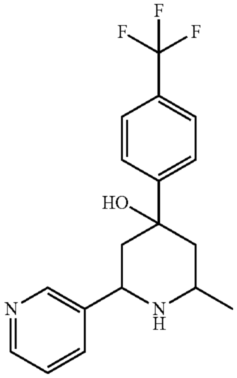 [SMILES: CC1CC(O)(c2ccc(C(F)(F)F)cc2)CC(c2cccnc2)N1]
I284
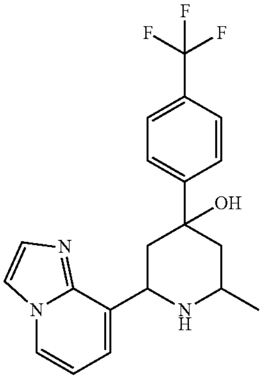 [SMILES: CC1CC(O)(c2ccc(C(F)(F)F)cc2)CC(c2cccn3ccnc23)N1]
TABLE 2-continued
Compounds I5 to I295
I285
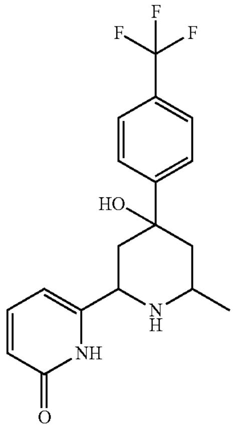 [SMILES: CC1CC(O)(c2ccc(C(F)(F)F)cc2)CC(c2cccc(=O)[nH]2)N1]
I286
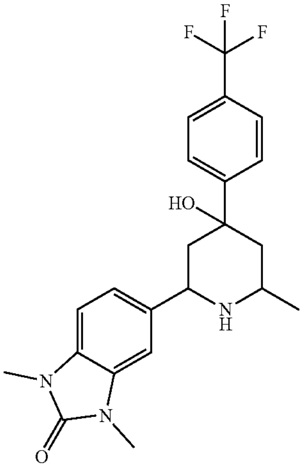
I287
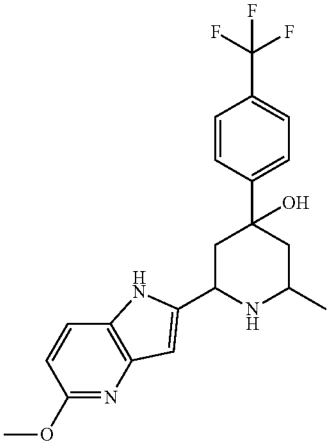

TABLE 2-continued
| Compounds I5 to I295 |
| --- |
| 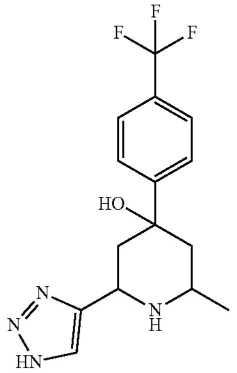 I288 |
| 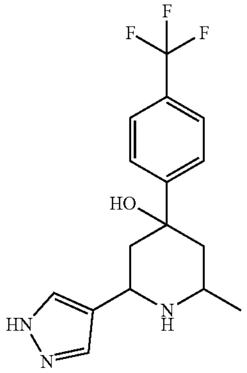 I289 |
| 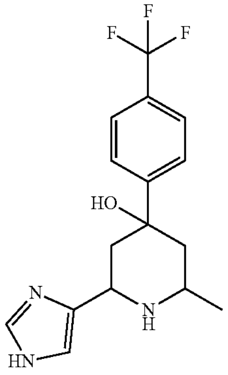 I290 |
| 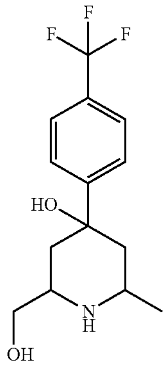 I291 |
TABLE 2-continued
| Compounds I5 to I295 |
| --- |
| 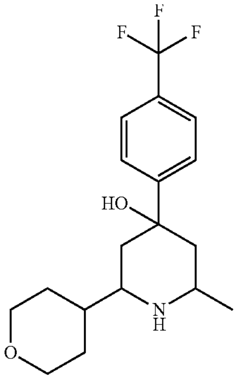 I292 |
| 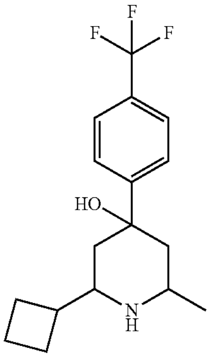 I293 |
| 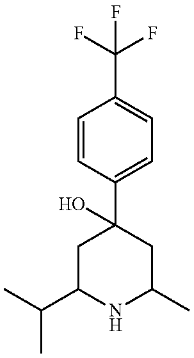 I294 |
| 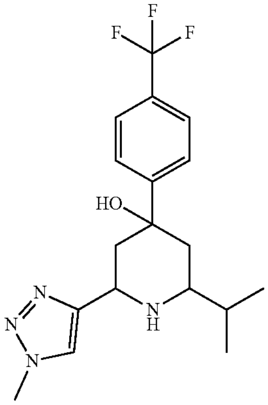 I295 |

TABLE 3
| Compounds 30 to 44 and Compound I296 |
| --- |
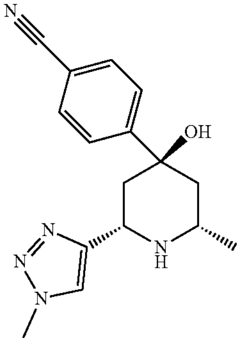 [SMILES: C[C@H]1C[C@@](O)(c2ccc(C#N)cc2)C[C@@H](c2cn(C)nn2)N1]
30
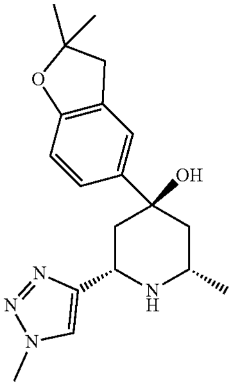 [SMILES: C[C@H]1C[C@@](O)(c2ccc3c(c2)CC(C)(C)O3)C[C@@H](c2cn(C)nn2)N1]
31
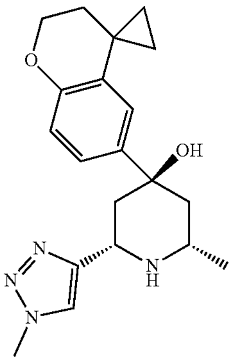 [SMILES: C[C@H]1C[C@@](O)(c2ccc3c(c2)C2(CCO3)CC2)C[C@@H](c2cn(C)nn2)N1]
32
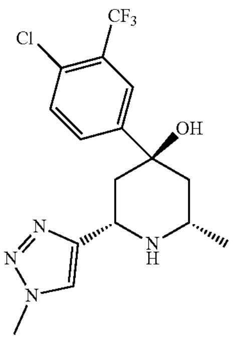
33
TABLE 3-continued
| Compounds 30 to 44 and Compound I296 |
| --- |
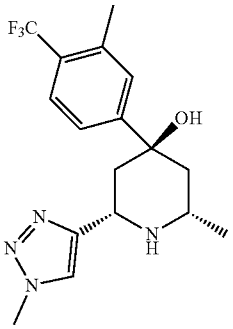 [SMILES: Cc1cc([C@@]2(O)C[C@@H](c3cn(C)nn3)N[C@@H](C)C2)ccc1C(F)(F)F]
34
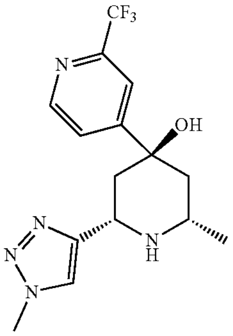 [SMILES: C[C@H]1C[C@@](O)(c2ccnc(C(F)(F)F)c2)C[C@@H](c2cn(C)nn2)N1]
35
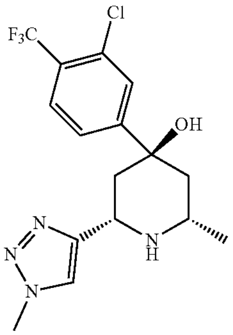
36
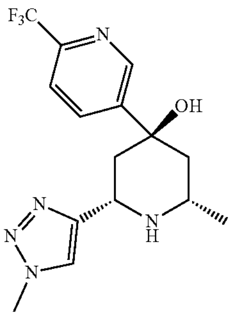
37

TABLE 3-continued
| Compounds 30 to 44 and Compound I296 | |
|---|---|
| 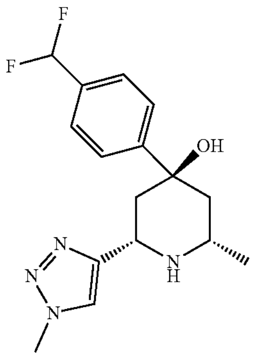 [SMILES: C[C@H]1C[C@@](O)(c2ccc(C(F)F)cc2)C[C@@H](c2cn(C)nn2)N1] | 38 |
| 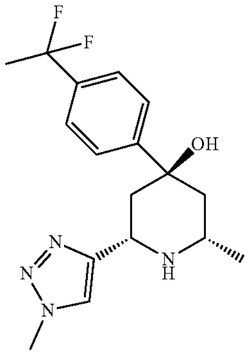 [SMILES: C[C@H]1C[C@@](O)(c2ccc(C(C)(F)F)cc2)C[C@@H](c2cn(C)nn2)N1] | 39 |
| 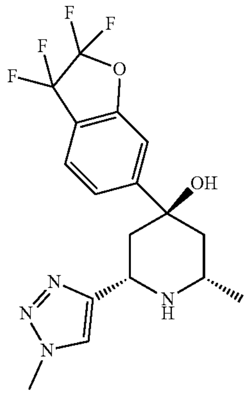 [SMILES: C[C@H]1C[C@@](O)(c2ccc3c(c2)OC(F)(F)C3(F)F)C[C@@H](c2cn(C)nn2)N1] | 40 |
| 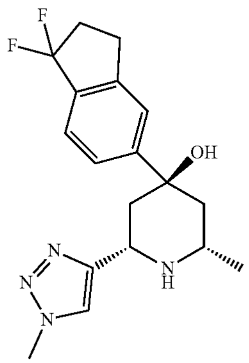 [SMILES: C[C@H]1C[C@@](O)(c2ccc3c(c2)CCC3(F)F)C[C@@H](c2cn(C)nn2)N1] | 41 |
| 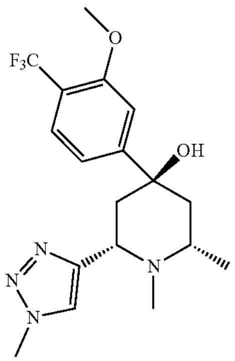 [SMILES: COc1cc([C@]2(O)C[C@H](C)N(C)[C@H](c3cn(C)nn3)C2)ccc1C(F)(F)F] | 42 |
| 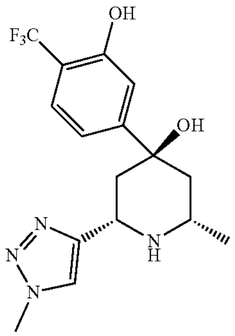 [SMILES: C[C@H]1C[C@@](O)(c2ccc(C(F)(F)F)c(O)c2)C[C@@H](c2cn(C)nn2)N1] | 43 |
| 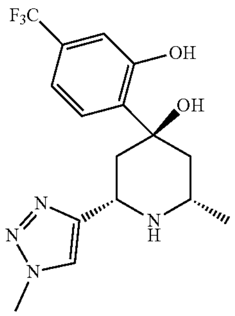 [SMILES: C[C@H]1C[C@@](O)(c2ccc(C(F)(F)F)cc2O)C[C@@H](c2cn(C)nn2)N1] | 44 |
| 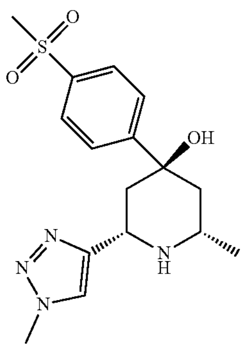 | I296 |

TABLE 4
| Compounds 45-68 |
| --- |
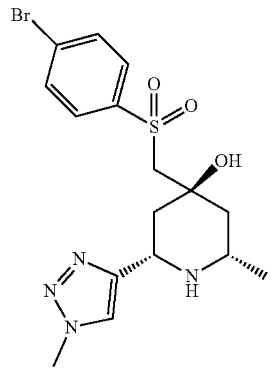 [SMILES: C[C@H]1C[C@@](O)(CS(=O)(=O)c2ccc(Br)cc2)C[C@@H](c2cn(C)nn2)N1]
45
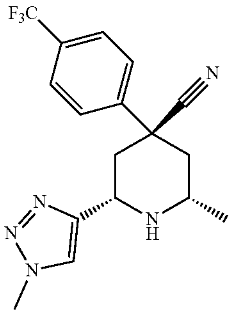 [SMILES: C[C@H]1C[C@@](C#N)(c2ccc(C(F)(F)F)cc2)C[C@@H](c2cn(C)nn2)N1]
46
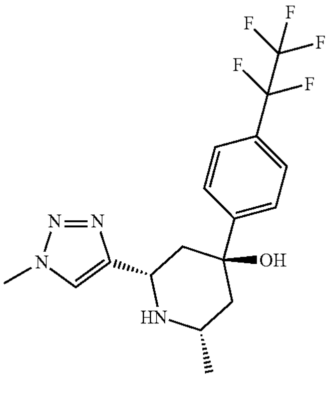 [SMILES: C[C@H]1C[C@@](O)(c2ccc(C(F)(F)C(F)(F)F)cc2)C[C@@H](c2cn(C)nn2)N1]
47
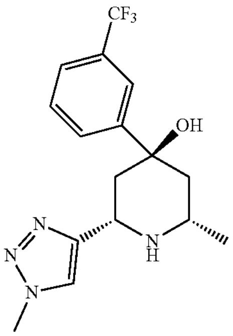 [SMILES: C[C@H]1C[C@@](O)(c2cccc(C(F)(F)F)c2)C[C@@H](c2cn(C)nn2)N1]
48
TABLE 4-continued
| Compounds 45-68 |
| --- |
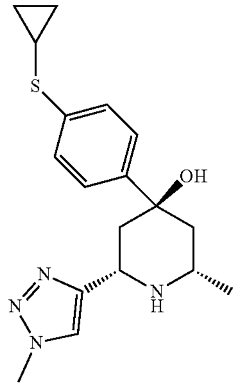 [SMILES: C[C@H]1C[C@@](O)(c2ccc(SC3CC3)cc2)C[C@@H](c2cn(C)nn2)N1]
49
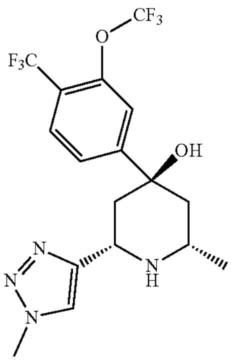 [SMILES: C[C@H]1C[C@@](O)(c2ccc(C(F)(F)F)c(OC(F)(F)F)c2)C[C@@H](c2cn(C)nn2)N1]
50
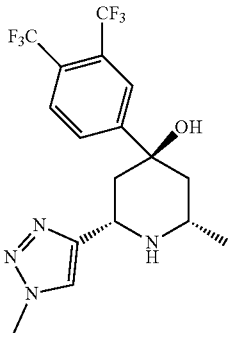 [SMILES: C[C@H]1C[C@@](O)(c2ccc(C(F)(F)F)c(C(F)(F)F)c2)C[C@@H](c2cn(C)nn2)N1]
51
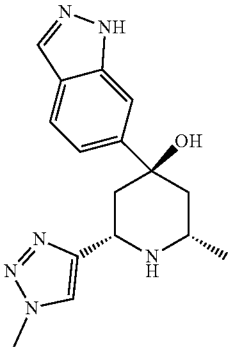 [SMILES: C[C@H]1C[C@@](O)(c2ccc3cn[nH]c3c2)C[C@@H](c2cn(C)nn2)N1]
52

TABLE 4-continued
| Compounds 45-68 |
| --- |
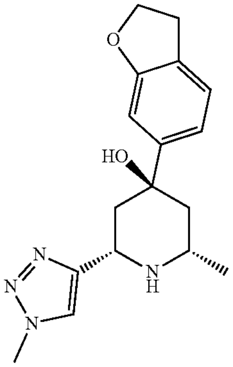 [SMILES: C[C@H]1C[C@@](O)(c2ccc3c(c2)OCC3)C[C@@H](c2cn(C)nn2)N1]
53
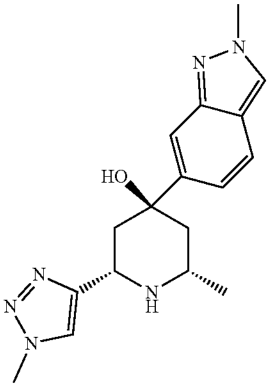 [SMILES: C[C@H]1C[C@@](O)(c2ccc3cn(C)nc3c2)C[C@@H](c2cn(C)nn2)N1]
54
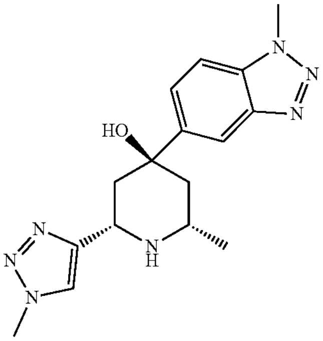 [SMILES: C[C@H]1C[C@@](O)(c2ccc3c(c2)nnn3C)C[C@@H](c2cn(C)nn2)N1]
55
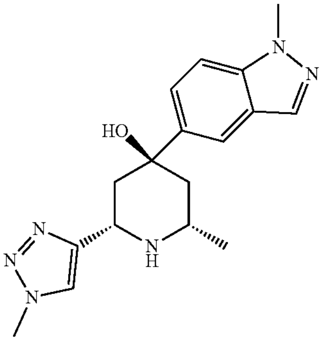 [SMILES: C[C@H]1C[C@@](O)(c2ccc3c(cnn3C)c2)C[C@@H](c2cn(C)nn2)N1]
56
TABLE 4-continued
| Compounds 45-68 |
| --- |
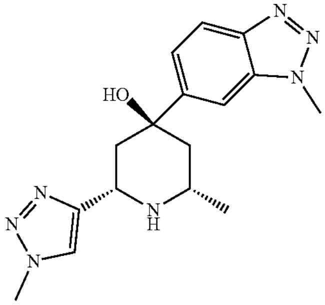 [SMILES: C[C@H]1C[C@@](O)(c2ccc3nnn(C)c3c2)C[C@@H](c2cn(C)nn2)N1]
57
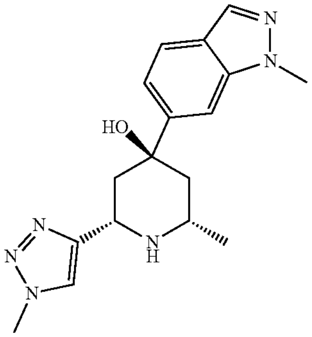 [SMILES: C[C@H]1C[C@@](O)(c2ccc3cnn(C)c3c2)C[C@@H](c2cn(C)nn2)N1]
58
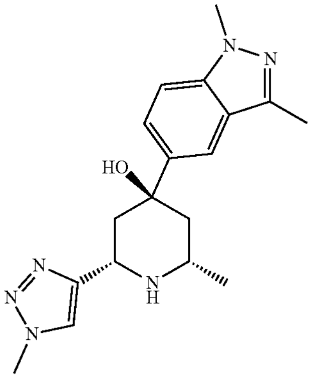 [SMILES: Cc1nn(C)c2ccc([C@@]3(O)C[C@@H](c4cn(C)nn4)N[C@@H](C)C3)cc12]
59
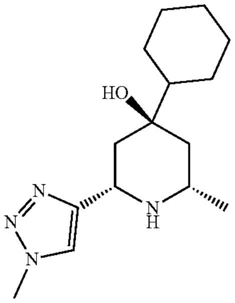 [SMILES: C[C@H]1C[C@@](O)(C2CCCCC2)C[C@@H](c2cn(C)nn2)N1]
60

TABLE 4-continued

| Compounds 45-68 | |
|---|---|
| 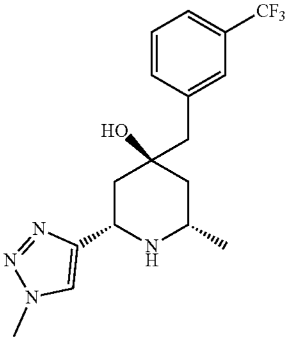 [SMILES: C[C@H]1C[C@@](O)(Cc2cccc(C(F)(F)F)c2)C[C@@H](c2cn(C)nn2)N1] | 61 |
| 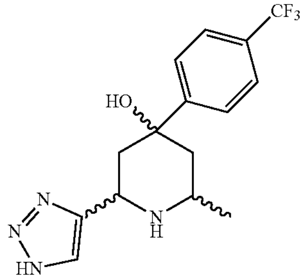 [SMILES: CC1CC(O)(c2ccc(C(F)(F)F)cc2)CC(c2c[nH]nn2)N1] | 62 |
| 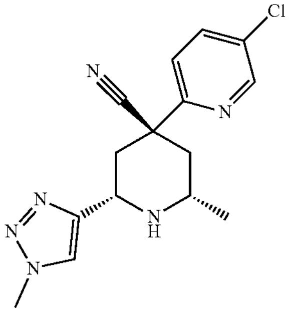 [SMILES: C[C@H]1C[C@@](C#N)(c2ccc(Cl)cn2)C[C@@H](c2cn(C)nn2)N1] | 63 |
| 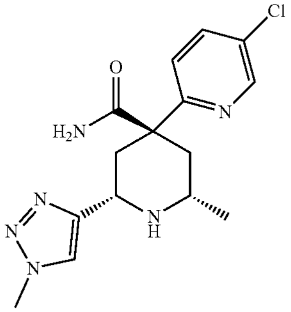 [SMILES: C[C@H]1C[C@@](C(N)=O)(c2ccc(Cl)cn2)C[C@@H](c2cn(C)nn2)N1] | 64 |
| 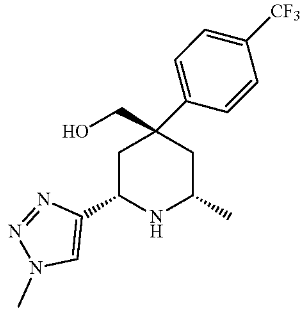 [SMILES: C[C@H]1C[C@@](CO)(c2ccc(C(F)(F)F)cc2)C[C@@H](c2cn(C)nn2)N1] | 65 |

TABLE 4-continued

| Compounds 45-68 | |
|---|---|
| 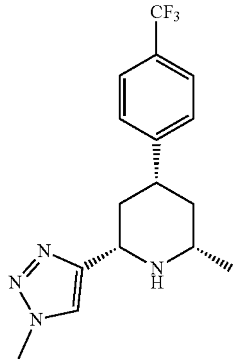 [SMILES: C[C@H]1C[C@@H](c2ccc(C(F)(F)F)cc2)C[C@@H](c2cn(C)nn2)N1] | 66 |
| 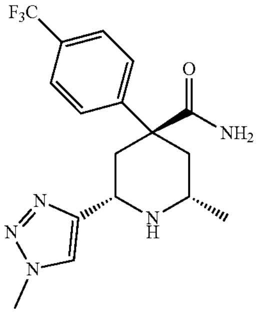 [SMILES: C[C@H]1C[C@@](C(N)=O)(c2ccc(C(F)(F)F)cc2)C[C@@H](c2cn(C)nn2)N1] | 67 |
| 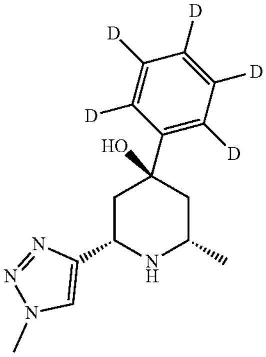 [SMILES: [2H]c1c([2H])c([2H])c([C@@]2(O)C[C@@H](c3cn(C)nn3)N[C@@H](C)C2)c([2H])c1[2H]] | 68 |

Some embodiments of the disclosure include derivatives of Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, or pharmaceutically acceptable salts of any of the foregoing. In some embodiments, the derivatives are silicon derivatives in which at least one carbon atom in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by silicon. In some embodiments, the derivatives are silicon derivatives in which at least one halogen atom (e.g., a fluorine) in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by a silicon derivative (e.g., —$Si(CH_3)_3$). In some embodiments, the derivatives are boron derivatives, in which at least one carbon atom in a compound, tautomer, deuterated derivative, or pharmaceutically acceptable salt chosen from Compounds 1 to 29, Compounds I5 to 1295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by boron. In other embodiments, the derivatives are phosphorus derivatives, in which at least one carbon atom in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by phosphorus.

In some embodiments, the derivative is a silicon derivative in which one carbon atom in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by silicon or a silicon derivative (e.g., —$Si(CH_3)_2$— or —$Si(OH)_2$—). The carbon replaced by silicon may be a non-aromatic carbon. In other embodiments, a fluorine has been replaced by a silicon derivative (e.g., —$Si(CH_3)_3$). In some embodiments, the silicon derivatives of the disclosure may include one or more hydrogen atoms replaced by deuterium. In some embodiments, a silicon derivative of compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, a tautomer thereof, a deuterated derivative of that compound or tautomer, or a pharmaceutically acceptable salt of any of the foregoing, may have silicon incorporated into a heterocycle ring.

In some embodiments, the derivative is a boron derivative in which one carbon atom in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by boron or a boron derivative.

In some embodiments, the derivative is a phosphorus derivative in which one carbon atom in a compound, tautomer, deuterated derivative, or pharmaceutically acceptable salt chosen from Compounds 1 to 29, Compounds I5 to I295, Compounds 30 to 44, and Compounds 45 to 68, or compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing, has been replaced by phosphorus or a phosphorus derivative.

Another aspect of the disclosure provides pharmaceutical compositions comprising at least one compound, tautomer, deuterated derivative, or pharmaceutically acceptable salt according to any one formula chosen from Formulae I, Ia, Ib, Ic, Ic-1, Ic-2, Ic-3, Ic-4, Ic-5, Ic-6, II, 11-1, 11-2, 11-3, 11-4, 11-5, 11-6, II-6a and II-6b, and Compounds 1 to 29, Compounds I5 to 1295, Compounds 30 to 44, and Compounds 45 to 68, tautomers thereof, deuterated derivatives of those compounds or tautomers, and pharmaceutically acceptable salts of any of the foregoing. In some embodiments, the pharmaceutical composition comprising at least one compound, tautomer, deuterated derivative, or pharmaceutically acceptable salt chosen from Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, and Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing is administered to a patient in need thereof.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, and lubricants.

It will also be appreciated that a pharmaceutical composition of this disclosure can be employed in combination therapies; that is, the pharmaceutical compositions described herein can further include at least one additional active therapeutic agent. Alternatively, a pharmaceutical composition comprising at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing can be administered as a separate composition concurrently with, prior to, or subsequent to, a composition comprising at least one other active therapeutic agent. In some embodiments, a pharmaceutical composition comprising at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing can be administered as a separate composition concurrently with, prior to, or subsequent to, a composition comprising at least one other active therapeutic agent.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988 to 1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as, e.g., human serum albumin), buffer substances (such as, e.g., phosphates, glycine, sorbic acid, and potassium sorbate), partial glyceride mixtures of saturated vegetable fatty acids, water, salts, and electrolytes (such as, e.g., protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as, e.g., lactose, glucose, and sucrose), starches (such as, e.g., corn starch and potato starch), cellulose and its derivatives (such as, e.g., sodium carboxymethyl cellulose, ethyl cellulose, and cellulose acetate), powdered tragacanth, malt, gelatin, talc, excipients (such as, e.g., cocoa butter and suppository waxes), oils (such as, e.g., peanut oil, cottonseed oil, safflower oil, sesame oil, olive oil, corn oil, and soybean oil), glycols (such as, e.g., propylene glycol and polyethylene glycol), esters (such as, e.g., ethyl oleate and ethyl laurate), agar, buffering agents (such as, e.g., magnesium hydroxide and aluminum hydroxide), alginic acid, pyrogen-free water, isotonic saline, Ringer's solution, ethyl alcohol, phosphate buffer solutions, non-toxic compatible lubricants (such as, e.g., sodium lauryl sulfate and magnesium stearate), coloring agents, releasing agents, coating agents, sweetening agents, flavoring agents, perfuming agents, preservatives, and antioxidants.

In some embodiments of the disclosure, the compounds and the pharmaceutical compositions described herein are used to treat FSGS and/or NDKD. In some embodiments, FSGS is mediated by APOL1. In some embodiments, NDKD is mediated by APOL1.

In some embodiments of the disclosure, the compounds and the pharmaceutical compositions described herein are used to treat cancer. In some embodiments, the cancer is mediated by APOL1.

In some embodiments of the disclosure, the compounds and the pharmaceutical compositions described herein are used to treat pancreatic cancer. In some embodiments, the pancreatic cancer is mediated by APOL1.

In some embodiments, the methods of the disclosure comprise administering to a patient in need thereof at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds and tautomers, and pharmaceutically acceptable salts of any of the foregoing. In some embodiments, the compound, tautomer, deuterated derivative, or pharmaceutically acceptable salt is chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing. In some embodiments, said patient in need thereof possesses APOL1 genetic variants, i.e., G1: S342G: 1384M and G2: N388del:Y389del.

Another aspect of the disclosure provides methods of inhibiting APOL1 activity comprising contacting said APOL1 with at least one compound, tautomer, deuterated derivative, or pharmaceutically acceptable salt chosen from compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, tautomers thereof, deuterated derivatives of those compounds or tautomers, and pharmaceutically acceptable salts of any of the foregoing. In some embodiments, the methods of inhibiting APOL1 activity comprise contacting said APOL1 with at least one compound, tautomer, deuterated derivative, or pharmaceutically acceptable salt chosen from Compounds 1 to 29, Compounds I5 to I295, Compounds 30 to 44, and Compounds 45 to 68, tautomers thereof, deuterated derivatives of those compounds or tautomers, and pharmaceutically acceptable salts of any of the foregoing.

Solid Forms

Some embodiments of the disclosure provide a solid form of Compound I6. In some embodiments, the solid form of Compound 16 is Form A. In some embodiments of the disclosure, Compound 16 Form A is substantially pure. In some embodiments of the disclosure, Compound 16 Form A is substantially crystalline.

In some embodiments, Compound 16 Form A is characterized by an X-ray powder diffractogram comprising a signal at a degrees two-theta value selected from 19.9±0.2 degrees two-theta, 20.0±0.2 degrees two-theta, and 10.9±0.2 degrees two-theta. In some embodiments, Compound 16 Form A is characterized by an X-ray powder diffractogram comprising two or more signals at 19.9±0.2 degrees two-theta, 20.0±0.2 degrees two-theta, and 10.9±0.2 degrees two-theta. In some embodiments, the Compound 16 Form A is characterized by an X-ray powder diffractogram comprising signals at 19.9±0.2 degrees two-theta, 20.0±0.2 degrees two-theta, and 10.9±0.2 degrees two-theta.

In some embodiments, Compound 16 Form A is characterized by an X-ray powder diffractogram comprising a signal at two or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at three or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at four or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at five or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at six or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at seven or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising a signal at eight or more degrees two-theta values selected from 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta. In some embodiments, Compound 16 Form A is characterized by an X-ray powder diffractogram comprising signals at 10.9±0.2 degrees two-theta, 14.1±0.2 degrees two-theta, 15.4±0.2 degrees two-theta, 16.1±0.2 degrees two-theta, 17.5±0.2 degrees two-theta, 18.2±0.2 degrees two-theta, 19.3±0.2 degrees two-theta, 19.9±0.2 degrees two-theta, 20.0±0.2 degrees two-theta, 20.5±0.2 degrees two-theta, 20.6±0.2 degrees two-theta, 21.4±0.2 degrees two-theta, 21.7±0.2 degrees two-theta, 22.8±0.2 degrees two-theta, 23.3±0.2 degrees two-theta, 23.8±0.2 degrees two-theta, 26.1±0.2 degrees two-theta, and 26.2±0.2 degrees two-theta.

In some embodiments, Compound 16 Form A is characterized by an X-ray powder diffractogram substantially similar to FIG. 1.

Figure 2:
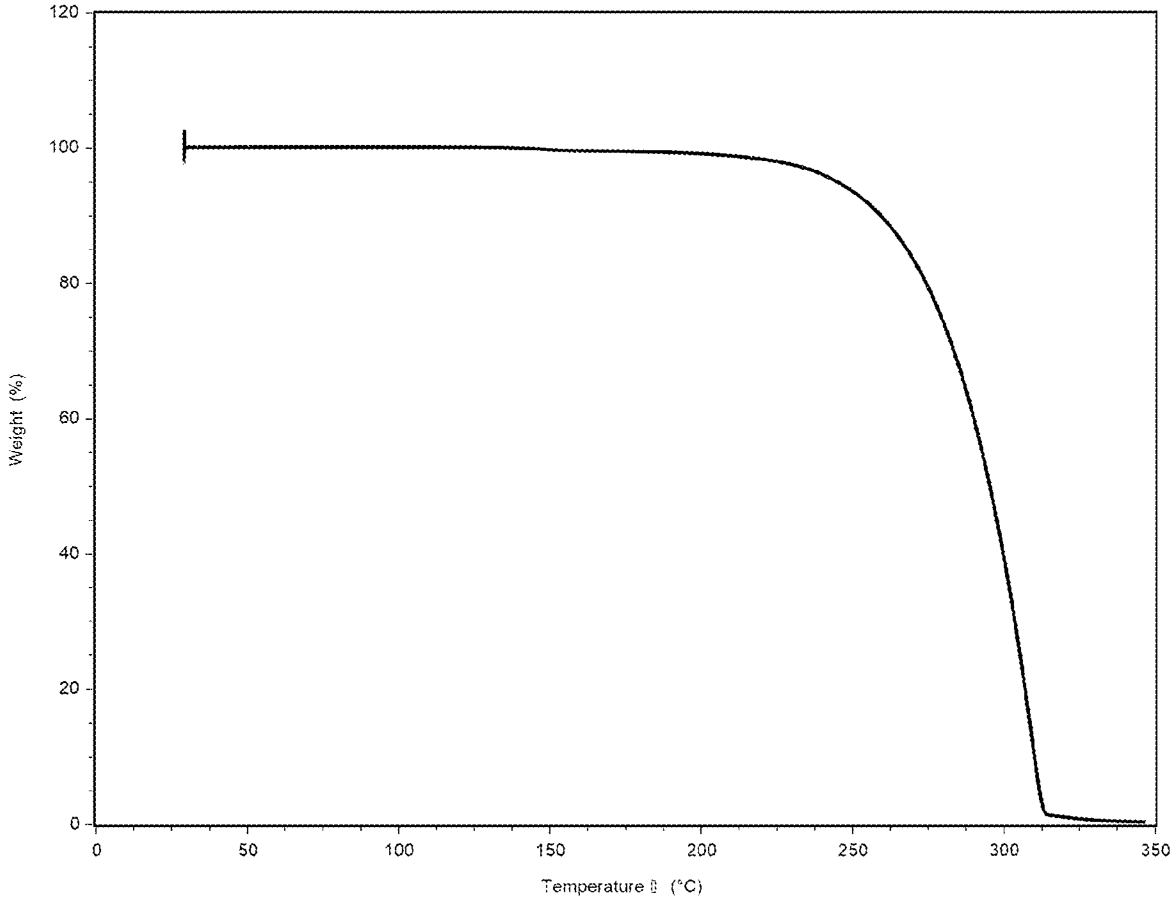
FIG. 2 depicts a TGA of Compound 16 Form A.

In some embodiments, Compound 16 Form A is characterized by a thermogravimetric analysis that shows minimal weight loss from ambient temperature to 250° C. In some embodiments, Compound 16 Form A is characterized by a TGA thermogram substantially similar to FIG. 2.

Figure 3:
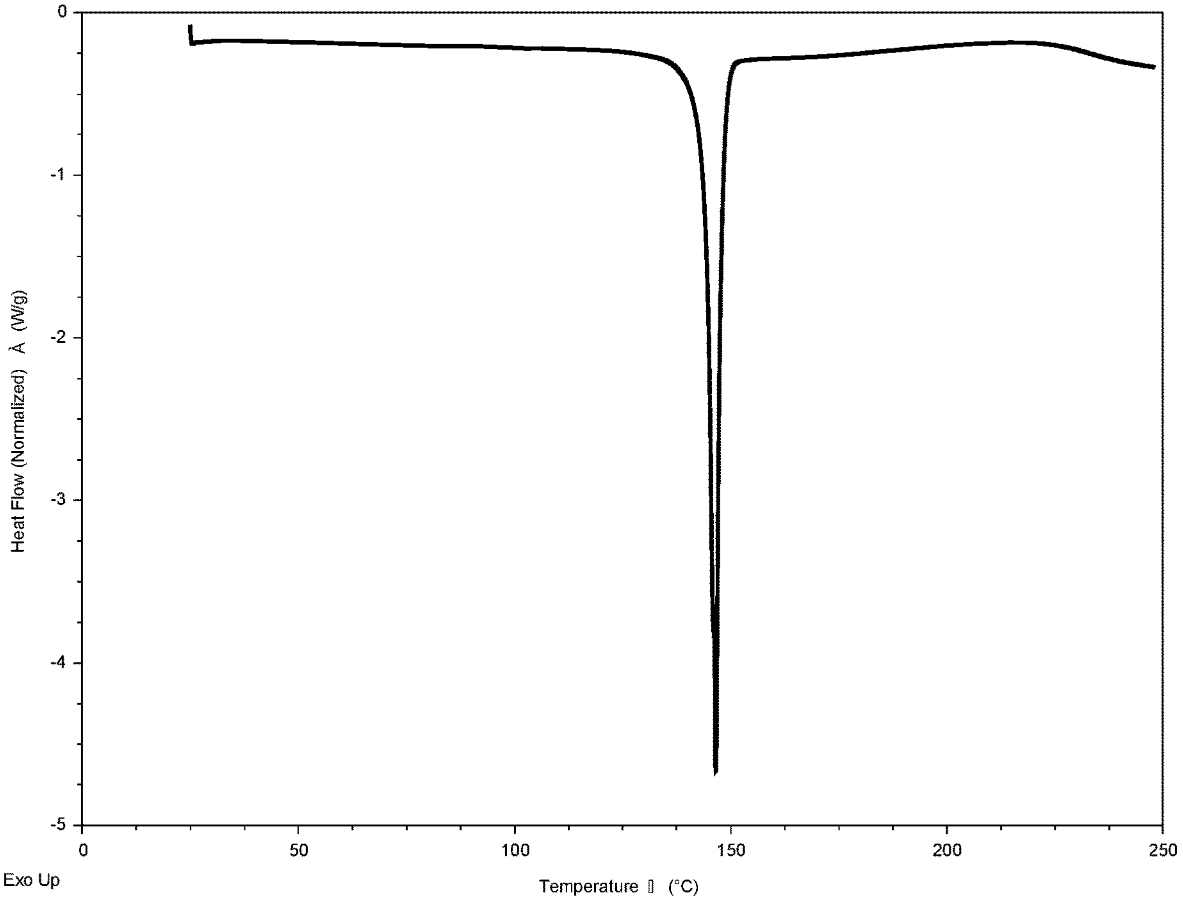
FIG. 3 depicts a DSC of Compound 16 Form A.

In some embodiments, Compound 16 Form A is characterized by a differential scanning calorimetry analysis showing one endotherm peak at 147° C. In some embodiments, Compound 16 Form A is characterized by a DSC thermogram substantially similar to FIG. 3.

In some embodiments, Compound 16 Form A is characterized by solid state NMR. In some embodiments, Compound 16 Form A is characterized by a $^{13}C$ SSNMR spectrum comprising one or more signals selected from 153.5±0.2 ppm, 151.5±0.2 ppm, 126.9±0.2 ppm, 125.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm. In some embodiments, Compound 16 Form A is characterized by a $^{13}C$ SSNMR spectrum comprising two or more signals selected from 153.5±0.2 ppm, 151.5±0.2 ppm, 126.9±0.2 ppm, 125.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm. In some embodiments, Compound 16 Form A is characterized by a $^{13}C$ SSNMR spectrum comprising three or more signal selected from 153.5±0.2 ppm, 151.5±0.2 ppm, 126.9±0.2 ppm, 125.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm. In some embodiments, Compound 16 Form A is characterized by a $^{13}C$ SSNMR spectrum comprising four or more signals selected from 153.5±0.2 ppm, 151.5±0.2 ppm, 126.9±0.2 ppm, 125.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm. In some embodiments, Compound 16 Form A is characterized by a $^{13}C$ SSNMR spectrum comprising five or more signals selected from 153.5±0.2 ppm, 151.5±0.2 ppm, 125.9±0.2 ppm, 126.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm. In some embodiments, Compound 16 Form A is characterized by a $^{13}C$ SSNMR spectrum comprising six or more signals selected from 153.5±0.2 ppm, 151.5±0.2 ppm, 125.9±0.2 ppm, 126.1±0.2 ppm, 123.9±0.2 ppm, 122.1±0.2 ppm, 73.6±0.2 ppm, 49.9±0.2 ppm, 47.2±0.2 ppm, 37.2±0.2 ppm, and 23.0±0.2 ppm.

Figure 4:
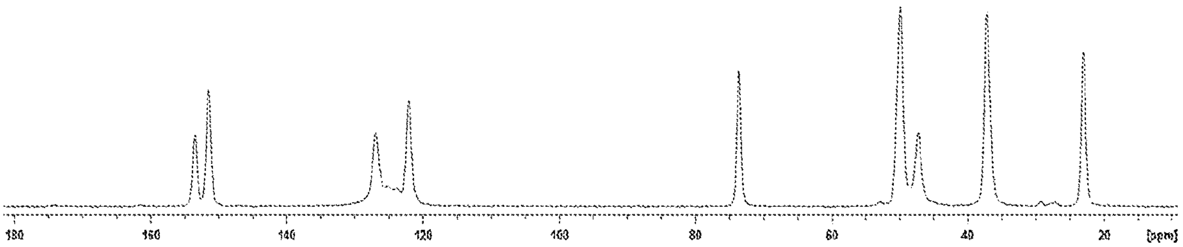
FIG. 4 depicts a $^{13}C$ SSNMR spectrum of Compound 16 Form A.

In some embodiments, Compound 16 Form A is characterized by a $^{13}C$ NMR spectrum substantially similar to FIG. 4.

In some embodiments, Compound 16 Form A is characterized by a $^{19}F$ SSNMR spectrum comprising a signal at −58.0±0.2 ppm.

In some embodiments Compound 16 Form A is characterized by an Orthorhombic crystal system, a $P2_12_12_1$ space group, and a unit cell having dimensions measured at 100 K on Bruker diffractometer equipped with Cu $K_\alpha$ radiation (λ=1.54178 Å) of:

| | | | |
|---|---|---|---|
| a | 5.0 ± 0.1 Å | α | 90° |
| b | 9.0 ± 0.1 Å | β | 90° |
| c | 34.5 ± 0.1 Å | γ | 90° |

In some embodiments Compound 16 Form A is characterized by an Orthorhombic crystal system, a $P2_12_12_1$ space group, and a unit cell having dimensions measured at 298 K on Bruker diffractometer equipped with Cu $K_\alpha$ radiation ($\lambda$=1.54178 Å), of:

| | | | |
|---|---|---|---|
| a | 5.1 ± 0.1 Å | α | 90° |
| b | 9.2 ± 0.1 Å | β | 90° |
| c | 34.5 ± 0.1 Å | γ | 90° |

Another aspect of the disclosure provides a method of making crystalline Compound 16 Form A by crystallizing Compound 16 in MTBE, filtering the crystallized compound, and vacuum drying at 60° C. overnight to yield Compound 16 Form A.

Non-Limiting Example Embodiments

Without limitation, some embodiments of the present disclosure include:

1. A compound represented by the formula:

Formula I

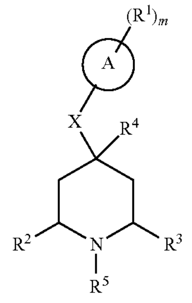

a tautomer thereof, a deuterated derivative of that compound or tautomer, or a pharmaceutically acceptable salt of any of the foregoing, wherein:

X is a bond (i.e., X is absent) or is chosen from —$(CH_2)$—, and —$(CH_2)SO_2$—;

Ring A is chosen from $C_6$ cycloalkyl, $C_6$ aryl and 5- and 6-membered heteroaryl groups; $R^1$, for each occurrence, is independently chosen from halogen, —$OR^c$, =O, cyano, phenyl, $C_1$-$C_6$ alkyl, $C_1$-$C_6$ alkoxy, $C_3$-$C_6$ carbocyclyl, 4- to 6-membered heterocyclyl, —C(=O)N$(R^c)_2$, —S-(cyclopropyl), and —$SO_2(R^c)$ groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 6 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(=O)$NH_2$, —C(=O)NH($C_1$-$C_4$ alkyl), and —C(=O)N($C_1$-$C_4$ alkyl)$_2$ groups; or wherein two $R^1$ groups taken together with the Ring A atoms connecting them form a 5 to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, 5- to 6-membered heteroaryl are each optionally substituted with 1 to 4 groups selected from halogen, —OH, and $C_1$-$C_4$ alkyl;

$R^2$ is chosen from cyano, $C_1$-$C_6$ alkyl, —C(=O)O($C_1$-$C_4$ alkyl), $C_2$-$C_6$ alkynyl, and

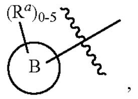, wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)$NR^hR^i$, —$NR^hR^i$, —$NR^h$C(=O)$R^k$, —$NR^h$C(=O)$OR^k$, —$NR^h$C(=O)$NR^iR^j$, —$NR^h$S(=O)$_pR^k$, —$OR^k$, —OC(=O)$R^k$, —OC(=O)$OR^k$, —OC(=O)$NR^hR^i$, —$[O(CH_2)_q]_r$O($C_1$-$C_6$ alkyl), —S(=O)$_pR^k$, —S(=O)$_pNR^hR^i$, —C(=O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5- to 10-membered heteroaryl (optionally substituted with 1 to 3 $R^m$ groups), cyano, —C(=O)$R^k$, —C(=O)$OR^k$, —C(=O)$NR^hR^i$, —$NR^hR^i$, —$NR^h$C(=O)$R^k$, —$NR^h$C(=O)$OR^k$, —$NR^h$C(=O)$NR^iR^j$, —$NR^h$S(=O)$R^k$, —$OR^k$, —OC(=O)$R^k$, —OC(=O)$OR^k$, —OC(=O)$NR^hR^i$, —S(=O)$_pR^k$, —S(=O)$_pNR^hR^i$, —O($C_6$ aryl) (optionally substituted with 1 to 3 $R^m$ groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$$R^k$, and —O$R^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from hydrogen, halogen, cyano, $C_1$-$C_6$ alkyl, $C_1$-$C_6$ haloalkyl, —($CH_2$)$_r$C(═O)N$R^n$$R^o$, —N$R^n$$R^o$, —N$R^o$C(═O)$R^p$, —N$R^n$S(═O)$_p$$R^p$, —($CH_2$)$_n$O$R^p$, —S(═O)$_p$$R^p$, —S(═O)$_p$N$R^n$$R^o$, —OS(═O)$_p$N$R^n$$R^o$, and —($CH_2$)$_n$C(═O)O$R^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

$R^5$ is chosen from hydrogen and $C_1$-$C_6$ alkyl;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

1a. A compound represented by the following structural formula:

Formula Ia

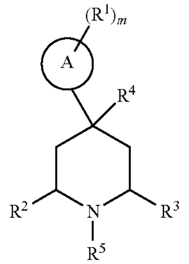

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, ═O, cyano, phenyl, $C_1$-$C_6$ alkyl, $C_1$-$C_6$ alkoxy, $C_3$-$C_6$ carbocyclyl, 4- to 6-membered heterocyclyl, —C(═O)N($R^c$)$_2$ and —$SO_2$($R^c$), groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl; $R^2$ is chosen from cyano, $C_1$-$C_6$ alkyl, —C(═O)O($C_1$-$C_4$ alkyl), $C_2$-$C_6$ alkynyl, and

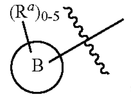

, wherein:

the $C_1$-$C_6$ alkyl of $R^2$ is optionally substituted with 1 to 3 groups independently chosen from halogen, cyano, —OH, —$NH_2$, —$NH(C_1$-$C_4$ alkyl), —$N(C_1$-$C_4$ alkyl$)_2$, $C_1$-$C_4$ alkoxy, —C(═O)$NH_2$, —C(═O)NH($C_1$-$C_4$ alkyl), —C(═O)N($C_1$-$C_4$ alkyl$)_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)$NR^hR^i$, —$NR^hR^i$, —$NR^hC$(═O)$R^k$, —$NR^hC$(═O)$OR^k$, —$NR^hC$(═O)$NR^iR^j$, —$NR^hS$(═O$)_pR^k$, —$OR^k$, —OC(═O)$R^k$, —OC(═O)$OR^k$, —OC(═O)$NR^hR^i$, —$[O(CH_2)_q]_rO(C_1$-$C_6$ alkyl), —S(═O$)_pR^k$, —S(═O$)_pNR^hR^i$, —C(═O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(═O)$R^k$, —C(═O)$OR^k$, —C(═O)$NR^hR^i$, —$NR^hR^i$, —$NR^hC$(═O)$R^k$, —$NR^hC$(═O)$OR^k$, —$NR^hC$(═O)$NR^iR^j$, —$NR^hS$(═O)$R^k$, —$OR^k$, —OC(═O)$R^k$, —OC(═O)$OR^k$, —OC(═O)$NR^hR^i$, —S(═O$)_pR^k$, —S(═O$)_pNR^hR^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O$)_pR^k$, and —$OR^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —$NH(C_1$-$C_4$ alkyl), —$N(C_1$-$C_4$ alkyl$)_2$, $C_1$-$C_4$ alkoxy, —C(═O)$NH_2$, —C(═O)NH($C_1$-$C_4$ alkyl), and —C(═O)N($C_1$-$C_4$ alkyl$)_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH ($C_1$-$C_4$ alkyl) (optionally substituted with —OH), —$N(C_1$-$C_4$ alkyl$)_2$, $C_1$-$C_5$ alkyl (optionally substituted with —OH or —S(═O$)_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl$)_2$ groups;

$R^4$ is chosen from halogen, cyano, $C_1$-$C_6$ alkyl, $C_1$-$C_6$ haloalkyl, —$(CH_2)_n$C(═O)$NR^nR^o$, —$NR^nR^o$, —$NR^oC$(═O)$R^p$, —$NR^nS$(═O$)_pR^p$, —$(CH_2)_nOR^p$, —S(═O$)_pR^p$, —S(═O$)_pNR^nR^o$, —OS(═O$)_pNR^nR^o$, and —$(CH_2)$~C(═O)$OR^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

$R^5$ is chosen from hydrogen and $C_1$-$C_6$ alkyl;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

1b. A compound represented by the following structural formula:

Formula Ib

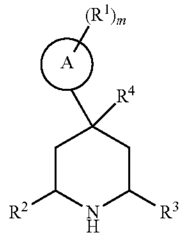

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, ═O, cyano, phenyl, $C_1$-$C_6$ alkyl, $C_1$-$C_6$ alkoxy, $C_3$-$C_6$ carbocyclyl, 4- to 6-membered heterocyclyl, —C(═O)N($R^c$)$_2$ and —$SO_2$($R^c$), groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl;

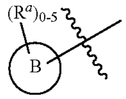

, $R^2$ is chosen from cyano, $C_1$-$C_6$ alkyl, —C(═O)O($C_1$-$C_4$ alkyl), $C_2$-$C_6$ alkynyl, and wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), —C(═O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)$NR^hR^i$, —$NR^hR^i$, —$NR^h$C(═O)$R^k$, —$NR^h$C(O)$OR^k$, —$NR^h$C(═O)$NR^iR^j$, —$NR^h$S(═O)$_pR^k$, —$OR^k$, —OC(═O)$R^k$, —OC(═O)$OR^k$, —OC(═O)$NR^hR^i$, —[O($CH_2$)$_q$]$_r$O($C_1$-$C_6$ alkyl), —S(═O)$_pR^k$, —S(═O)$_p NR^hR^i$, —C(═O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(═O)$R^k$, —C(═O)$OR^k$, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$R^k$, —$OR^k$, —OC(═O)$R^k$, —OC(═O)$OR^k$, —OC(═O)$NR^hR^i$, —S(═O)$_pR^k$, —S(═O)$_p NR^hR^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_pR^k$, and —$OR^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-

$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from halogen, cyano, $C_1$-$C_6$ alkyl, $C_1$-$C_6$ haloalkyl, —$(CH_2)_n$C(═O)NR$^n$R$^o$, —NR$^n$R$^o$, —NR$^o$C(═O)R$^p$, —NR$^n$S(═O)$_p$R$^p$, —$(CH_2)_n$OR$^p$, —S(═O)$_p$R$^p$, —S(═O)$_p$NR$^n$R$^o$, —OS(═O)$_p$NR$^n$R$^o$, and —$(CH_2)_n$C(═O)OR$^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

1c. A compound represented by the following structural formula:

Formula Ic

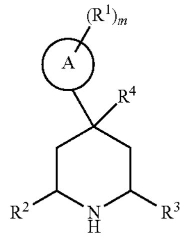

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, ═O, cyano, phenyl, $C_1$-$C_6$ alkyl, $C_1$-$C_6$ alkoxy, $C_3$-$C_6$ carbocyclyl, 4- to 6-membered heterocyclyl, and —C(═O)N($R^c$)$_2$ groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups; and the phenyl of $R^1$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkyl, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

$R^2$ is chosen from cyano, $C_1$-$C_6$ alkyl, —C(═O)O($C_1$-$C_4$ alkyl), $C_2$-$C_6$ alkynyl, and

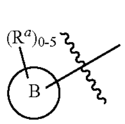

, wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), —C(═O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)NR$^h$R$^i$, —NR$^h$R$^i$, —NR$^h$ C(═O)R$^k$, —NR$^h$ C(O)OR$^k$, —NR$^h$C(═O)NR$^i$R$^j$, —NR$^h$S(═O)$_p$R$^k$, —OR$^k$, —OC(═O)R$^k$, —OC(═O)OR$^k$, —OC(═O)NR$^h$R$^i$, —[O$(CH_2)_q]_r$O($C_1$-$C_6$ alkyl), —S(═O)$_p$R$^k$, —S(═O)$_p$NR$^h$R$^i$, —C(═O)OR$^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(═O)R$^k$, —C(═O)OR$^k$, —C(═O)NR$^h$R$^i$, —NR$^h$R$^i$, —NR$^h$C(═O)R$^k$, —NR$^h$C(═O)OR$^k$, —NR$^h$C(═O)NR$^i$R$^j$, —NR$^h$S(═O)R$^k$, —OR$^k$, —OC(═O)R$^k$, —OC(═O)OR$^k$, —OC(═O)NR$^h$R$^i$, —S(═O)$_p$R$^k$, —S(═O)$_p$NR$^h$R$^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —NR$^h$R$^i$, and —OR$^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$R$^k$, and —OR$^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, —C(═O)O($C_1$-$C_4$ alkyl), $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), and —C(═O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —$NH_2$, —NH($C_1$-$C_4$ alkyl) (optionally substituted with —OH), —N($C_1$-$C_4$ alkyl)$_2$, $C_1$-$C_5$ alkyl (optionally substituted with —OH or —S(═O)$_2$($C_1$-$C_4$ alkyl)), $C_1$-$C_4$ alkoxy, —C(═O)$NH_2$, —C(═O)NH($C_1$-$C_4$ alkyl), —NHC(═O)($C_1$-$C_4$ alkyl), —C(═O)($C_1$-$C_4$ alkoxy), and —C(═O)N($C_1$-$C_4$ alkyl)$_2$ groups;

$R^4$ is chosen from halogen, cyano, $C_1$-$C_6$ alkyl, $C_1$-$C_6$ haloalkyl, —(CH$_2$)$_n$C(═O)NR$^n$R$^o$, —NR$^n$R$^o$, —NR$^o$C(═O)R$^p$, —NR$^n$S(═O)$_p$R$^p$, —(CH$_2$)$_n$OR$^p$, —S(═O)$_p$R$^p$, —S(═O)$_p$NR$^n$R$^o$, —OS(═O)$_p$NR$^n$R$^o$, and —(CH$_2$)~C(═O)OR$^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

2. The compound, tautomer, deuterated derivative, or pharmaceutically acceptable salt according to any one of Embodiments 1 to 1b, wherein the compound is represented by the following structural formula:

Formula II

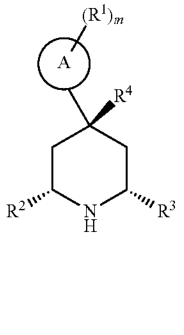

a tautomer thereof, a deuterated derivative of that compound or tautomer, or a pharmaceutically acceptable salt of any of the foregoing, wherein $R^1$, $R^2$, $R^3$, $R^4$, Ring A, and m are as defined in any one of Embodiments 1 to 1b.

3. The compound, tautomer, deuterated derivative, or pharmaceutically acceptable salt according to any one of Embodiments 1 to 2, wherein $R^4$ is —OH; and all other variables not specifically defined herein are as defined in any one of Embodiments 1 to 2.

4. The compound, tautomer, deuterated derivative, or pharmaceutically acceptable salt according to any one of Embodiments 1 to 3, wherein $R^3$ is chosen from $C_1$-$C_4$ alkyl groups; and all other variables not specifically defined herein are as defined in any one of Embodiments 1 to 3.

5. The compound, tautomer, deuterated derivative, or pharmaceutically acceptable salt according to any one of Embodiments 1 to 4, wherein $R^3$ is —$CH_3$; and all other variables not specifically defined herein are as defined in any one of Embodiments 1 to 4.

6. The compound, tautomer, deuterated derivative, or pharmaceutically acceptable salt according to any one of Embodiments 1 to 5, wherein $R^2$ is chosen from $C_1$-$C_4$ alkyl and

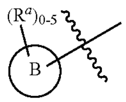

groups, wherein:

the $C_1$-$C_4$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_2$ alkoxy, $C_3$-$C_6$ cycloalkyl, 5- to 6-membered heterocyclyl, phenyl, and 5- to 6-membered heteroaryl groups;

and all other variables not specifically defined herein are as defined in any one of Embodiments 1 to 5.

7. The compound, tautomer, deuterated derivative, or pharmaceutically acceptable salt according to any one of Embodiments 1 to 6, wherein $R^2$ is chosen from —$CH_3$ and

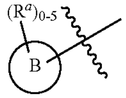

groups;

and all other variables not specifically defined herein are as defined in any one of Embodiments 1 to 6.

8. The compound, tautomer, deuterated derivative, or pharmaceutically acceptable salt according to any one of Embodiments 1 to 7, wherein the compound is represented by one of the following structural formulae:

Formula Ic-4

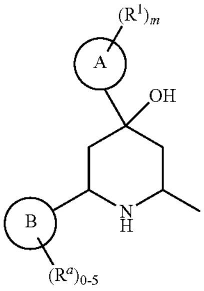

Formula IID

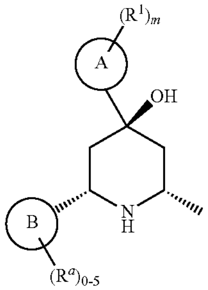

a tautomer thereof, a deuterated derivative of that compound or tautomer, or a pharmaceutically acceptable salt of any of the foregoing, wherein all variables not specifically defined herein are as defined in any one of Embodiments 1 to 7.

9. The compound, tautomer, deuterated derivative, or pharmaceutically acceptable salt according to Embodiment 8, wherein Ring B is chosen from cyclopropyl, 5- to 10-membered heterocyclyl, phenyl, and 5- to 9-membered heteroaryl groups; each of which is optionally substituted with 1, 2, 3, 4, or 5 $R^a$ groups; and all other variables not specifically defined herein are as defined in any one of Embodiments 1 to 8.

10. The compound, tautomer, deuterated derivative, or pharmaceutically acceptable salt according to Embodiment 8, wherein Ring B is chosen from cyclopropyl, 5- to 10-membered heterocyclyl comprising 1 to 3 heteroatoms chosen from N and O, phenyl, and 5- to 9-membered heteroaryl comprising 1 to 3 heteroatoms chosen from N and O; each of which is optionally substituted with 1, 2, 3, 4, or 5 $R^a$ groups; and all other variables not specifically defined herein are as defined in any one of Embodiments 1 to 8.

11. The compound, tautomer, deuterated derivative, or pharmaceutically acceptable salt according to Embodiment 8, wherein Ring B is chosen from cyclopropyl, 5-membered heterocyclyl comprising 1 to 3 heteroatoms chosen from N and O, 6-membered heterocyclyl comprising 1 to 3 heteroatoms chosen from N and O, 9-membered heterocyclyl comprising 1 to 3 heteroatoms chosen from N and O, 10-membered heterocyclyl comprising 1 to 3 heteroatoms chosen from N and O, phenyl, 5-membered heteroaryl comprising 1 to 3 heteroatoms chosen from N and O, 6-membered heteroaryl comprising 1 to 3 heteroatoms chosen from N and O, and 9-membered heteroaryl comprising 1 to 3 heteroatoms chosen from N and O; each of which is optionally substituted with 1, 2, 3, 4, or 5 $R^a$ groups; and all other variables not specifically defined herein are as defined in any one of Embodiments 1 to 8.

12. The compound, tautomer, deuterated derivative, or pharmaceutically acceptable salt according to Embodiment 8, wherein Ring B is chosen from

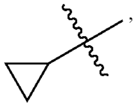, 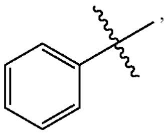, 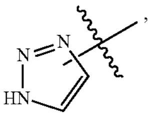,

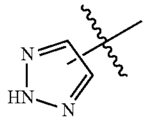, 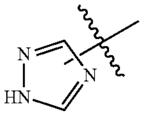, 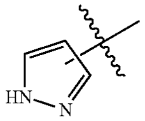,

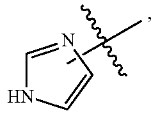, 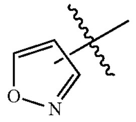, 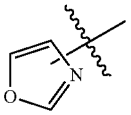,

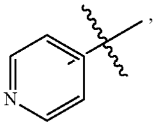, 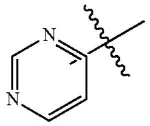, 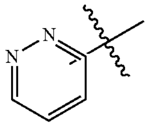,

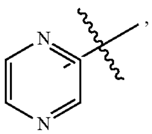, 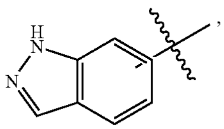,

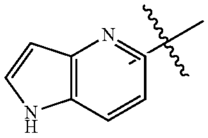, 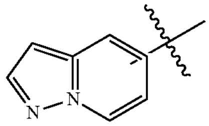,

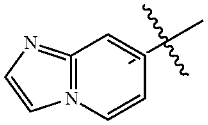, 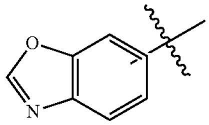,

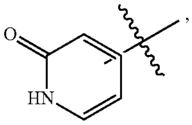, 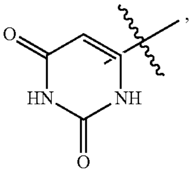,

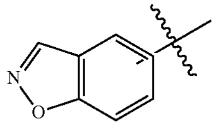, 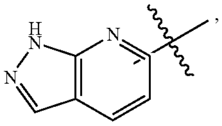,

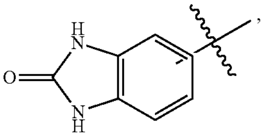, 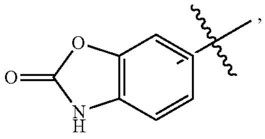,

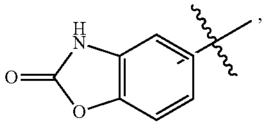, 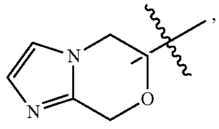,

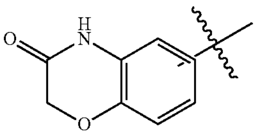, and

-continued
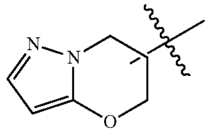;
each of which is optionally substituted with 1, 2, 3, 4, or 5 $R^a$ groups; and all other variables not specifically defined herein are as defined in any one of Embodiments 1 to 8.
13. The compound, tautomer, deuterated derivative, or pharmaceutically acceptable salt according to Embodiment 8, wherein Ring B is chosen from
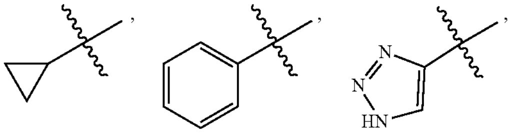
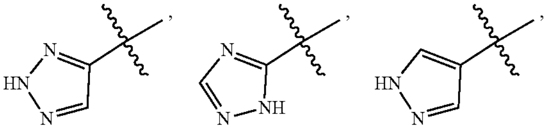
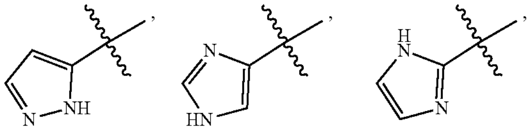
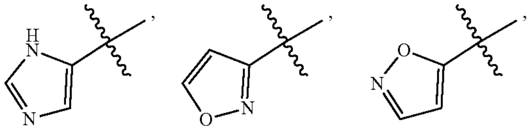
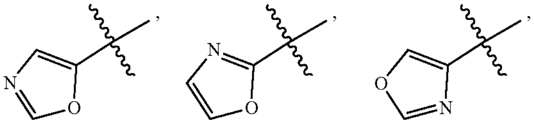
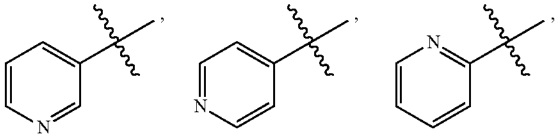
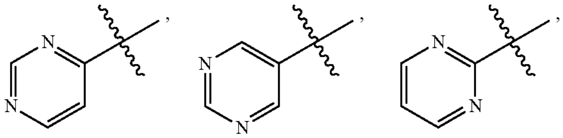
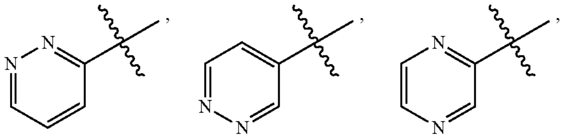
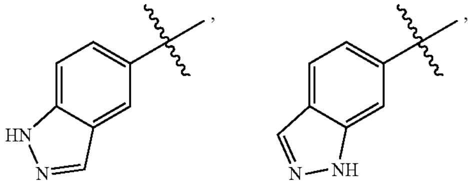
-continued
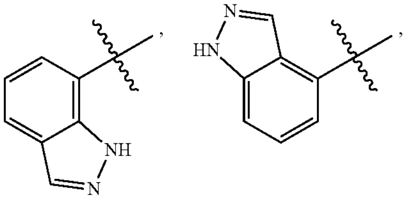
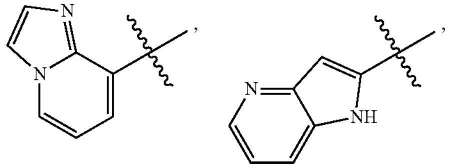
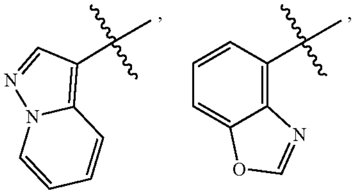
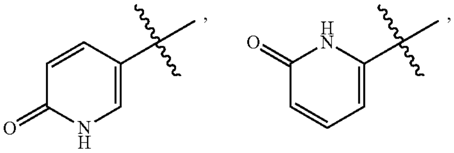
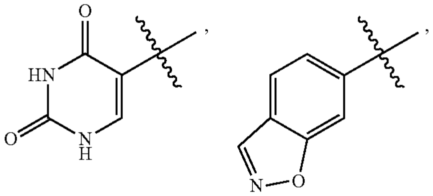
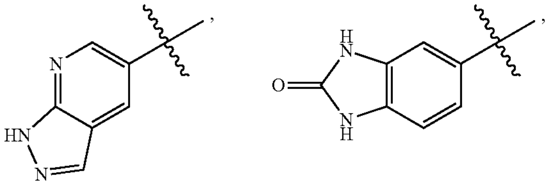
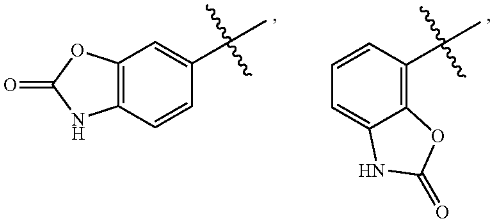
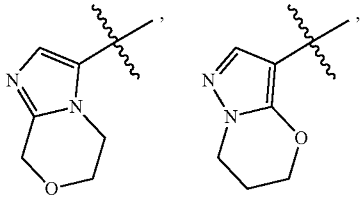
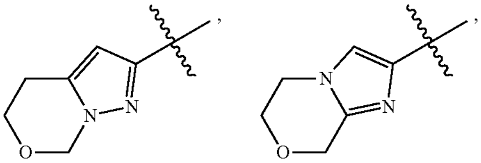

-continued

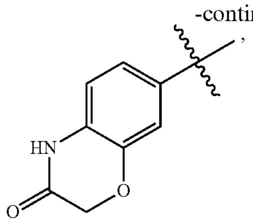,
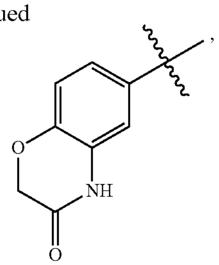,
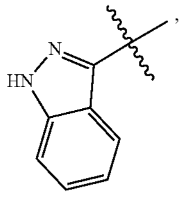, and
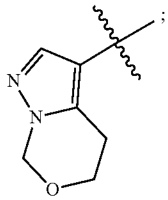;

each of which is optionally substituted with 1, 2, 3, 4, or 5 $R^a$ groups; and all other variables not specifically defined herein are as defined in any one of Embodiments 1 to 8.

14. The compound, tautomer, deuterated derivative, or pharmaceutically acceptable salt according to Embodiment 8, wherein Ring B is

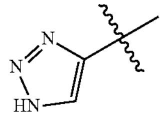 [SMILES: *c1c[nH]nn1]

which is optionally substituted with 1 $R^a$ group; and all other variables not specifically defined herein are as defined in any one of Embodiments 1 to 8.

15. The compound, tautomer, deuterated derivative, or pharmaceutically acceptable salt according to any one of Embodiments 1 to 14, wherein $R^1$, for each occurrence, is independently chosen from hydrogen, halogen, cyano, —OH, $C_1$-$C_4$ alkyl, $C_1$-$C_4$ alkoxy, —C(═O)N($R^c$)$_2$, and $C_3$-$C_6$ cycloalkyl groups, wherein:
   $R^c$, for each occurrence, is independently chosen from hydrogen and $C_1$-$C_2$ alkyl groups;
   the $C_1$-$C_4$ alkyl of $R^1$ is optionally substituted with 1 to 3 groups independently chosen from halogen, cyano, —OH, and $C_1$-$C_2$ alkoxy groups;
   the $C_1$-$C_4$ alkoxy of $R^1$ is optionally substituted with 1 to 3 independently chosen from halogen groups; and
   the $C_3$-$C_6$ cycloalkyl of $R^1$ is optionally substituted with 1 to 3 groups independently chosen from halogen, cyano, —OH, and $C_1$-$C_2$ alkoxy groups;
and all other variables not specifically defined herein are as defined in any one of Embodiments 1 to 14.

16. The compound, tautomer, deuterated derivative, or pharmaceutically acceptable salt according to any one of Embodiments 1 to 15, wherein $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:
   $R^c$, for each occurrence, is independently chosen from hydrogen and $C_1$-$C_2$ alkyl groups;
   the $C_1$-$C_4$ alkyl of $R^1$ is optionally substituted with 1 to 3 groups independently chosen from halogen and —OH;
   the $C_1$-$C_4$ alkoxy of $R^1$ is optionally substituted with 1 to 3 independently chosen from halogen groups; and
   the $C_3$-$C_6$ cycloalkyl of $R^1$ is optionally substituted with 1 to 3 groups independently chosen from halogen and —OH;
and all other variables not specifically defined herein are as defined in any one of Embodiments 1 to 15.

17. The compound, tautomer, deuterated derivative, or pharmaceutically acceptable salt according to any one of Embodiments 1 to 16, wherein $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:
   $R^c$, for each occurrence, is independently chosen from hydrogen and $C_1$-$C_2$ alkyl groups;
   the $C_1$-$C_4$ alkyl of $R^1$ is optionally substituted with 1 to 3 groups independently chosen from halogen and —OH; and
   the $C_1$-$C_4$ alkoxy of $R^1$ is optionally substituted with 1 to 3 independently chosen from halogen groups;
and all other variables not specifically defined herein are as defined in any one of Embodiments 1 to 16.

18. The compound, tautomer, deuterated derivative, or pharmaceutically acceptable salt according to any one of Embodiments 1 to 17, wherein $R^1$, for each occurrence, is independently chosen from F, Cl, Br, —$CH_3$, —$CH(CH_3)_2$, —$CF_3$, —$OCH_3$, —$OCF_3$, —C(═O)N($CH_3$)$_2$, and cyclopropyl;
and all other variables not specifically defined herein are as defined in any one of Embodiments 1 to 17.

18a. The compound, tautomer, deuterated derivative, or pharmaceutically acceptable salt according to any one of Embodiments 1 to 14, wherein $R^1$, for each occurrence, is independently chosen from —$SO_2$($R^c$) groups, wherein $R^c$ is independently chosen from $C_1$-$C_4$ alkyl groups;
and all other variables not specifically defined herein are as defined in any one of Embodiments 1 to 14.

18b. The compound, tautomer, deuterated derivative, or pharmaceutically acceptable salt according to any one of Embodiments 1 to 14, wherein $R^1$, for each occurrence, is independently chosen from —$SO_2$($R^c$) groups, wherein $R^c$ is independently chosen from $C_1$ alkyl groups;
and all other variables not specifically defined herein are as defined in any one of Embodiments 1 to 14.

18c. The compound, tautomer, deuterated derivative, or pharmaceutically acceptable salt according to any one of Embodiments 1, la-1, la-2, and 2 to 14, wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring,
   wherein the 5- to 6-membered cycloalkyl, 5- to 8-membered heterocyclyl, 5- to 6-membered aryl, and 5- to 6-membered heteroaryl are each optionally substituted with 1 to 4 groups selected from halogen, —OH, and $C_1$-$C_4$ alkyl; and all other variables not specifically defined herein are as defined in any one of Embodiments 1 to 14.

18d. The compound, tautomer, deuterated derivative, or pharmaceutically acceptable salt according to any one of Embodiments 1 to 14, wherein two $R^1$ groups taken together with the Ring A atoms connecting them form a group chosen from

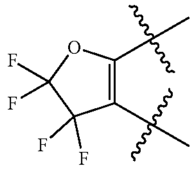,
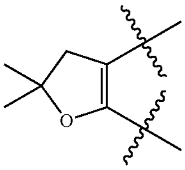,
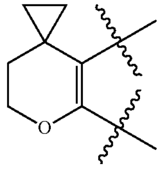, and
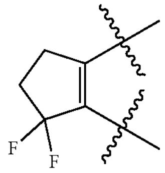;

and all other variables not specifically defined herein are as defined in any one of Embodiments 1 to 14.

19. The compound, tautomer, deuterated derivative, or pharmaceutically acceptable salt according to any one of Embodiments 1 to 18, wherein m is 1; and all other variables not specifically defined herein are as defined in any one of Embodiments 1 to 18.

20. The compound, tautomer, deuterated derivative, or pharmaceutically acceptable salt according to any one of Embodiments 1 to 18, wherein m is 2; and all other variables not specifically defined herein are as defined in any one of Embodiments 1 to 18.

21. The compound, tautomer, deuterated derivative, or pharmaceutically acceptable salt according to any one of Embodiments 1 to 20, wherein $R^a$, for each occurrence, is independently chosen from halogen, cyano, $C_1$-$C_6$ alkyl, $C_1$-$C_4$ alkoxy, $C_1$-$C_6$ haloalkyl, $C_1$-$C_6$ haloalkoxy, —C(═O)$NR^hR^i$, —$NR^hR^i$, —$NR^h$C(O)$R^k$, —$OR^k$, —$[O(CH_2)_q]_r O(C_1$-$C_6$ alkyl), —S(═O)$_2R^k$, —S(═O)$_2NR^hR^i$, $C_3$-$C_6$ cycloalkyl, 5 to 10-membered heterocyclyl, phenyl, and 5- to 8-membered heteroaryl groups, wherein:

the $C_1$-$C_6$ alkyl of $R^a$ is optionally substituted with 1 to 3 groups independently chosen from cyano, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_pR^k$, —$OR^k$, —S(═O)$_2R^k$, —S(═O)$_pNR^hR^i$, and $C_3$-$C_6$ cycloalkyl groups;

the $C_3$-$C_6$ cycloalkyl, the 5- to 10-membered heterocyclyl, the phenyl, and the 5- to 8-membered heteroaryl of $R^a$ are each optionally substituted with 1 to 3 groups independently chosen from halogen, $C_1$-$C_2$ alkyl, and —$OR^k$ groups, wherein:

$R^h$, $R^i$, and $R^j$, for each occurrence, are each independently chosen from hydrogen, $C_1$-$C_2$ alkyl, cyclopropyl, and cyclobutyl groups, wherein:

the $C_1$-$C_2$ alkyl of any one of $R^h$, $R^i$, and $R^j$ is optionally substituted with 1 to 3 groups independently chosen from halogen and —OH;

$R^k$, for each occurrence, is each independently chosen from hydrogen and $C_1$-$C_4$ alkyl groups, wherein:

the $C_1$-$C_4$ alkyl of $R^1$ is optionally substituted with 1 to 3 groups independently chosen from halogen and —OH; and q and r are each an integer chosen from 1, 2, and 3;

and all other variables not specifically defined herein are as defined in any one of Embodiments 1 to 20.

22. The compound, tautomer, deuterated derivative, or pharmaceutically acceptable salt according to any one of Embodiments 1 to 21, wherein $R^a$, for each occurrence, is independently chosen from halogen, cyano, $C_1$-$C_6$ alkyl, $C_1$-$C_4$ alkoxy, $C_1$-$C_4$ haloalkyl, $C_1$-$C_4$ haloalkoxy, —C(═O)$NR^hR^i$, —$NR^hR^i$, —$NR^h$C(═O)$R^k$, —$OR^k$, —$[O(CH_2)_q]_r O(C_1$-$C_4$ alkyl), —S(═O)$_2R^k$, —S(═O)$_2NR^hR^i$, cyclopropyl, cyclobutyl, 5- to 6-membered heterocyclyl, phenyl, and 5- to 6-membered heteroaryl, wherein:

the $C_1$-$C_6$ alkyl of $R^a$ is optionally substituted with 1 to 3 groups independently chosen from cyano, —C(═O)$NR^hR^i$, —S(═O)$_2R^k$, —$NR^hR^i$, —$OR^k$, cyclopropyl, and cyclobutyl groups, wherein:

the cyclopropyl, the cyclobutyl, the 5- to 6-membered heterocyclyl, the phenyl, and the 5 to 6-membered heteroaryl of $R^a$ are each optionally substituted with 1 to 3 groups independently chosen from halogen, —$CH_3$, —OH, and —$OCH_3$; wherein:

$R^h$ and $R^i$, for each occurrence, are each independently chosen from hydrogen, —$CH_3$, cyclopropyl, and cyclobutyl groups, wherein:

the —$CH_3$ of any one of $R^h$ and $R^i$ is optionally substituted with 1 to 3 groups independently chosen from F, $C_1$, and —OH;

$R^k$, for each occurrence, is each independently chosen from hydrogen and —$CH_3$, wherein:

the —$CH_3$ of $R^k$ is optionally substituted with 1 to 3 groups independently chosen from halogen and —OH;

and all other variables not specifically defined herein are as defined in any one of Embodiments 1 to 21.

23. The compound, tautomer, deuterated derivative, or pharmaceutically acceptable salt according to any one of Embodiments 1 to 22, wherein $R^a$, for each occurrence, is independently chosen from F, Cl, Br, cyano, $C_1$-$C_6$ alkyl, $C_1$-$C_2$ alkoxy, $C_1$-$C_2$ haloalkyl, —C(═O)$NR^hR^i$, —$NR^hR^i$, —$NR^h$C(═O)$R^k$, —$OR^k$, —$[O(CH_2)_q]_r O(C_1$-$C_2$ alkyl), —S(═O)$_2R^k$, —S(═O)$_2NR^hR^i$, cyclopropyl, cyclobutyl, 5-membered heterocyclyl, phenyl, and 6-membered heteroaryl groups, wherein:

the $C_1$-$C_6$ alkyl of $R^a$ is optionally substituted with 1 to 3 groups independently chosen from cyano, —C(═O)$NR^hR^i$, —$OR^k$, —S(═O)$_2R^k$, and cyclopropyl;

the cyclopropyl, the cyclobutyl, the 5- to 6-membered heterocyclyl, the phenyl, and the 5- to 6-membered heteroaryl of $R^a$ are each optionally substituted with 1 to 3 groups independently chosen from halogen, —$CH_3$, —OH, and —$OCH_3$, wherein:

$R^h$ and $R^i$, for each occurrence, are each independently chosen from hydrogen, —$CH_3$, and cyclopropyl; wherein:

the —$CH_3$ of any one of $R^h$ and $R^i$ is optionally substituted with 1 to 3 groups independently chosen from F, $C_1$, and —OH;

$R^k$, for each occurrence, is each independently chosen from hydrogen and —$CH_3$; and q and r are each an integer independently chosen from 1 and 2;

and all other variables not specifically defined herein are as defined in any one of Embodiments 1 to 22.

24. The compound, tautomer, deuterated derivative, or pharmaceutically acceptable salt according to any one of Embodiments 1 to 23, wherein $R^a$, for each occurrence, is independently chosen from F, cyano, —OH, —$CH_3$, —$CF_3$, —$CH(CH_3)_2$, —$(CH_2)_2OH$, —$(CH_2)_2OCH_3$, —$CH_2CH(OH)C_2H_5$, —$CH_2C(CH_3)(CH_2OH)_2$, —$OCH_3$, —$OCH_2CH_3$, —$[O(CH_2)_2]_2OCH_3$, —$CH_2C$(═O)$NHCH_3$, $—(CH_2)_2SO_2CH_3$, $—CH_2C(=O)N(CH_3)_2$, $—CH_2$(cyclopropyl), $—C(=O)NH_2$, $—C(=O)NH$(cyclopropyl), $—NH_2$, $—NHCH_3$, $—N(CH_3)_2$, $—NHC(CH_3)_2CH_2OH$, $—NHC(=O)CH_3$, $—SO_2CH_3$, $—SO_2NH_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide; and all other variables not specifically defined herein are as defined in any one of Embodiments 1 to 23.

25. The compound, tautomer, deuterated derivative, or pharmaceutically acceptable salt according to any one of Embodiments 1 to 24, wherein $R^a$, for each occurrence, is independently chosen from $—CH_3$ and $—(CH_2)_2SO_2CH_3$; and all other variables not specifically defined herein are as defined in any one of Embodiments 1 to 24.

26. The compound, tautomer, deuterated derivative, or pharmaceutically acceptable salt according to any one of Embodiments 1 to 25, wherein Ring A is chosen from phenyl, thiophenyl, and pyridinyl; and all other variables not specifically defined herein are as defined in any one of Embodiments 1 to 25.

27. The compound, tautomer, deuterated derivative, or pharmaceutically acceptable salt according to any one of Embodiments 1 to 26, wherein Ring A is phenyl; and all other variables not specifically defined herein are as defined in any one of Embodiments 1 to 26.

27a. The compound, tautomer, deuterated derivative, or pharmaceutically acceptable salt according to any one of Embodiments 1 and 2 to 27, wherein $R^5$ is chosen from hydrogen, methyl, and propyl; and all other variables not specifically defined herein are as defined in any one of Embodiments 1 and 2 to 27.

27b. The compound, tautomer, deuterated derivative, or pharmaceutically acceptable salt according to any one of Embodiments 1 and 2 to 27a, wherein $R^5$ is hydrogen; and all other variables not specifically defined herein are as defined in any one of Embodiments 1 and 2 to 27a.

28. A compound, tautomer, deuterated derivative, or pharmaceutically acceptable salt chosen from the compounds of Table 1, tautomers thereof, deuterated derivative of those compounds and tautomers, and pharmaceutically acceptable salts of any of the foregoing.

28a. A compound, tautomer, deuterated derivative, or pharmaceutically acceptable salt chosen from the compounds of Table 2, tautomers thereof, deuterated derivatives of those compounds and tautomers, and pharmaceutically acceptable salts of any of the foregoing.

28b. A compound, tautomer, deuterated derivative, or pharmaceutically acceptable salt chosen from the compounds of Table 3, tautomers thereof, deuterated derivatives of those compounds and tautomers, and pharmaceutically acceptable salts of any of the foregoing.

29. A pharmaceutical composition comprising at least one compound, tautomer, deuterated derivative, or pharmaceutically acceptable salt according to any one of Embodiments 1 to 28b and a pharmaceutically acceptable carrier.

30. A method of treating focal segmental glomerulosclerosis and/or non-diabetic kidney disease comprising administering to a patient in need thereof at least one compound according to any one of Embodiments 1 to 28b or the pharmaceutical composition according to Embodiment 29.

31. Use of at least one compound, tautomer, deuterated derivative, or pharmaceutically acceptable salt according to any one of Embodiments 1 to 28b or a pharmaceutical composition according to Embodiment 29 for the manufacture of the medicament for treating focal segmental glomerulosclerosis and/or non-diabetic kidney disease.

32. At least one compound, tautomer, deuterated derivative, or pharmaceutically acceptable salt according to any one of Embodiments 1 to 28b or the pharmaceutical composition according to Embodiment 29 for use in treating focal segmental glomerulosclerosis and/or non-diabetic kidney disease.

33. A method of inhibiting APOL1 activity comprising contacting said APOL1 with at least one compound, tautomer, deuterated derivative, or pharmaceutically acceptable salt according to any one of Embodiments 1 to 28b or the pharmaceutical composition according to Embodiment 29.

34. Use of at least one compound, tautomer, deuterated derivative, or pharmaceutically acceptable salt according to any one of Embodiments 1 to 28b or the pharmaceutical composition according to Embodiment 29 for the manufacture of a medicament for inhibiting APOL1 activity.

35. At least one compound, tautomer, deuterated derivative, or pharmaceutically acceptable salt according to any one of Embodiments 1 to 28b or a pharmaceutical composition according to Embodiment 29 for use in inhibiting APOL1 activity.

36. A method of treating an APOL1-mediated disease comprising administering to a patient in need thereof at least one compound according to any one of Embodiments 1 to 28b or the pharmaceutical composition according to Embodiment 29.

37. The method according to Embodiment 36, wherein the APOL1-mediated disease is cancer.

38. The method according to Embodiment 36 or Embodiment 37, wherein the APOL1-mediated disease is pancreatic cancer.

39. Use of at least one compound, tautomer, deuterated derivative, or pharmaceutically acceptable salt according to any one of Embodiments 1 to 28b or the pharmaceutical composition according to Embodiment 29 for the manufacture of a medicament for treating an APOL1-mediated disease.

40. The use according to Embodiment 39, wherein the APOL1-mediated disease is cancer.

41. The use according to Embodiment 39 or Embodiment 40, wherein the APOL1-mediated disease is pancreatic cancer.

42. At least one compound, tautomer, deuterated derivative, or pharmaceutically acceptable salt according to any one of Embodiments 1 to 28b or the pharmaceutical composition according to Embodiment 29 for use in treating an APOL1-mediated disease.

43. The at least one compound, tautomer, deuterated derivative, or pharmaceutically acceptable salt for use according to Embodiment 42, wherein the APOL1-mediated disease is cancer.

44. The at least one compound, tautomer, deuterated derivative, or pharmaceutically acceptable salt for use according to Embodiment 42 or Embodiment 43, wherein the APOL1-mediated disease is pancreatic cancer.

45. A method of inhibiting APOL1 activity comprising contacting said APOL1 with at least one compound, tautomer, deuterated derivative, or pharmaceutically acceptable salt according to any one of Embodiments 1 to 28b or a pharmaceutical composition according to Embodiment 29.

46. Use of at least one compound, tautomer, deuterated derivative, or pharmaceutically acceptable salt according to any one of Embodiments 1 to 28b or a pharmaceutical composition according to Embodiment 29 for the manufacture of a medicament for inhibiting APOL1 activity.

47. At least one compound, tautomer, deuterated derivative, or pharmaceutically acceptable salt according to any one of Embodiments 1 to 28b or a pharmaceutical composition according to Embodiment 29 for use in inhibiting APOL1 activity.

48. A silicon derivative of the at least one compound, tautomer, deuterated derivative, or pharmaceutically acceptable salt according to any one of Embodiments 1 to 28b.

49. A pharmaceutical composition comprising a silicon derivative of Embodiment 48.

50. A method of treating focal segmental glomerulosclerosis and/or non-diabetic kidney disease comprising administering to a patient in need thereof the silicon derivative according to Embodiment 48 or the pharmaceutical composition according to Embodiment 49.

51. Use of the silicon derivative according to Embodiment 48 or the pharmaceutical composition according to Embodiment 49 for the manufacture of a medicament for treating focal segmental glomerulosclerosis and/or non-diabetic kidney disease.

52. The silicon derivative according to Embodiment 48 or the pharmaceutical composition according to Embodiment 49 for use in treating focal segmental glomerulosclerosis and/or non-diabetic kidney disease.

53. A method of treating an APOL1-mediated disease comprising administering to a patient in need thereof the silicon derivative according to Embodiment 48 or the pharmaceutical composition according to Embodiment 49.

54. The method according to Embodiment 53, wherein the APOL1-mediated disease is cancer.

55. The method according to Embodiment 53 or Embodiment 54, wherein the APOL1-mediated disease is pancreatic cancer.

56. Use of the silicon derivative according to Embodiment 48 or the pharmaceutical composition according to Embodiment 49 for the manufacture of a medicament for treating an APOL1-mediated disease.

57. The use according to Embodiment 56, wherein the APOL1-mediated disease is cancer.

58. The use according to Embodiment 56 or Embodiment 57, wherein the APOL1-mediated disease is pancreatic cancer.

59. The silicon derivative according to Embodiment 48 or the pharmaceutical composition according to Embodiment 49 for use in treating an APOL1-mediated disease.

60. The silicon derivative or pharmaceutical composition for use according to Embodiment 59, wherein the APOL1-mediated disease is cancer.

61. The silicon derivative or pharmaceutical composition for use according to Embodiment 59 or Embodiment 60, wherein the APOL1-mediated disease is pancreatic cancer.

62. A boron derivative of the at least one compound, tautomer, deuterated derivative, or pharmaceutically acceptable salt according to any one of Embodiments 1 to 28b.

63. A pharmaceutical composition comprising a boron derivative of Embodiment 62.

64. A method of treating focal segmental glomerulosclerosis and/or non-diabetic kidney disease comprising administering to a patient in need thereof a boron derivative according to Embodiment 62 or a pharmaceutical composition according to Embodiment 63.

65. Use of the boron derivative according to Embodiment 62 or a pharmaceutical composition according to Embodiment 63 for the manufacture of a medicament for treating focal segmental glomerulosclerosis and/or non-diabetic kidney disease.

66. The boron derivative according to Embodiment 62 or a pharmaceutical composition according to Embodiment 63 for use in treating focal segmental glomerulosclerosis and/or non-diabetic kidney disease.

67. A method of treating an APOL1-mediated disease comprising administering to a patient in need thereof a boron derivative according to Embodiment 62 or a pharmaceutical composition according to Embodiment 63.

68. The method according to Embodiment 67, wherein the APOL1-mediated disease is cancer.

69. The method according to Embodiment 67 or Embodiment 68, wherein the APOL1-mediated disease is pancreatic cancer.

70. Use of the boron derivative according to Embodiment 62 or the pharmaceutical composition according to Embodiment 63 for the manufacture of a medicament for treating an APOL1-mediated disease.

71. The use according to Embodiment 70, wherein the APOL1-mediated disease is cancer.

72. The use according to Embodiment 70 or Embodiment 71, wherein the APOL1-mediated disease is pancreatic cancer.

73. The boron derivative according to Embodiment 62 or the pharmaceutical composition according to Embodiment 63 for use in treating an APOL1-mediated disease.

74. The boron derivative or pharmaceutical composition for use according to Embodiment 73, wherein the APOL1-mediated disease is cancer.

75. The boron derivative or pharmaceutical composition for use according to Embodiment 73 or Embodiment 74, wherein the APOL1-mediated disease is pancreatic cancer.

76. A phosphorus derivative of at least one compound, tautomer, deuterated derivative or pharmaceutically acceptable salt according to any one of Embodiments 1 to 28b.

77. A pharmaceutical composition comprising a phosphorus derivative of Embodiment 76.

78. A method of treating focal segmental glomerulosclerosis and/or non-diabetic kidney disease comprising administering to a patient in need thereof a phosphorus derivative according to Embodiment 76 or a pharmaceutical composition according to Embodiment 77.

79. Use of the phosphorus derivative according to Embodiment 76 or the pharmaceutical composition according to Embodiment 77 for the manufacture of a medicament for treating focal segmental glomerulosclerosis and/or non-diabetic kidney disease.

80. The phosphorus derivative according to Embodiment 76 or the pharmaceutical composition according to Embodiment 77 for use in treating focal segmental glomerulosclerosis and/or non-diabetic kidney disease.

81. A method of treating an APOL1-mediated disease comprising administering to a patient in need thereof a phosphorus derivative according to Embodiment 76 or the pharmaceutical composition according to Embodiment 77.

82. The method according to Embodiment 81, wherein the APOL1-mediated disease is cancer.

83. The method according to Embodiment 81 or Embodiment 82, wherein the APOL1-mediated disease is pancreatic cancer.

84. Use of the phosphorus derivative according to Embodiment 76 or the pharmaceutical composition according to Embodiment 77 for the manufacture of a medicament for treating an APOL1-mediated disease.

85. The use according to Embodiment 84, wherein the APOL1-mediated disease is cancer.

86. The use according to Embodiment 84 or Embodiment 85, wherein the APOL1-mediated disease is pancreatic cancer.

87. The phosphorus derivative according to Embodiment 76 or a pharmaceutical composition according to Embodiment 77 for use in treating an APOL1-mediated disease.

88. The phosphorus derivative or pharmaceutical composition for use according to Embodiment 87, wherein the APOL1-mediated disease is cancer.

89. The phosphorus derivative or pharmaceutical composition for use according to Embodiment 87 or Embodiment 88, wherein the APOL1-mediated disease is pancreatic cancer.

90. The compound, tautomer, deuterated derivative, or pharmaceutically acceptable salt according to Embodiment 1, wherein the variable X is a bond (i.e., X is not present).

91. A compound represented by the formula:

Formula II-6a

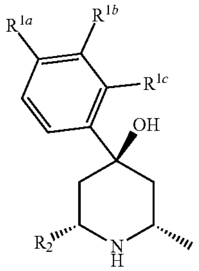

a tautomer thereof, a deuterated derivative of that compound or tautomer, or a pharmaceutically acceptable salt of any of the foregoing, wherein:

$R^{1a}$ and $R^{1b}$ are independently chosen from halogen, H, $C_1$-$C_4$ alkyl, and $C_1$-$C_4$ haloalkyl groups;

$R^{1c}$ is chosen from halogen, H, CH3, —OH, and CH3OH; and $R^2$ is chosen from cyano, $C_1$-$C_6$ alkyl, —C(═O)O($C_1$-$C_4$ alkyl), $C_2$-$C_6$ alkynyl, and

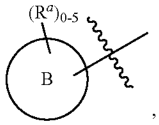

, wherein:

the $C_1$-$C_6$ alkyl of $R^2$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), —C(═O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)$NR^hR^i$, —$NR^hR^i$, —$NR^h$ C(═O)$R^k$, —$NR^h$ C(═O)$OR^k$, —$NR^h$C(═O)$NR^iR^j$, —$NR^h$S(═O)$_pR^k$, —$OR^k$, —OC(═O)$R^k$, —OC(═O)$OR^k$, —OC(═O)$NR^hR^i$, —[O(CH$_2$)$_q$]$_r$O($C_1$-$C_6$ alkyl), —S(═O)$_pR^k$, —S(═O)$_p$$NR^hR^i$, —C(═O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5 to 10-membered heteroaryl (optionally substituted with 1 to 3 $R^m$groups), cyano, —C(═O)$R^k$, —C(═O)$OR^k$, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$R^k$, —$OR^k$, —OC(═O)$R^k$, —OC(═O)$OR^k$, —OC(═O)$NR^hR^i$, —S(═O)$_pR^k$, —S(═O)$_p$$NR^hR^i$, —O($C_6$ aryl) (optionally substituted with 1 to 3 $R^m$groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_p$R$^k$, and —OR$^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups.

92. A compound represented by the formula:

II-6b

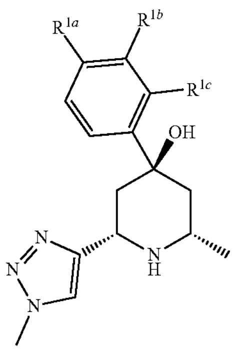

a tautomer thereof, a deuterated derivative of that compound or tautomer, or a pharmaceutically acceptable salt of any of the foregoing, wherein:

$R^{1a}$ and $R^{1b}$ are independently chosen from halogen, H, $C_1$-$C_4$ alkyl, and $C_1$-$C_4$ haloalkyl groups; and $R^{1c}$ is chosen from halogen, H, CH3, —OH, and CH3OH.

93. A pharmaceutical composition comprising the compound, tautomer, deuterated derivative, or pharmaceutically acceptable salt according to Embodiment 91 or Embodiment 92.

94. A method of treating an APOL1-mediated disease comprising administering to a patient in need thereof the compound, tautomer, deuterated derivative, or pharmaceutically acceptable salt according to Embodiment 91 or Embodiment 92, or the pharmaceutical composition according to Embodiment 93.

95. The method according to Embodiment 94, wherein the APOL1-mediated disease is cancer.

96. The method according to Embodiment 94 or Embodiment 95, wherein the APOL1-mediated disease is pancreatic cancer.

97. A method of treating focal segmental glomerulosclerosis and/or non-diabetic kidney disease comprising administering to a patient in need thereof the compound, tautomer, deuterated derivative, or pharmaceutically acceptable salt according to Embodiment 91 or Embodiment 92, or the pharmaceutical composition according to Embodiment 93.

98. Use of the compound, tautomer, deuterated derivative, or pharmaceutically acceptable salt according to Embodiment 91 or Embodiment 92, or the pharmaceutical composition according to Embodiment 93 for the manufacture of a medicament for treating an APOL1-mediated disease.

99. The use according to Embodiment 98, wherein the APOL1-mediated disease is cancer.

100. The use according to Embodiment 98 or Embodiment 99, wherein the APOL1-mediated disease is pancreatic cancer.

101. Use of the compound, tautomer, deuterated derivative, or pharmaceutically acceptable salt according to Embodiment 91 or Embodiment 92, or the pharmaceutical composition according to Embodiment 93 for the manufacture of the medicament for treating focal segmental glomerulosclerosis and/or non-diabetic kidney disease.

102. The compound, tautomer, deuterated derivative, or pharmaceutically acceptable salt according to Embodiment 91 or Embodiment 92 or the pharmaceutical composition according to Embodiment 93 for use in treating an APOL1-mediated disease.

103. The compound, tautomer, deuterated derivative, or pharmaceutically acceptable salt according to Embodiment 91 or Embodiment 92 or the pharmaceutical composition according to Embodiment 93, for use in treating an APOL1-mediated cancer.

104. The compound, tautomer, deuterated derivative, or pharmaceutically acceptable salt according to Embodiment 91 or Embodiment 92 or the pharmaceutical composition according to Embodiment 93, for use in treating APOL1-mediated pancreatic cancer.

105. The compound, tautomer, deuterated derivative, or pharmaceutically acceptable salt according to Embodiment 91 or Embodiment 92 or the pharmaceutical composition according to Embodiment 93, for use in treating focal segmental glomerulosclerosis and/or non-diabetic kidney disease.

EXAMPLES

In order that the disclosure described herein may be more fully understood, the following examples are set forth. It should be understood that these examples are for illustrative purposes only and are not to be construed as limiting this disclosure in any manner.

The compounds of the disclosure may be made according to standard chemical practices or as described herein. Throughout the following synthetic schemes and in the descriptions for preparing compounds of Formulae I, Ia, Ib, Ic, Ic-1, Ic-2, Ic-3, Ic-4, Ic-5, Ic-6, II, II-1, II-2, II-3, II-4, II-5, II-6, II-6a and II-6b, Compounds 1 to 29, Compounds I5 to I295, Compounds 30 to 44, and Compounds 45 to 68, a tautomer thereof, a deuterated derivative of that compound or tautomer, or a pharmaceutically acceptable salt of any of the foregoing, the following abbreviations are used:

Abbreviations

AIBN=azobisisobutyronitrile
ARP=assay ready plate
BBBPY=4,4'-Di-tert-butyl-2,2'-dipyridyl
$BF_3$=boron trifluoride
$BF_3$·$OEt_2$=boro trifluoride diethyl etherate
$Boc_2O$=di-tert-butyl dicarbonate
CBzCl=benzyl chloroformate
CDMT=2-chloro-4,6-dimethoxy-1,3,5-triazine
DAST=diethylaminosulfur trifluoride
DBU=1,8-diazabicyclo[5.4.0]undec-7-ene
DCM=dichloromethane
DIBAL-H=diisobutylaluminum hydride
DIPEA=N,N-Diisopropylethylamine or N-ethyl-N-isopropyl-propan-2-amine
DMAP=dimethylamino pyridine DMA=dimethyl acetamide
DME=dimethoxyethane
DMEM=Dulbecco's modified Eagle's medium
DMF=dimethylformamide
DMPU=N,N'-dimethylpropyleneurea
DMSO=dimethyl sulfoxide
DPPA=diphenylphosphoryl azide
dppb=1-4-bis[P(Ph)2]-butane
EtOAc=ethyl acetate
EtOH=ethanol
$Et_2O$=diethyl ether
FBS=fetal bovine serum
FLU=fluorescent values
HATU=[dimethylamino(triazolo[4,5-b]pyridin-3-yloxy) methylene]-dimethyl-ammonium (Phosphorus Hexafluoride Ion)
HDMC=N-[(5-Chloro-3-oxido-1H-benzotriazol-1-yl)-4-morpholinylmethylene]-N-methylmethanaminium hexafluorophosphate
HEPES=4-(2-hydroxyethyl)-1-piperazineethanesulfonic acid
HBSS=Hank's balanced salt solution
IPA=isopropyl alcohol
$Ir[df(CF_3)ppy]_2(dtbbpy)PF_6$=phosphorus hexafluoride
LDA=lithium diisopropyl amide
LED=light emitting diode
MeCN=acetonitrile
MeI=methyl iodide
MeOH=methanol
MsOH=methanesulfonic acid
MTBE or TBME=Methyl tert-butyl ether
n-BuLi=n-butyllithium
NBS=N-bromosuccinimide
NMM=N-methyl morpholine
NMP=N-methyl pyrrolidine
PBS=phosphate-buffered saline
$Pd(dppf)_2Cl_2$=[1,1'-Bis(diphenylphosphino)ferrocene]dichloropalladium(II)
$PdCl_2(PPh_3)_2$=Bis(triphenylphosphine)palladium(II) dichloride
$Pd_2dba_3$=Tris(dibenzylideneacetone)dipalladium
PP=polypropylene
psig=pounds per square inch gauge
PTSA=p-Toluenesulfonic acid monohydrate
rt=room temperature
SFC=supercritical fluid chromatography
T3P=2,4,6-Tripropyl-1,3,5,2,4,6-trioxatriphosphorinane-2,4,6-trioxide
TBAF=tetra-n-butylammonium fluoride
TBSCl=tert-butyldimethylsilyl chloride
TBME=methyl tert-butyl ether
TEA=triethylamine
Tet=tetracycline
TFA or TFAA=trifluoroacetic acid
TfOH=triflic acid
THF=tetrahydrofuran
2-Me-THF=2=methyltetrahydrofuran
THP=tetrahydropyran
TMSCl=trimethylsilyl chloride
TMSS=Tris(trimethylsilyl)silane

Example 1. Synthesis of Compounds

All the specific and generic compounds, and the intermediates disclosed for making those compounds, are considered to be part of the disclosure disclosed herein.

Synthesis of Starting Materials

Preparations describe synthetic routes to intermediates used in the synthesis of Compounds 1 to 29, Compounds I5 to I295, Compound I296, Compounds 30 to 44, and Compounds 45-68.

General Schemes

In some embodiments, processes for preparing compounds of Formula I comprise the reactions described in Schemes 1-10. In the schemes below, A is CH or N and $R^1$, $R^2$, and $R^3$ are as defined above.

Scheme 1 shows a process for the preparation of a compound of formula 1-2 from piperidinone S1. The piperidinone S1 can be optionally substituted with a protecting group reagent such as allyl bromide to provide the protected piperidinone depicted by S2. Suitable aryl halides are treated with hexyl lithium in a solvent such as THF, which are then combined with S2 to form compounds depicted by formula 1-1. This is followed by deprotection of the allyl group to provide compounds depicted by formula 1-2.

Scheme 1
Representatative scheme using n-hexyllithium to form aryl lithium nucleophiles for 1,2-addition

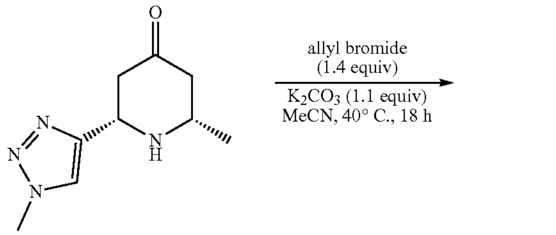

S1

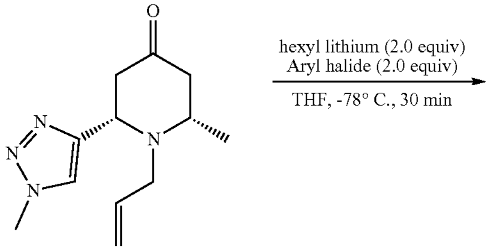

S2
73%

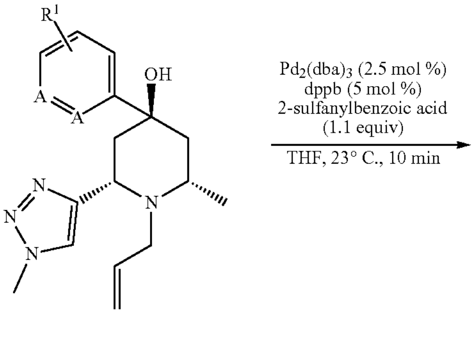

1-1

-continued

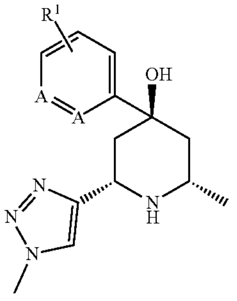

1-2

Scheme 2 shows an alternative process for the preparation of a compound of formula 2-2 from the protected piperidinone S2. Suitable aryl halides are treated with t-butyllithium in a solvent such as THF, which are then combined with S2 to form compounds depicted by formula 2-1. This is followed by deprotection of the allyl group to provide compounds depicted by formula 2-2.

Scheme 2

Representatative scheme using tert-butyllithium to form aryl lithium nucleophiles for 1,2-addition

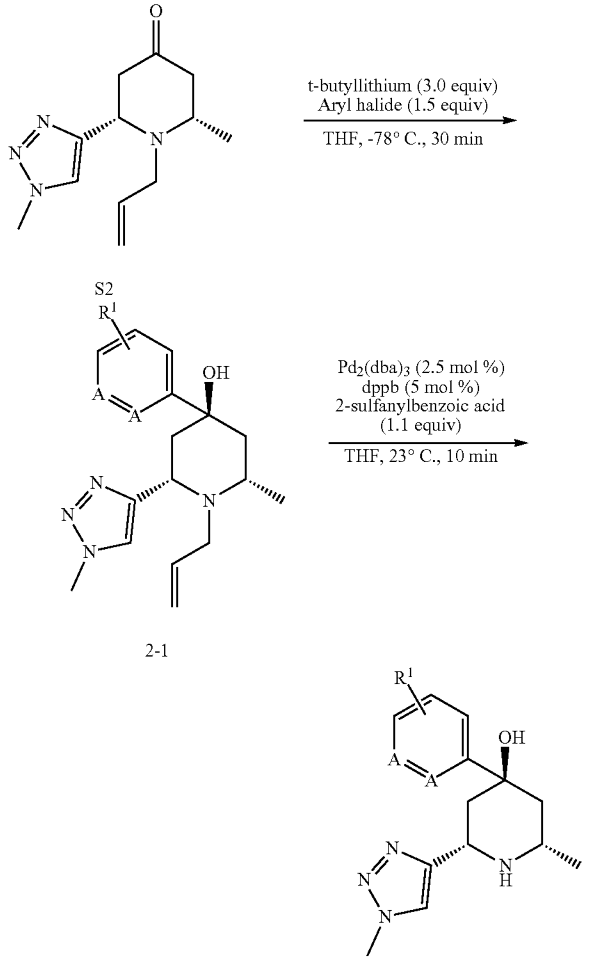

2-2

Scheme 3 shows an alternative process for the preparation of a compound of formula 3-2 from the protected piperidinone S2. Suitable aryl halides are treated with n-butyllithium in a solvent such as THF, which are then combined with S2 to form compounds depicted by formula 3-1. This is followed by deprotection of the allyl group to provide compounds depicted by formula 3-2.

Scheme 3

Representative scheme using n-butyllithium to form aryl lithium nucleophiles for 1,2-addition

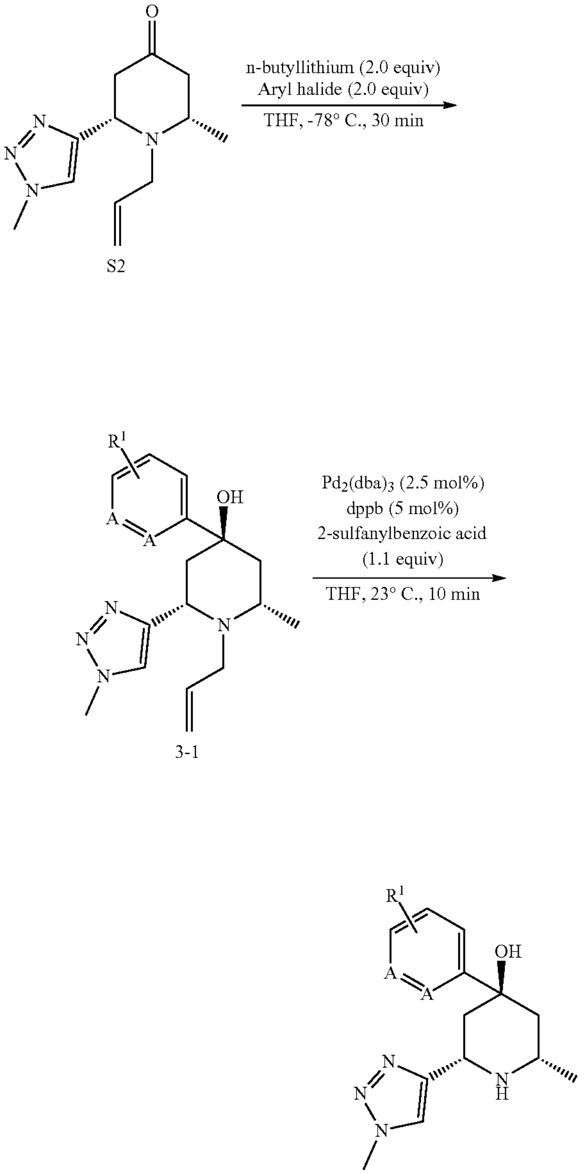

3-2

Scheme 4 shows an alternative process for the preparation of a compound of formula 4-2 from the protected piperidinone S2. Suitable aryl halides are treated with s-butyllithium in a solvent such as THF, which are then combined with S2 to form compounds depicted by formula 4-1. This is followed by deprotection of the allyl group to provide compounds depicted by formula 4-2.

Scheme 4
Representative scheme using sec-butyllithium to form aryl lithium nucleophiles for 1,2-addition

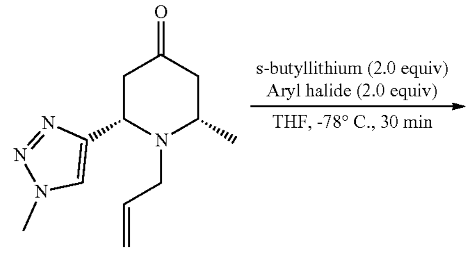

S2

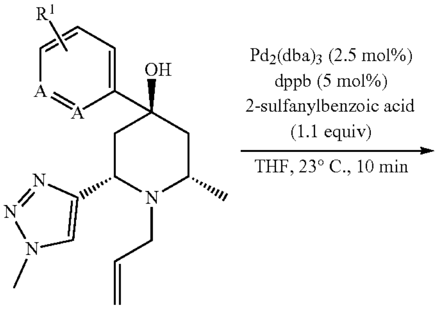

4-1

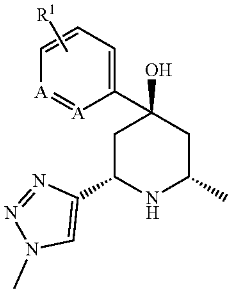

4-2

Scheme 5 shows an alternative process for the preparation of a compound of formula 5-2 from the protected piperidinone S2. Suitable aryl lithiate reagents in a solvent such as THF are combined with S2 to form compounds depicted by formula 5-1. This is followed by deprotection of the allyl group to provide compounds depicted by formula 5-2.

Scheme 5
Representative scheme of 1,2-addition using phenyl lithium to aryl lithium nucleophiles

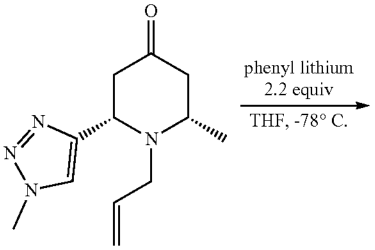

S2

-continued

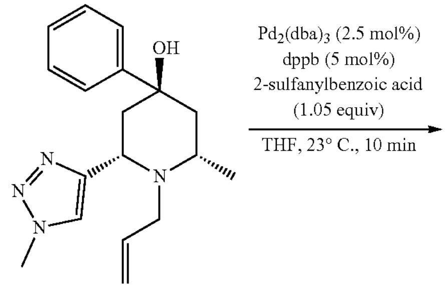

5-1
40%
6:5 trans:cis

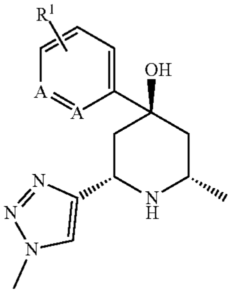

5-2

Scheme 6 shows an alternative process for the preparation of a compound of formula 6-2 from the protected piperidinone S2. Suitable aryl Grignard reagents (ArMgX), which in some embodiments are prepared by treatment of appropriate aryl halides with magnesium in a solvent such as THF, are then combined with S2 to form compounds depicted by formula 6-1. This is followed by deprotection of the allyl group to provide compounds depicted by formula 6-2.

Scheme 6
Representative scheme of 1,2-addition using arylmagnesium bromide nucleophiles

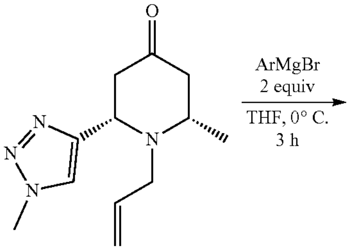

S2

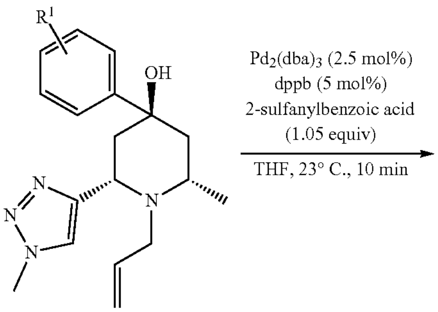

6-1

-continued

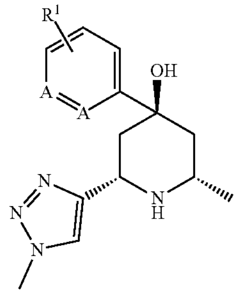

6-2

Scheme 7 shows an alternative process for the preparation of a compound of formula 7-2 from the protected piperidinone S2. Suitable aryl halides may be treated with iPrMgCl—LiCl in a solvent such as THF, then combined with S2 to form compounds depicted by formula 7-1, followed by deprotection of the allyl group to provide compounds depicted by formula 7-2.

Scheme 7
Representative scheme to generate arylmagnesium halide nucelophiles and their addition

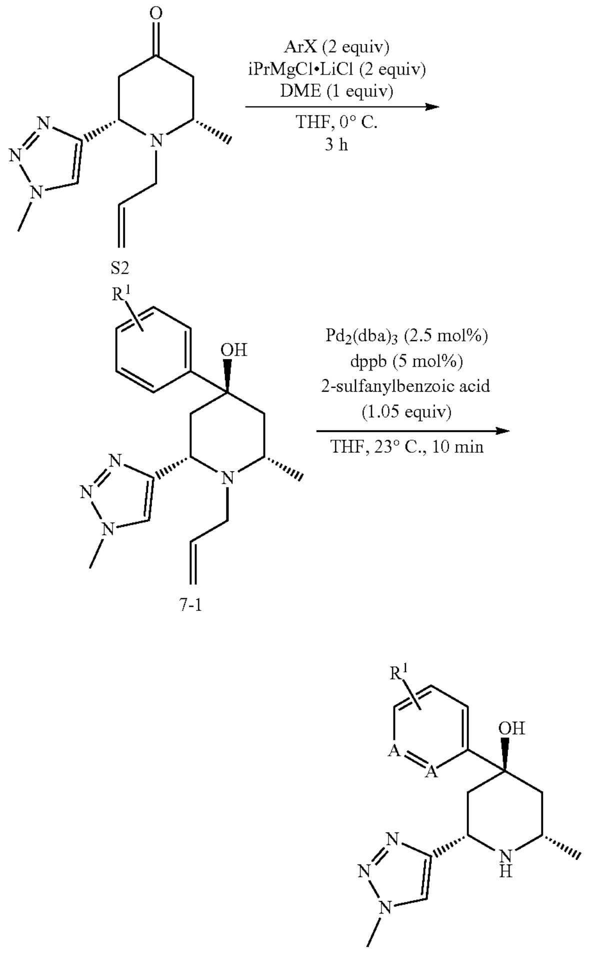

S2

7-1

7-2

Scheme 8 shows an alternative process for the preparation of a compound of formula 8-2 from the protected piperidinone S2. Suitable aryl Grignard reagents (ArMgX), which in some embodiments are prepared by treatment of appropriate aryl halides with magnesium in a solvent such as THF, are then combined with $LaCl_3 \cdot 2LiCl$ and S2 to form compounds depicted by formula 8-1. This is followed by deprotection of the allyl group to provide compounds depicted by formula 8-2.

Scheme 8
Representative scheme using arylmagnesium halide Grignard reagents with $LaCl_3$•2LiCl as nucleophiles

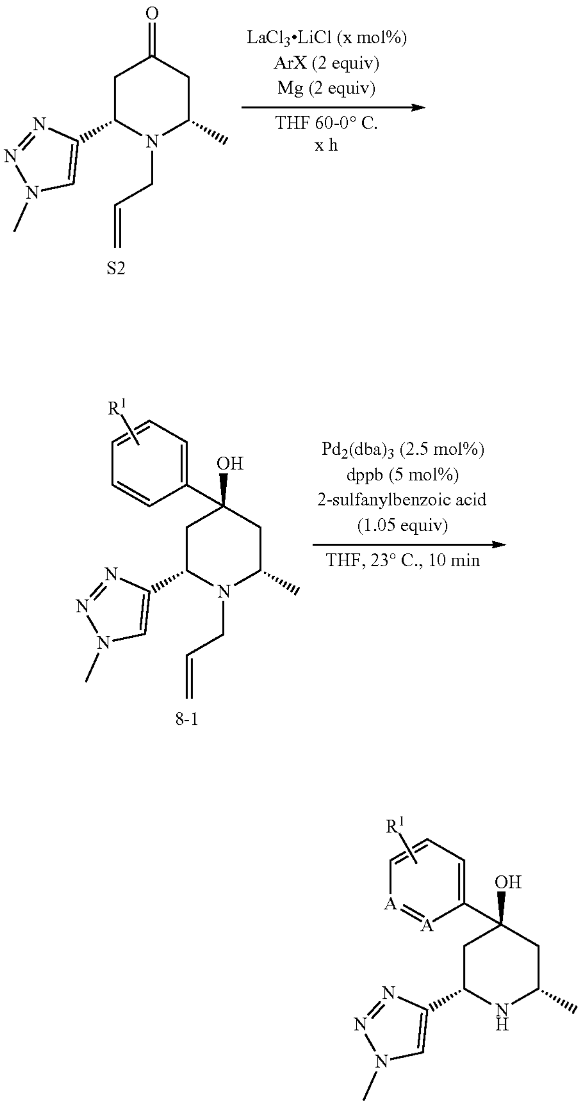

S2

8-1

8-2

Scheme 8a shows an alternative process for the preparation of a compound of formula 16 from piperidinones of formula S1. Note that this chemistry can proceed in the absence of a N-protecting group. Suitable aryl Grignard reagents (ArMgX), which in some embodiments are prepared by treatment of appropriate aryl halides with magnesium in a solvent such as THF or 2-MeTHF, are then combined with S1 to form compounds depicted by formula 16.

Scheme 8a
Representative scheme to generate arylmagnesium halide nucleophiles and their addition

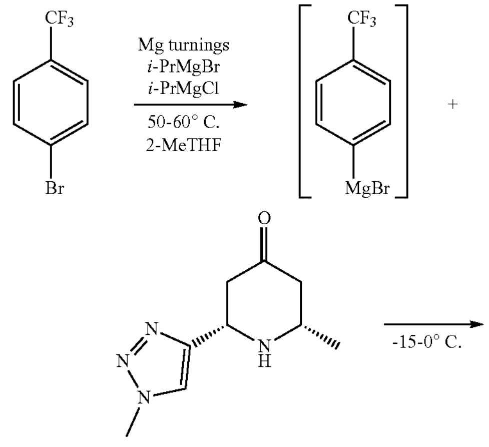

S1

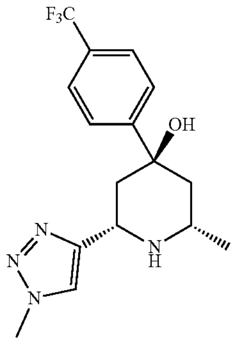

16

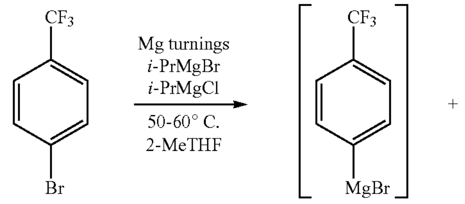

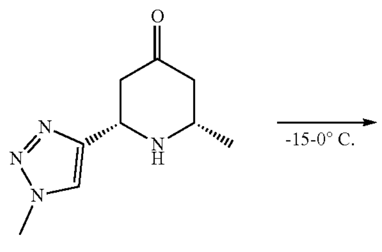

S1

-continued

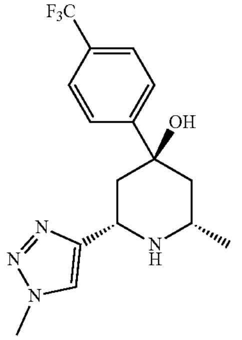

16

Scheme 9 shows an alternative process for the preparation of a compound of formula 9-6 from N-protected beta-amino acids of formula 9-1. $PG^4$ may be Boc or any suitable nitrogen protecting group. Compound 9-2 dimagnesium salt may be coupled to compounds of formula 9-1 using a reagent such as CDI in a solvent such as THF. Condensation of compounds of formula 9-3 with aldehydes of formula 9-4 affords compounds of formula 9-5. In some embodiments, the reaction may be performed by treatment of a compound of formula 9-3 with an acid such as TFA in a solvent such as dichloromethane, followed by the addition of aldehyde of formula 9-4. A compound of formula 9-6 may be prepared from a compound of formula 9-5 by treatment with an acid such as methanesulfonic acid in a solvent such as dichloromethane. The reaction may be performed in the presence of added heat (e.g., reflux conditions).

Scheme 9
Representative scheme to synthesize 2,6-disubstituted piperidinones

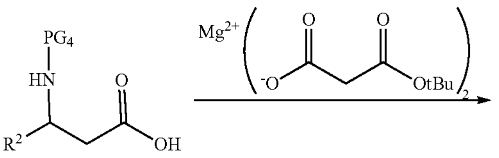

9-1

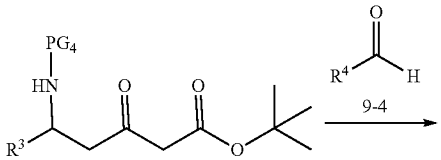

9-3

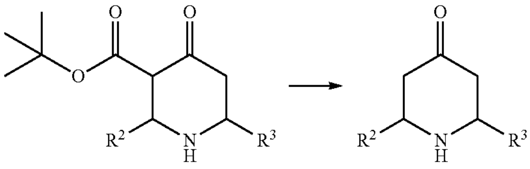

9-5 9-6

Scheme 10 shows a process for the preparation of a compound of formula 10-3 from piperidinone 9-6. The piperidinone 9-6 can be optionally substituted with a protecting group reagent such as allyl bromide to provide the protected piperidinone depicted by formula 10-1. Suitable aryl halides such as 1-iodo-4-(trifluoromethyl)benzene are treated with hexyl lithium in a solvent such as THF, which are then combined with formula 10-1 to form compounds depicted by formula 10-2. This is followed by deprotection of the allyl group to provide compounds depicted by formula 10-3.

Scheme 10
General scheme of allyl protection, 1,2-addition, and deprotection

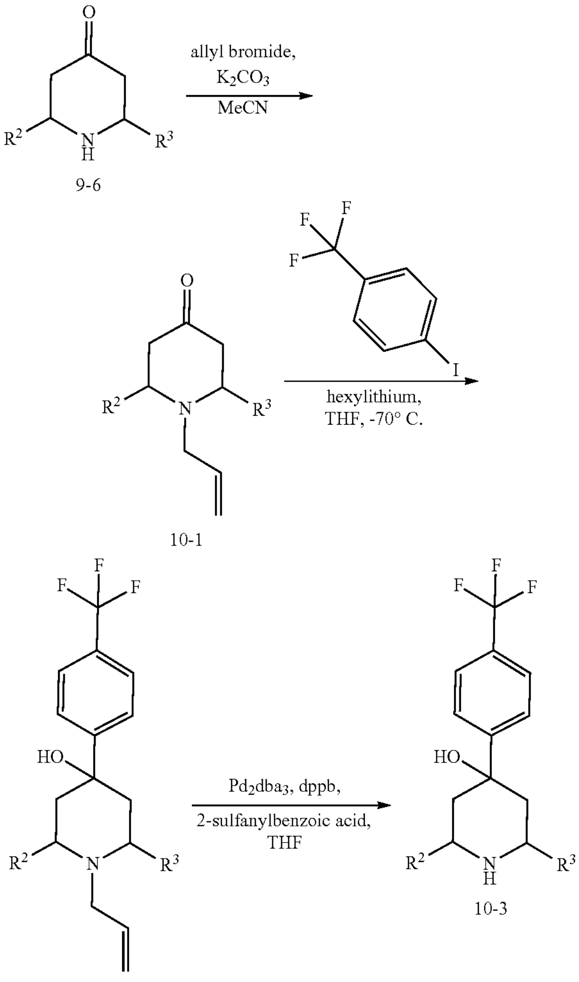

9-6, 10-1, 10-2, 10-3

Preparation S1

(2S,6S)-1-allyl-2-methyl-6-(1-methyl-1H-1,2,3-triazol-4-yl)piperidin-4-one (S1)

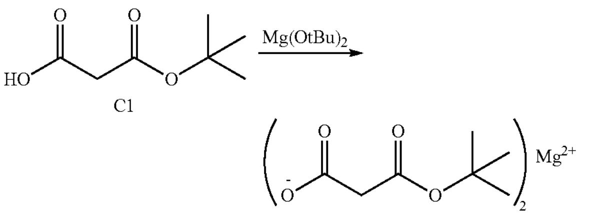

C1, C2

-continued

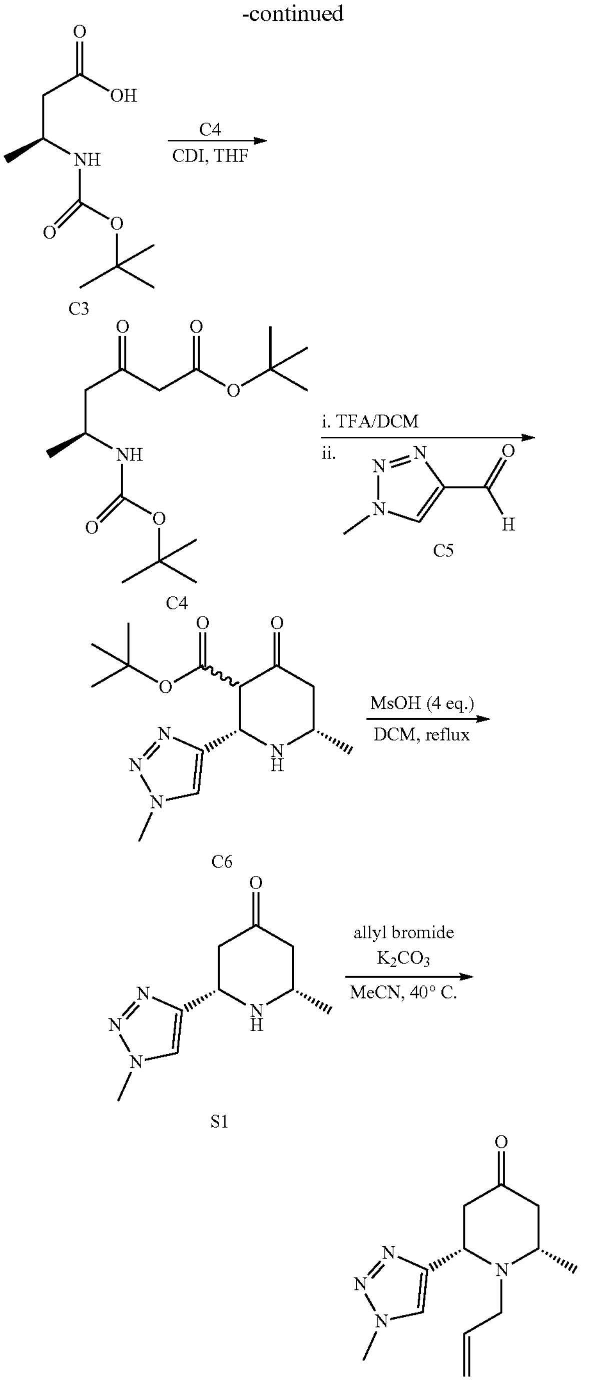

C3, C4, C5, C6, S1, S2

Step 1. Synthesis of bis[(3-tert-butoxy-3-oxo-propanoyl)oxy]magnesium (C2)

A solution of 3-tert-butoxy-3-oxo-propanoic acid (C1) (321.51 g, 1.907 mol) in THF (2 L) was cooled to 5° C. in an ice-bath, and $Mg(OEt)_2$ (111.33 g, 953.5 mmol) was added. The reaction was stirred for 30 minutes at 0° C., removed from the cooling bath, and stirred at room temperature overnight. The reaction was filtered over a plug of Celite®, and the plug was washed with additional THF. The clear, colorless filtrate was evaporated in vacuo to afford a wet solid. The solid was triturated with 1 L of diethyl ether and filtered. The filter-cake was washed with $Et_2O$ and dried in vacuo. The filtrate was evaporated in vacuo again and was then triturated with a small volume of $Et_2O$ and filtered to afford a second crop of the product. The crops were combined and dried in vacuo to afford the title compound C2 (294.49 g, 90%) as a white solid. $^1H$ NMR (300 MHz, Methanol-$d_4$) δ 4.92 (s, 4H), 1.48 (s, 18H).

Step 2. Synthesis of tert-butyl (5S)-5-(tert-butoxycarbonylamino)-3-oxo-hexanoate (C4)

To a solution of (3S)-3-(tert-butoxycarbonylamino)butanoic acid (C3) (170.15 g, 837.2 mmol) in THF (1.5 L) was added CDI (149.8 g, 923.8 mmol). The milky suspension cleared over the next few minutes. Gas evolution was observed. The reaction was stirred at room temperature for 3 hours. Bis[(3-tert-butoxy-3-oxo-propanoyl)oxy]magnesium (C2) (172.19 g, 502.6 mmol) was added. Another milky suspension was formed that cleared after stirring for 30 minutes. The reaction was stirred for 48 hours. The reaction was poured into 1.5 L of 1 M HCl and extracted with MTBE (1 L). The pH was confirmed to be approximately 3. The extract was washed with saturated $NaHCO_3$, dried over $MgSO_4$, filtered, and concentrated in vacuo to afford the title compound C4 (248.5 g, 99%) as a clear oil. $^1H$ NMR (300 MHz, Chloroform-d) δ 4.90 (d, J=18.1 Hz, 1H), 4.04 (dt, J=13.8, 6.6 Hz, 1H), 3.47-3.22 (m, 2H), 2.76 (qd, J=17.0, 5.7 Hz, 2H), 1.48 (s, 9H), 1.44 (s, 9H), 1.23 (d, J=6.8 Hz, 3H).

Step 3. Synthesis of tert-butyl (2S,3R,6S)-6-methyl-2-(1-methyltriazol-4-yl)-4-oxo-piperidine-3-carboxylate (C6)

To a solution of tert-butyl (5S)-5-(tert-butoxycarbonylamino)-3-oxo-hexanoate (C4) (248.5 g, 824.5 mmol) in DCM (1.5 L) was added TFA (240 mL, 3.115 mol), and the reaction was stirred overnight. The reaction was evaporated in vacuo at 25° C. The solid that remained was triturated with 500 mL of pentane and filtered. The filter cake was washed with pentane, and most of the solvent was pulled off of the filter-cake. The cake was transferred back to the reaction flask and dissolved in 1 L of DCM. 1-Methyltriazole-4-carbaldehyde (120.7 g, 1.086 mol) was added. The reaction was stirred at room temperature overnight. Brine (100 mL) was added, and then 6 M NaOH was added until the aqueous layer remained alkaline when the funnel was shaken. The organic layer was isolated, and the aqueous layer was extracted with DCM (1 L). The organic layers were combined, dried over $MgSO_4$, and filtered over a plug of silica gel. The plug was eluted with 10% MeOH/EtOAc. The filtrate was evaporated in vacuo to afford a solid that was triturated with MTBE (500 mL) and filtered. The filter cake was washed with MTBE and dried in vacuo to give a crop of product. The mother liquor from the trituration was concentrated. The solid that precipitated was filtered to provide a second crop of the product. The crops were combined to give the title compound C6 (105.45 g, 43%) as a white solid. $^1H$ NMR (300 MHz, Chloroform-d) δ 7.48 (s, 1H), 4.52 (d, J=11.0 Hz, 1H), 4.09 (s, 3H), 3.61 (dd, J=11.0, 1.0 Hz, 1H), 3.21 (ddd, J=11.7, 6.1, 2.9 Hz, 1H), 2.55 (dd, J=13.7, 2.9 Hz, 1H), 2.37-2.13 (m, 1H), 1.98 (s, 1H), 1.39 (s, 9H), 1.29 (d, J=6.3 Hz, 3H).

Step 4. Synthesis of (2S,6S)-2-methyl-6-(1-methyltriazol-4-yl)piperidin-4-one (S1)

To a solution of tert-butyl (2S,3R,6S)-6-methyl-2-(1-methyltriazol-4-yl)-4-oxo-piperidine-3-carboxylate (C6) (70.59 g, 239.8 mmol) in DCM (750 mL) was added MsOH (62 mL, 955.4 mmol) and the reaction was heated to reflux for 6 hours. The reaction was cooled down to room temperature and then poured into a separatory funnel. Brine (100 mL) was added, and then 6 M NaOH was added until the aqueous layer remained alkaline after shaking. The organic layer was separated, and the aqueous layer was extracted with DCM (2×500 mL). The organic layers were combined, dried over $MgSO_4$, filtered, and concentrated in vacuo to afford the title compound S1 (43.74 g, 94%) as an off-white solid. $^1H$ NMR (300 MHz, Chloroform-d) δ 7.46 (s, 1H), 4.20 (dd, J=10.1, 5.1 Hz, 1H), 4.06 (s, 3H), 3.11 (dqd, J=12.3, 6.2, 3.0 Hz, 1H), 2.73-2.48 (m, 2H), 2.40 (ddd, J=14.1, 3.0, 1.5 Hz, 1H), 2.25-2.00 (m, 2H), 1.23 (d, J=6.2 Hz, 3H).

Step 5. (2S,6S)-1-allyl-2-methyl-6-(1-methyl-1H-1,2,3-triazol-4-yl)piperidin-4-one (S2)

To a suspension of (2S,6S)-2-methyl-6-(1-methyltriazol-4-yl)piperidin-4-one (S1) (10.0 g, 50.5 mmol) and $K_2CO_3$ (8.0 g, 57.9 mmol) in MeCN (100 mL) was added allyl bromide (5.5 mL, 63.6 mmol), and the mixture was heated to 40° C. and stirred for 18 hours. The suspension was then filtered, rinsed with MeCN, and concentrated to about 3 volumes. The mixture was diluted with TBME/EtOAc/DCM 1:1:1 (300 mL) and water (250 mL). The aqueous layer was extracted with DCM (2×150 mL). The combined organic layer was washed with saturated brine (250 mL), dried with $MgSO_4$, filtered, and concentrated. The mixture was suspended in TBME (180 mL) and refluxed. Upon reflux, full dissolution to a yellow solution was observed. The mixture was removed from the bath and stirred. After about 5 minutes, significant precipitation was observed. At this time, the mixture was cooled with an ice bath for 10 minutes, filtered, and rinsed with TBME (2×15 mL). Dissolution was observed, so subsequent rinses were carried out using heptane (3×20 mL). The addition of heptane caused a significant amount of precipitation in the mother liquor, which was filtered and rinsed with heptane (3×10 mL) to yield the second crop. The crops were combined to yield the title compound S2 (2S,6S)-1-allyl-2-methyl-6-(1-methyltriazol-4-yl)piperidin-4-one (8.42 g, 71%) as an off-white solid. $^1H$ NMR (300 MHz, Chloroform-d) δ 7.48 (s, 1H), 5.91 (ddt, J=16.9, 11.1, 6.4 Hz, 1H), 5.13 (t, J=14.6 Hz, 2H), 4.23 (dd, J=10.9, 3.8 Hz, 1H), 4.12 (d, J=1.3 Hz, 3H), 3.44 (dd, J=16.0, 6.8 Hz, 1H), 3.17 (dd, J=16.0, 6.3 Hz, 1H), 3.06 (dt, J=10.5, 5.4 Hz, 1H), 2.88 (dd, J=14.6, 10.9 Hz, 1H), 2.59 (dd, J=14.8, 3.7 Hz, 1H), 2.53-2.34 (m, 2H), 1.27 (d, J=6.2 Hz, 3H).

Preparation S3

2-methyl-6-(1-(2-(methylsulfonyl)ethyl)-1H-pyrazol-4-yl)piperidin-4-one (S3)

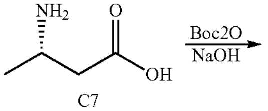

C7

-continued

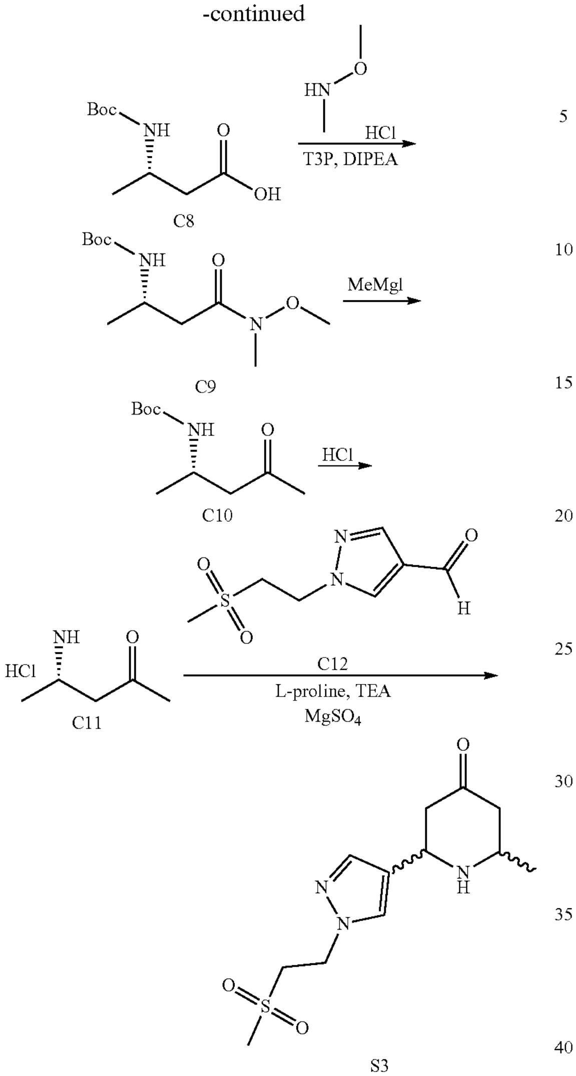

Step 1. Synthesis of (3S)-3-(tert-butoxycarbonylamino)butanoic acid (C8)

To a solution of (3S)-3-aminobutanoic acid (C7) (100 g, 969.7 mmol) in dioxane (600 mL) was added aqueous NaOH solution (950 mL of 1 M, 950.0 mmol) over 15 minutes, followed by $Boc_2O$ (300 g, 1.375 mol). The reaction mixture was stirred at room temperature for 12 hours. The reaction was partitioned with MTBE (1 L) and water (300 mL). The layers were separated, and the aqueous layer was extracted again with MTBE (500 mL). The aqueous layer was then acidified with 1 M HCl until pH=2 and extracted with DCM (3×600 mL). The combined organic layers were washed with brine, dried over $MgSO_4$, filtered, and concentrated in vacuo to yield the title compound C8 (176 g, 89%) as a white solid. $^1H$ NMR (300 MHz, Chloroform-d) δ 4.92 (s, 1H), 4.04 (s, 1H), 2.56 (dd, J=5.5, 2.9 Hz, 2H), 1.44 (s, 9H), 1.25 (d, J=6.8 Hz, 3H).

Step 2. Synthesis of tert-butyl N—[(S)-3-[methoxy (methyl)amino]-1-methyl-3-oxo-propyl]carbamate (C9)

To a solution of (3S)-3-(tert-butoxycarbonylamino)butanoic acid (C8) (160 g, 787.3 mmol) in DCM (1.5 L) was added N-methoxymethanamine (Hydrochloride salt) (81 g, 830.4 mmol), followed by the addition of DIPEA (560 mL, 3.215 mol) over 10 minutes. The reaction mixture was cooled to 0° C., and T3P (600 g of 50% w/w in EtOAc, 942.9 mmol) was added over 45 minutes. After the addition, the cooling bath was removed, and the reaction was stirred at room temperature for 1 hour. The reaction mixture was cooled to 10° C., and aqueous 1 M NaOH solution (700 mL) was added. The solution was stirred for 15 minutes. The organic phase was separated, washed with aqueous saturated ammonium chloride solution (200 mL) and brine (200 mL), dried, filtered through a silica gel plug, and concentrated in vacuo to afford the title compound C9 (180 g, 93%) as a clear, colorless viscous oil. $^1H$ NMR (300 MHz, Chloroform-d) δ 5.30 (s, 1H), 4.06 (ddd, J=14.3, 9.7, 6.0 Hz, 1H), 3.68 (s, 3H), 3.17 (s, 3H), 2.71 (dd, J=15.6, 5.2 Hz, 1H), 2.54 (dd, J=15.7, 5.7 Hz, 1H), 1.43 (s, 9H), 1.24 (d, J=6.8 Hz, 3H).

Step 3. Synthesis of tert-butyl N—[(S)-1-methyl-3-oxo-butyl]carbamate (C10)

To a solution of tert-butyl N-[(1S)-3-[methoxy(methyl) amino]-1-methyl-3-oxo-propyl]carbamate (C9) (220 g, 893.2 mmol) in THF (4 L) at 0° C. was added iodo(methyl) magnesium (900 mL of 3M, 2.7 mol) over 40 minutes. The resulting reaction mixture was stirred at 0° C. for 4 hours. The reaction was quenched with saturated ammonium chloride solution (2 L), followed by MTBE (1 L) and water (2 L). The mixture was stirred for 30 minutes, and the organic layer was separated. The aqueous phase was extracted with MTBE (1 L), and the combined organic layers were washed with saturated ammonium chloride solution (1 L), dried over $MgSO_4$, filtered, and concentrated in vacuo. Purification by silica gel chromatography (Gradient: 0-70% EtOAc in heptane) yielded the title compound C10 (115 g, 64%) as a white solid. $^1H$ NMR (300 MHz, Chloroform-d) δ 4.83 (s, 1H), 4.12-3.87 (m, 1H), 2.69 (dd, J=16.5, 5.2 Hz, 1H), 2.63-2.47 (m, 1H), 2.15 (d, J=2.3 Hz, 3H), 1.43 (d, J=2.4 Hz, 9H), 1.20 (dd, J=6.8, 2.4 Hz, 3H).

Step 4. Synthesis of (4S)-4-aminopentan-2-one (Hydrochloride Salt) (C11)

To a solution of tert-butyl N-[(1S)-1-methyl-3-oxo-butyl] carbamate (C10) (16.3 g, 80.2 mmol) in MeOH (30 mL) was added hydrogen chloride (50 mL of 4 M in dioxane, 200.0 mmol) over 3 minutes. The reaction was stirred at room temperature for 5 hours and then concentrated under reduced pressure. The residue was co-evaporated with EtOH (2×30 mL) and dried under vacuum to afford the title compound C11 (12 g, 98%) as a pink viscous oil. $^1H$ NMR (300 MHz, Chloroform-d) δ 8.06 (s, 3H), 3.48 (d, J=6.8 Hz, 1H), 2.88 (dd, J=18.0, 5.8 Hz, 1H), 2.75 (dd, J=18.0, 7.2 Hz, 1H), 2.13 (s, 3H), 1.17 (d, J=6.6 Hz, 3H).

Step 5. Synthesis of 2-methyl-6-(1-(2-(methylsulfonyl)ethyl)-1H-pyrazol-4-yl)piperidin-4-one (S3)

To a mixture of (4S)-4-aminopentan-2-one (hydrochloride salt) C11 (580 mg, 4.088 mmol) in EtOH (13 mL) was added 1-(2-methylsulfonylethyl)pyrazole-4-carbaldehyde (760 mg, 3.758 mmol), L-proline (94 mg, 0.8165 mmol), magnesium sulfate (600 mg, 4.985 mmol), and TEA (600 μL, 4.305 mmol). The reaction mixture was stirred at room temperature overnight. TLC indicated incomplete reaction, so additional 1-(2-methylsulfonylethyl)pyrazole-4-carbaldehyde (C12) (150 mg, 0.74 mmol) was added and the reaction was stirred overnight. The reaction mixture was filtered and concentrated under reduced pressure. The crude residue was quenched with saturated sodium bicarbonate solution and extracted with DCM (x3). The combined organic extracts were washed with brine, dried over magnesium sulfate, filtered, and concentrated in vacuo. The crude was purified via silica gel chromatography (0-60% of 20% MeOH/DCM in DCM) to yield the title compound S3 (500 mg, 38%) in 7:1 cis to trans ratio as an orange oil. Additionally, the enantiomeric ratio at the stereocenter from C11 was eroded to ~85%. $^1$H NMR (300 MHz, Chloroform-d) δ 7.58 (s, 1H), 7.53 (s, 1H), 4.60 (t, J=6.3 Hz, 2H), 4.00 (dd, J=11.6, 3.3 Hz, 1H), 3.65 (t, J=6.2 Hz, 2H), 3.10 (dqd, J=12.1, 6.0, 2.9 Hz, 1H), 2.58-2.51 (m, 4H), 2.48-2.37 (m, 2H), 2.17 (dd, J=14.1, 11.6 Hz, 1H), 1.26 (d, J=6.1 Hz, 3H) (cis isomer).

Compound 1
(2S,6R)-4-(3-chlorophenyl)-2,6-dimethyl-piperidin-4-ol) (1)

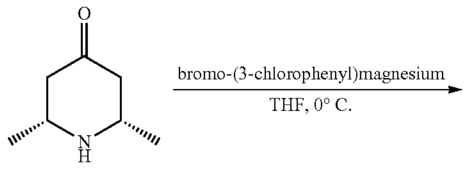

C13

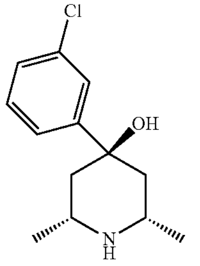

1

A THF solution of bromo-(3-chlorophenyl)magnesium (3.2 mL of 0.5 M, 1.60 mmol) was diluted with THF (4.8 mL) and then cooled to 0° C. To this solution was added (2S,6R)-2,6-dimethylpiperidin-4-one (C13) (100 mg, 0.786 mmol) as a solution in THF (2 mL), and the reaction was stirred at 0° C. for 1 hour and then warmed to room temperature and stirred for 3 hours. At this time, the mixture was quenched with water (5 mL) and diluted with DCM (5 mL). The aqueous layer was extracted with additional DCM (3x5 mL). The combined organic layer was passed over a phase separator and concentrated in vacuo. The crude residue was purified by silica gel chromatography (Gradient: 0-20% MeOH in DCM) to yield the title compound 1 as a ~3:1 mixture of diastereomers. The oil was then repurified by silica gel chromatography (Gradient: 0-20% MeOH in DCM) to yield the purified title Compound 1 (60.5 mg, 30%) as a yellow solid. $^1$H NMR (300 MHz, Chloroform-d) δ 7.70-7.14 (m, 4H), 3.22 (ddd, J=11.2, 6.1, 2.3 Hz, 2H), 1.80-1.68 (m, 2H), 1.64-1.48 (m, 2H), 1.13 (d, J=6.4 Hz, 6H). ESI-MS m/z calc. 239.1077, found 240.09 (M+H)$^+$.

Compound 2
4-(3-chlorophenyl)-2-methyl-6-[1-(2-methylsulfonylethyl)pyrazol-4-yl]piperidin-4-ol (2)

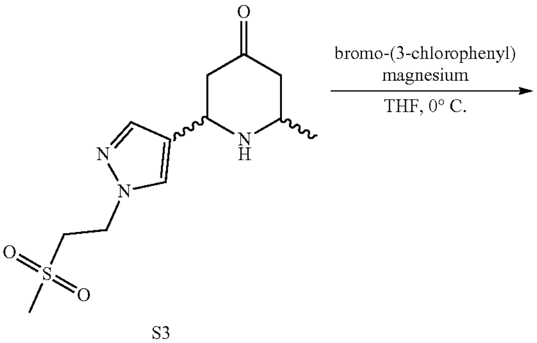

S3

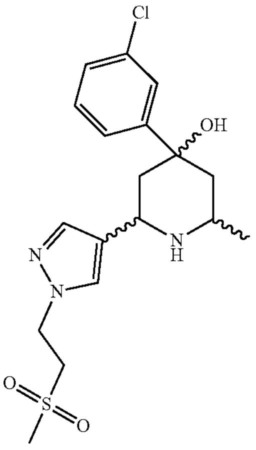

2

Compound 2 was prepared from compound S3 following the method described for Compound 1. The reaction was purified by silica gel chromatography (Gradient: 0-20% MeOH in DCM) and then reversed-phase HPLC (Method: Waters XSelect CSH C18 OBD Prep Column; 30×150 mm, 5 micron. Gradient: Acetonitrile in Water with 0.1% Trifluoroacetic Acid) to afford the title Compound 2 (2.0 mg, 2%) as a yellow solid. $^1$H NMR (300 MHz, Methanol-d4) δ 7.74 (s, 1H), 7.62 (s, 1H), 7.56 (t, J=2.0 Hz, 1H), 7.33 (t, J=7.8 Hz, 1H), 7.50-7.13 (m, 2H), 4.60 (t, J=6.5 Hz, 2H), 4.32 (dd, J=11.4, 3.4 Hz, 1H), 3.67 (t, J=6.5 Hz, 2H), 3.47-3.34 (m, 1H), 2.73 (s, 3H), 2.07-1.86 (m, 2H), 1.84-1.59 (m, 2H), 1.19 (d, J=6.4 Hz, 3H). ESI-MS m/z calc. 397.12268, found 398.26 (M+H)$^+$.

Compound 3
(2S,4R,6S)-4-(3-chlorophenyl)-2-methyl-6-(1-methyltriazol-4-yl)piperidin-4-ol (3)

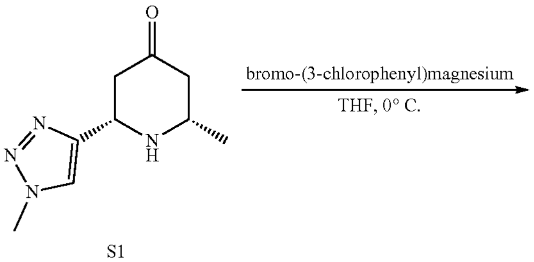

S1

-continued

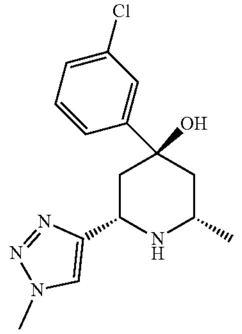

3

Compound 3 was prepared from compound S1 following the method described for Compound 1. The reaction mixture was purified by reversed-phase HPLC (Method: Waters XSelect CSH C18 OBD Prep Column; 30×150 mm, 5 micron. Gradient: Acetonitrile in Water with 10 mM Ammonium Hydroxide) to afford the title Compound 3 (2 mg, 1%) as a yellow solid. $^1$H NMR (300 MHz, Methanol-d4) δ 7.85 (s, 1H), 7.62-7.50 (m, 2H), 7.46-7.28 (m, 2H), 4.10 (s, 3H), 3.84 (dd, J=12.3, 2.4 Hz, 1H), 2.85-2.73 (m, 2H), 2.55 (dt, J=13.4, 2.5 Hz, 1H), 1.98-1.84 (m, 1H), 1.60 (dd, J=13.4, 11.8 Hz, 1H), 1.19 (d, J=6.3 Hz, 3H). ESI-MS m/z calc. 306.12473, found 307.32 (M+H)$^+$.

Compound 4
(2S,4S,6S)-4-(4-chlorophenyl)-2-methyl-6-(1-methyltriazol-4-yl)piperidin-4-ol (4)

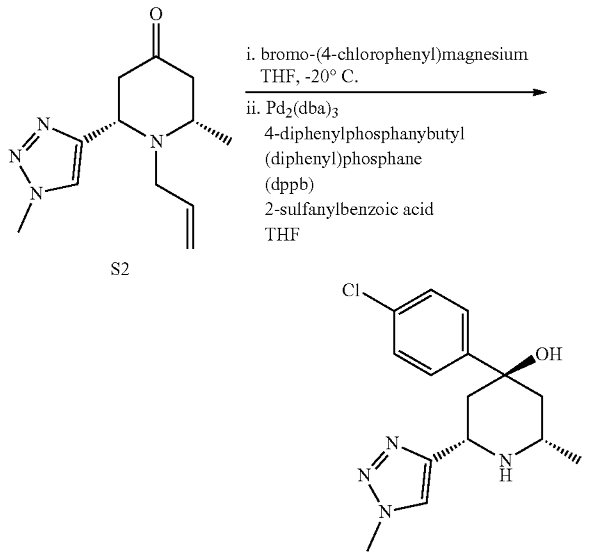

4

To a mixture of compound S2 (100 mg, 0.4268 mmol) in THF (2 mL) was added a diethyl ether solution of bromo-(4-chlorophenyl)magnesium (1 mL of 1 M, 1.000 mmol) at −20° C. (1:15). After addition, UPLC was obtained, which indicated complete conversion. The mixture was quenched with saturated aqueous ammonium chloride and then warmed to room temperature. The suspension was diluted with water (1 mL) and ethyl acetate (4 mL). The aqueous layer was washed with additional ethyl acetate (2×2 mL), and the combined organic layer was passed over a phase separator, concentrated, and minimally diluted in DCM and loaded onto a silica gel column for purification (Gradient: 0-10% MeOH in DCM) to afford the intermediate.

In an inert glovebox, to a mixture of $Pd_2(dba)_3$ (4 mg, 0.004368 mmol) and dppb (5 mg, 0.01172 mmol) in THF (0.5 mL) was added 2-sulfanylbenzoic acid (30 mg, 0.1946 mmol). The mixture was stirred under argon for 10 minutes (9:30). At this time, to the mixture was added the intermediate (60 mg, 0.1730 mmol) in THF (1 mL), and the reaction was stirred at room temperature for 20 minutes. At this time, the reaction was diluted with TBME (6 mL) and 1 M HCl (5 mL). The layers were mixed, and the organic layer was removed and extracted with 1 M HCl (5 mL). The organic layer was removed, and the combined aqueous layer was filtered through a 0.45 micron filter, washed with additional TBME (5 mL), pH adjusted with a combination of saturated aqueous sodium bicarbonate and 6 M NaOH until pH ~11. The hazy mixture was then extracted with DCM (3×5 mL), and the combined organic layer was passed over a phase separator and concentrated to yield the title Compound 4 (37.5 mg, 65%) as a pale yellow oil. $^1$H NMR (300 MHz, Chloroform-d) δ 7.50-7.43 (m, 2H), 7.41 (s, 1H), 7.32-7.26 (m, 2H), 4.51 (dd, J=9.6, 4.8 Hz, 1H), 4.03 (s, 3H), 3.79-3.68 (m, 1H), 3.38 (dtd, J=12.6, 6.3, 2.7 Hz, 1H), 2.07-1.92 (m, 2H), 1.88-1.75 (m, 2H), 1.59 (dd, J=13.6, 11.2 Hz, 1H), 1.14 (d, J=6.3 Hz, 3H). ESI-MS m/z calc. 306.12473, found 307.15 (M+H)$^+$.

Compound 5
(2S,4S,6S)-2-methyl-6-(1-methyltriazol-4-yl)-4-(p-tolyl)piperidin-4-ol (5)

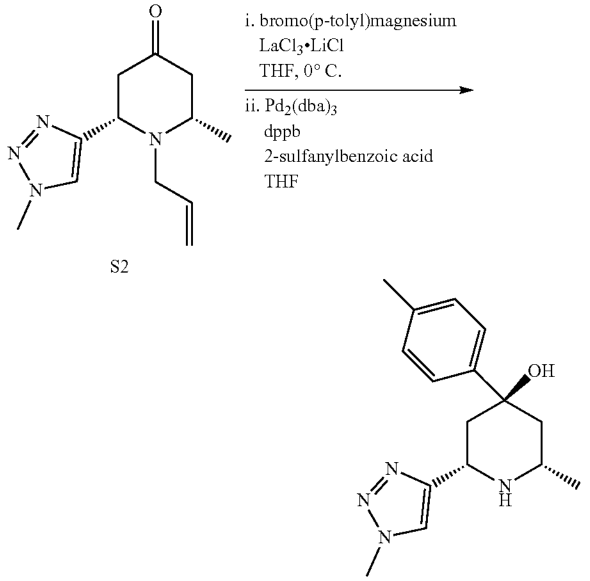

5

Compound S2 (20 mg, 0.08536 mmol) was diluted with a THF solution of chlorolithium; trichlorolanthanum (145 μL of 0.6 M, 0.0870 mmol) and cooled to −20° C. At this time, bromo(p-tolyl)magnesium (200 μL of 1 M, 0.200 mmol was added at −20° C. (1:15). After addition, UPLC was obtained, which indicated complete conversion. The mixture was quenched with saturated aqueous ammonium chloride (2 mL) and ethyl acetate (2 mL) and then warmed to room temperature. The aqueous layer was extracted with additional ethyl acetate (2×2 mL), and the combined organic layer was dried with magnesium sulfate, filtered, and concentrated in vacuo. The crude residue was used in the next step without further purification.

The crude mixture was diluted with THF (0.2 mL), and 2-sulfanylbenzoic acid (14 mg, 0.09080 mmol) was added. In an inert glovebox, a solution of dppb (2 mg, 0.004690 mmol) and $Pd_2(dba)_3$ (2 mg, 0.002184 mmol) in THF (0.2 mL) was prepared and, after 5 minutes of mixing, the light brown mixture was added to the intermediate mixture and the formed solution was stirred for 5 minutes. At this time, the reaction was diluted with ethyl acetate (1 mL) and 1 M TFA (2×0.75 mL). The aqueous layer was combined and purified by reversed-phase HPLC (Method: Waters XSelect CSH C18 OBD Prep Column; 30×150 mm, 5 micron. Gradient: 5-98% Acetonitrile in Water with 0.1% Trifluoroacetic Acid). The title Compound 5 (8.3 mg, 24%) was isolated as a clear amorphous solid $^1$H NMR (400 MHz, DMSO-d6) δ 9.27 (s, 1H), 8.89 (s, 1H), 8.24 (s, 1H), 7.38 (d, J=8.0 Hz, 2H), 7.19 (d, J=7.9 Hz, 2H), 5.65 (s, 1H), 4.79 (d, J=10.9 Hz, 1H), 4.09 (s, 3H), 3.72 (s, 1H), 2.40 (t, J=13.3 Hz, 1H), 2.29 (s, 3H), 2.07 (d, J=13.9 Hz, 1H), 2.03-1.85 (m, 2H), 1.28 (d, J=6.5 Hz, 3H).

ESI-MS m/z calc. 286.17935, found 287.36 $(M+H)^+$.

Compound 6
(2S,4S,6S)-2-methyl-6-(1-methyltriazol-4-yl)-4-(m-tolyl)piperidin-4-ol (6)

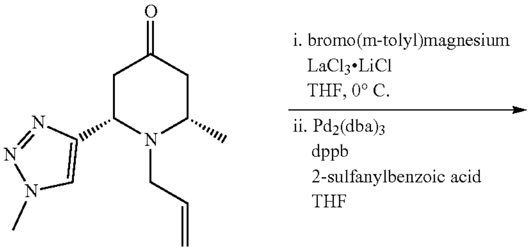

S2

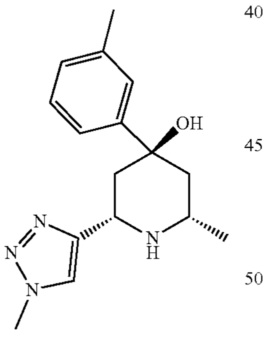

6

Compound 6 was synthesized from compound S2 following the method described for Compound 5, with purification by reversed-phase HPLC (Method: Waters XSelect CSH C18 OBD Prep Column; 30×150 mm, 5 micron. Gradient: 5-98% Acetonitrile in Water with 0.1% Trifluoroacetic Acid) to afford the title Compound 6 (8.3 mg, 24%) as a white solid. $^1$H NMR (400 MHz, DMSO-d6) δ 9.28 (s, 1H), 8.88 (s, 1H), 8.24 (s, 1H), 7.30 (d, J=10.4 Hz, 3H), 7.10 (t, J=4.1 Hz, 1H), 5.67 (s, 1H), 4.81 (d, J=11.7 Hz, 1H), 4.09 (s, 3H), 3.72 (s, 1H), 2.42 (t, J=13.4 Hz, 1H), 2.33 (s, 3H), 2.13-2.00 (m, 1H), 1.93 (dd, J=27.8, 13.0 Hz, 2H), 1.29 (d, J=6.5 Hz, 3H). ESI-MS m/z calc. 286.17935, found 287.32 $(M+H)^+$.

Compound 7
(2S,4S,6S)-2-methyl-6-(1-methyltriazol-4-yl)-4-(phenyl)piperidin-4-ol (7)

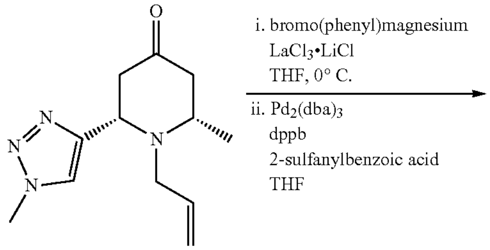

S2

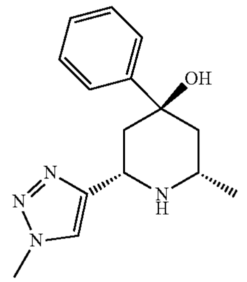

7

Compound 7 was synthesized from compound S2 following the method described for Compound 5, with purification by reversed-phase HPLC (Method: Waters XSelect CSH C18 OBD Prep Column; 30×150 mm, 5 micron. Gradient: 5-98% Acetonitrile in Water with 0.1% Trifluoroacetic Acid) to afford the title Compound 7 (8.9 mg, 25%) as a white solid. $^1$H NMR (400 MHz, DMSO-d6) δ 9.29 (s, 1H), 8.91 (s, 1H), 8.25 (s, 1H), 7.50 (d, J=7.7 Hz, 2H), 7.40 (t, J=7.6 Hz, 2H), 7.30 (d, J=7.3 Hz, 1H), 5.72 (s, 1H), 4.82 (s, 1H), 4.09 (s, 3H), 3.74 (s, 1H), 2.43 (t, J=13.3 Hz, 1H), 2.09 (d, J=14.1 Hz, 1H), 2.05-1.95 (m, 1H), 1.91 (d, J=14.0 Hz, 1H), 1.29 (d, J=6.5 Hz, 3H). ESI-MS m/z calc. 272.1637, found 273.32 $(M+H)^+$.

Compound 8
(2S,4S,6S)-4-(4-isopropylphenyl)-2-methyl-6-(1-methyltriazol-4-yl)piperidin-4-ol (8)

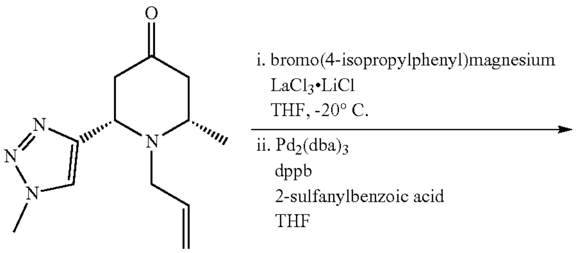

S2

-continued

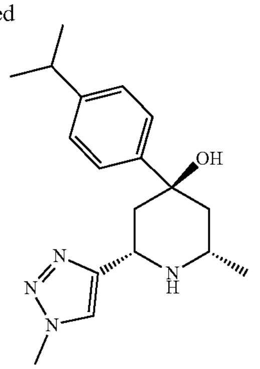

8 i. To a solution of compound S2 (80 mg, 0.3414 mmol) in THF (0.4 mL) was added a THF solution of chlorolithium; trichlorolanthanum (580 μL of 0.6 M, 0.3480 mmol), and the mixture was cooled to −20° C. At this time, bromo-(4-isopropylphenyl)magnesium (1.2 mL of 0.5 M, 0.6000 mmol) was added at −20° C. After 10 minutes, the mixture was quenched with saturated aqueous ammonium chloride (0.1 mL) and then warmed to room temperature. The suspension was diluted with water (2 mL) and EtOAc (2 mL), extracted with EtOAc (2×2 mL), dried over $Na_2SO_4$, filtered, and concentrated in vacuo to yield a crude residue.

ii. The crude mixture was diluted with THF (0.4 mL), and 2-sulfanylbenzoic acid (56 mg, 0.3632 mmol) was added. In a glovebox, a solution of dppb (4 mg, 0.009379 mmol) and $Pd_2(dba)_3$ (4 mg, 0.004368 mmol) was prepared and, after 30 minutes of mixing, the light brown mixture was added to the intermediate solution. The mixtures were stirred. After 30 minutes, full conversion was observed. The mixture was diluted with TBME (5 mL), followed by 1 M HCl (2×5 mL). The aqueous layer was removed and combined and then pH adjusted with aqueous NaOH (6 M, 1.7 mL) followed by saturated aqueous ammonium chloride to achieve pH ~9. The mixture was diluted and extracted with TBME (3×10 mL), and the combined organic layer was filtered through a phase separator and concentrated to a crude residue, which was purified by reversed-phase HPLC (Method: Waters XBridge Prep $C_8$ Column; 30×150 mm, 5 micron. Gradient: 5-98% Acetonitrile in Water with 10 mM Ammonium Hydroxide) to afford the title Compound 8 (23 mg, 21%) as a white solid. $^1$H NMR (400 MHz, Chloroform-d) δ 7.49-7.38 (m, 3H), 7.23 (d, J=8.3 Hz, 2H), 4.53 (p, J=7.0 Hz, 1H), 4.05 (s, 3H), 3.47-3.34 (m, 1H), 2.90 (hept, J=6.9 Hz, 1H), 2.11-2.05 (m, 2H), 1.89-1.63 (m, 3H), 1.25 (d, J=7.0 Hz, 6H), 1.16 (d, J=6.3 Hz, 3H). ESI-MS m/z calc. 314.21066, found 315.32 (M+H)$^+$.

Compound 9

(2S,4S,6S)-4-(3-chloro-4-fluoro-phenyl)-2-methyl-6-(1-methyltriazol-4-yl)piperidin-4-ol (9)

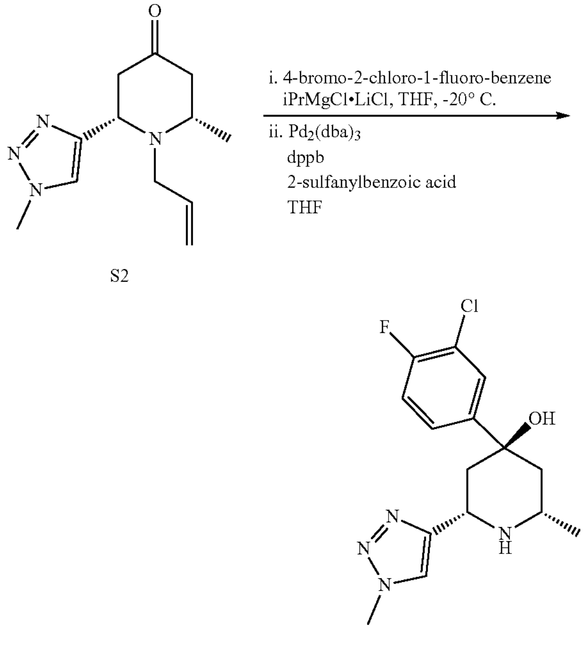

S2

9 i. A mixture of 4-bromo-2-chloro-1-fluoro-benzene (54 mg, 0.258 mmol) was diluted in THF (0.25 mL). To the mixture cooled to −20° C. was added Turbo Grignard (200 μL of 1.3 M, 0.260 mmol). The mixtures were stirred for 30 minutes (11:00), at which time a THF (0.25 mL) solution of compound S2 (20 mg, 0.0854 mmol) was added and the reactions were stirred for 45 minutes. At this time, saturated aqueous ammonium chloride was added, and the mixture was diluted with ethyl acetate (2 mL) and separated. The aqueous layer was extracted with additional ethyl acetate (2 mL), and the combined organic layer was passed over a phase separator, concentrated, and used in the next step directly.

ii. A mixture of $Pd_2(dba)_3$ (2 mg, 0.00218 mmol) and 4-diphenylphosphanylbutyl (diphenyl)phosphane (2 mg, 0.00469 mmol) in THF (0.25 mL) was stirred at room temperature under argon for 15 minutes. At this time, the intermediate from step i, (2S,4S,6S)-1-allyl-4-(3-chloro-4-fluorophenyl)-2-methyl-6-(1-methyl-1H-1,2,3-triazol-4-yl) piperidin-4-ol, and 2-sulfanylbenzoic acid (15 mg, 0.0973 mmol) in THF (0.25 mL) was added and the mixture was stirred for 10 minutes. The reaction was extracted with 1 M HCl (2×750 μL) and directly purified by reversed-phase HPLC. (Method: Waters XSelect CSH C18 OBD Prep Column; 30×150 mm, 5 micron. Gradient: 5-98% Acetonitrile in Water with 5 mM Hydrochloric Acid.) The title Compound 9 was isolated as a white solid. (7.6 mg, 23%)$^1$H NMR (300 MHz, Methanol-d4) δ 8.08 (s, 1H), 7.68 (dd, J=7.1, 2.4 Hz, 1H), 7.50 (ddd, J=8.7, 4.5, 2.4 Hz, 1H), 7.27 (t, J=8.9 Hz, 1H), 4.96 (dd, J=12.5, 3.1 Hz, 1H), 4.13 (s, 3H), 3.98-3.81 (m, 1H), 2.51 (dd, J=14.5, 12.5 Hz, 1H), 2.23 (d, J=14.3 Hz, 1H), 2.08-1.97 (m, 2H), 1.42 (d, J=6.6 Hz, 3H). ESI-MS m/z calc. 324.11533, found 325.34 (M+H)$^+$.

Compound 10
(2S,4S,6S)-4-(3-chloro-4-fluoro-phenyl)-2-methyl-6-(1-methyltriazol-4-yl)piperidin-4-ol (10)

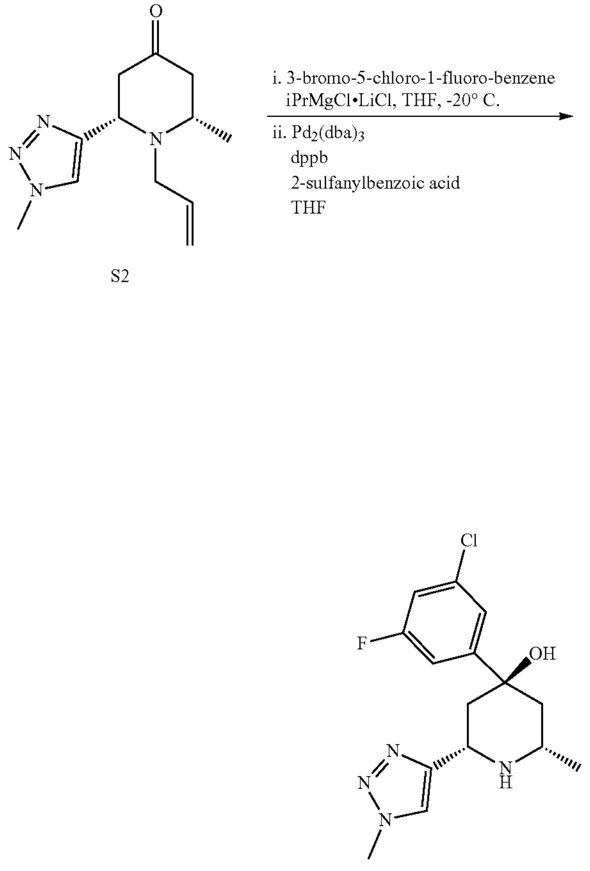

S2

10 i. A mixture of 1-bromo-3-chloro-5-fluoro-benzene (67 mg, 0.320 mmol) was diluted in THF (0.25 mL). To the mixture cooled to −20° C. was added Turbo Grignard (250 μL of 1.3 M, 0.325 mmol) followed by diglyme (50 μL, 0.349 mmol). The mixtures were stirred for 30 minutes, at which time a THF (0.25 mL) solution of compound S2 (25 mg, 0.107 mmol) was added and the reactions were stirred for 45 minutes. At this time, saturated aqueous ammonium chloride was added, and the mixture was diluted with ethyl acetate (2 mL) and separated. The aqueous layer was extracted with additional ethyl acetate (2 mL), and the combined organic layer was passed over a phase separator, concentrated, and used in the next step directly.

ii. A mixture of $Pd_2(dba)_3$ (2.5 mg, 0.00273 mmol) and 4-diphenylphosphanylbutyl (diphenyl)phosphane (2.5 mg, 0.00586 mmol) in THF (0.25 mL) was stirred at room temperature under argon for 15 minutes. At this time, the intermediate and 2-sulfanylbenzoic acid (18 mg, 0.117 mmol) in THF (0.25 mL) were added, and the mixture was stirred for 10 minutes. The reaction was extracted with 1 M HCl (2×750 μL) and directly purified by reversed-phase HPLC. (Method: Waters XSelect CSH C18 OBD Prep Column; 30×150 mm, 5 micron. Gradient: Acetonitrile in Water with 5 mM Hydrochloric Acid.) The title Compound 10 was isolated as a white solid (17 mg, 43%). $^1$H NMR (300 MHz, Methanol-d4) δ 8.08 (s, 1H), 7.68 (dd, J=7.1, 2.4 Hz, 1H), 7.50 (ddd, J=8.7, 4.5, 2.4 Hz, 1H), 7.27 (t, J=8.9 Hz, 1H), 4.96 (dd, J=12.5, 3.1 Hz, 1H), 4.13 (s, 3H), 3.98-3.81 (m, 1H), 2.51 (dd, J=14.5, 12.5 Hz, 1H), 2.23 (d, J=14.3 Hz, 1H), 2.08-1.97 (m, 2H), 1.42 (d, J=6.6 Hz, 3H). ESI-MS m/z calc. 324.781, found 325.29 $(M+H)^+$.

Compound 11
(2S,4S,6S)-4-(3-fluoro-4-methyl-phenyl)-2-methyl-6-(1-methyltriazol-4-yl)piperidin-4-ol (11)

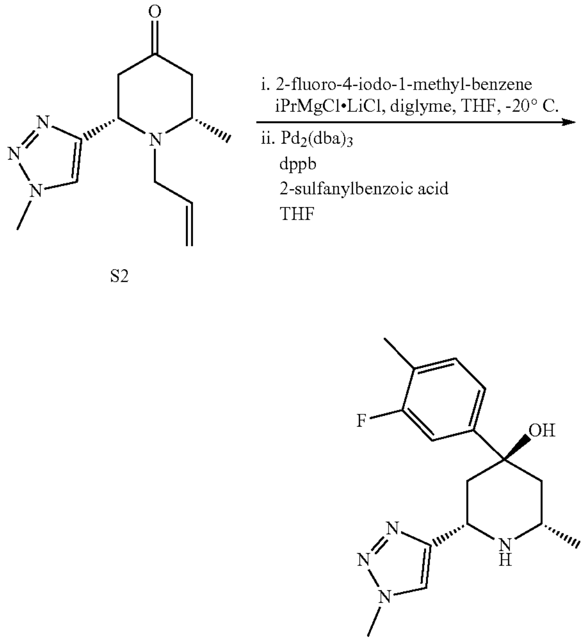

S2

11

Compound 11 was synthesized from compound S2 following the method described for Compound 10. Purification by reversed-phase HPLC (Method: Waters XSelect CSH C18 OBD Prep Column; 30×150 mm, 5 micron. Gradient: 5-98% Acetonitrile in Water with 5 mM Hydrochloric Acid) afforded the title Compound 11 (18.3 mg, 50%) as a white solid. $^1$H NMR (400 MHz, DMSO-d6) δ 9.46-9.18 (m, 2H), 8.32 (s, 1H), 7.30 (t, J=8.0 Hz, 1H), 7.27-7.14 (m, 2H), 5.80 (s, 1H), 4.77 (t, J=11.2 Hz, 1H), 4.09 (s, 3H), 3.70 (s, 1H), 2.46 (s, 1H), 2.22 (d, J=1.7 Hz, 3H), 2.08 (t, J=13.3 Hz, 2H), 1.88 (d, J=14.1 Hz, 1H), 1.31 (d, J=6.4 Hz, 3H). ESI-MS m/z calc. 304.363, found 305.34 $(M+H)^+$.

Compound 12
(2S,4S,6S)-4-(4-fluoro-3-methyl-phenyl)-2-methyl-6-(1-methyltriazol-4-yl)piperidin-4-ol (12)

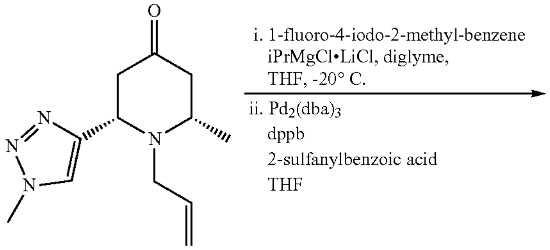

S2

-continued

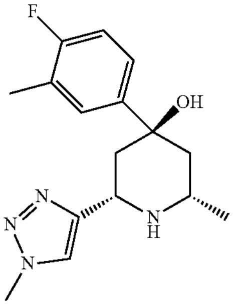

12

Compound 12 was synthesized from compound S2 following the method described for Compound 10. Purification by reversed-phase HPLC (Method: Waters XSelect CSH C18 OBD Prep Column; 30×150 mm, 5 micron. Gradient: Acetonitrile in Water with 5 mM Hydrochloric Acid) afforded the title Compound 12 (4.6 mg, 12%) as a white solid. $^1$H NMR (400 MHz, DMSO-d6) δ 9.37 (s, 2H), 8.34 (s, 1H), 7.43-7.31 (m, 2H), 7.31-7.05 (m, 2H), 5.71 (s, 1H), 4.76 (t, J=11.2 Hz, 1H), 4.09 (s, 3H), 3.69 (s, 1H), 2.25 (d, J=1.9 Hz, 3H), 2.08 (t, J=15.7 Hz, 2H), 1.88 (d, J=13.9 Hz, 1H), 1.31 (d, J=6.4 Hz, 3H). ESI-MS m/z calc. 304.363, found 305.34 (M+H)$^+$.

Compound 13

(2S,4S,6S)-4-(4-fluoro-3-methyl-phenyl)-2-methyl-6-(1-methyltriazol-4-yl)piperidin-4-ol (13)

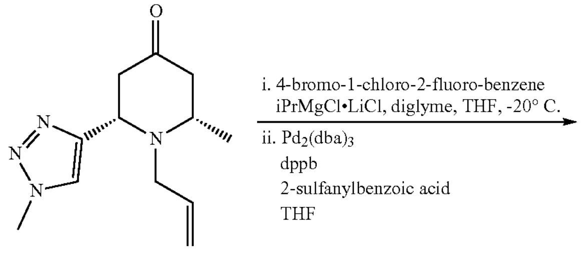

S2

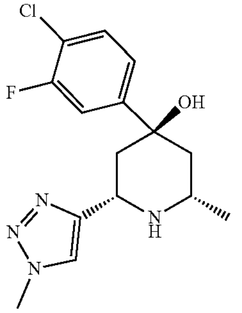

13

Compound 13 was synthesized from compound S2 following the method described for Compound 10. Purification by reversed-phase HPLC (Method: Waters XSelect CSH C18 OBD Prep Column; 30×150 mm, 5 micron. Gradient: 5-98% Acetonitrile in Water with 5 mM Hydrochloric Acid) afforded the title Compound 13 (23 mg, 59%) as a white solid. $^1$H NMR (300 MHz, Methanol-d4) δ 8.12 (s, 1H), 7.54-7.41 (m, 2H), 7.36 (dd, J=8.5, 2.2 Hz, 1H), 4.97 (dd, J=12.5, 3.1 Hz, 1H), 4.13 (s, 3H), 3.97-3.82 (m, 1H), 2.55 (dd, J=14.5, 12.6 Hz, 1H), 2.22 (d, J=13.8 Hz, 1H), 2.11-2.01 (m, 2H), 1.43 (d, J=6.6 Hz, 3H). ESI-MS m/z calc. 324.781, found 325.29 (M+H)$^+$.

Compound 14

(2S,6S)-2-methyl-6-(1-methyltriazol-4-yl)-4-[5-(trifluoromethyl)-3-thienyl]piperidin-4-ol (14)

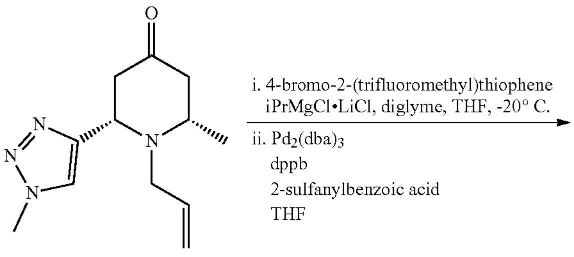

S2

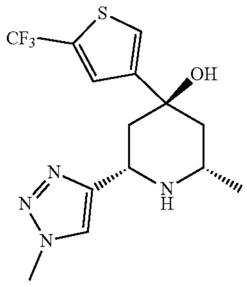

14

Compound 14 was synthesized from compound S2 following the method described for Compound 10. Purification by reversed-phase HPLC (Method: Waters XSelect CSH C18 OBD Prep Column; 30×150 mm, 5 micron. Gradient: Acetonitrile in Water with 5 mM Hydrochloric Acid) afforded the title Compound 14 (21 mg, 51%) as a white solid. ESI-MS m/z calc. 346.371, found 347.28 (M+H)$^+$.

Compound 15

(2S,4S,6S)-4-(4-fluorophenyl)-2-methyl-6-(1-methyltriazol-4-yl)piperidin-4-ol (15)

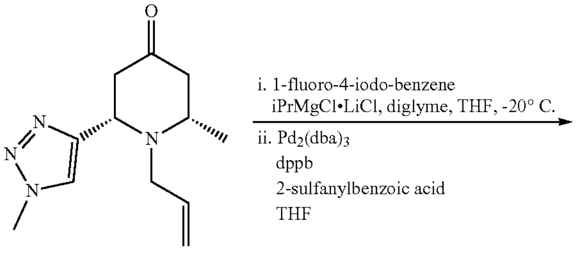

S2

-continued

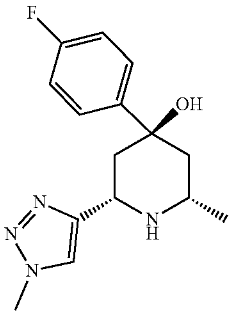

15

Compound 15 was synthesized from compound S2 following the method described for Compound 10. Purification by reversed-phase HPLC (Method: Waters XSelect CSH C18 OBD Prep Column; 30×150 mm, 5 micron. Gradient: 5-98% Acetonitrile in Water with 5 mM Hydrochloric Acid) afforded the title Compound 15 (17 mg, 46%) as a white solid. $^1$H NMR (400 MHz, DMSO-d6) δ 9.47 (d, J=10.1 Hz, 1H), 9.18 (d, J=10.2 Hz, 1H), 8.28 (s, 1H), 7.79-7.61 (m, 1H), 7.36 (dt, J=11.0, 5.4 Hz, 1H), 7.30-7.08 (m, 2H), 6.02 (s, 1H), 4.82 (t, J=11.4 Hz, 1H), 4.09 (s, 3H), 3.75 (s, 1H), 2.70 (t, J=13.3 Hz, 1H), 2.24 (t, J=13.1 Hz, 1H), 2.10 (d, J=14.0 Hz, 1H), 1.91 (d, J=13.9 Hz, 1H), 1.30 (d, J=6.5 Hz, 3H). ESI-MS m/z calc. 290.336, found 291.34 $(M+H)^+$.

Compound 16
(2S,4S,6S)-2-methyl-6-(1-methyltriazol-4-yl)-4-[4-(trifluoromethyl)phenyl]piperidin-4-ol (16)

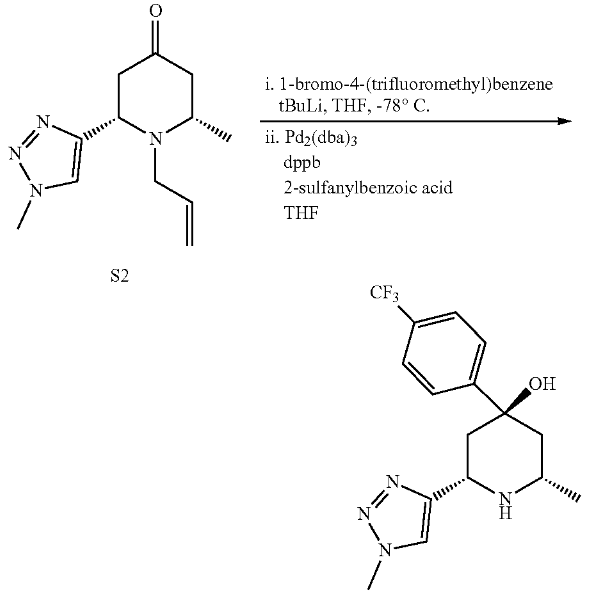

S2

16

Step i: A THF (10 mL) solution of 1-bromo-4-(trifluoromethyl)benzene (600 µL, 4.285 mmol) was cooled to −78° C. At this time, a pentane solution of tBuLi (5 mL of 1.7 M, 8.500 mmol) was added dropwise over 20 minutes, and the yellow suspension was stirred at this temperature for 30 minutes. At this time, a THF solution of compound S2 (5 mL of 0.427 M, 2.135 mmol) was added dropwise over 20 minutes. After 30 minutes, the reaction was quenched with saturated aqueous ammonium chloride (10 mL) and diluted with ether (20 mL) and water (10 mL). The aqueous layer was extracted with additional ether (20 mL), and the combined organic layer was washed with brine (20 mL), dried with magnesium sulfate, filtered, and concentrated. The crude material was minimally dissolved in DCM and loaded onto a silica gel column for purification (Gradient: 0-10% MeOH in DCM). The product-containing fractions were pooled and concentrated. The sequence was repeated twice more and combined for the next step, about 60% yield per reaction.

Alternative Preparation of Step i:

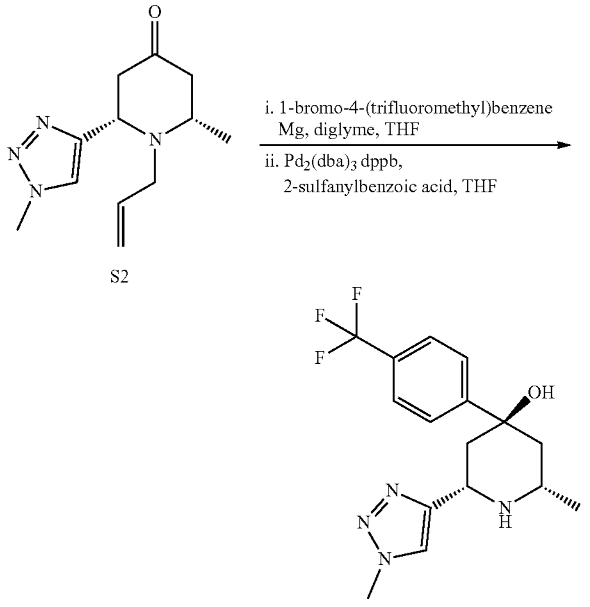

S2

16

To a suspension of magnesium (1.712 g, 70.44 mmol) in THF (100 mL) under nitrogen atmosphere was added one drop of 1,2-dibromoethane followed by 1-bromo-4-(trifluoromethyl)benzene (14.88 g, 66.13 mmol). The mixture was sonicated for 5 minutes and allowed to stir at ambient temperature for 1 hour. The solution was cooled to −10° C. to −15° C. via salt ice bath, and diglyme (3.123 mL, 21.81 mmol) was added, followed by a THF solution of (2S,6S)-1-allyl-2-methyl-6-(1-methyltriazol-4-yl)piperidin-4-one (49.98 mL of 0.427 M, 21.34 mmol), dropwise. Stirring was continued for 45 minutes. The mixture was quenched with water (50 mL) and pH adjusted to pH ~9 with ammonium chloride (50 mL), extracted with ether (2×100 mL), and the organic layer was washed with brine (50 mL) and dried with magnesium sulfate, filtered, and concentrated. The concentrate was minimally diluted in DCM and loaded onto a silica gel column for purification (Gradient: 0-10% MeOH in DCM). The product-containing fractions were pooled and concentrated to yield (2S,4S,6S)-1-allyl-2-methyl-6-(1-methyltriazol-4-yl)-4-[4-(trifluoromethyl)phenyl]piperidin-4-ol (4.350 g, 51%) ESI-MS m/z calc. 380.1824, found 381.2 $(M+H)^+$ as an off-white solid, which was used in the next step.

Step ii: To the intermediate (1.756 g, 4.496 mmol) diluted with THF (5 mL) was added 2-sulfanylbenzoic acid (740 mg, 4.607 mmol). In an inert glovebox, a solution of dppb (20 mg, 0.04690 mmol) and $Pd_2(dba)_3$ (20 mg, 0.02184 mmol) in THF (5 mL) was prepared and, after 10 minutes of mixing, the light brown solution was added to the previous mixture. The newly formed brown solution was stirred for 35 minutes. At this time, the mixture was diluted with TBME (30 mL), followed by 1 M HCl (2×20 mL). The aqueous layer was removed and combined and then pH adjusted with aqueous NaOH (7.4 mL of 6 M, 44.40 mmol), followed by ~1 mL saturated aqueous ammonium chloride to achieve pH ~9. The mixture was diluted and extracted with TBME (3×20 mL), and the combined organic layer was dried with brine (20 mL) that was pH adjusted with saturated aqueous ammonium chloride to pH ~9. The organic layer was dried with magnesium sulfate, and to the suspension was added MP-TMT resin (350 mg, 0.66 mmol/g) and the suspension was stirred for 2 hours, and then filtered and concentrated. The foam was diluted in 30 mL TBME and to the yellow solution was added a dioxane solution of HCl (1.2 mL of 4 M, 4.800 mmol) dropwise, which immediately resulted in a loss of color in the mixture and a white precipitate. The suspension was stirred for 3 minutes and then filtered, rinsed with additional TBME, and dried for 3 days at 70° C. to yield the title Compound 16 (1.463 g, 84%) as an off-white solid. $^1H$ NMR (300 MHz, Methanol-d4) δ 7.85 (s, 1H), 7.72 (d, J=8.3 Hz, 2H), 7.64 (d, J=8.3 Hz, 2H), 4.49 (dd, J=9.1, 5.5 Hz, 1H), 4.08 (s, 3H), 3.40 (dtd, J=12.9, 6.5, 2.9 Hz, 1H), 2.14-2.02 (m, 2H), 1.86-1.76 (m, 1H), 1.67 (dd, J=13.6, 11.2 Hz, 1H), 1.19 (d, J=6.4 Hz, 3H). ESI-MS m/z calc. 340.1511, found 341.14 $(M+H)^+$.

Preparation and Characterization of Compound 16 Form A

To (2S,4S,6S)-1-allyl-2-methyl-6-(1-methyltriazol-4-yl)-4-[4-(trifluoromethyl) phenyl]piperidin-4-ol (1.534 g, 3.928 mmol) diluted with THF (4.365 mL) was added 2-sulfanylbenzoic acid (646.0 mg, 4.022 mmol). In an inert glovebox, a solution of dppb (17.47 mg, 0.04096 mmol) and $Pd_2dba_3$ (17.47 mg, 0.01908 mmol) in THF (4.365 mL) was prepared and after 10 min of mixing the light brown solution was added to the previous mixture. The newly formed brown solution was stirred for 35 min. At this time, the mixture was diluted with TBME (30 mL) followed by 1 N HCl (2×20 mL). The aqueous layer was removed and combined and then pH adjusted with aqueous NaOH (6.463 mL of 6 M, 38.78 mmol) followed by ~1 mL sat. aq. ammonium chloride to achieve pH ~9. The mixture was diluted and extracted with TBME (3×20 mL), and the combined organic layer was dried with brine (10 mL) that was pH adjusted with sat. aq. ammonium chloride to pH ~9. The organic layer was dried with magnesium sulfate, and filtered through a pad of Florisil and slowly rotovated while allowing for crystallization to a dense white solid.

Material was diluted in MTBE to homogenize, and then slowly concentrated while observing a dense white solid precipitating out of solution. The resulting white solid was dried in vacuum oven overnight at 60° C.

X-Ray Powder Diffraction

The X-ray powder diffraction (XRPD) diffractogram of Compound 16 Form A was acquired at room temperature in transmission mode using a PANalytical Empyrean system equipped with a sealed tube source and a PIXcel 3D Medipix-3 detector (Malvern Pa.Nalytical Inc, Westborough, Massachusetts). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.0131303° and 49s per step. The results are depicted in FIG. 1 and the table below:

| XRPD Peaks | Angle (°2θ ± 0.2) | Intensity % |
|---|---|---|
| 1 | 19.9 | 100.0 |
| 2 | 20.0 | 60.3 |
| 3 | 10.9 | 28.5 |
| 4 | 20.6 | 26.6 |
| 5 | 20.5 | 24.0 |
| 6 | 16.1 | 20.4 |
| 7 | 17.5 | 19.6 |
| 8 | 19.3 | 19.6 |
| 9 | 22.8 | 16.9 |
| 10 | 26.1 | 15.8 |
| 11 | 23.8 | 15.0 |
| 12 | 21.7 | 14.4 |
| 13 | 18.2 | 14.4 |
| 14 | 23.3 | 13.3 |
| 15 | 26.2 | 12.9 |
| 16 | 14.1 | 12.9 |
| 17 | 21.4 | 10.9 |
| 18 | 15.4 | 10.1 |

Thermogravimetric Analysis (TGA):

Thermal gravimetric analysis of Compound 16 Form A was measured using the TA5500 Discovery TGA. A sample with a weight of approximately 1-10 mg in a open platinum pan. The program was set to heat from ambient at a heating rate of 10° C. per min to 350° C. with nitrogen purge. The TGA thermogram shows minimal weight loss from ambient until 250° C. The TGA thermogram is shown as FIG. 2.

Differential Scanning Calorimetry Analysis (DSC):

DSC analysis of Compound 16 Form A was measured using the TA Instruments TA2500 DSC. A sample with a weight between 1-10 mg was weighed into an aluminum crimp sealed pan with a pinhole. This pan was placed in the sample position in the calorimeter cell. An empty pan was placed in the reference position. The calorimeter cell was closed, and a flow of nitrogen was passed through the cell. The program was set with a heat rate at 10° C. per min to a temperature of 250° C. The thermogram (FIG. 3) shows one endotherm peak at 147° C.

Solid State NMR

A Bruker-Biospin 400 MHz wide-bore spectrometer equipped with Bruker-Biospin 4 mm HFX probe was used. Samples were packed into 4 mm $ZrO_2$ rotors and spun under Magic Angle Spinning (MAS) condition with spinning speed typically set to 12.5 kHz. The proton relaxation time was measured using $^1H$ MAS $T_1$ saturation recovery relaxation experiment in order to set up proper recycle delay of the $^{13}C$ cross-polarization (CP) MAS experiment. The fluorine relaxation time was measured using $^{19}F$ MAS $T_1$ saturation recovery relaxation experiment in order to set up proper recycle delay of the $^{19}F$ MAS experiment. The CP contact time of carbon CPMAS experiments was set to 2 ms. A CP proton pulse with linear ramp (from 50% to 100%) was employed. The carbon Hartmann-Hahn match was optimized on external reference sample (glycine). Carbon and fluorine spectra were recorded with proton decoupling using TPPM15 decoupling sequence with the field strength of approximately 100 kHz. The results are shown in FIG. 4 ($^{13}C$ CPMAS) and in the tables below:

$^{13}C$ CPMAS SSNMR

| Peak # | Chem Shift [ppm] | Intensity [rel] |
|---|---|---|
| 1 | 153.5 | 3.57 |
| 2 | 151.5 | 5.83 |

-continued

| $^{13}$C CPMAS SSNMR | | |
|---|---|---|
| Peak # | Chem Shift [ppm] | Intensity [rel] |
| 3 | 126.9 | 3.7 |
| 4 | 125.1 | 1.05 |
| 5 | 123.9 | 0.95 |
| 6 | 122.1 | 5.34 |
| 7 | 73.6 | 6.95 |
| 8 | 49.9 | 10 |
| 9 | 47.2 | 3.72 |
| 10 | 37.2 | 9.7 |
| 11 | 23.0 | 7.77 |

| 19F SSNMR | | |
|---|---|---|
| Peak # | Chem Shift [ppm] | Intensity [rel] |
| 1 | −58.0 | 10 |

Single Crystal Elucidation:

Single crystals having the Compound 16 Form A structure were grown from DVS cycling experiment at room temperature (25±2° C.) from 0%-95%-0% Relative Humidity. X-ray diffraction data were acquired at 100 K on a Bruker diffractometer equipped with Cu $K_\alpha$ radiation (λ=1.54178 Å) and a CMOS detector. The structure was solved and refined using SHELX programs (Sheldrick, G. M., Acta Cryst., (2008) A64, 112-122) and results are summarized below.

Single Crystal Elucidation of Compound 16 Form A at 100 K

| Crystal System | Orthorhombic |
|---|---|
| Space Group | P212121 |
| a (Å) | 5.02810(10) |
| b (Å) | 9.0057(2) |
| c (Å) | 34.4600(8) |
| α (°) | 90 |
| β (°) | 90 |
| γ (°) | 90 |
| V (Å$^3$) | 1560.40(6) |
| Z/Z' | 4/1 |
| Temperature | 100K |

Single Crystal Elucidation of Compound 16 Form A at 298 K

| Crystal System | Orthorhombic |
|---|---|
| Space Group | P212121 |
| a (Å) | 5.11990(10) |
| b (Å) | 9.1779(2) |
| c (Å) | 34.4956(8) |
| α (°) | 90 |
| β (°) | 90 |
| γ (°) | 90 |
| V (Å$^3$) | 1620.95(6) |
| Z/Z' | 4/1 |
| Temperature | 298K |

Compound 17
(2S,4S,6S)-4-(6-chloro-3-pyridyl)-2-methyl-6-(1-methyltriazol-4-yl)piperidin-4-ol (17)

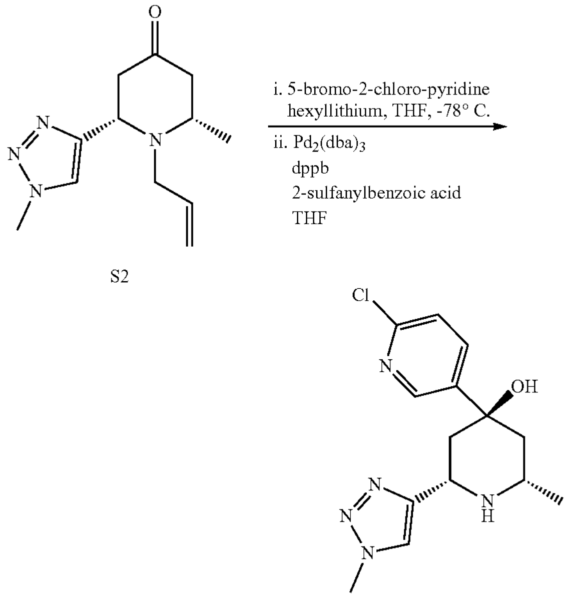

S2

17

Step i: A mixture of 5-bromo-2-chloro-pyridine (38 mg, 0.198 mmol) in THF (0.2 mL) was cooled to −78° C. At this time, hexyllithium (85 μL of 2.3 M, 0.196 mmol) was added, and the mixture was stirred at this temperature for 15 minutes. The reaction turned blue within 5 minutes. At this time, a THF solution of compound S2 (0.2 mL of 0.5 M, 0.100 mmol) was added over 30 seconds. After 5 minutes, the mixture was diluted with saturated aqueous ammonium chloride (2 mL) and ethyl acetate (2 mL). The aqueous layer was extracted with additional ethyl acetate (2×2 mL), and the combined organic layer was dried with magnesium sulfate, filtered, concentrated, and minimally diluted in DCM and loaded onto a silica gel column for purification (0-10% MeOH in DCM). Two spots were isolated, correlating to the major and minor diastereomers. The product containing fractions were pooled and concentrated.

Step ii: The intermediate was diluted with THF (250 μL), and 2-sulfanylbenzoic acid (17 mg, 0.110 mmol) was added. In a glovebox, a solution of dppb (2 mg, 0.00469 mmol) and $Pd_2(dba)_3$ (2 mg, 0.00218 mmol) in THF (250 μL) was prepared and, after 5 minutes of mixing, the light brown mixture was added to the intermediate solutions. The mixtures were stirred (8:20). After 5 minutes, full conversion was observed. The mixture was diluted and split with 1 M HCl (2×750 μL). The combined aqueous layer was pH adjusted with saturated aqueous sodium bicarbonate (1 mL), followed by extraction with DCM (3×5 mL). The organic layer was passed over a phase separator and concentrated to yield the title compound afford the title Compound 17 (7.6 mg, 16%) as a white solid. $^1$H NMR (300 MHz, Methanol-d4) δ 8.55 (d, J=2.6 Hz, 1H), 8.06 (s, 1H), 7.98 (dd, J=8.4, 2.7 Hz, 1H), 7.50 (d, J=8.4 Hz, 1H), 4.99 (d, J=12.5 Hz, 1H), 4.13 (s, 3H), 3.94 (s, 1H), 2.58-2.45 (m, 1H), 2.29 (d, J=14.9 Hz, 1H), 2.20-1.97 (m, 2H), 1.43 (d, J=6.6 Hz, 3H). ESI-MS m/z calc. 307.12, found 308.32 (M+H)$^+$.

Compound 18
(2S,4S,6S)-4-(5-chloro-3-pyridyl)-2-methyl-6-(1-methyltriazol-4-yl)piperidin-4-ol (18)

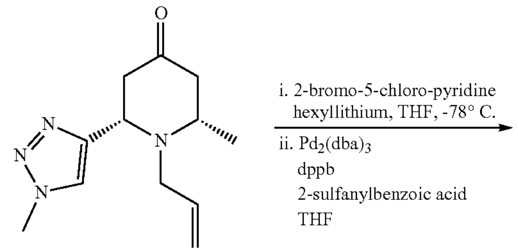

S2

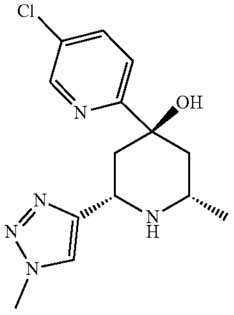

18

Compound 18 was synthesized from compound S2 following the method described for Compound 17. Purification by reversed-phase HPLC (Method: Waters XSelect CSH C18 OBD Prep Column; 30×150 mm, 5 micron. Gradient: Acetonitrile in Water with 0.1% trifluoroacetic acid) afforded the title Compound 18 (3.1 mg, 5%) as a clear oil. $^1$H NMR (300 MHz, Methanol-d4) δ 8.54 (s, 1H), 8.04 (s, 1H), 7.89 (d, J=8.9 Hz, 1H), 7.75 (d, J=8.7 Hz, 1H), 4.95 (d, J=15.1 Hz, 1H), 4.12 (s, 3H), 3.89 (s, 1H), 2.79-2.66 (m, 1H), 2.35-2.22 (m, 1H), 2.17 (d, J=14.9 Hz, 1H), 1.99 (d, J=13.7 Hz, 1H), 1.41 (d, J=6.5 Hz, 3H). ESI-MS m/z calc. 307.12, found 308.36 $(M+H)^+$.

Compound 19
(2S,4S,6S)-4-(4-chloro-3-methoxy-phenyl)-2-methyl-6-(1-methyltriazol-4-yl)piperidin-4-ol (19)

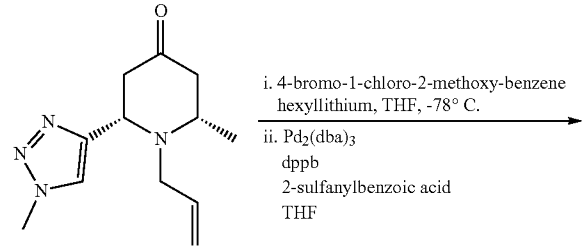

S2

-continued

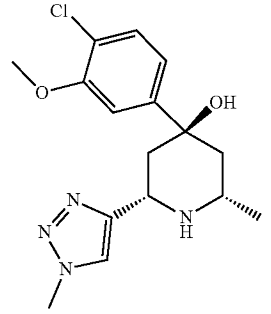

19

Compound 19 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 19 (3.8 mg, 8%) as a clear oil. $^1$H NMR (300 MHz, Methanol-d4) δ 8.06 (s, 1H), 7.37 (d, J=8.2 Hz, 1H), 7.26 (s, 1H), 7.05 (d, J=8.5 Hz, 1H), 4.97 (d, J=12.3 Hz, 1H), 4.13 (s, 3H), 3.92 (s, 4H), 2.57-2.45 (m, 1H), 2.24 (d, J=14.5 Hz, 1H), 2.05 (d, J=10.6 Hz, 2H), 1.42 (d, J=6.6 Hz, 3H). ESI-MS m/z calc. 336.135, found 337.30 $(M+H)^+$.

Compound 20
(2S,4S,6S)-4-(4-chloro-2-methoxy-phenyl)-2-methyl-6-(1-methyltriazol-4-yl)piperidin-4-ol (20)

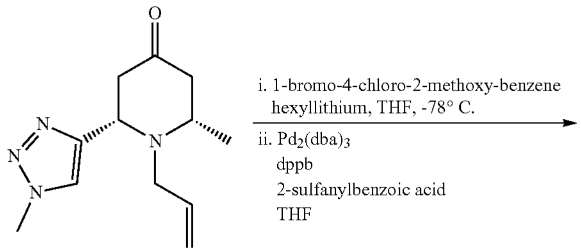

S2

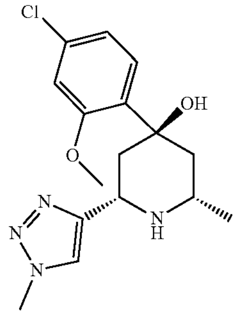

20

Compound 20 was synthesized from compound S2 following the method described for Compound 17. Purification by reversed-phase HPLC (Method: Waters XSelect CSH C18 OBD Prep Column; 30×150 mm, 5 micron. Gradient: Acetonitrile in Water with 0.1% trifluoroacetic acid) afforded the title Compound 20 (7.3 mg, 16%) as a clear oil. $^1$H NMR (300 MHz, Methanol-d4) δ 8.03 (s, 1H), 7.59 (d, J=8.4 Hz, 1H), 7.07 (d, J=1.8 Hz, 1H), 7.04-6.94 (m, 1H), 4.96 (d, J=12.7 Hz, 1H), 4.12 (s, 3H), 3.90 (s, 4H), 3.03 (s, 1H), 2.65-2.52 (m, 1H), 2.03 (s, 1H), 1.88 (d, J=14.4 Hz, 1H), 1.39 (d, J=6.8 Hz, 3H). ESI-MS m/z calc. 336.135, found 337.35 $(M+H)^+$.

Compound 21

(2S,4S,6S)-4-(4-chloro-2-methyl-phenyl)-2-methyl-6-(1-methyltriazol-4-yl)piperidin-4-ol (21)

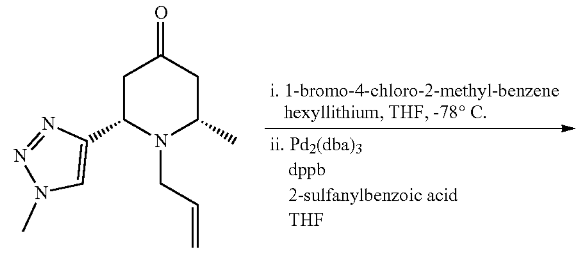

S2

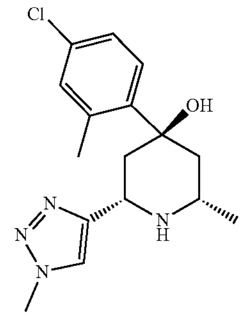

21

Compound 21 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 21 (3.8 mg, 9%) as a clear oil. $^1$H NMR (300 MHz, Methanol-d4) δ 8.08 (s, 1H), 7.42 (d, J=8.5 Hz, 1H), 7.23 (s, 1H), 7.19 (d, J=8.6 Hz, 1H), 5.05-4.97 (m, 1H), 4.14 (s, 3H), 3.96 (s, 1H), 2.63 (s, 3H), 2.48 (dd, J=21.7, 13.0 Hz, 2H), 2.29 (d, J=14.3 Hz, 1H), 2.10-1.97 (m, 1H), 1.42 (d, J=6.6 Hz, 3H). ESI-MS m/z calc. 320.140, found 321.32 $(M+H)^+$.

Compound 22

(2S,4S,6S)-4-(4-chloro-2-fluoro-phenyl)-2-methyl-6-(1-methyltriazol-4-yl)piperidin-4-ol (22)

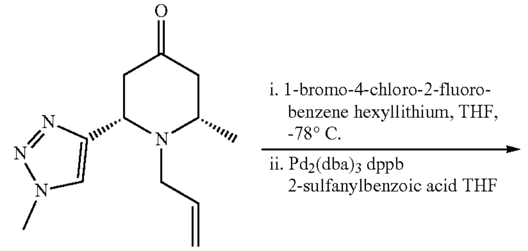

S2

-continued

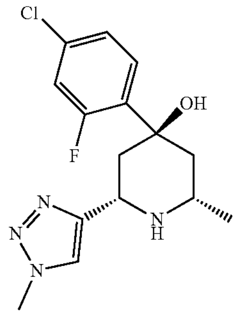

22

Compound 22 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 22 (5.7 mg, 12%) as a clear oil. $^1$H NMR (300 MHz, Methanol-d4) δ 8.04 (s, 1H), 7.69 (t, J=8.6 Hz, 1H), 7.34 (s, 2H), 4.99 (d, J=12.2 Hz, 1H), 4.12 (s, 3H), 3.92 (s, 1H), 2.84-2.72 (m, 1H), 2.38-2.26 (m, 1H), 2.20 (d, J=14.5 Hz, 1H), 2.03 (d, J=14.6 Hz, 1H), 1.40 (d, J=6.6 Hz, 3H). ESI-MS m/z calc. 324.115, found 325.29 $(M+H)^+$.

Compound 23

(2S,4S,6S)-4-[4-chloro-3-(trifluoromethoxy)phenyl]-2-methyl-6-(1-methyltriazol-4-yl)piperidin-4-ol (23)

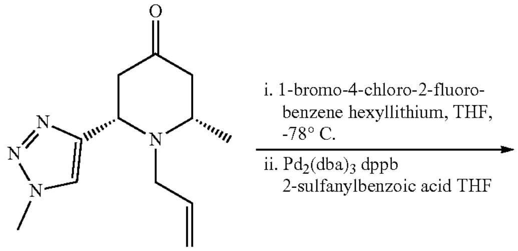

S2

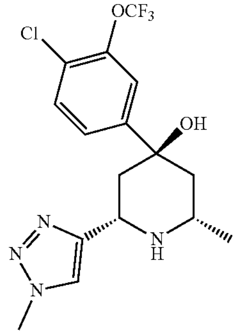

23

Compound 23 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 23 (22.3 mg, 44%) as a white solid. $^1$H NMR (300 MHz, Methanol-d4) δ 8.06 (s, 1H), 7.64 (s, 1H), 7.62 (d, J=8.7 Hz, 1H), 7.52 (dd, J=8.6, 2.1 Hz, 1H), 4.98 (dd, J=12.4, 3.1 Hz, 1H), 4.13 (s, 3H), 3.90 (p, J=7.0, 6.5 Hz, 1H), 2.52 (dd, J=14.4, 12.6 Hz, 1H), 2.23 (d, J=14.6 Hz, 1H), 2.11-1.94 (m, 2H), 1.42 (d, J=6.6 Hz, 3H). ESI-MS m/z calc. 390.107, found 391.22 $(M+H)^+$.

Compound 24
2-chloro-5-[(2S,4S,6S)-4-hydroxy-2-methyl-6-(1-methyltriazol-4-yl)piperidyl]-N,N-dimethyl-benzamide (24)

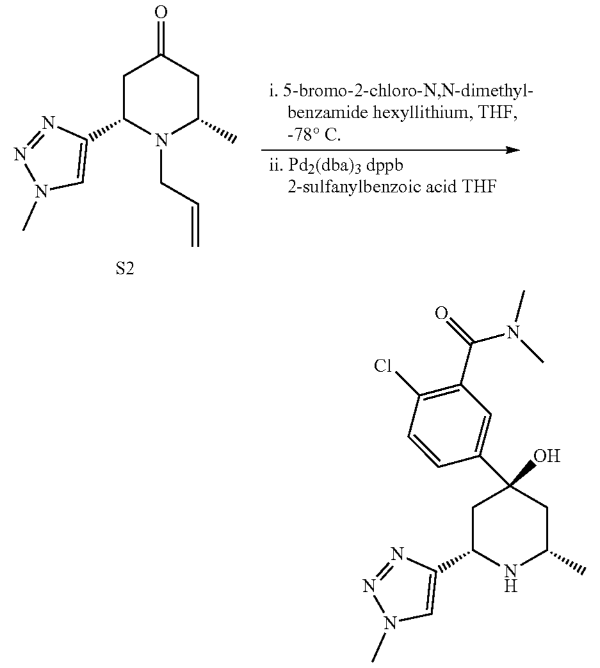

S2

24

Compound 24 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 24 (3 mg, 6%) as a clear oil. $^1H$ NMR (300 MHz, Methanol-d4) δ 8.05 (s, 1H), 7.59 (s, 1H), 7.52 (d, J=8.3 Hz, 2H), 4.97 (d, J=15.8 Hz, 1H), 4.13 (s, 3H), 3.95-3.89 (m, 1H), 3.13 (s, 3H), 2.89 (s, 3H), 2.50 (s, 1H), 2.21 (s, 1H), 2.06 (d, J=5.7 Hz, 2H), 1.41 (d, J=6.6 Hz, 3H). ESI-MS m/z calc. 377.162, found 378.3 $(M+H)^+$.

Compound 25
(2S,4S,6S)-4-[3-fluoro-4-(trifluoromethyl)phenyl]-2-methyl-6-(1-methyltriazol-4-yl)piperidin-4-ol (25)

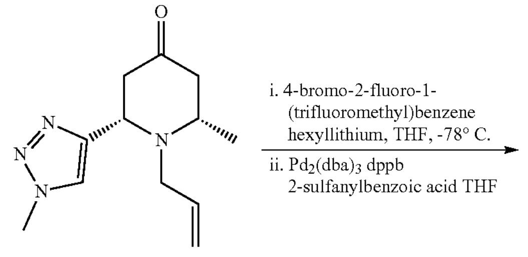

S2

-continued

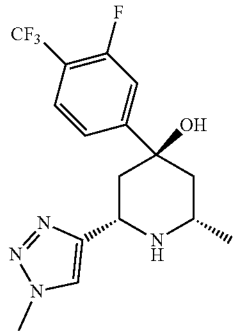

25

Compound 25 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 25 (8.4 mg, 17%) as a white solid. $^1H$ NMR (300 MHz, Methanol-d4) δ 8.06 (s, 1H), 7.74 (t, J=8.0 Hz, 1H), 7.58-7.49 (m, 2H), 5.03-4.95 (m, 1H), 4.13 (s, 3H), 3.92 (dd, J=10.9, 5.9 Hz, 1H), 2.58-2.47 (m, 1H), 2.24 (d, J=14.2 Hz, 1H), 2.06 (d, J=10.4 Hz, 2H), 1.42 (d, J=6.6 Hz, 3H). ESI-MS m/z calc. 358.142, found 359.29 $(M+H)^+$.

Compound 26
(2S,4S,6S)-4-(4-chloro-3-methyl-phenyl)-2-methyl-6-(1-methyltriazol-4-yl)piperidin-4-ol (26)

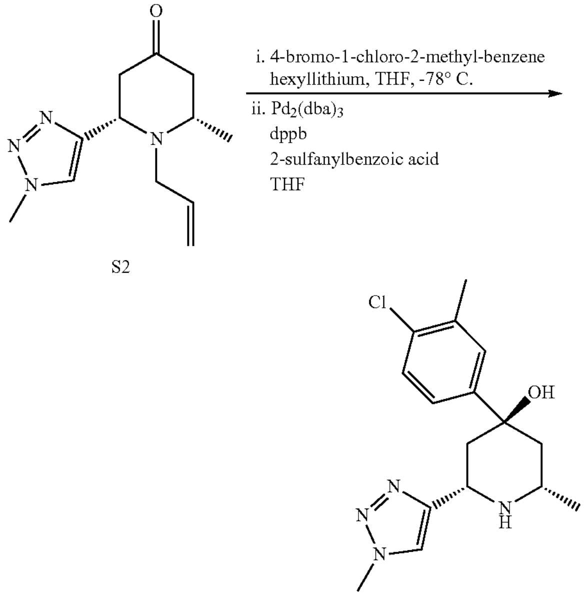

S2

26

Compound 26 was synthesized from compound S2 following the method described for Compound 17. Purification by reversed-phase HPLC (Method: Waters XSelect CSH C18 OBD Prep Column; 30×150 mm, 5 micron. Gradient: 5-98% Acetonitrile in Water with 0.1% trifluoroacetic acid) afforded the title Compound 26 (12.6 mg, 28%) as a white solid. $^1H$ NMR (300 MHz, Methanol-d4) δ 8.06 (s, 1H), 7.47 (d, J=1.8 Hz, 1H), 7.35 (d, J=4.2 Hz, 2H), 4.96 (dd, J=12.4, 3.1 Hz, 1H), 4.13 (s, 3H), 3.91 (dt, J=11.3, 5.6 Hz, 1H), 2.55-2.41 (m, 1H), 2.40 (s, 3H), 2.22 (d, J=14.6 Hz, 1H), 2.03 (d, J=10.8 Hz, 2H), 1.41 (d, J=6.6 Hz, 3H). ESI-MS m/z calc. 320.140, found 321.28 $(M+H)^+$.

Compound 27

(2S,4R,6S)-4-[4-bromophenyl)-2-methyl-6-(1-methyltriazol-4-yl)piperidin-4-ol (27)

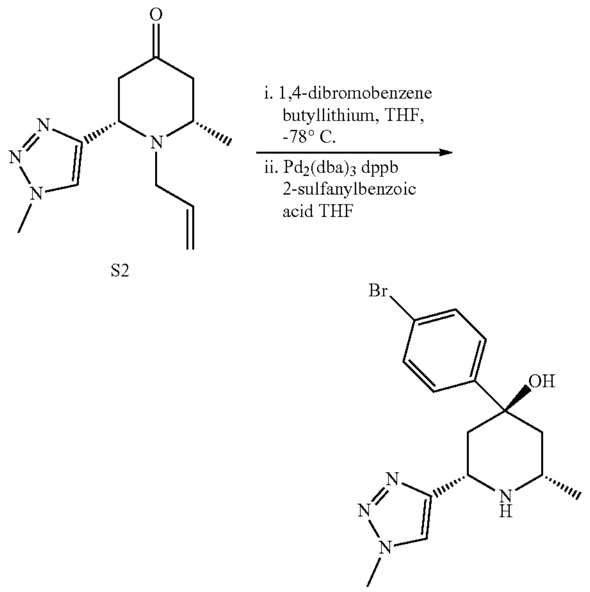

27

Step i: A mixture of 1,4-dibromobenzene (120.8 mg, 0.512 mmol) in THF (800 μL) was cooled to −78° C. At this time, butyllithium (260 μL of 1.6 M, 0.416 mmol) was added dropwise, and the mixture was stirred at −78° C. for 15 minutes. At this time, a THF (800 μL) solution of compound S2 (80 mg, 0.3414 mmol) was added dropwise, and the reaction was stirred for 15 minutes. The mixture was diluted with saturated aqueous ammonium chloride (10 mL), water (10 mL), and ethyl acetate (10 mL). The aqueous layer was extracted with additional ethyl acetate (2×10 mL), and the combined organic layer was dried with sodium sulfate, filtered, and concentrated to a crude residue.

Step ii: The intermediate was diluted with THF (400 μL) and 2-sulfanylbenzoic acid (56 mg, 0.363 mmol) was added. In an inert glovebox, a solution of dppb (4 mg, 0.00938 mmol) and $Pd_2(dba)_3$ (4 mg, 0.00437 mmol) in THF (400 μL) was prepared and, after 30 minutes of mixing, the light brown mixture was added to the intermediate solution. The mixtures were stirred. After 30 minutes, UPLC indicated complete conversion. The mixture was diluted with TBME (5 mL), followed by 1 M HCl (2×5 mL). The aqueous layer was removed and combined and then pH adjusted with aqueous NaOH (6 M, 1.7 mL) followed by saturated aqueous ammonium chloride to achieve pH ~9. The mixture was diluted and extracted with TBME (3×10 mL), and the combined organic layer was filtered through a phase separator and concentrated to a crude residue, which was purified via reverse phase chromatography Purification by reversed-phase HPLC (Method: Waters XBridge Prep $C_8$ Column; 30×150 mm, 5 micron. Gradient: 5-98% Acetonitrile in Water with 10 mM Ammonium Hydroxide) yielded the title Compound 27 (16.6 mg, 14%) as a white solid. $^1H$ NMR (400 MHz, Chloroform-d) δ 7.55-7.41 (m, 5H), 4.07 (s, 3H), 3.98 (dd, J=12.0, 2.6 Hz, 1H), 2.90-2.80 (m, 1H), 2.79-2.72 (m, 1H), 2.51-2.43 (m, 1H), 2.01 (t, J=12.4 Hz, 1H), 1.73-1.57 (m, 1H), 1.17 (d, J=6.1 Hz, 3H). ESI-MS m/z calc. 350.0742, found 351.17 $(M+H)^+$.

Compound 28

(2S,4R,6S)-4-(4-bromophenyl)-2-methyl-6-(1-methyltriazol-4-yl)piperidin-4-ol (28)

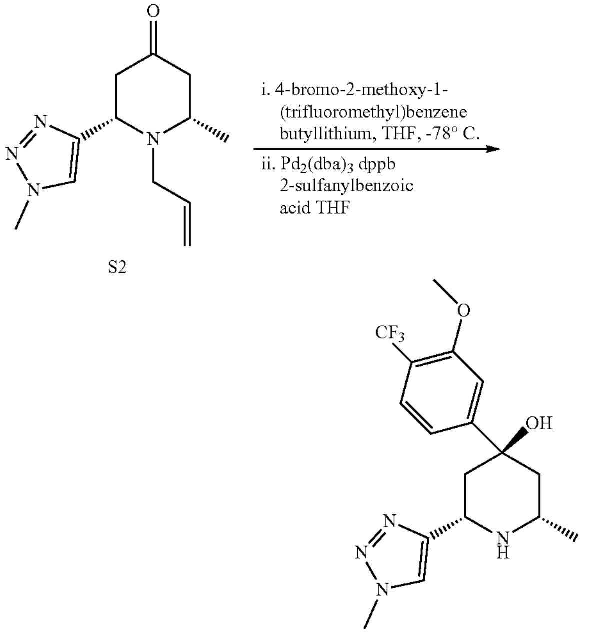

28

Step i: A mixture of 4-bromo-2-methoxy-1-(trifluoromethyl)benzene (220 mg, 0.863 mmol) in THF (1000 μL) was cooled to −78° C. At this time, sec-butyllithium (600 μL of 1.4 M, 0.840 mmol) was added, and the mixture was stirred at this temperature for 40 minutes. At this time, a THF (1,000 μL) solution of compound S2 (100 mg, 0.427 mmol) was added over 30 seconds. The mixture was then stirred for 2 minutes, and then quenched with 2 mL saturated aqueous ammonium chloride and ethyl acetate (4 mL). The aqueous layer was extracted with additional ethyl acetate (2×4 mL), and the combined organic layer was washed with brine (5 mL), dried with magnesium sulfate, filtered, and concentrated. The mixture was minimally diluted with DCM and loaded onto a silica gel column for purification (Gradient: 0-8% MeOH in DCM). The product-containing fractions were pooled and concentrated and found to be only about 80% purity, with the remainder being the starting material. The mixture was redissolved in DCM and loaded onto another silica gel column for purification (0-6% MeOH in DCM). The product-containing fractions were pooled and concentrated.

Step ii: In an inert glovebox, a solution of dppb (2 mg, 0.004690 mmol) and $Pd_2(dba)_3$ (2 mg, 0.002184 mmol) in THF (0.5 mL) was prepared and, after 5 minutes of mixing, the light brown mixture was added to a solution of the intermediate and 2-sulfanylbenzoic acid (15 mg, 0.09729 mmol) in THF (0.5 mL). The mixture was stirred for 5 minutes. At this time, the mixtures were diluted with TBME (2 mL) and extracted with 1 M HCl (2×1 mL), which was then pH adjusted to pH>10 and then extracted with DCM (2 mL). The organic layer was passed over a phase separator, concentrated to a minimal volume, and then diluted in DCM for silica gel purification (Gradient: 0-10% MeOH in DCM). The product-containing fractions were pooled and concentrated to yield the title Compound 28 (26 mg, 14%) as a white solid. $^1$H NMR (300 MHz, Methanol-d4) δ 7.87 (s, 1H), 7.53 (d, J=8.1 Hz, 1H), 7.35 (s, 1H), 7.18 (d, J=8.2 Hz, 1H), 4.51 (dd, J=10.9, 3.8 Hz, 1H), 4.08 (d, J=1.5 Hz, 3H), 3.93 (d, J=1.5 Hz, 3H), 3.43 (ddd, J=12.5, 6.5, 3.3 Hz, 1H), 2.19-2.01 (m, 2H), 1.81 (dd, J=13.6, 2.4 Hz, 1H), 1.70 (dd, J=13.4, 11.4 Hz, 1H), 1.23-1.15 (m, 3H). ESI-MS m/z calc. 370.162, found 371.14 $(M+H)^+$.

Compound 29
(2S,4S,6S)-4-(4-cyclopropylphenyl)-2-methyl-6-(1-methyltriazol-4-yl)piperidin-4-ol (29)

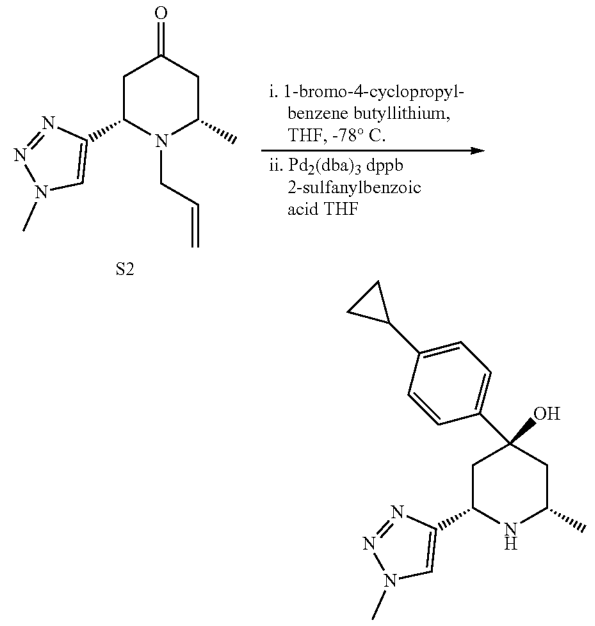

S2

29

Step i: A mixture of 1-bromo-4-cyclopropyl-benzene (120 mg, 0.609 mmol) in THF (800 μL) was cooled to −78° C. At this time, butyllithium (260 μL of 1.6 M, 0.416 mmol) was added dropwise, and the mixture was stirred at −78° C. for 10 minutes. To the reaction was added $LaCl_3 \cdot LiCl$ (580 μL of 0.6 M, 0.348 mmol), and the reaction was stirred for 5 minutes. At this time, a THF (800 μL) solution of compound S2 (80 mg, 0.341 mmol) was added dropwise. The mixture was diluted with saturated aqueous ammonium chloride (10 mL), water (10 mL), and ethyl acetate (10 mL). The aqueous layer was extracted with additional ethyl acetate (2×10 mL), and the combined organic layer was dried with sodium sulfate, filtered, and concentrated.

Step ii: The intermediate was diluted with THF (400 μL) and 2-sulfanylbenzoic acid (55 mg, 0.357 mmol) was added. In a glovebox, a solution of dppb (4 mg, 0.00938 mmol) and $Pd_2(dba)_3$ (4 mg, 0.00437 mmol) in THF (400 μL) was prepared and, after 30 minutes of mixing, the light brown mixture was added to the intermediate solution. The mixture was stirred for 30 minutes. The mixture was diluted with TBME (5 mL) followed by 1 M HCl (2×5 mL). The aqueous layer was removed and combined and then pH adjusted with aqueous NaOH (6N, 1.7 mL) followed by saturated aqueous ammonium chloride to achieve pH ~9. The mixture was diluted and extracted with TBME (3×10 mL), and the combined organic layer was filtered through a phase separator and concentrated to a crude residue, which was purified via reverse phase chromatography (Purification by reversed-phase HPLC. Method: Waters XBridge Prep C8 Column; 30×150 mm, 5 micron. Gradient: 5-98% Acetonitrile in Water with 10 mM Ammonium Hydroxide) to yield the title Compound 29 (19.4 mg, 18%) as a white solid. $^1$H NMR (400 MHz, Chloroform-d) δ 7.47 (s, 1H), 7.45-7.38 (m, 2H), 7.07 (d, J=8.0 Hz, 2H), 4.54 (dd, J=10.7, 3.8 Hz, 1H), 4.06 (d, J=1.1 Hz, 3H), 3.43 (s, 1H), 2.19-1.99 (m, 2H), 1.97-1.68 (m, 4H), 1.18 (d, J=6.3 Hz, 3H), 1.01-0.92 (m, 2H), 0.75-0.61 (m, 2H). ESI-MS m/z calc. 312.195, found 313.33 $(M+H)^+$.

Compound 30
4-[(2S,4S,6S)-4-hydroxy-2-methyl-6-(1-methyltriazol-4-yl)-4-piperidyl]benzonitrile (30)

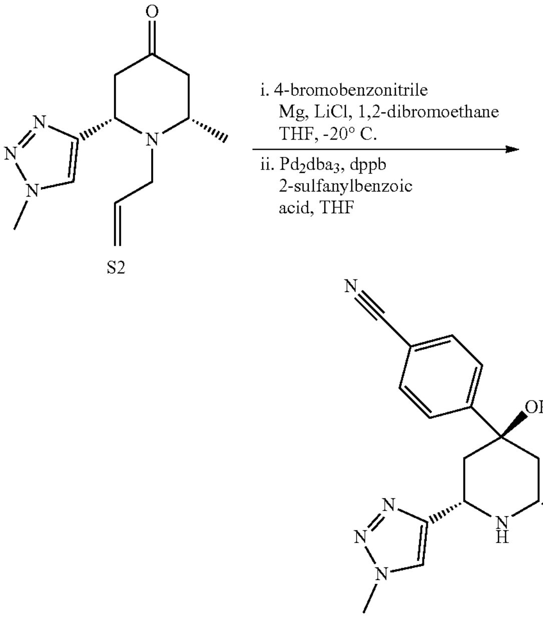

S2

30

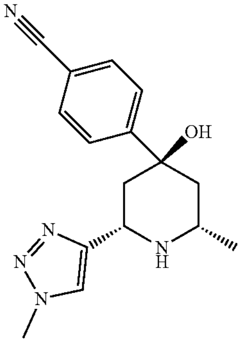

30

To a mixture of Mg (17 mg, 699 μmol) in THF (500 μL), LiCl (430 uL of 0.5 M in THF) a drop of 1,2-dibromoethane was added, followed by 4-bromobenzonitrile (117 mg, 643 μmol). The mixture was stirred for 1 h at rt and then heated to 40° C. After 1 h, the formed solution was cooled to −20° C. in a dry ice/acetone bath and a solution of (2S,6S)-1-allyl-2-methyl-6-(1-methyl-1H-1,2,3-triazol-4-yl)piperidin-4-one S2 (50 mg, 213 μmol) in THF (500 μL) was added.

After 5 min, the reactions were quenched with sat. aq. ammonium chloride (2 mL), diluted with TBME (5 mL) and water (3 mL). The organic layer was passed over a phase separator and concentrated and diluted in DMSO (1 mL). Purification by reversed-phase HPLC. Method: C18 Waters Sunfire column (30×150 mm, 5 micron). Gradient: MeCN in $H_2O$ with 0.2% formic acid. The pure product-containing fractions were pooled, concentrated, and diluted with THF (500 μL), at which time 2-sulfanylbenzoic acid (32.9 mg, 0.213 mmol) was added and the mixture was evacuated and back-filled with nitrogen (3×). In an inert glove box, a solution of $Pd_2dba_3$ (1 mg, 107 μmol) and DPPB (1 mg, 213 μmol) in THF (500 μL) was prepared and the mixture was stirred until mostly homogeneous and yellow-brown, about 5 min. At this time, a THF (500 μL) solution of the tertiary alcohol and 2-sulfanylbenzoic acid was evacuated and back-filled with nitrogen 3 times and then stirred at rt. At this time, the catalyst solution was added and the mixture was allowed to continue stirring under nitrogen. After 1 h, the mixture was diluted with TBME (1 mL) and extracted with 1 M HCl (2×1 mL) and the aqueous layer was washed with TBME (2×1 mL). The combined aqueous layers were pH adjusted to pH 9 with 6 M NaOH and sat. aq. ammonium chloride if necessary. The cloudy aqueous layer was extracted with TBME (2×1 mL), and the combined organic layer was washed with brine (1 mL), dried with magnesium sulfate, passed over a florisil cartridge and washed with methanol (2×1 mL). The combined organics were concentrated to yield the title compound 30 (2.9 mg, 4%) as a white solid. $^1$H NMR (300 MHz, Methanol-d4) δ 7.84 (s, 1H), 7.72 (s, 4H), 4.47 (dd, J=9.2, 5.3 Hz, 1H), 4.08 (s, 3H), 3.45-3.35 (m, 1H), 2.10-1.96 (m, 2H), 1.81-1.72 (m, 1H), 1.64 (dd, J=13.6, 11.2 Hz, 1H), 1.17 (d, J=6.4 Hz, 3H). LCMS m/z 298.08 $[M+H]^+$.

Compound 31

(2S,4S,6S)-4-(2,2-dimethyl-3H-benzofuran-6-yl)-2-methyl-6-(1-methyltriazol-4-yl)piperidin-4-ol (31)

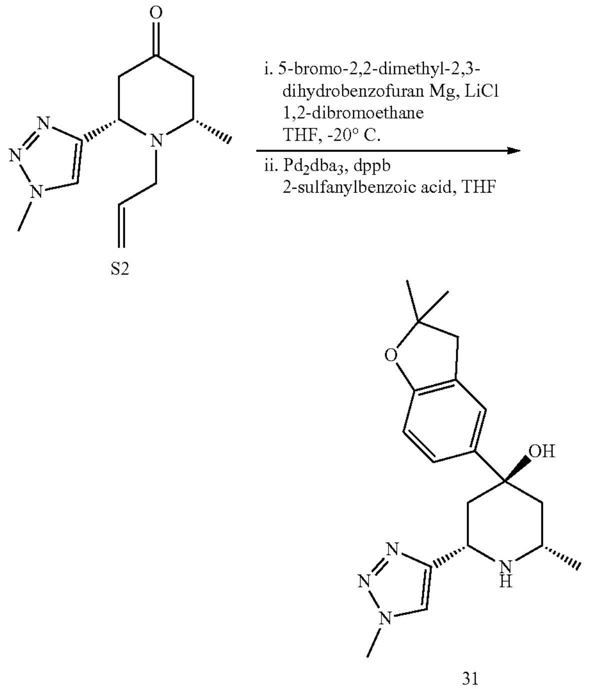

31

Compound 31 was synthesized from compound S2 following the method described for compound 30 with the appropriate aryl halide. The title compound 31 (8.7 mg, 11%) was isolated as a white solid. $^1$H NMR (300 MHz, Methanol-d4) δ 7.83 (s, 1H), 7.13-7.05 (m, 1H), 6.95 (dd, J=7.8, 1.7 Hz, 1H), 6.85 (d, J=1.6 Hz, 1H), 4.45 (dd, J=8.5, 6.1 Hz, 1H), 4.08 (s, 3H), 3.41-3.36 (m, 1H), 3.34 (s, 1H), 2.98 (d, J=1.1 Hz, 2H), 2.06-1.98 (m, 2H), 1.78 (dd, J=13.4, 2.5 Hz, 1H), 1.61 (dd, J=13.7, 11.3 Hz, 1H), 1.42 (s, 6H), 1.16 (d, J=6.4 Hz, 3H). LCMS m/z 343.13 $[M+H]^+$.

Compound 32

(2S,4S,6S)-2-methyl-6-(1-methyltriazol-4-yl)-4-spiro[chromane-4,1′-cyclopropane]-7-yl-piperidin-4-ol (32)

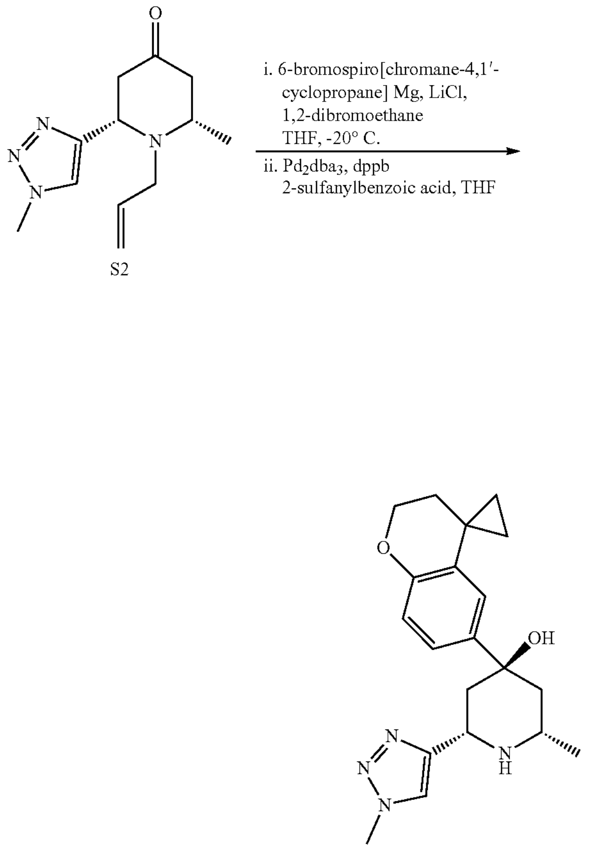

32

Compound 32 was synthesized from compound S2 following the method described for compound 30 with the appropriate aryl halide. The title compound 32 (14.5 mg, 19%) was isolated as a white solid. $^1$H NMR (300 MHz, Methanol-d4) δ 7.82 (s, 1H), 6.94 (dd, J=8.1, 2.0 Hz, 1H), 6.91 (d, J=1.9 Hz, 1H), 6.66 (d, J=8.1 Hz, 1H), 4.44 (dd, J=9.4, 5.3 Hz, 1H), 4.28-4.15 (m, 2H), 4.07 (s, 3H), 3.41-3.35 (m, 1H), 2.06-1.90 (m, 2H), 1.87-1.80 (m, 2H), 1.77 (dt, J=13.8, 2.3 Hz, 1H), 1.58 (dd, J=13.7, 11.3 Hz, 1H), 1.16 (d, J=6.4 Hz, 3H), 1.05-0.98 (m, 2H), 0.88-0.77 (m, 2H). LCMS m/z 355.14 $[M+H]^+$.

Compound 33
(2S,4S,6S)-4-[4-chloro-3-(trifluoromethyl)phenyl]-2-methyl-6-(1-methyltriazol-4-yl)piperidin-4-ol (33)

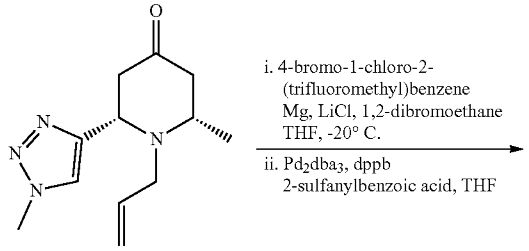

S2

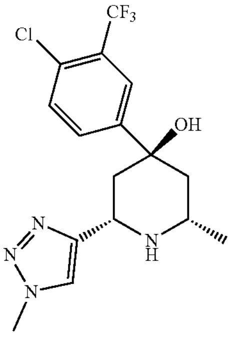

33

Compound 33 was synthesized from compound S2 following the method described for compound 30 with the appropriate aryl halide, with a modified work up and isolation for the final step as follows: The reaction mixture was diluted with TBME (500 μL) and extracted with 1 M HCl (3×500 μL). The combined aqueous layer was submitted for reversed phase purification to isolate the final product (Method: C18 Waters Sunfire column (30×150 mm, 5 micron). Gradient: MeCN in $H_2O$ with 0.2% formic acid.). Fractions were concentrated to yield the title compound 33 (formic acid salt) (2.9 mg, 4%) as a white solid $^1$H NMR (300 MHz, Methanol-d4) δ 8.06 (s, 1H), 7.99 (d, J=2.3 Hz, 1H), 7.78 (dd, J=8.5, 2.3 Hz, 1H), 7.67 (d, J=8.5 Hz, 1H), 4.95 (d, J=3.1 Hz, 1H), 4.15 (s, 3H), 3.87 (dt, J=11.2, 5.8 Hz, 1H), 2.48 (t, J=13.4 Hz, 1H), 2.23 (d, J=14.0 Hz, 1H), 2.14-1.95 (m, 2H), 1.41 (d, J=6.6 Hz, 3H). LCMS m/z 375.25 [M+H]$^+$.

Compound 34
(2S,4S,6S)-2-methyl-6-(1-methyltriazol-4-yl)-4-[3-methyl-4-(trifluoromethyl)phenyl]piperidin-4-ol (34)

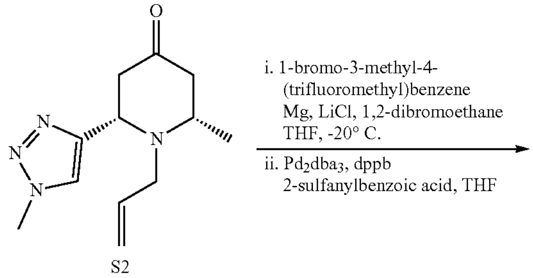

S2

-continued

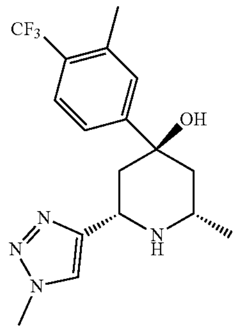

34

Compound 34 was synthesized from compound S2 following the method described for compound 30 with the appropriate aryl halide with the modification from compound 33. Fractions were concentrated to yield the title compound 34 (formic acid salt) (19.7 mg, 23%) as a white solid $^1$H NMR (300 MHz, Methanol-d4) δ 8.06 (s, 1H), 7.68 (d, J=8.3 Hz, 1H), 7.58 (s, 1H), 7.53 (d, J=8.1 Hz, 1H), 4.95 (dd, J=12.3, 3.1 Hz, 1H), 4.15 (s, 3H), 3.90 (dd, J=10.3, 5.8 Hz, 1H), 2.56-2.51 (m, 3H), 2.51-2.42 (m, 1H), 2.23 (d, J=14.0 Hz, 1H), 2.04 (d, J=10.0 Hz, 2H), 1.42 (d, J=6.6 Hz, 3H). LCMS m/z 355.28 [M+H]$^+$.

Compound 35
(2S,4S,6S)-2-methyl-6-(1-methyltriazol-4-yl)-4-[2-(trifluoromethyl)-4-pyridyl]piperidin-4-ol (35)

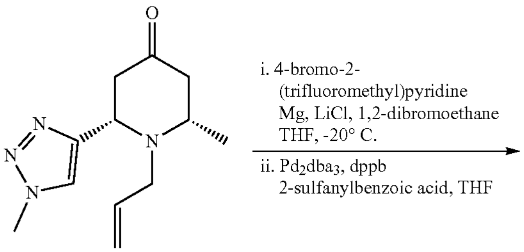

S2

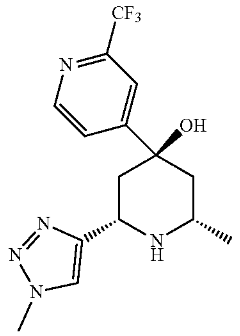

35

Compound 35 was synthesized from compound S2 following the method described for compound 30 with the appropriate aryl halide with the modification from compound 33. Fractions were concentrated to yield the title compound 35 (16.9 mg, 23%) as a white solid $^1$H NMR (300 MHz, Methanol-d4) δ 8.77 (d, J=5.2 Hz, 1H), 8.17 (s, 1H), 8.03 (dd, J=1.8, 0.8 Hz, 1H), 7.84 (dd, J=5.1, 1.8 Hz, 1H), 5.04 (dd, J=12.6, 3.1 Hz, 1H), 4.16 (s, 3H), 3.98 (ddd, J=11.0, 6.5, 4.1 Hz, 1H), 2.66 (dd, J=14.5, 12.5 Hz, 1H), 2.31-2.22 (m, 1H), 2.22-2.02 (m, 2H), 1.47 (d, J=6.6 Hz, 3H). LCMS m/z 342.31 $[M+H]^+$.

Compound 36
(2S,4S,6S)-4-[3-chloro-4-(trifluoromethyl)phenyl]-2-methyl-6-(1-methyltriazol-4-yl)piperidin-4-ol (36)

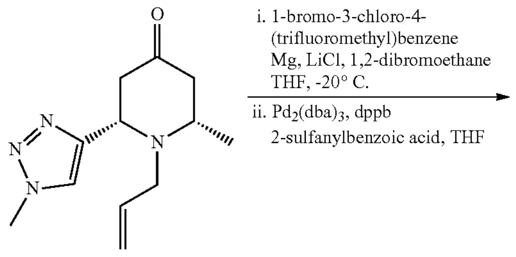

S2

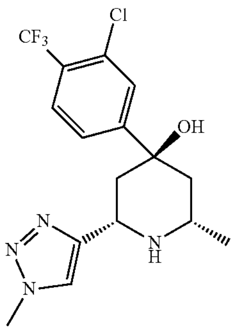

36

Compound 35 was synthesized from compound S2 following the method described for compound 30 with the appropriate aryl halide with the modification from compound 33. Fractions were concentrated to yield the title compound 36 (19.7 mg, 24%) as a white solid. $^1H$ NMR (300 MHz, Methanol-d4) δ 8.11 (s, 1H), 7.88-7.80 (m, 2H), 7.67 (d, J=8.3 Hz, 1H), 5.02 (dd, J=12.4, 3.1 Hz, 1H), 4.16 (s, 3H), 4.02-3.83 (m, 1H), 2.65-2.48 (m, 1H), 2.27 (d, J=14.0 Hz, 1H), 2.10 (d, J=8.3 Hz, 2H), 1.45 (d, J=6.6 Hz, 3H). LCMS m/z 375.29 $[M+H]^+$.

Compound 37
(2S,4S,6S)-2-methyl-6-(1-methyltriazol-4-yl)-4-[4-(trifluoromethyl)-3-pyridyl]piperidin-4-ol (37)

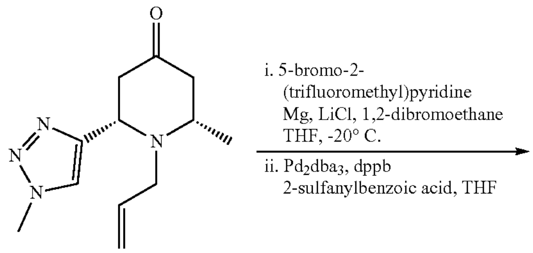

S2

-continued

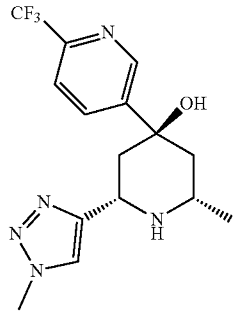

37

Compound 37 was synthesized from compound S2 following the method described for compound 30 with the appropriate aryl halide with the modification from compound 33. Fractions were concentrated to yield the title compound 35 (26.5 mg, 24%) as a white solid $^1H$ NMR (300 MHz, Methanol-d4) δ 8.93 (s, 1H), 8.23 (d, J=8.2 Hz, 1H), 8.11 (s, 1H), 7.89 (d, J=8.4 Hz, 1H), 5.05 (dd, J=12.6, 3.2 Hz, 1H), 4.16 (s, 3H), 3.99 (s, 1H), 2.61 (t, J=13.5 Hz, 1H), 2.34 (d, J=14.2 Hz, 1H), 2.14 (d, J=11.0 Hz, 2H), 1.47 (d, J=6.6 Hz, 3H). LCMS m/z 342.31 $[M+H]^+$.

Compound 38
(2S,4S,6S)-4-(4-(difluoromethyl)phenyl)-2-methyl-6-(1-methyl-1H-1,2,3-triazol-4-yl)piperidin-4-ol (38)

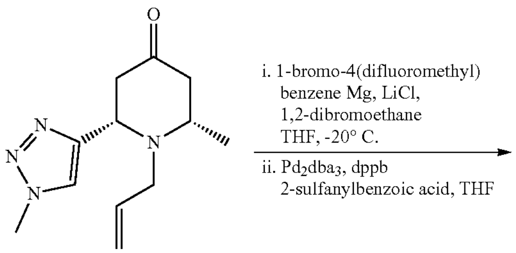

S2

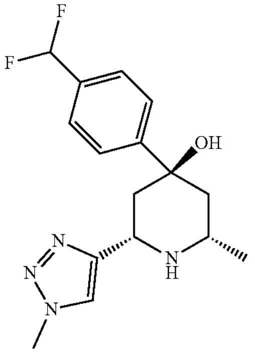

38

Compound 38 was synthesized from compound S2 following the method described for compound 30 with the appropriate aryl halide with the modification from compound 33, in addition the allyl intermediate was not purified. Fractions were concentrated to yield the title compound 38 (formic acid) (60 mg. 37%) as a white solid. $^1H$ NMR (400 MHz, DMSO-d6) δ 8.20 (s, 1H), 7.97 (s, 1H), 7.64 (d, J=8.1 Hz, 2H), 7.54 (d, J=8.1 Hz, 2H), 7.02 (t, J=56.0 Hz, 1H), 5.28 (s, 1H), 4.40 (dd, J=9.3, 5.1 Hz, 1H), 4.02 (s, 3H), 2.00-1.90 (m, 2H), 1.69 (d, J=13.0 Hz, 1H), 1.61-1.51 (m, 1H), 1.09 (d, J=6.3 Hz, 3H). LCMS m/z 323.25 $[M+H]^+$.

Compound 39
(2S,4S,6S)-2-methyl-6-(1-methyltriazol-4-yl)-4-[4-(trifluoromethyl)-3-pyridyl]piperidin-4-ol (39)

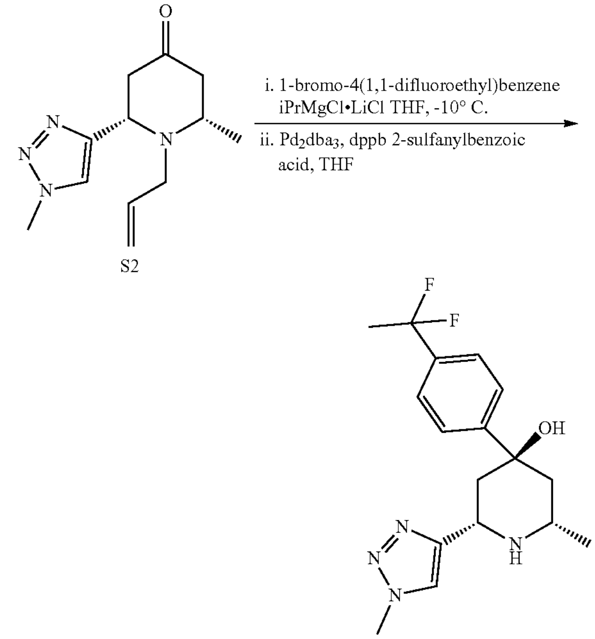

S2

39

To an oven dried vial containing 1-bromo-4(1,1-difluoroethyl)benzene (566 m, 2.56 mmol) was added 2-methyltetrahydrofuran (2.3 mL) followed by isopropylmagnesium chloride-lithium chloride complex (2.3 mL of 1.3 M, 2.99 mmol) and stirred at rt for 4 h. At this time, the reaction mixture was cooled to −10° C. and solid S2 was added in one portion and stirred for 1 h. The reaction mixture was quenched with water and sat. aq. ammonium chloride and then extracted with ethyl acetate (2×). The organic layer was passed over a phase separator and concentrated. The residual oil was brought into an inert glove box and the vial was charged with 2-sulfanylbenzoic acid (53 mg, 0.344 mmol) and dissolved in THF (300 μL). A separate vial was charged with $Pd_2dba_3$ (3 mg, 3.28 μmol), dppb (3 mg, 7.04 μmol), and THF (300 μL) and then stirred for 10 min. This solution was added to the other mixture and the reaction was stirred for 3 h. At this time, the mixture was diluted with TBME followed by extraction with 1 M HCl (2×). The aqueous layer was removed and combined and then pH adjusted with aqueous 6 M NaOH followed by sat. aq. ammonium chloride to achieve pH ~9. The mixture was diluted and extracted with TBME (3×10 mL), and the combined organic layer was filtered through a phase separator, and concentrated to a crude residue. Purification by reversed-phase HPLC. (Method: Waters XSelect CSH C18 OBD Prep Column; 30×150 mm, 5 micron. Gradient: Aceonitrile in Water with 0.2 Formic Acid.) afforded the title compound 39 (31.7 mg, 31%) as a white solid. $^1H$ NMR (400 MHz, DMSO-d6) δ 8.29 (d, J=1.2 Hz, 2H), 7.94 (s, 1H), 7.62-7.49 (m, 4H), 4.35 (dd, J=9.0, 5.2 Hz, 1H), 4.01 (s, 3H), 3.28 (t, J=8.6 Hz, 1H), 1.96 (t, J=18.8 Hz, 3H), 1.88 (d, J=4.0 Hz, 1H), 1.71-1.45 (m, 2H), 1.06 (d, J=6.3 Hz, 3H). LCMS m/z 337.30 $[M+H]^+$.

Compound 40
(2S,4S,6S)-2-methyl-6-(1-methyltriazol-4-yl)-4-[4-(trifluoromethyl)-3-pyridyl]piperidin-4-ol (40)

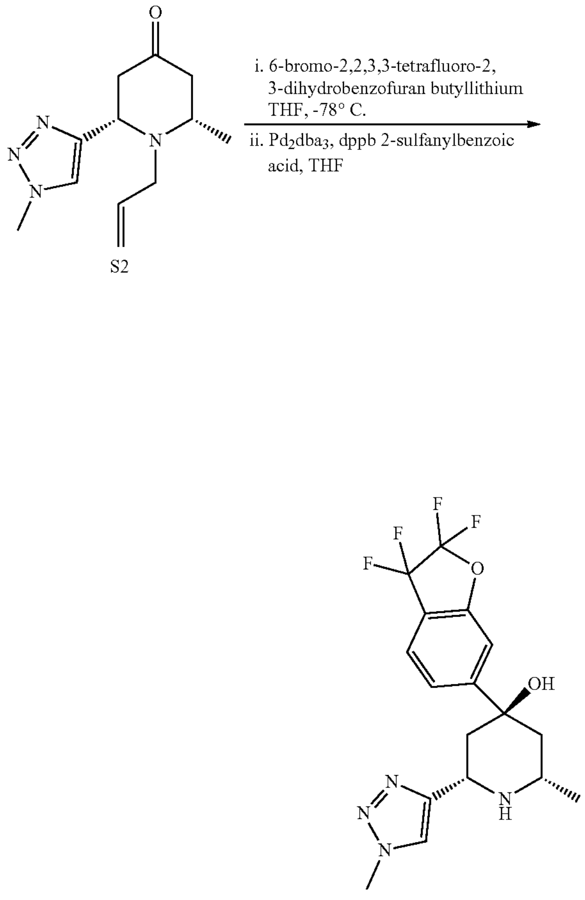

S2

40

Compound 40 was synthesized from compound S2 following the method described for compound 29 with the appropriate aryl halide to yield the title compound 40 (16 mg, 19%) as a white solid. $^1H$ NMR (400 MHz, DMSO-d6) δ 8.19 (s, 1H), 7.94 (s, 1H), 7.91-7.84 (m, 1H), 7.54 (dd, J=8.1, 1.4 Hz, 1H), 7.48 (s, 1H), 5.46 (s, 1H), 4.34 (dd, J=8.6, 5.6 Hz, 1H), 4.01 (s, 3H), 1.97-1.87 (m, 2H), 1.66 (d, J=12.9 Hz, 1H), 1.53 (dd, J=13.1, 11.0 Hz, 1H), 1.06 (d, J=6.3 Hz, 3H). LCMS m/z 387.3 $[M+H]^+$.

Compound 41
(2S,4S,6S)-4-(1,1-difluoro-2,3-dihydro-1H-inden-5-yl)-2-methyl-6-(1-methyl-1H-1,2,3-triazol-4-yl)piperidin-4-ol (41)

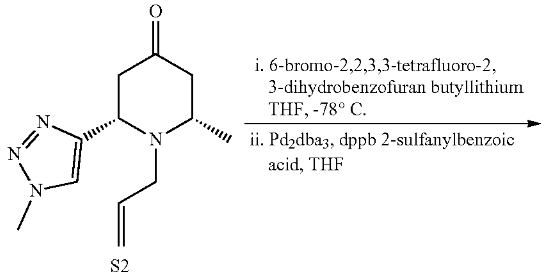

S2

-continued

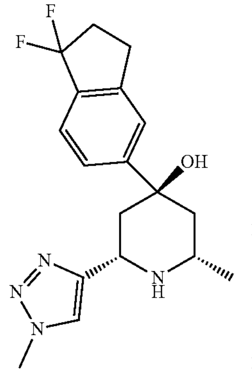

41

Compound 41 was synthesized from compound S2 following the method described for compound 29 with the appropriate aryl halide to yield the title compound 41 (33.2 mg, 31%) as a white solid. $^1$H NMR (400 MHz, DMSO-d6) δ 8.23 (s, 1H), 8.01 (s, 1H), 7.51 (s, 3H), 4.45 (dd, J=11.6, 2.9 Hz, 1H), 4.02 (s, 3H), 3.38 (ddd, J=9.9, 6.3, 3.2 Hz, 1H), 3.03 (tt, J=6.7, 3.1 Hz, 2H), 2.67-2.52 (m, 2H), 2.13-1.99 (m, 1H), 1.93 (dt, J=13.4, 2.6 Hz, 1H), 1.75-1.58 (m, 2H), 1.11 (d, J=6.3 Hz, 3H). LCMS m/z 349.31 $[M+H]^+$.

Compound 42

(2S,4S,6S)-4-(triflyoromethyl)phenyl]-1,2-dimethyl-6-(1-methyltriazol-4-yl)piperidin-4-ol (42)

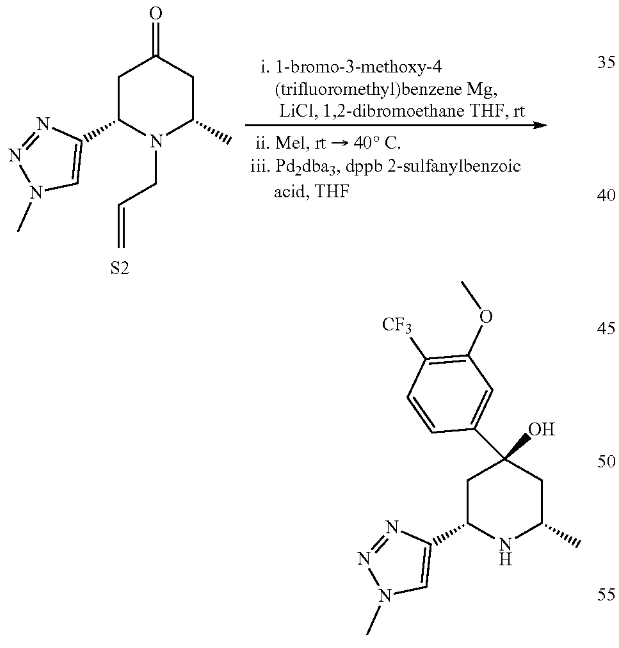

S2

42

To a mixture of Mg (17 mg, 699 μmol) in THF (500 μL), LiCl (430 uL of 0.5 M in THF was added 1,2-dibromoethane, followed by 1-bromo-3-methoxy-4(trifluoromethyl) benzene (165 mg, 647 μmol). The mixture was stirred for 1 h at rt and then heated to 40° C. After 1 h, compound S2 (50 mg, 209 μmol) was added as a solution in THF (500 μL) at rt. At this time, MeI (60 μL, 964 μmol) was added and the reaction was stirred. After 25 min, the reaction was heated to 40° C. The reaction was stirred for 18 h. At this time, the reaction mixture was diluted with sat. aq. ammonium chloride (1 mL) and DCM (3 mL). The layers were phase separated and the aqueous layer was washed with additional DCM (3 mL). The combined organic layer was concentrated and minimally diluted in DCM for column chromatography (silica gel, 0-10% MeOH:DCM). The product-containing fractions were pooled and concentrated. To the crude oil and 2-sulfanylbenzoic acid (10 mg, 65 μmol) in an inert glove box was charged THF (125 μL) followed by a THF (125 μL) solution of $Pd_2dba_3$ (0.25 mg, 0.261 μmol)/DPPB (approximately 0.25 mg, 0.523 μmol). The mixture was sealed and removed from the glove box and stirred for 1 h. At this time, the mixture was diluted with TBME (500 μL) and 1 M HCl (500 μL). The organic layer was extracted with 2 additional portions of 1 M HCl (2×500 mL). The combined aqueous layer was pH adjusted with at. NaOH and sat. aq. ammonium chloride to a pH of ~9. The aqueous layer was extracted with TBME (3×500 μL), and the combined organic layer was washed with brine, dried with magnesium sulfate, filtered, and concentrated to yield the title compound 42 (12.2 mg, 15%). $^1$H NMR (300 MHz, Chloroform-d) δ 7.48 (s, 1H), 7.44 (d, J=8.2 Hz, 1H), 7.23 (s, 1H), 7.04 (d, J=8.3 Hz, 1H), 4.01 (d, J=8.3 Hz, 1H), 3.98 (s, 3H), 3.86 (s, 3H), 3.14 (s, 1H), 2.80 (s, 1H), 2.28 (t, J=12.9 Hz, 1H), 2.13 (s, 3H), 2.03-1.91 (m, 1H), 1.88 (dt, J=13.8, 3.2 Hz, 1H), 1.76 (dt, J=13.8, 2.9 Hz, 1H), 1.16 (d, J=6.3 Hz, 3H). LCMS m/z 385.16 $[M+H]^+$.

Compound 43

(2S,4S,6S)-4-[3-hydroxy-4-(trifluoromethyl)phenyl]-2-methyl-6-(1-methyltriazol-4yl)piperidin-4-ol (43)

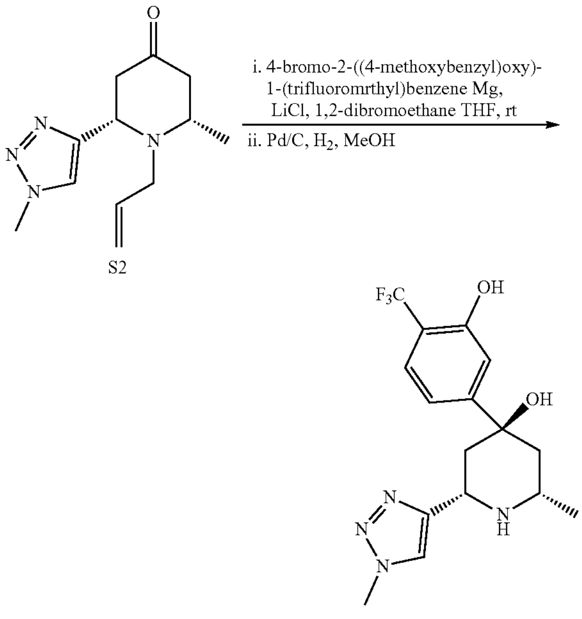

S2

43

To a mixture of LiCl (28 mg, 661 μmol) and Mg (15 mg, 617 μmol) turnings was added 1,2-dibromoethane (1 μL, 11.6 μmol) followed by THF (1000 μL). The reaction mixture was heated to 50° C. and stirred for 1 h. At this time, all solid magnesium was consumed. The solution was cooled to −20° C. and to the solution was added a solution of piperidone S2 (50 mg, 209 μmol) in THF (500 μL) After 5 min, the mixture was diluted with sat. aq. ammonium chloride (10 mL) and TBME (10 mL). The layers were phase separated and the organic layer was washed with brine (10 mL). The organic layer was dried with magnesium sulfate, filtered, and concentrated. The crude oil was dissolved in DCM (1 mL) and loaded on to a silica gel column for purification (0-10% MeOH:DCM). The product containing fractions were pooled and concentrated. To the purified oil was added Pd/C (50 mg of 2.5% w/w, 11.8 μmol) followed by MeOH (1 mL), and the mixture was stirred under 40 psig hydrogen for 21 h. At this time, the mixture was passed through a 0.45 micron membrane filter, rinsed with methanol (0.5 mL) and concentrated. The crude concentrate was dissolved in DMSO (1 mL) and purified by reversed-phase HPLC (Method: C18 Waters Sunfire column (30×150 mm, 5 micron). Gradient: MeCN in $H_2O$ with 0.2% formic acid). The title compound 43 (5.5 mg, 7%) was isolated as a white solid. $^1$H NMR (300 MHz, Methanol-d4) δ 8.08 (s, 1H), 7.53 (d, J=8.2 Hz, 1H), 7.23 (s, 1H), 7.07 (d, J=8.2 Hz, 1H), 4.99 (dd, J=12.4, 3.1 Hz, 1H), 4.15 (s, 3H), 4.05-3.80 (m, 1H), 2.58-2.48 (m, 1H), 2.24 (d, J=13.9 Hz, 1H), 2.06 (d, J=8.5 Hz, 2H), 1.44 (d, J=6.6 Hz, 3H). LCMS m/z 357.31 $[M+H]^+$.

The process of producing Compound 33 also produces Compound 33a

43a

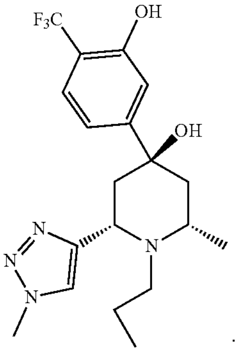

In some embodiments, Compound 33a is specifically excluded from the formulae of this disclosure by proviso.

-continued

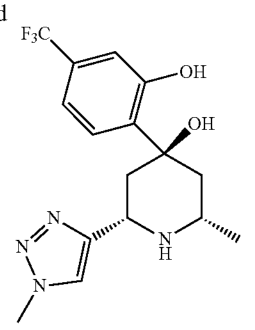

44

To a mixture of LiCl (28 mg, 661 μmol) and Mg (15 mg, 617 μmol) turnings was added 1,2-dibromoethane (1 μL, 11.6 μmol) followed by THF (1000 μL). The reaction mixture was heated to 50° C. and stirred for 1 h. At this time, all solid magnesium was consumed. The solution was cooled to −20° C. and to the solution was added a solution of S2 (50 mg, 209 μmol) in THF (500 μL). After 5 min, the reaction mixture was diluted with sat. aq. ammonium chloride (10 mL) and TBME (10 mL). The layers were phase separated and the organic layer was washed with brine (10 mL). The organic layer was dried with magnesium sulfate, filtered, and concentrated. At this time, the crude oil was taken up in aqueous HCl (1000 μL of 37% w/w, 12.18 mmol)/MeOH (1 mL), which was then heated to 50° C. (3:15). After 45 min, the mixture was diluted with water (10 mL) and TBME (10 mL). The organic layer was extracted with 1 M HCl (3×5 mL). The combined aqueous layer was pH adjusted with 6 M aq. NaOH to a pH ~8 and extracted with DCM (3×15 mL). The combined organic layer was dried with magnesium sulfate, filtered, and concentrated. To the residual oil was added 2-sulfanylbenzoic acid (16 mg, 104 μmol) and in an inert glove box was charged THF (250 μL) followed by a THF (250 μL) solution of $Pd_2dba_3$ (0.5 mg, 0.546 μmol)/DPPB (0.5 mg, 1.17 μmol). The mixture was stirred for 1 h, at which time the mixture was diluted with TBME (500 μL) and extracted with 1 M HCl (3×500 μL). The aqueous layer was then directly purified by reversed-phase HPLC. Method: C18 Waters Sunfire column (30×150 mm, 5 micron). Gradient: MeCN in $H_2O$ with 0.2% formic acid. The title compound 44 formic acid salt (15.7 mg, 18%) was isolated as a white solid. $^1$H NMR (300 MHz, Methanol-d4) δ 8.05 (s, 1H), 7.72 (d, J=8.2 Hz, 1H), 7.19 (d, J=8.1 Hz, 1H), 7.11 (d, J=1.8 Hz, 1H), 5.03-4.95 (m, 1H), 4.14 (s, 3H), 3.90 (dd, J=7.5, 4.1 Hz, 1H), 3.17-3.03 (m, 1H), 2.68 (dd, J=14.5, 12.2 Hz, 1H), 2.24-2.09 (m, 1H), 2.02-1.93 (m, 1H), 1.42 (d, J=6.6 Hz, 3H). LCMS m/z 357.31 $[M+H]^+$.

Compound 44

(2S,4S,6S)-4-[2-hydroxy-4-(trifluoromethyl)phenyl]-2-methyl-6-(1-methyltriazol-4-yl)piperidin-4-ol (44)

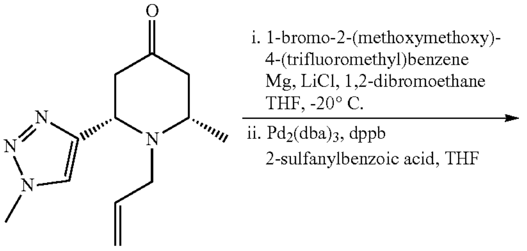

S2

Compound 45

(2S,4S,6S)-4-(((4-bromophenyl)sulfonyl)methyl)-2-methyl-6-(1-methyl-1H-1,2,3-triazol-4-yl)piperidin-4-ol (45)

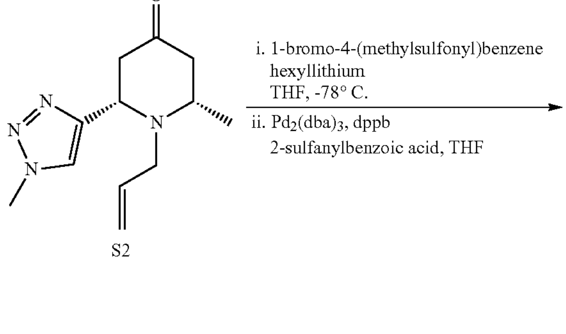

S2

-continued

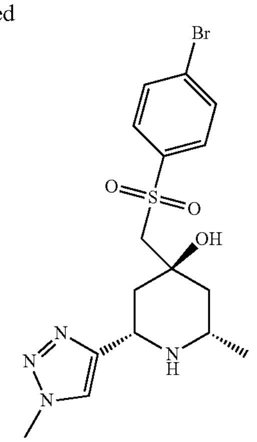

45

To a mixture of 1-bromo-4-methylsulfonyl-benzene (150 mg, 638 μmol) in THF (1 mL) cooled to −78° C. was added a hexane solution of hexyllithium (280 μL of 2.3 M, 644 μmol). After 5 min, a solution of piperidone S2 (50 mg, 213 μmol) in THF (500 μL) was added and the mixture was allowed to warm to rt. At this time, the mixture was quenched with sat. aq. ammonium chloride (1 mL). The crude mixture was warmed to rt, diluted with TBME (5 mL) and water (2 mL). The organic layer was removed and washed with brine (5 mL), dried with magnesium sulfate, filtered and concentrated. To this crude mixture was added 2-sulfanylbenzoic acid (33 mg, 214 μmol), at which time the reaction was transferred to an inert glove box, when THF (0.5 mL) and a THF (0.5 mL) solution of $Pd_2dba_3$ (1 mg, 1.09 μmol)/dppb (1 mg, 2.35 μmol) was added. The reaction stirred for 1 h, at which time the mixture was diluted with TBME (500 μL) and extracted with 1 N HCl (3×500 μL). The aqueous layers were combined and were purified by reversed-phase HPLC (Method: C18 Waters Sunfire column (30×150 mm, 5 micron). Gradient: MeCN in $H_2O$ with 0.2% formic acid). The title compound 45 (4.9 mg, 5%) was isolated as a clear oil. $^1H$ NMR (300 MHz, Methanol-d4) δ 8.05 (s, 1H), 7.96-7.80 (m, 4H), 4.16 (s, 3H), 3.77 (s, 1H), 3.59 (s, 2H), 3.29 (d, J=1.6 Hz, 1H), 2.43 (d, J=11.3 Hz, 2H), 2.27 (d, J=14.2 Hz, 1H), 1.96 (dd, J=14.5, 12.2 Hz, 1H), 1.40 (d, J=6.6 Hz, 3H). LCMS m/z 428.95 $[M+H]^+$ Compound 46
(2S,4S,6S)-2-methyl-6-(1-methyltriazol-4-yl)-4-[4-(trifluoromethyl)phenyl]piperidine-4-carbonitrile (46)

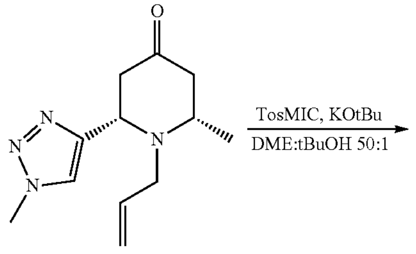

S2

-continued

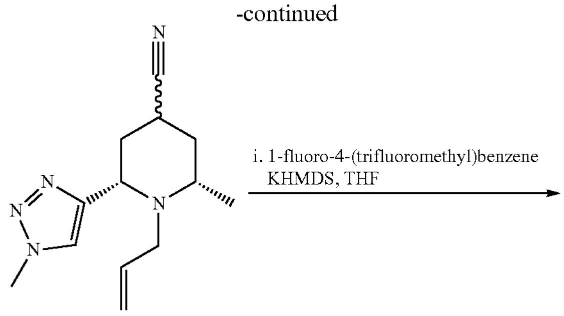

C12

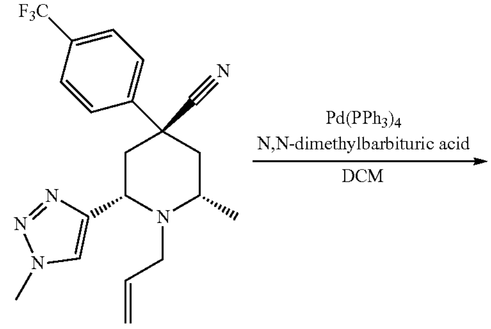

C13

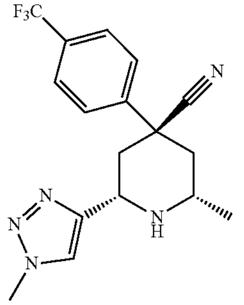

46

Step 1. Synthesis of (2S,6S)-1-allyl-2-methyl-6-(1-methyl-1H-1,2,3-triazol-4-yl)piperidine-4-carbonitrile (C12)

To a solution of piperidone S2 (150 mg, 0.608 mmol) in DME (5 mL)/tBuOH (0.1 mL) was added dropwise t-BuOK in THF (1.25 mL of 1 M, 1.2500 mmol). The reaction was stirred at room temperature for 3 hours. Water (10 mL) was added, the phases were separated, and the aqueous phase extracted with EtOAc (3×15 mL). The organic phases were combined, washed with brine (40 mL), dried over sodium sulfate and the solvent removed under reduced pressure. Purification by silica gel chromatography (0-15% MeOH in DCM) yielded the title compound C12 (111 mg, 59%) as a light orange solid. $^1H$ NMR (400 MHz, CDCl3) δ 7.48 (s, 1H), 7.44 (s, 1H), 6.02-5.77 (m, 2H), 5.19-4.98 (m, 3H), 4.19-4.02 (m, 5H), 3.85 (dd, J=11.6, 2.7 Hz, 1H), 3.39-3.25 (m, 2H), 3.10-2.94 (m, 2H), 2.67-2.54 (m, 2H), 2.20 (br dd, J=13.0, 3.0 Hz, 1H), 2.15-1.99 (m, 2H), 1.93 (q, J=12.4 Hz, 1H), 1.78-1.65 (m, 2H), 1.26 (d, J=5.0 Hz, 2H), 1.21 (d, J=6.1 Hz, 4H). LCMS m/z 246.2 $[M+H]^+$

Step 2. Synthesis of (2S,4S,6S)-1-allyl-2-methyl-6-(1-methyl-1H-1,2,3-triazol-4-yl)-4-(4-(trifluoromethyl)phenyl)piperidine-4-carbonitrile (C13)

To a solution of piperidine C12 (85 mg, 0.3461 mmol) and 1-fluoro-4-(trifluoromethyl)benzene (78 mg, 0.06 mL, 0.473 mmol) in freshly distilled THF (2 mL) at room temperature was added dropwise KHMDS in THF (0.5 mL of 1 M, 0.500 mmol). The reaction was stirred for 3 hours before addition of water (5 mL) and few drops of saturated solution of $NH_4Cl$ until pH 8-9 was reached. The aqueous phase was extracted with EtOAc (3×10 mL), the combined organic phase was dried over anhydrous sodium sulfate, filtered then concentrated in vacuo. Purification by silica gel chromatography (Column 40 g Combiflash Isco, gradient: 0-15% MeOH in DCM) yielded (2S,4S,6S)-1-allyl-2-methyl-6-(1-methyltriazol-4-yl)-4-[4-(trifluoromethyl)phenyl]piperidine-4-carbonitrile (94 mg, 70%) as a tacky yellow solid. LCMS m/z 390.2 $[M+H]^+$

Step 3. Synthesis of (2S,4S,6S)-2-methyl-6-(1-methyltriazol-4-yl)-4-[4-(trifluoromethyl)phenyl]piperidine-4-carbonitrile (46)

To a solution of (2S,4S,6S)-1-allyl-2-methyl-6-(1-methyltriazol-4-yl)-4-[4-(trifluoromethyl)phenyl]piperidine-4-carbonitrile (73 mg, 0.1873 mmol) and N,N-dimethylbarbituric acid (40 mg, 0.2408 mmol) in DCM (2 mL) was added $Pd(PPh_3)_4$ (20 mg, 0.0171 mmol). The reaction was stirred for 2 hours. The solvent was removed under vacuum then the residue dissolved with a 1M aqueous solution of hydrochloric acid (10 mL). The aqueous phase was washed with MTBE (3×10 mL) then the pH was adjusted to 8-9 by addition of a 1M aqueous solution of sodium hydroxide. The aqueous solution was then extracted with MeTHF (3×20 mL), dried over sodium sulfate and the solvent removed under vacuum. Purification by reversed-phase chromatography (column: $C_{18}$; gradient: 5% of MeCN in basic buffer (NH4CO3/NH4OH 0.1M) followed by 5-100% MeCN in water) yielded, after overnight freeze-drying, the title compound 46 (48 mg, 73%) as a white solid. $^1H$ NMR (400 MHz, DMSO-d6) δ 8.01 (s, 1H), 7.86-7.79 (m, 4H), 4.25 (br d, J=10.9 Hz, 1H), 4.03 (s, 3H), 3.23-3.13 (m, 1H), 2.98-2.70 (m, 1H), 2.40 (br d, J=13.2 Hz, 1H), 2.19 (br d, J=12.6 Hz, 1H), 1.99 (br t, J=12.2 Hz, 1H), 1.65 (br t, J=11.9 Hz, 1H), 1.15 (d, J=6.1 Hz, 3H). 19F NMR (377 MHz, DMSO-d6) δ −61.12 (s, 3F). LCMS m/z 350.2 $[M+H]^+$ Compound 47
(2S,4S,6S)-2-methyl-6-(1-methyltriazol-4-yl)-4-[4-(1,1,2,2,2-pentafluoroethyl)phenyl]piperidin-4-ol (47)

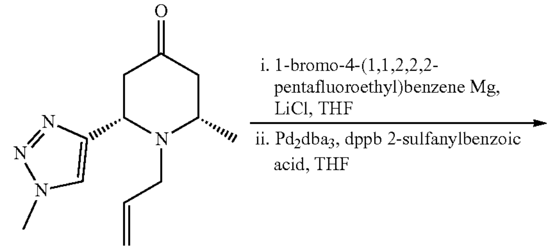

S2

-continued

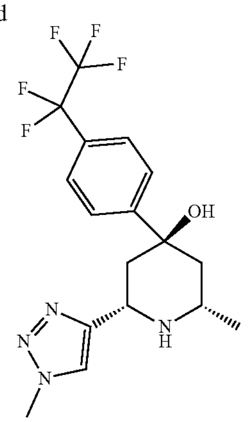

47

To an oven dried vial containing magnesium (12 mg, 0.4559 mmol) was added 1-bromo-4-(1,1,2,2,2-pentafluoroethyl)benzene (106 mg, 0.3854 mmol) as a solution with LiCl (1.4 mL of 0.285 M, 0.3990 mmol) in THF. The reaction was stirred at room temperature overnight. At this time, the mixture was cooled to −15° C. and piperidone S2 (46 mg, 0.196 mmol) was added as a solution in THF (300 μL) and stirred for 30 min. The mixture was diluted with sat. aq. ammonium chloride, water, and DCM. The aqueous layer was extracted with additional DCM, and the combined organic layer was filtered through a phase separator and concentrated, to which was added 2-sulfanylbenzoic acid (32 mg, 0.208 mmol). In an inert glovebox, a solution of $Pd_2(dba)_3$ (1.9 mg, 0.00208 mmol) and dppb (1.9 mg, 0.00446 mmol) in THF (950 μL) was added to the mixture. The resulting brown solution was stirred for 3 h. The mixture was diluted with TBME followed by extraction with 1 N HCl (2×10 mL). The aqueous layer was removed and combined and then pH adjusted with aqueous 6N NaOH followed by sat. aq. ammonium chloride to achieve pH ~9. The mixture was diluted and extracted with TBME (3×10, mL), and the combined organic layer was filtered through a phase separator and concentrated to a crude residue. The residue was diluted with DMSO and purified by reversed-phase HPLC. (Method: Waters XSelect CSH C18 OBD Prep Column; 30×150 mm, 5 micron. Gradient: Acetonitrile in Water with 0.2% Formic Acid.) to yield the title compound 47 (29.8 mg, 39%) as a white solid. $^1H$ NMR (300 MHz, DMSO-d6) δ 8.24 (s, 1H), 8.05 (s, 1H), 7.76 (d, J=8.4 Hz, 2H), 7.68 (d, J=8.4 Hz, 2H), 4.48 (dd, J=11.7, 3.0 Hz, 1H), 4.02 (s, 3H), 3.51-3.32 (m, 1H), 2.10 (dd, J=13.4, 11.7 Hz, 1H), 1.96 (d, J=13.0 Hz, 1H), 1.83-1.60 (m, 2H), 1.13 (d, J=6.4 Hz, 3H). 19F NMR (282 MHz, DMSO-d6) δ −84.07 (t, J=2.3 Hz), −113.29 (d, J=2.4 Hz). LCMS m/z 391.28 $[M+H]^+$

Compounds 48-59

Compounds 48-59 were prepared from piperidone S2 and the relevant halide as described for compound 47. Halides were obtained from commercial sources.

Method of Preparation, Structure and Physicochemical Data for Compounds 48-59.

| Product | Piperidone and halide | $^1$H NMR; LCMS m/z [M + H]$^+$ |
|---|---|---|
| Compound 48 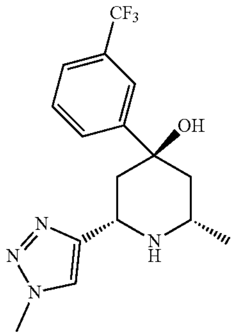 | S2; 1-bromo-3-(trifluoromethyl) benzene | $^1$H NMR (300 MHz, Methanol-d$_4$) δ 8.05 (s, 1H), 7.89 (s, 1H), 7.84-7.67 (m, 1H), 7.68-7.53 (m, 2H), 4.95 (d, J = 12.1 Hz, 1H), 4.12 (s, 3H), 3.89 (q, J = 7.3 Hz, 1H), 2.51 (t, J = 13.7 Hz, 1H), 2.22 (d, J = 14.5 Hz, 1H), 2.15-2.01 (m, 2H), 1.40 (d, J = 6.5 Hz, 3H); LCMS m/z 391.280 (M + H)$^+$ |
| Compound 49 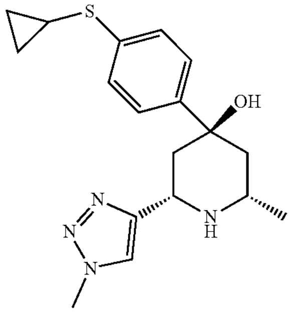 [SMILES: C[C@H]1C[C@@](O)(c2ccc(SC3CC3)cc2)C[C@@H](c2cn(C)nn2)N1] | S2; 1-bromo-4-cyclopropylsulfanyl-benzene | $^1$H NMR (300 MHz, Methanol-d$_4$) δ 8.03 (s, 1H), 7.47 (d, J = 8.6 Hz, 2H), 7.38 (d, J = 8.6 Hz, 2H), 4.94 (s, 1H), 4.13 (s, 3H), 3.86 (s, 1H), 2.44 (s, 1H), 2.31-2.16 (m, 2H), 2.00 (d, J = 14.8 Hz, 2H), 1.39 (d, J = 6.6 Hz, 3H), 1.14-1.02 (m, 2H), 0.60 (dt, J = 6.5, 4.4 Hz, 2H); LCMS m/z 345.29 [M + H]$^+$ |
| Compound 50 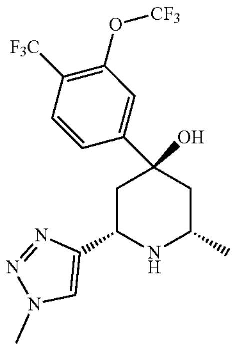 [SMILES: C[C@H]1C[C@@](O)(c2ccc(C(F)(F)F)c(OC(F)(F)F)c2)C[C@@H](c2cn(C)nn2)N1] | S2; 4-bromo-2-(trifluoromethoxy)-1-(trifluoromethyl) benzene | $^1$H NMR (300 MHz, Methanol-d$_4$) δ 8.44 (s, 1H), 8.01 (s, 1H), 7.84 (d, J = 8.3 Hz, 1H), 7.76 (s, 1H), 7.67 (d, J = 8.3 Hz, 1H), 4.88 (s, 1H), 4.12 (s, 3H), 3.88-3.67 (m, 1H), 2.50-2.35 (m, 1H), 2.19 (d, J = 14.2 Hz, 1H), 1.98 (d, J = 10.5 Hz, 2H), 1.37 (d, J = 6.6 Hz, 3H) ; LCMS m/z 425.29 [M + H]$^+$ |
| Compound 51 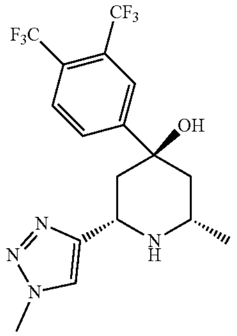 [SMILES: C[C@H]1C[C@@](O)(c2ccc(C(F)(F)F)c(C(F)(F)F)c2)C[C@@H](c2cn(C)nn2)N1] | S2; 4-bromo-1,2-bis(trifluoromethyl) benzene | $^1$H NMR (300 MHz, Methanol-d$_4$) δ 8.37 (s, 1H), 8.15 (s, 1H), 8.08-7.93 (m, 3H), 4.95 (d, J = 12.8 Hz, 1H), 4.12 (s, 3H), 3.98-3.80 (m, 1H), 2.61-2.41 (m, 1H), 2.23 (d, J = 14.5 Hz, 1H), 2.08-2.00 (m, 2H), 1.40 (dd, J = 6.6, 2.8 Hz, 3H); LCMS m/z 409.30 [M + H]$^+$ |

-continued

| Product | Piperidone and halide | $^1$H NMR; LCMS m/z $[M + H]^+$ |
|---|---|---|
| Compound 52<br>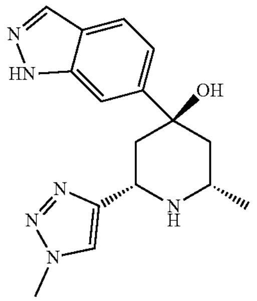 [SMILES: C[C@H]1C[C@@](O)(c2ccc3cn[nH]c3c2)C[C@@H](c2cn(C)nn2)N1] | S2;<br>6-bromo-1-(tetrahydro-2H-pyran-2-yl)-1H-indazole | $^1$H NMR (300 MHz, Methanol-$d_4$) δ 8.04-7.97 (m, 1H), 7.94 (s, 1H), 7.79-7.73 (m, 2H), 7.34 (dd, J = 8.8, 1.4 Hz, 1H), 4.70 (dd, J = 11.9, 3.0 Hz, 1H), 4.10 (s, 3H), 3.72-3.53 (m, 1H), 2.43-1.76 (m, 4H), 1.29 (d, J = 6.5 Hz, 3H); LCMS m/z 313.31 $[M + H]^+$ |
| Compound 53<br>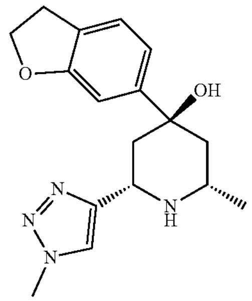 [SMILES: C[C@H]1C[C@@](O)(c2ccc3c(c2)OCC3)C[C@@H](c2cn(C)nn2)N1] | S2;<br>6-bromo-2,3-dihydrobenzofuran | $^1$H NMR (300 MHz, Methanol-$d_4$) δ 8.39 (s, 1H), 8.09 (s, 1H), 7.21 (dd, J = 7.7, 1.2 Hz, 1H), 7.01 (dd, J = 7.8, 1.7 Hz, 1H), 6.94 (d, J = 1.7 Hz, 1H), 4.95 (dd, J = 12.5, 3.1 Hz, 1H), 4.54 (t, J = 8.7 Hz, 2H), 4.13 (s, 3H), 3.89 (dp, J = 9.4, 6.6 Hz, 1H), 3.18 (td, J = 8.7, 1.1 Hz, 2H), 2.51 (dd, J = 14.5, 12.5 Hz, 1H), 2.26-1.95 (m, 3H), 1.41 (d, J = 6.6 Hz, 3H); LCMS m/z 315.34 $[M + H]^+$ |
| Compound 54<br>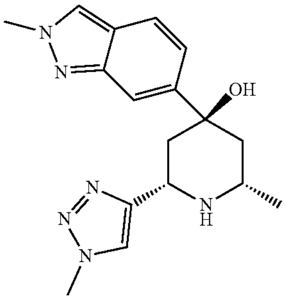 | S2;<br>6-bromo-2-methyl-2H-indazole | LCMS m/z 327.36 $[M + H]^+$ |
| Compound 55<br>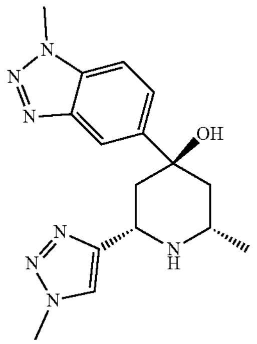 [SMILES: C[C@H]1C[C@@](O)(c2ccc3c(c2)nnn3C)C[C@@H](c2cn(C)nn2)N1] | S2;<br>5-bromo-1-methyl-1H-benzo[d][1,2,3]triazole | LCMS m/z 328.39 $[M + H]^+$ |

-continued

| Product | Piperidone and halide | $^1H$ NMR; LCMS m/z $[M + H]^+$ |
|---|---|---|
| Compound 56 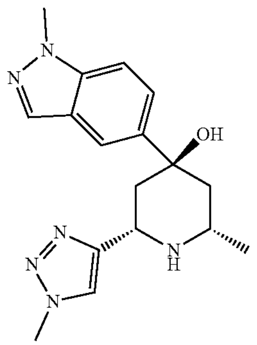 [SMILES: C[C@H]1C[C@@](O)(c2ccc3c(cnn3C)c2)C[C@@H](c2cn(C)nn2)N1] | S2; 5-bromo-1-methyl-1H-indazole | $^1H$ NMR (300 MHz, Methanol-$d_4$) δ 8.42 (d, J = 27.0 Hz, 1H), 8.14 (s, 1H), 8.04-7.92 (m, 2H), 7.68 (dd, J = 8.9, 1.7 Hz, 1H), 7.59 (dt, J = 9.0, 0.9 Hz, 1H), 5.02 (dd, J = 12.5, 3.1 Hz, 1H), 4.14 (s, 3H), 4.07 (s, 3H), 4.01-3.89 (m, 1H), 2.66 (dd, J = 14.4, 12.6 Hz, 1H), 2.31 (ddd, J = 14.5, 3.2, 1.9 Hz, 1H), 2.24-2.09 (m, 2H), 1.45 (d, J = 6.6 Hz, 3H) ; LCMS m/z 327.36 $[M + H]^+$ |
| Compound 57 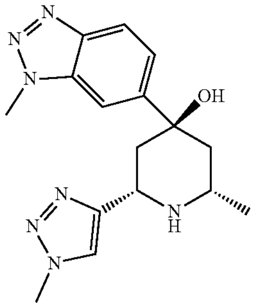 | S2; 6-bromo-1-methyl-1H-benzo[d][1,2,3]triazole | LCMS m/z 328.31 $[M + H]^+$ |
| Compound 58 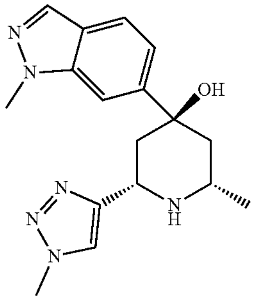 | S2; 6-bromo-1-methyl-1H-indazole | $^1H$ NMR (300 MHz, Methanol-$d_4$) δ 8.15 (s, 1H), 7.98 (d, J = 0.9 Hz, 1H), 7.83-7.73 (m, 2H), 7.37 (dd, J = 8.6, 1.5 Hz, 1H), 5.03 (dd, J = 12.5, 3.1 Hz, 1H), 4.14 (s, 3H), 4.09 (s, 3H), 4.06-3.89 (m, 1H), 2.71 (dd, J = 14.5, 12.6 Hz, 1H), 2.37-2.07 (m, 3H), 1.46 (d, J = 6.6 Hz, 3H); LCMS m/z 327.36 $[M + H]^+$ |
| Compound 59 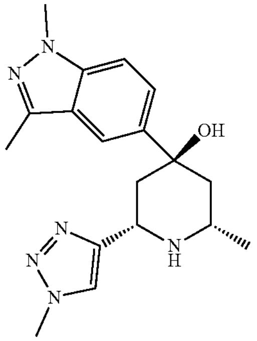 | S2; 5-bromo-1,3-dimethyl-1H-indazole | LCMS m/z 341.36 $[M + H]^+$ |

Compound 60
(2S,4S,6S)-4-cyclohexyl-2-methyl-6-)1-methyltriazol-4-yl)piperidin-4-ol
(60)

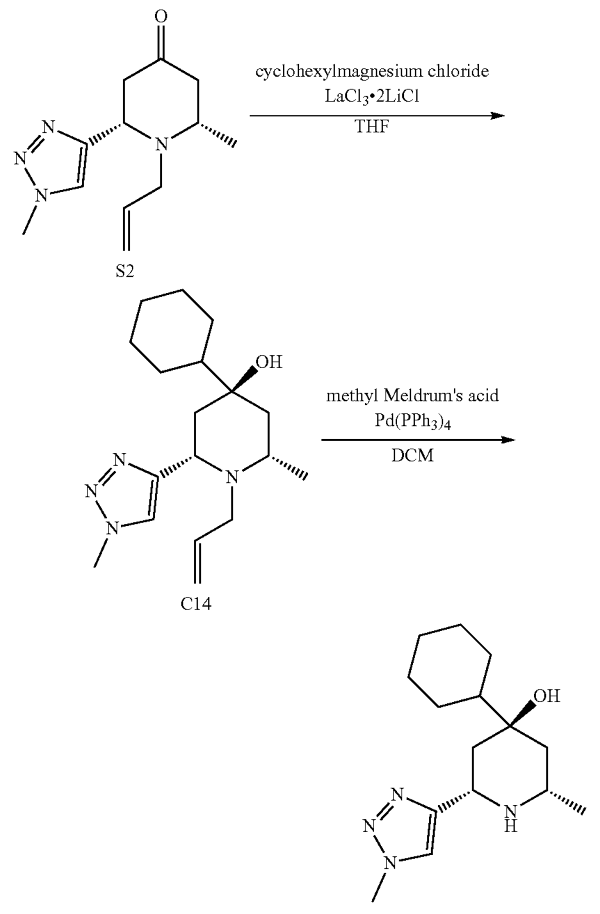

S2

C14

60

Step 1: Synthesis of (2S,4S,6S)-1-allyl-4-cyclohexyl-2-methyl-6-(1-methyltriazol-4-yl)piperidin-4-ol (C14)

In a flame dried, nitrogen-flushed flask equipped with a septum and a magnetic stirring bar was placed lanthanum (III) chloride bis(lithium chloride) complex solution (0.8 mL of 0.6 M, 0.480 mmol). In another flame dried, nitrogen-flushed flask was placed piperidone S2 (102.3 mg, 0.437 mmol). The solid was transferred to the lanthanum-containing flask using anhydrous THF (3 mL) as solvent. The mixture was stirred at ambient temperature for 1 hour. The reaction was cooled to 0° C. and cyclohexylmagnesium chloride (0.5 mL of 1 M, 0.500 mmol) was added dropwise. The reaction mixture was stirred at 0° C. for 1 hour. The reaction was quenched with water and the aqueous layer was extracted with ethyl acetate. The combined extracts were dried over sodium sulfate and evaporated under vacuum. The crude residue was purified by reversed-phase chromatography (Column: C18. Gradient: 0-100% MeCN in basic buffer ($NH_4HCO_3$/$NH_4OH$ 0.1 M)) to afford, after overnight freeze-drying the title compound C14 (53.3 mg, 36%) as a white solid. LCMS m/z 319.3 $[M+H]^+$ Step 2: Synthesis of (2S,4S,6S)-4-cyclohexyl-2-methyl-6-(1-methyltriazol-4-yl)piperidin-4-ol (60)

Piperidine C14 (53.3 mg, 0.159 mmol), methyl Meldrum's acid (44.2 mg, 0.2711 mmol) and $Pd(PPh_3)_4$ (22.5 mg, 0.0191 mmol) were placed under nitrogen, followed by addition of DCM (8 mL). The yellow solution was then stirred at ambient temperature for 2 hours. Then the mixture was dried under vacuum and purified by reversed phase chromatography (Column: C18, 30 g. Gradient: 0-100% MeCN in basic buffer ($NH_4HCO_3$/$NH_4OH$ 0.1 M)) afforded, after freeze-drying, the title compound 60 (31.9 mg, 70%) as a white solid. $^1H$ NMR (400 MHz, DMSO-$d_6$) δ 7.84 (s, 1H), 4.11 (br d, J=9.4 Hz, 1H), 3.97 (s, 3H), 3.92-3.89 (m, 1H), 3.11-3.01 (m, 1H), 1.95 (br s, 1H), 1.82-1.57 (m, 6H), 1.45-1.38 (m, 1H), 1.29 (t, J=12.2 Hz, 1H), 1.21-0.90 (m, 10H). LCMS m/z 279.2 $[M+H]^+$ Compound 61
(2S,4S,6S)-2-methyl-6-(1-methyltriazol-4-yl)-4-[[3-(trifluoromethyl)phenyl]methyl]piperidin-4-ol (61)

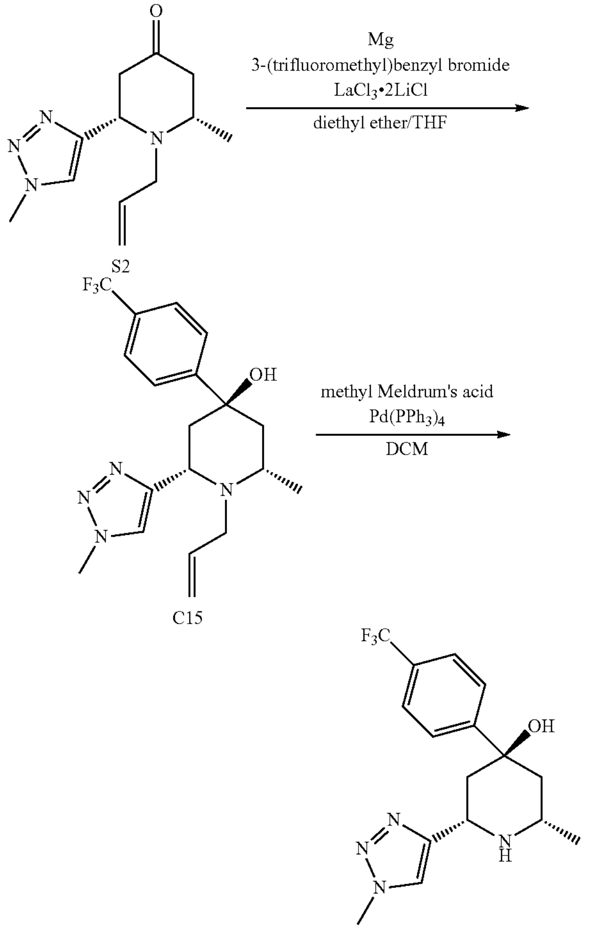

S2

C15

61

Step 1: Synthesis of(2S,4S,6S)-1-allyl-2-methyl-6-(1-methyltriazol-4-yl)-4-[[3-(trifluoromethyl)phenyl]methyl]piperidin-4-ol (C15)

In a flame dried, nitrogen-flushed flask equipped with a septum and a magnetic stirring bar was placed magnesium (147 mg, 6.065 mmol) and a small amount of iodine in diethyl ether (8 mL). The solution was stirred for 15 minutes. Then was added 3-(trifluoromethyl)benzyl bromide (1.064 g, 0.68 mL, 4.45 mmol) dropwise. The solution was heated at 40° C. until the boiling observed. Then the mixture was stirred at room temperature for 1 hour. A green Grignard solution was obtained (8 mL, 0.56 M). In a flame dried, nitrogen-flushed flask equipped with a septum and a magnetic stirring bar was placed piperidone S2 (125 mg, 0.535 mmol) in THF (3 mL). Then lanthanum(III) chloride bis (lithium chloride) complex solution (0.8 mL of 0.6 M, 0.480 mmol) was added and the mixture was stirred at room temperature for 1 hour. The reaction was cooled to 0° C. and the previously prepared Grignard (2 mL, 1.12 mmol, 2 eq) was added dropwise, and the reaction mixture was stirred at 0° C. for 1 hour. The reaction was quenched with water and the aqueous layer was extracted with ethyl acetate. The combined extracts were dried over sodium sulfate and evaporated under vacuum. The crude residue was purified by reversed-phase chromatography (Column: C18. Gradient: 0-100% MeCN in basic buffer ($NH_4HCO_3$/$NH_4OH$ 0.1 M)) to afford, after overnight freeze-drying, the title compound C15 (37.3 mg, 17%) as a white solid. $^1H$ NMR (400 MHz, CDCl3) δ 7.54-7.50 (m, 2H), 7.47-7.39 (m, 3H), 6.06-5.95 (m, 1H), 5.21-5.16 (m, 1H), 5.15-5.09 (m, 1H), 4.16 (dd, J=11.3, 3.5 Hz, 1H), 4.09 (s, 3H), 3.35 (dd, J=16.0, 7.1 Hz, 1H), 3.10-2.96 (m, 3H), 2.89 (dqd, J=11.7, 6.1, 2.8 Hz, 1H), 1.94-1.79 (m, 2H), 1.68 (s, 1H), 1.59-1.50 (m, 1H overlapped with water), 1.17 (d, J=6.1 Hz, 3H); $^{19}F$ NMR (377 MHz, CDCl3) δ −62.53 (s, 3F). LCMS m/z 395.2 $[M+H]^+$ Step 2: Synthesis of (2S,4S,6S)-2-methyl-6-(1-methyltriazol-4-yl)-4-[[3-(trifluoromethyl)phenyl] methyl]piperidin-4-ol (61)

Piperidine C15 (37.3 mg, 0.0898 mmol), methyl Meldrum's acid (54.5 mg, 0.334 mmol) and $Pd(PPh_3)_4$ (17.3 mg, 0.0147 mmol) were placed under nitrogen, then was added $CH_2Cl_2$ (6 mL). The yellow solution was then stirred at rt for 2 hours. Then the mixture was dried under vacuum and purified by reversed phase chromatography (Column: C18, 30 g. Gradient: 0-100% MeCN in basic buffer ($NH_4HCO_3$/$NH_4OH$ 0.1 M)) followed by another purification by reversed phase chromatography (Column: C18, 15.5 g. Gradient: 0-100% MeCN in water) followed by another purification in reversed-phase preparative chromatography (Column: C18. Gradient 0-95% acetonitrile in acidic water (formic acid 0.1 M)) to afford the product as a salt. At this time, the product was obtained as a free base by purification in reversed phase chromatography (Column: C18, 15.5 g. Gradient: 0-100% MeCN in basic buffer ($NH_4HCO_3$/$NH_4OH$ 0.1 M)), to afford, after freeze-drying the title compound 61 (10 mg, 31%) as a white solid. $^1H$ NMR (400 MHz, DMSO-d6) δ 7.80 (s, 1H), 7.57-7.46 (m, 4H), 4.43 (s, 1H), 4.08 (br d, J=9.8 Hz, 1H), 3.97 (s, 3H), 3.05-2.96 (m, 1H), 2.76 (s, 2H), 2.04 (br s, 1H), 1.62 (br d, J=12.8 Hz, 1H), 1.40-1.30 (m, 2H), 1.05 (t, J=12.0 Hz, 1H), 0.94 (d, J=6.2 Hz, 3H). $^{19}F$ NMR (377 MHz, DMSO-d6) δ −60.81 (s, 3F); LCMS m/z 355.2 $[M+H]^+$ Preparation of C17

2-(tetrahydro-2H-pyran-2-yl)-2H-1,2,3-triazole-4-carbaldehyde (C7)

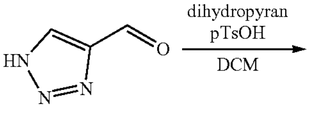

C16

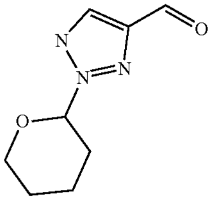

C17

1H-1,2,3-triazole-4-carbaldehyde (C16) was obtained from commercial sources. To a mixture of $C_{16}$ (1 g, 10.30 mmol) and 3,4-dihydro-2H-pyran (1000 μL, 10.96 mmol) in DCM (20 mL) cooled to 0° C. was added p-TsOH·$H_2O$ (100 mg, 0.526 mmol). The mixture was warmed to rt and stirred (1:30). After 10 min, a bright purple color appeared and solids began to dissolve. The mixture was stirred for 3 h. At this time, the mixture was diluted with sat. aq. sodium bicarbonate (5 mL), shaken, and phase separated. The aqueous layer was washed with DCM (2×5 mL). The combined organic layer was concentrated and diluted in minimal DCM for silica gel purification (0-50% EtOAc:heptane). Two regioisomers were isolated, only the major was kept. The title compound C17 (1094 mg, 57%) was isolated as a clear oil. $^1H$ NMR (300 MHz, Chloroform-d) δ 10.17 (s, 1H), 8.15 (s, 1H), 5.83 (dd, J=8.6, 2.7 Hz, 1H), 4.18-4.02 (m, 1H), 3.89-3.73 (m, 1H), 2.56-2.35 (m, 1H), 2.25-2.07 (m, 2H), 1.94-1.63 (m, 3H). LCMS m/z 181.73 $[M+H]^+$ Compound 62

2-methyl-6-(1H-triazol-4-yl)-4-[4-(trifluoromethyl)phenyl])piperidin-4-ol (62)

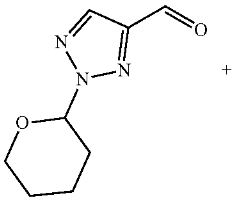

C17

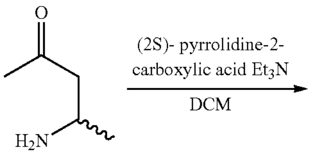

-continued

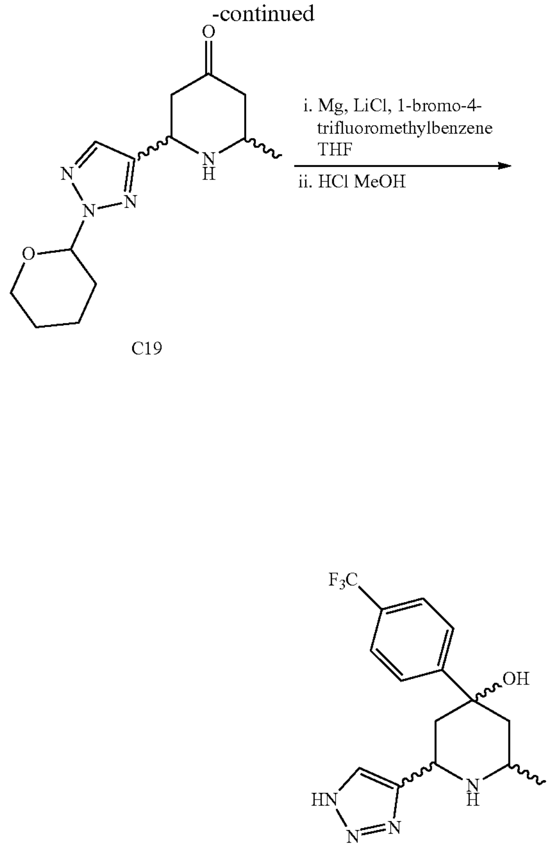

C19

62

Step 1: Synthesis of 2-methyl-6-(1-tetrahydropyran-2-yltriazol-4-yl)piperidin-4-one (C19)

Intermediate C18 (4-aminopentane-2-one hydrochloride salt) was obtained from commercial sources. Ketone C18 (hydrochloride salt) (250 mg, 1.817 mmol) was dissolved in ethanol (10 mL) and the mixture was cooled to 0° C. To the mixture was added compound S9 (346 mg, 1.910 mmol), $Et_3N$ (270 μL, 1.937 mmol) followed by (2S)-pyrrolidine-2-carboxylic acid (45 mg, 0.391 mmol). The mixture was stirred at 0° C. After 1.5 h, the reaction was warmed to rt and stirred. After 20 h, the mixture was concentrated, dissolved in DCM (10 mL) and sat. aq. sodium bicarbonate (5 mL). The aqueous layer was extracted with additional DCM (2×10 mL), and the combined organic layer was dried, minimally dissolved in DCM, and loaded onto a silica gel column for purification (0-10% MeOH:DCM). The product containing fractions (visualized by KMnO4) were pooled and concentrated to yield the title compound C19 (313 mg, 65%) as a yellow oil. $^1$H NMR (300 MHz, Chloroform-d) δ 7.64 (s, 1H), 5.69 (dd, J=9.3, 2.6 Hz, 1H), 4.25 (ddd, J=11.3, 3.9, 1.2 Hz, 1H), 4.13-4.00 (m, 1H), 3.76 (ddd, J=11.6, 9.7, 3.1 Hz, 1H), 3.15 (dqd, J=12.3, 6.2, 2.9 Hz, 1H), 2.75-2.66 (m, 1H), 2.66-2.54 (m, 1H), 2.52-2.35 (m, 2H), 2.30-2.17 (m, 1H), 2.17-1.98 (m, 3H), 1.82-1.64 (m, 3H), 1.29 (dd, J=6.2, 0.6 Hz, 3H),

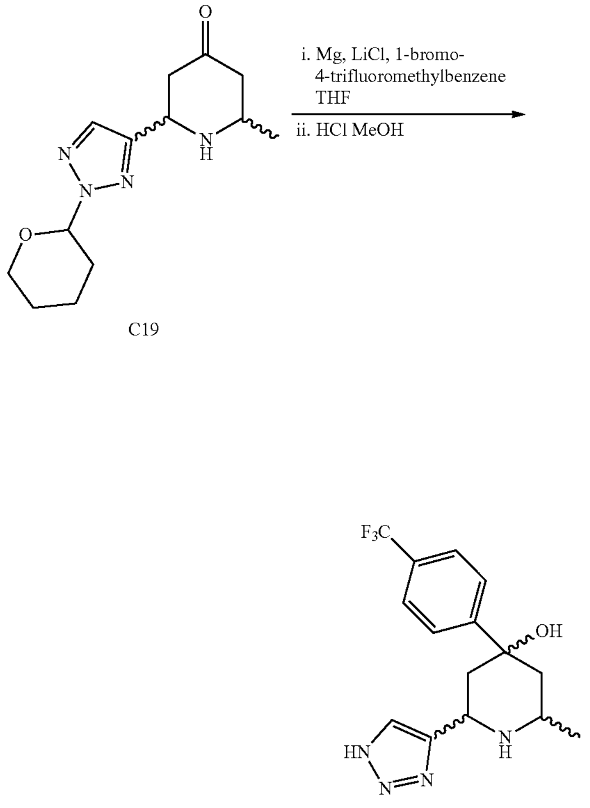

C19

62

Step 3: Synthesis of 2-methyl-6-(1H-triazol-4-yl)-4-[4-(trifluoromethyl)phenyl]piperidin-4-ol (62)

To a mixture of 1-bromo-4-(trifluoromethyl)benzene (200 mg, 0.8889 mmol), LiCl (37 mg, 0.8728 mmol), and Mg (21 mg, 0.8640 mmol) was added THF (1 mL) and the mixture was sonicated until Grignard initiation was observed. At this time, the dark brown solution was cooled to −10° C., at which time a THF (1 mL) solution of piperidone C19 (100 mg, 0.329 mmol) was added. The mixture was stirred for 5 min and then quenched with water (4 mL) and TBME (4 mL). The organic layer was removed, concentrated, and diluted in minimal DCM for silica gel purification (0-10% MeOH:DCM, 1 wt % ammonia modifier). The product-containing fractions were pooled and concentrated. To the residue was added MeOH (0.2 mL) and HCl (25 μL of 4 M, 0.1000 mmol) in dioxane was added. The reaction mixture was stirred at rt. After 1 h, the mixture was concentrated and rediluted in TBME and water (1 mL each). The organic layer was washed with 1 N HCl (1 mL) and the combined aqueous layer was purified by reversed-phase HPLC (Method: C18 Waters Sunfire column (30×150 mm, 5 micron). Gradient: MeCN in $H_2O$ with 0.2% formic acid). The title compound 62 formic acid salt (13.7 mg, 10%) was isolated as a white solid. $^1$H NMR (300 MHz, Methanol-d4) δ 7.96 (s, 1H), 7.76 (d, J=9.2 Hz, 2H), 7.71 (d, J=8.4 Hz, 2H), 5.04 (dd, J=12.5, 3.1 Hz, 1H), 3.93 (h, J=7.0 Hz, 1H), 2.54 (dd, J=14.4, 12.5 Hz, 1H), 2.28 (dd, J=14.6, 3.2 Hz, 1H), 2.14-2.01 (m, 2H), 1.42 (d, J=6.6 Hz, 3H). LCMS m/z 327.27 $[M+H]^+$ Compound 63

(2S,4S,6S)-4-(5-chloropyridin-2-yl)-2-methyl-6-(1-methyl-1H-1,2,3-triazol-4-yl)piperidine-4-carbonitrile

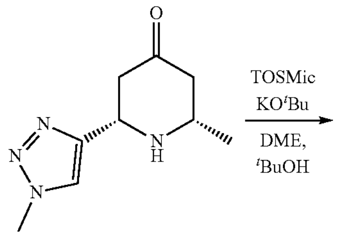

S1

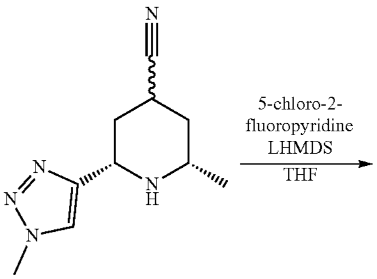

C20

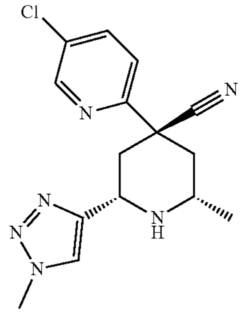

63

Step 1: Synthesis of (2S,6S)-2-methyl-6-(1-methyl-1H-1,2,3-triazol-4-yl)piperidine-4-carbonitrile (C20)

To a solution of piperidone S1 (5 g, 24.97 mmol) and TOSMic (5.12 g, 26.22 mmol) in DME (150 mL)/tBuOH (5 mL) cooled to 0° C. was added KO$^t$Bu (6 g, 53.47 mmol) in four portions. The reaction was then allowed to warm to rt and stirred, at which time a brown-yellow solid began to precipitate heavily. After 15 min, the reaction was filtered and rinsed with additional DME (3×5 mL). The filtrate was concentrated and partitioned between water (100 mL) and DCM (100 mL). Sat. aq. ammonium chloride (25 mL) was added to lower the pH to about 9, resulting in a milky organic layer. The organic layer was removed and the aqueous layer was extracted with additional DCM (2×150 mL). The aqueous layer was then diluted with brine (100 mL) followed by sodium chloride (~3 g) to re-saturate the mixture. This salted layer was further extracted with DCM (3×150 mL). The pooled organic layer was dried with magnesium sulfate, filtered, and concentrated. The orange solid was diluted with DCM (30 ml) and about 75 mL of TBME, which caused an immediate precipitation. The suspension was sonicated for 5 minutes and then filtered and rinsed with additional TBME to yield the title compound C20 (2.82 g, 55%) as a yellow solid, 4:1 mixture of nitrile diastereomers. $^1$H NMR (300 MHz, DMSO-d6) δ 7.92 (s, 1H), 4.01 (d, J=1.1 Hz, 3H), 3.80 (dd, J=11.3, 2.6 Hz, 1H), 2.99 (tt, J=12.4, 3.8 Hz, 1H), 2.72 (ddd, J=11.0, 6.3, 2.5 Hz, 1H), 2.39 (s, 1H), 2.23-1.98 (m, 1H), 1.98-1.74 (m, 1H), 1.66-1.37 (m, 1H), 1.34-1.11 (m, 1H), 1.04 (dd, J=6.3, 5.1 Hz, 3H).

Step 2: Synthesis of (2S,4S,6S)-4-(5-chloropyridin-2-yl)-2-methyl-6-(1-methyl-1H-1,2,3-triazol-4-yl)piperidine-4-carbonitrile (63)

To a mixture of 5-chloro-2-fluoro-pyridine (863 mg, 6.561 mmol) and piperidine C20 (1 g, 4.87 mmol) in THF (15 mL) cooled to 0° C. was added KHMDS (9.8 mL of 1 M in THF, 9.80 mmol) over 3 min. Upon completion of addition, water and sat. aq. sodium bicarbonate (10 mL each) were added followed by TBME (30 mL). The organic layer was removed and the aqueous layer was extracted with additional TBME (30 mL). The combined organic layer was dried with magnesium sulfate, filtered and concentrated. The crude oil was minimally dissolved in DCM and loaded on to a silica gel column for purification (0-10% MeOH·DCM). The product-containing fractions were pooled and concentrated to yield the title compound 63 (1.31 g, 80%) as a brown glass. $^1$H NMR (300 MHz, Chloroform-d) δ 8.40 (dd, J=2.5, 0.8 Hz, 1H), 7.57 (dd, J=8.5, 2.5 Hz, 1H), 7.42 (dd, J=8.5, 0.8 Hz, 1H), 7.34 (s, 1H), 4.41-4.29 (m, 1H), 3.92 (s, 3H), 3.24 (dqd, J=12.5, 6.2, 2.4 Hz, 1H), 2.30-2.19 (m, 1H), 2.12 (dd, J=13.2, 11.6 Hz, 1H), 1.98 (dt, J=13.2, 2.3 Hz, 1H), 1.70 (dd, J=13.2, 11.4 Hz, 2H), 1.07 (d, J=6.2 Hz, 3H). LCMS m/z 317.02 $[M+H]^+$ Compound 64

(2S,4S,6S)-4-(5-chloropyridin-2-yl)-2-methyl-6-(1-methyl-1H-1,2,3-triazol-4-yl)piperidine-4-carboxamide

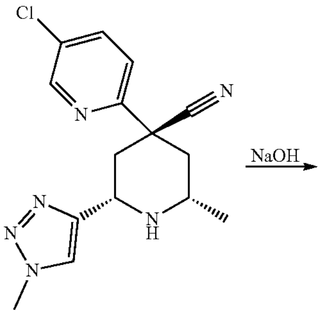

63

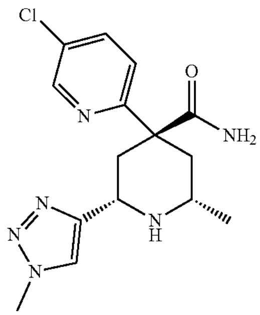

64

To a pressure vessel was added compound 63 (50 mg, 0.158 mmol) and aqueous NaOH (1 mL of 2 M, 2.00 mmol). The biphasic mixture was heated to 140° C. and stirred for 90 min. At this time, the mixture was pH adjusted with ~500 uL 2 N HCl to a pH of about 10, at which time the mixture was extracted with DCM (2×1 mL). The combined organic layer was concentrated to yield the title compound 64 (23 mg, 43%) as an off-white solid. $^1$H NMR (300 MHz, Chloroform-d) δ 8.48 (d, J=2.5 Hz, 1H), 7.62 (dd, J=8.5, 2.6 Hz, 1H), 7.49 (s, 1H), 7.32 (d, J=8.6 Hz, 1H), 6.46 (s, 1H), 5.68 (s, 1H), 4.32 (dd, J=11.8, 2.4 Hz, 1H), 4.05 (s, 3H), 3.27-3.09 (m, 1H), 2.94 (dt, J=13.3, 2.5 Hz, 1H), 2.69 (dt, J=13.4, 2.4 Hz, 1H), 2.03 (s, 1H), 1.85 (dd, J=13.4, 11.8 Hz, 1H), 1.42 (dd, J=13.3, 11.3 Hz, 1H), 1.18 (d, J=6.2 Hz, 3H). LCMS m/z 335.07 $[M+H]^+$ Compound 65
((2S,4S,6S)-2-methyl-6-(1-methyl-1H-1,2,3-triazol-4-yl)-4-(4-(trifluoromethyl)phenyl)piperidin-4-yl)methanol

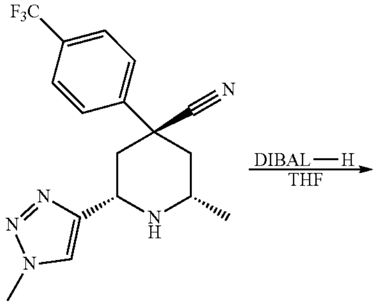

46

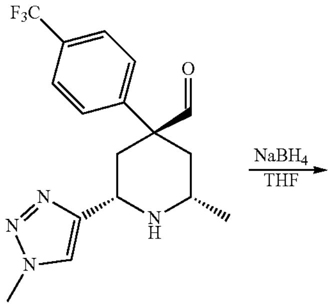

C21

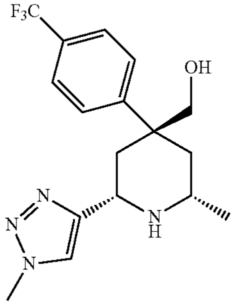

65

Step 1: Synthesis of (2S,4S,6S)-2-methyl-6-(1-methyl-1H-1,2,3-triazol-4-yl)-4-(4-(trifluoromethyl)phenyl)piperidine-4-carbaldehyde (C21)

To a THF (1 mL) solution of piperidine 46 (50 mg, 0.1431 mmol) cooled to −78° C. was added diisobutylalumane (290 μL of 1 M, 0.290 mmol) dropwise and the mixture was stirred at −78° C. After 90 min, the reaction mixture was warmed to −35° C. After 40 min at this temperature, the mixture was cooled to −78° C. once again and additional diisobutylalumane (290 μL of 1 M, 0.290 mmol) was added dropwise and the mixture continued to stir at this temperature, and then allowed to warm up to rt for 18 h. At this time, the mixture was cooled back to −78° C. and quenched with 15% citric acid (1 mL). TBME (3 mL) was added and the resulting suspension was filtered. The aqueous layer was extracted with TBME (2×1 mL). The combined organic layer was dried with magnesium sulfate, filtered and concentrated to yield the title compound C21 (45 mg, 86%) as a clear oil. $^1$H NMR (300 MHz, Chloroform-d) δ 9.50 (d, J=1.0 Hz, 1H), 7.71-7.60 (m, 2H), 7.48 (s, 1H), 7.47-7.36 (m, 2H), 4.18 (dd, J=11.9, 2.7 Hz, 1H), 4.08 (s, 3H), 3.02 (dtd, J=12.3, 6.2, 2.4 Hz, 1H), 2.87 (dt, J=13.2, 2.5 Hz, 1H), 2.57 (dt, J=13.2, 2.4 Hz, 1H), 1.93 (ddd, J=13.1, 12.0, 1.1 Hz, 1H), 1.57 (d, J=12.4 Hz, 1H), 1.22 (d, J=6.2 Hz, 3H). 19F NMR (282 MHz, CDCl3) δ −62.71. LCMS m/z 353.12 $[M+H]^+$ Step 2: Synthesis of ((2S,4S,6S)-2-methyl-6-(1-methyl-1H-1,2,3-triazol-4-yl)-4-(4-(trifluoromethyl)phenyl)piperidin-4-yl)methanol (65)

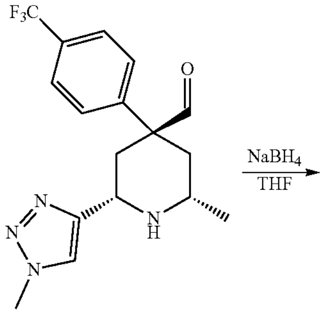

C21

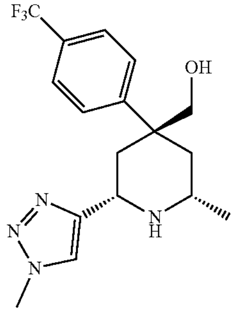

65

To a mixture of aldehyde C21 (22 mg, 0.0624 mmol) in THF (1 mL) was added $NaBH_4$ (10 mg, 0.264 mmol) After 1 h, the reaction was diluted with sat. aq. ammonium chloride (1 mL) and TBME (1 mL) and the mixture was stirred overnight. At this time, the organic layer was removed and the aqueous layer was extracted with additional TBME (1 mL). The combined organic layer was concentrated and diluted in MeOH for reversed-phase purification (Method: Waters XSelect CSH C18 OBD Prep Column; 30×150 mm, 5 micron. Gradient: Acetonitrile in Water with 10 mM Ammonium Hydroxide). The product containing fraction was concentrated to yield the title compound 65 (11.5 mg, 48%) was isolated as a white solid. $^1$H NMR (300 MHz, Methanol-d4) δ 7.86 (s, 1H), 7.61 (s, 4H), 4.29 (dd, J=12.2, 2.7 Hz, 1H), 4.09 (s, 3H), 4.01-3.89 (m, 2H), 3.22 (dqd, J=12.4, 6.3, 2.7 Hz, 1H), 2.56 (dt, J=13.4, 2.5 Hz, 1H), 2.30 (dt, J=13.5, 2.5 Hz, 1H), 1.73 (dd, J=13.4, 12.3 Hz, 1H), 1.38 (dd, J=13.5, 11.7 Hz, 1H), 1.21 (d, J=6.2 Hz, 3H). 19F NMR (282 MHz, Methanol-d4) δ −63.91. LCMS m/z 355.37 $[M+H]^+$ Compound 66

(2S,4R,6S)-2-methyl-6-(1-methyl-1H-1,2,3-triazol-4-yl)-4-(4-(trifluoromethyl)phenyl)piperidine

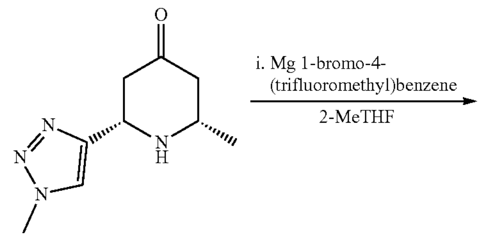

S1

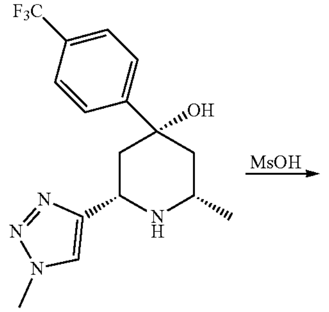

C22

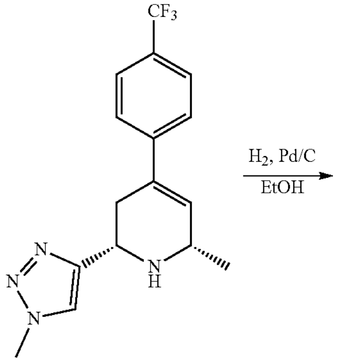

C23

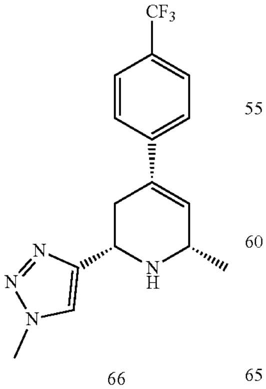

66

Step 1: Synthesis of (2S,4R,6S)-2-methyl-6-(1-methyl-1H-1,2,3-triazol-4-yl)-4-(4-(trifluoromethyl)phenyl)piperidin-4-ol (C22)

To a suspension of Mg (4.8 g, 197.5 mmol) in 2-MeTHF (400 mL) under nitrogen was added 1-bromo-4-(trifluoromethyl)benzene (27.9 mL, 199.3 mmol) followed by iodine (180 mg, 0.709 mmol). The mixture was then heated to 45° C. until no evidence of solid magnesium was observed. The reaction mixture was cooled to rt and stirred overnight. At this time, the mixture was sonicated in a 30° C. sonicator bath for a brief time and then the mixture was cooled to −10° C. Piperidone S1 (15 g, 77.23 mmol) was added in portions over 20 min, maintaining an internal temperature below −5° C. Upon completion of addition, additional 2-MeTHF (50 mL) was added. After 15 min, the mixture was diluted with water (100 mL), sat. aq. ammonium chloride (100 mL), and the formed biphasic was diluted with EtOAc (250 mL). The formed layers were split and the aqueous layer was extracted with additional EtOAc (100 mL). The combined organic layer was dried with sodium sulfate, filtered and concentrated. The crude mixture was diluted with DCM and loaded on to a silica gel column for purification (100% EtOAc-2% $Et_3N$:8% MeOH:90% EtOAc). The product-containing fractions were pooled and concentrated and submitted for SFC purification (DAICEL CHIRALPAK® AD-H 20×250 mm column, 40% MeOH:$CO_2$, 75 mL/min flow rate). The product containing fractions were pooled and concentrated to yield the title compound C22 (1.53 g, 6%) as an orange glass. LCMS m/z 340.10 $[M+H]^+$ Step 2: Synthesis of (2S,6S)-6-methyl-2-(1-methyl-1H-1,2,3-triazol-4-yl)-4-(4-(trifluoromethyl)phenyl)-1,2,3,6-tetrahydropyridine (C23)

To a mixture of piperidine $C_{22}$ (100 mg, 0.294 mmol) in DCM (2 mL) was added MsOH (60 μL, 0.925 mmol), which immediately caused precipitation. The suspension was heated to reflux for 10 min, at which time MeOH (0.5 mL) was added. The thin suspension was stirred at reflux for 4 h. At this time, MsOH (500 μL, 7.71 mmol) was added, which resulted in a clear solution. After stirring overnight, the reaction was heated to 70° C. open to the air. After stirring overnight, the reaction mixture was cooled to rt, diluted with DCM (8 mL) and the oiled-out mixture was added dropwise to sat. aq. sodium bicarbonate (10 mL). The layers were split and the organic layer was passed over a phase separator, concentrated to a minimal volume and loaded on to a silica gel column for purification (0-10% MeOH:DCM). The product-containing fraction was concentrated to yield the title compound C23 (55 mg, 58%) as a clear oil. LCMS m/z 323.19 $[M+H]^+$ Step 3: Synthesis of (2S,4R,6S)-2-methyl-6-(1-methyltriazol-4-yl)-4-[4-(trifluoromethyl)phenyl]piperidine (66)

To a solution of alkene C23 (55 mg, 0.171 mmol) from the first step was added Pd/C (30 mg, 0.0141 mmol) followed by ethanol (2 mL). The mixture was pressure purged with 60 psig nitrogen (5×) and 50 psig hydrogen (3×) and stirred under 50 psig hydrogen (5:00). After stirring overnight, the mixture was once again purged with 60 psig nitrogen (5×), filtered over Celite®, rinsed with additional ethanol (~3 mL) and concentrated. The crude mixture was dissolved in minimal DCM and loaded on to a silica gel column for purification (0-25% MeOH:DCM, 1% $NH_3$ modifier). Two product containing fractions were kept separated and evaluated by $^{1}$H NMR. The first fraction was found to contain the title compound 66 (12.6 mg, 13%) as a white solid. $^{1}$H NMR (300 MHz, MeOD) δ 7.84 (s, 1H), 7.65-7.54 (m, 2H), 7.47 (d, J=7.9 Hz, 2H), 4.08 (s, 4H), 3.11-3.01 (m, 1H), 3.01-2.90 (m, 1H), 2.22-2.10 (m, 1H), 1.91 (ddt, J=12.9, 4.2, 2.2 Hz, 1H), 1.71 (td, J=12.6, 11.5 Hz, 1H), 1.39 (td, J=12.6, 11.0 Hz, 1H), 1.21 (d, J=6.3 Hz, 3H). LCMS m/z 325.26 $[M+H]^+$ Compound 67

(2S,4S,6S)-2-methyl-6-(1-methyl-1H-1,2,3-triazol-4-yl)-4-(4-(trifluoromethyl)piperidine-4-carboxamide (67)

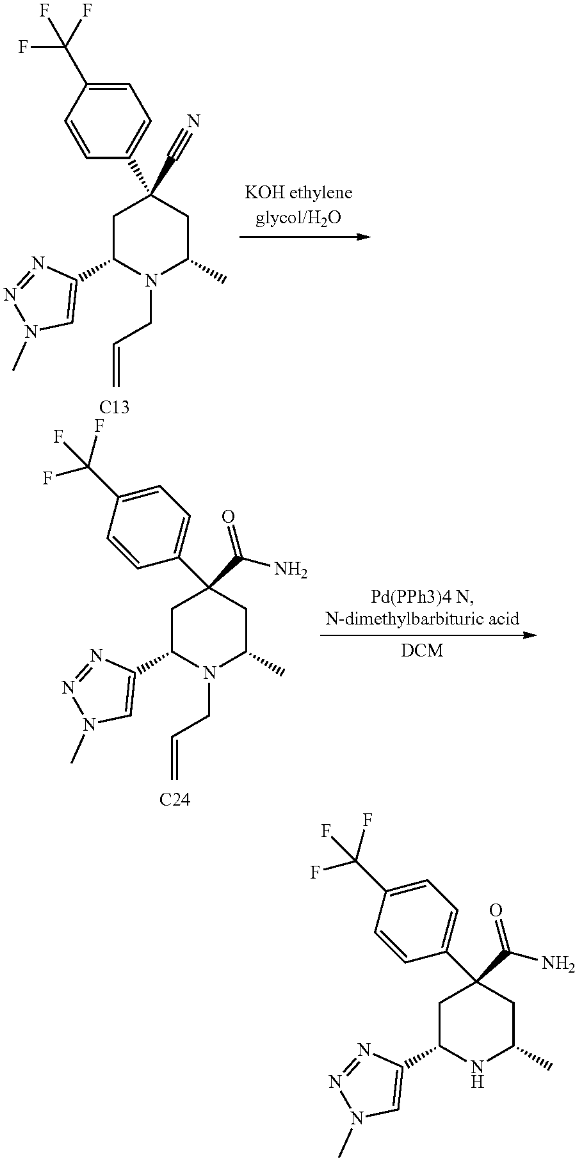

C13

C24

67

Step 1: Preparation of (2S,4S,6S)-1-allyl-2-methyl-6-(1-methyltriazol-4-yl)-4-[4 (trifluoromethyl)phenyl]piperidine-4-carboxamide (C24)

To a solution of (2S,4S,6S)-1-allyl-2-methyl-6-(1-methyl-1H-1,2,3-triazol-4-yl)-4-(4-(trifluoromethyl)phenyl)piperidine-4-carbonitrile C13 (120 mg, 0.3041 mmol) in ethylene glycol (3 mL)/water (0.3 mL) was added KOH (400 mg, 7.1294 mmol). The reaction was warmed-up to 120° C. and stirred at this temperature for 6 hours. The reaction was cooled down to room temperature and directly loaded onto the C18 column. Purification by reversed-phase chromatography (column: $C_{18}$; gradient: 0-100% MeCN in water) afforded, after overnight freeze-drying, (2S,4S,6S)-1-allyl-2-methyl-6-(1-methyltriazol-4-yl)-4-[4 (trifluoromethyl) phenyl]piperidine-4-carboxamide (105 mg, 84%) as a white powder. $^{1}$H NMR (400 MHz, DMSO-d6) δ 7.99 (s, 1H), 7.68 (d, J=8.3 Hz, 2H), 7.57 (d, J=8.2 Hz, 2H), 7.34 (s, 1H), 7.11 (s, 1H), 5.89 (ddt, J=17.1, 10.4, 6.5 Hz, 1H), 5.13-5.01 (m, 2H), 4.01 (s, 3H), 3.93 (br d, J=10.8 Hz, 1H), 3.19 (br dd, J=15.8, 7.3 Hz, 1H), 2.83 (br dd, J=15.8, 5.7 Hz, 1H), 2.78-2.70 (m, 1H), 2.70-2.59 (m, 2H), 1.80 (t, J=12.3 Hz, 1H), 1.50 (br t, J=12.1 Hz, 1H), 1.12 (d, J=6.0 Hz, 3H). $^{19}$F NMR (377 MHz, DMSO-d6) δ −60.87 (s, 3F). ESI-MS m/z calc. 407.1933, found 408.2 $(M+1)^+$

Step 2: Synthesis of (2S,4S,6S)-2-methyl-6-(1-methyl-1H-1,2,3-triazol-4-yl)-4-(4-(trifluoromethyl) phenyl)piperidine-4-carboxamide (67)

To a solution of (2S,4S,6S)-1-allyl-2-methyl-6-(1-methyltriazol-4-yl)-4-[4-(trifluoromethyl)phenyl]piperidine-4-carboxamide $C_{24}$ (103 mg, 0.2515 mmol) and N,N-dimethylbarbituric acid (54 mg, 0.3251 mmol) in DCM (2 mL) was added $Pd(PPh_3)_4$ (30 mg, 0.0257 mmol). The reaction was stirred for 1.5 hours. The solvent was removed under vacuum then the residue dissolved with a 1M aqueous solution of hydrochloric acid (10 mL). The aqueous phase was washed with MTBE (3×10 mL) then the pH was adjusted to 8-9 by addition of a 1M aqueous solution of sodium hydroxide. The aqueous solution was then extracted with MeTHF (3×20 mL), dried over sodium sulfate and the solvent removed under vacuum. Purification by reversed-phase chromatography (column: $C_{18}$; gradient: 5-100% MeCN in water) yielded, after overnight freeze-drying, (2S,4S,6S)-2-methyl-6-(1-methyltriazol-4-yl)-4-[4-(trifluoromethyl)phenyl]piperidine-4-carboxamide 67 (50 mg, 54%) as a white solid. $^{1}$H NMR (400 MHz, DMSO-d6) δ 7.92 (s, 1H), 7.70 (br d, J=8.3 Hz, 2H), 7.60 (br d, J=8.3 Hz, 2H), 7.33 (s, 1H), 7.12 (s, 1H), 4.05-3.92 (m, 4H), 2.96-2.88 (m, 1H), 2.85 (d, J=13.0 Hz, 1H), 2.59 (br d, J=13.0 Hz, 1H), 2.28-2.10 (m, 1H), 1.50 (br t, J=12.2 Hz, 1H), 1.22 (br t, J=12.0 Hz, 1H), 1.07 (d, J=6.1 Hz, 3H); $^{19}$F NMR (377 MHz, DMSO-d6) δ −60.84 (s, 3F). ESI-MS m/z calc. 367.162, found 368.2 $(M+1)^+$.

Compound 68

(2S,4S,6S)-2-methyl-6-(1-methyl-1H-1,2,3-triazol-4-yl)-4-(4-(trifluoromethyl)phenyl-2,3,5,6-d4)piperidin-4-ol (68)

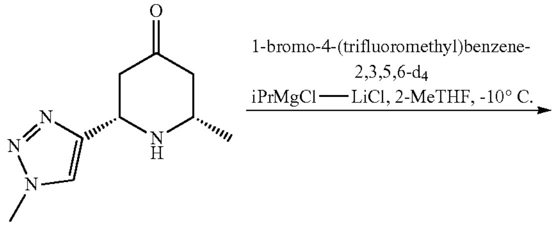

S1

-continued

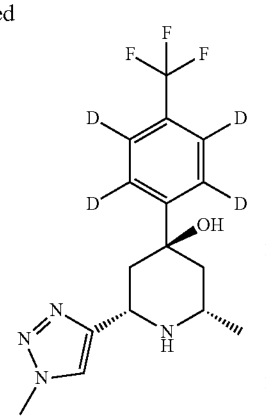

68

To a round bottom flask was added magnesium turnings (1.7 g, 65.24 mmol). The flask was charged with 2-MeTHF (98.6 mL) with N2 flowing through the reactor headspace. At this time, isopropylmagnesium chloride (0.21 g, 1.01 mL, 2M in THF) was added with stirring. The solution was heated to 50° C. for 20 min, at which time 1-bromo-4-(trifluoromethyl)benzene-2,3,5,6-d4 was added slowly via syringe pump. The formed dark solution was then cooled to −10° C. (2S,6S)-2-methyl-6-(1-methyl-1H-1,2,3-triazol-4-yl)piperidin-4-one S1 (4.93 g, 25.4 mmol) was added, after which the reaction was stirred at room temperature for 1.5 hours, and then quenched with $NH_4Cl$ (100 mL), and $H_2O$ (100 mL). The mixture was extracted four times with 2-MeTHF, and the combined fractions dried over sodium sulfate, filtered, and concentrated. Purification by chiral SFC chromatography provided, after drying, (2S,4S,6S)-2-methyl-6-(1-methyl-1H-1,2,3-triazol-4-yl)-4-(4-(trifluoromethyl)phenyl-2,3,5,6-d4)piperidin-4-ol 68 (3.11 g).

Compounds I5-I296

Compounds I5-I296 can be prepared in manners analogous to those described for Compounds 1-30, Compounds 31-44, and Compounds 45-68 disclosed above.

Example 2. MultiTox-Fluor Multiplex Cytotoxicity Assay for Detecting and Measuring APOL1 Inhibitor Properties The MultiTox-Fluor Multiplex Cytotoxicity Assay is a single-reagent-addition, homogeneous, fluorescence assay that measures the number of live and dead cells simultaneously in culture wells. The assay measures cell viability and cytotoxicity by detecting two distinct protease activities. The live-cell protease activity is restricted to intact viable cells and is measured using a fluorogenic, cell-permeant peptide glycyl-phenylalanylamino fluorocoumarin (GF-AFC) substrate. The substrate enters intact cells, where it is cleaved to generate a fluorescent signal proportional to the number of living cells. This live-cell protease activity marker becomes inactive upon loss of membrane integrity and leakage into the surrounding culture medium. A second, cell-impermeant, fluorogenic peptide substrate (bis-AAF-R110 Substrate) is used to measure dead-cell protease that has been released from cells that have lost membrane integrity. A ratio of dead to live cells is used to normalize data.

Briefly, the tet-inducible transgenic APOL1 T-REx-HEK293 cell lines were incubated with 50 ng/mL tet to induce APOL1 in the presence of 3-(2-(4-fluorophenyl)-1H-indol-3-yl)-N-((3S,4R)-4-hydroxy-2-oxopyrrolidin-3-yl) propenamide at 10.03, 3.24, 1.13, 0.356, 0.129, 0.042, 0.129, 0.0045, 0.0015, 0.0005 μM in duplicate for 24 hours in a humidified 37° C. incubator. The MultiTox reagent was added to each well and placed back in the incubator for an additional 30 minutes. The plate was read on the EnVision plate reader. A ratio of dead to live cells was used to normalize, and data was imported, analyzed, and fit using Genedata Screener (Basel, Switzerland) software. Data was normalized using percent of control, no tet (100% viability), and 50 ng/mL tet treated (0% viability), and fit using Smart Fit. The reagents, methods, and complete protocol for the MultiTox assay are described below.

| Reagent | Catalog Number | Vendor |
|---|---|---|
| 384 well, transparent, flat bottom tissue culture treated, Poly-D lysine coated | 356663 | Coming (Coming, NY) |
| 384 well round bottom polypropylene plates | 3656 | CoStar (Coming, NY) |
| Universal plate lids | 250002 | Thermo Fisher (Waltham) |
| Axygen 30 μL tips for Bravo 384 well | VT-384-31UL-R-S | Coming (Coming, NY) |
| MultiTox-Fluor Multiplex Cytotoxicity Assay | G9202 | Promega (Madison, WI) |
| 225 $cm^2$ flask, angled neck, treated, vented cap | 431082 | Coming (Coming, NY) |
| Dulbecco's Phosphate-Buffered Saline (DPBS), calcium and magnesium-free | 14190-136 | Thermo Fisher (Waltham) |
| Dulbecco's Modified Eagle Medium (DMEM), high glucose, no glutamine, no sodium pyruvate | 11960-077 | Thermo Fisher (Waltham) |
| Fetal Bovine Serum (FBS), tetracycline-free, US-Sourced | 631368 | Takara (Kusatsu, Japan) |
| L-Glutamine, 200 mM | 25030-081 | Thermo Fisher (Waltham) |
| Reagent | Catalog Number | Vendor |
| Penicillin-Streptomycin, 10,000 Units/mL | 15140-122 | Thermo Fisher (Waltham) |
| Blasticidin S HCl, 10 mg/mL | A11139-03 | Thermo Fisher (Waltham) |
| Tetracycline hydrochloride | T7660 -5G | Sigma (St. Louis, MO) |
| Puromycin dihydrochloride, 10 mg/mL | Al 1138-03 | Thermo Fisher (Waltham) |
| Trypsin-EDTA | 25300-054 | Thermo Fisher (Waltham) |
| InstrumentModel | Supplier | Location |
| Bravo16050-101 | Agilent Technologies | Santa Clara, CA |
| MultidropN/A Combi | Thermo Scientific | Waltham, MA |
| EnVisionN/A | PerkinElmer | Waltham, MA |

Multi-Tox Assay Protocol

Human embryonic kidney (HEK293) cell lines containing a tet-inducible expression system (T-REx™; Invitrogen, Carlsbad, CA) and Adeno-associated virus site 1 pAAVS1-Puro-APOL1 G0 or pAAVS1-Puro-APOL1 G1 or pAAVS1-Puro-APOL1 G2 Clones G0 DC2.13, G1 DC3.25, and G2 DC4.44 were grown in a T-225 flask at ~90% confluency in cell growth media (DMEM, 10% Tet-free FBS, 2 mM L-glutamine, 100 Units/mL penicillin-streptomycin, 5 μg/mL blasticidin S HCl, 1 μg/mL puromycin dihydrochloride). Cells were washed with DPBS and then trypsinized to dissociate from the flask. Media was used to quench the trypsin, cells were then pelleted at 200 g and resuspended in fresh cell assay media (DMEM, 2% Tet-free FBS, 2 mM L-glutamine, 100 Units/mL penicillin-streptomycin). Cells were counted and diluted to $1.17\times10^6$ cells/mL. 20 μL of cells (23,400/well) were dispensed in every well of a 384-well Poly-D-Lysine coated plate using the Multidrop dispenser. The plates were then incubated at room temperature for one hour.

Tetracycline is needed to induce APOL1 expression. 1 mg/mL tet stock in water was diluted to 250 ng/mL (5×) in cell assay media. 60 μL of cell assay media (no tet control) was dispensed in columns 1 and 24, and 60 μL of 5×tet in 384-PP-round bottom plate was dispensed in columns 2 to 23 with the Multidrop dispenser.

Assay ready plates from the Global Compound Archive were ordered using template 384_APOL1Cell_DR10n2_50 uM_v3. Compounds were dispensed at 200 nL in DMSO. The final top concentration was 10 μM with a 10 point 3-fold dilution in duplicate in the MultiTox assay.

20 μL was transferred from the 5×tet plate to the ARP and mixed, then 5 μL of 5×tet and the compounds were transferred to the cell plate and mixed using the Bravo. The cell plate was placed in the humidified 37° C. 5% $CO_2$ incubator for 24 hours.

The MultiTox-Fluor Multiplex Cytotoxicity Assay was performed in accordance with the manufacturer's protocol. After cells were incubated with tet and compound for 24 hours, 25 μL of 1×MultiTox reagent was added to each well using the Multidrop dispenser; the plates were placed on a plate shaker (600 rpm) for 2 minutes, then centrifuged briefly and placed back in the 37° C. incubator for 30 minutes. The cell viability (excitation: 400 nm, emission: 486 nm) and cytotoxicity (excitation: 485 nm, emission: 535 nm) were read using the EnVision plate reader. A ratio of dead (cytotoxicity) to live (viability) cells was reported. Data was exported and analyzed in Genedata. Data was normalized using percent of control, no tet (100% viability), and 50 ng/mL tet treated (0% viability), and fit using Smart Fit settings in Genedata.

Potency Data for Compounds 1 to 29

The compounds of Formula I are useful as inhibitors of APOL1 activity. Table 6 below illustrates the $IC_{50}$ of Compounds 1 to 68 using procedures described above. The procedures above may also be used to determine the potency of Compounds I5 to I295, and Compound I296. In the table below, the following meanings apply. For $IP_{50}$ (i.e., $IC_{50}$ for cell proliferation), "+++" means ≤50 nM; "++" means between 50 nM and 500 nM; "+" means ≥500 nM. RND=100% inhibition at 10 μm. ND=Not determined.

Potency Data for Compounds 1 to 68

| Compound No. | $IP_{50}$ (nM) |
|---|---|
| 1 | + |
| 2 | ++ |
| 3 | ++ |
| 4 | +++ |
| 5 | ++ |
| 6 | ++ |
| 7 | + |
| 8 | +++ |
| 9 | ++ |
| 10 | ++ |
| 11 | ++ |
| 12 | ++ |
| 13 | +++ |
| 14 | ++ |
| 15 | + |
| 16 | +++ |
| 17 | ++ |
| 18 | ++ |
| 19 | +++ |
| 20 | + |
| 21 | ++ |
| 22 | +++ |
| 23 | +++ |
| 24 | ++ |
| 25 | +++ |
| 26 | +++ |
| 27 | +++ |
| 28 | +++ |
| 29 | +++ |
| 30 | ++ |
| 31 | + |
| 32 | ++ |
| 33 | +++ |
| 34 | +++ |
| 35 | + |
| 36 | +++ |
| 37 | ++ |
| 38 | +++ |
| 39 | +++ |
| 40 | +++ |
| 41 | RND |
| 42 | ++ |
| 43 | +++ |
| 44 | ++ |
| 45 | + |
| 46 | ++ |
| 47 | +++ |
| 48 | ++ |
| 49 | ++ |
| 50 | +++ |
| 51 | +++ |
| 52 | +++ |
| 53 | + |
| 54 | + |
| 55 | + |
| 56 | + |
| 57 | + |
| 58 | +++ |
| 59 | ++ |
| 60 | + |
| 61 | + |
| 62 | +++ |
| 63 | + |
| 64 | + |
| 65 | ++ |
| 66 | ++ |
| 67 | ++ |
| 68 | ND |

OTHER EMBODIMENTS

This disclosure provides merely non-limiting example embodiments of the disclosed subject matter. One skilled in the art will readily recognize from the disclosure and claims, that various changes, modifications and variations can be made therein without departing from the spirit and scope of the disclosure as defined in the following claims.

The invention claimed is:

1. A compound represented by the formula:

Formula Ib

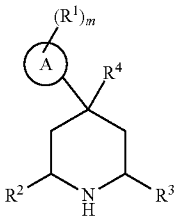

a tautomer thereof, a deuterated derivative of that compound or tautomer, or a pharmaceutically acceptable salt of any of the foregoing, wherein:

Ring A is chosen from $C_6$ aryl and 5- and 6-membered heteroaryl groups;

$R^1$, for each occurrence, is independently chosen from halogen, —OH, =O, cyano, phenyl, $C_1$-$C_6$ alkyl, $C_1$-$C_6$ alkoxy, $C_3$-$C_6$ carbocyclyl, 4- to 6-membered heterocyclyl, —C(=O)N($R^c$)$_2$, and —SO$_2$($R^c$) groups, wherein:

$R^c$, for each occurrence, is independently chosen from hydrogen and $C_1$-$C_4$ alkyl groups;

the 4- to 6-membered heterocyclyl of $R^1$ comprises one heteroatom chosen from nitrogen and oxygen;

the $C_1$-$C_6$ alkyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, and $C_1$-$C_4$ alkoxy groups;

the $C_1$-$C_6$ alkoxy of $R^1$ is optionally substituted with 1 to 3 groups independently chosen from —OH, cyano, and halogen groups;

the $C_3$-$C_6$ carbocyclyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$ groups; and the phenyl of $R^1$ is optionally substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkyl, $C_1$-$C_4$ alkoxy, —C(=O)NH$_2$, —C(=O)NH($C_1$-$C_4$ alkyl), and —C(=O)N($C_1$-$C_4$ alkyl)$_2$ groups; or wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, 5- to 6-membered heteroaryl are each optionally substituted with 1 to 4 groups chosen from halogen, —OH, and $C_1$-$C_4$ alkyl;

$R^2$ is chosen from $C_1$-$C_6$ alkyl, —C(=O)O($C_1$-$C_4$ alkyl), $C_2$-$C_6$ alkynyl, and

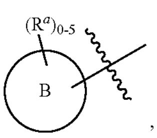

, wherein:

the $C_1$-$C_6$ alkyl of $R^2$ is substituted with 1 to 3 groups independently chosen from halogen, cyano, —OH, —NH$_2$, —NH($C_1$-$C_4$ alkyl), —N($C_1$-$C_4$ alkyl)$_2$, $C_1$-$C_4$ alkoxy, —C(=O)NH$_2$, —C(=O)NH($C_1$-$C_4$ alkyl), —C(=O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —[O(CH$_2$)$_q$]$_r$O($C_1$-$C_6$ alkyl), —S(=O)$_p$R$^k$, —S(=O)$_p$NR$^h$R$^i$, —C(=O)OR$^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 R$^m$ groups), 5- to 10-membered heterocyclyl (optionally substituted with 1 to 3 R$^m$ groups), 5- to 10-membered heteroaryl (optionally substituted with 1 to 3 R$^m$ groups), cyano, —C(=O)R$^k$, —C(=O)OR$^k$, —C(=O)NR$^h$R$^i$, —NR$^h$R$^i$, —NR$^h$C(=O)R$^k$, —NR$^h$C(=O)OR$^k$, —NR$^h$C(=O)NR$^i$R$^j$, —NR$^h$S(=O)$_p$R$^k$, —OR$^k$, —OC(=O)R$^k$, —OC(=O)OR$^k$, —OC(=O)NR$^h$R$^i$, —S(=O)$_p$R$^k$, —S(=O)$_p$NR$^h$R$^i$, —O($C_6$ aryl) (optionally substituted with 1 to 3 R$^m$ groups), and $C_3$-$C_6$ carbocyclyl groups (optionally substituted with 1 to 3 R$^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —NR$^h$R$^i$, and —OR$^k$ groups, wherein:

R$^h$, R$^i$, and R$^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of R$^h$, R$^i$, and R$^j$ is optionally substituted with 1 to 3 groups independently chosen from halogen, cyano, and —OH groups;

R$^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of R$^k$ is optionally substituted with 1 to 3 groups independently chosen from halogen, cyano, and —OH groups;

R$^m$, for each occurrence, is independently chosen from halogen, cyano, oxo, $C_1$-$C_6$ alkyl, $C_1$-$C_6$ alkoxy, —S(=O)$_p$R$^k$, and —OR$^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups;

$R^3$ is chosen from $C_1$-$C_6$ alkyl, $C_3$-$C_{12}$ carbocyclyl, 3- to 12-membered heterocyclyl, and 5- to 10-membered heteroaryl groups, wherein:

the $C_1$-$C_6$ alkyl of $R^3$ is optionally substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(=O)$NH_2$, —C(=O)NH ($C_1$-$C_4$ alkyl), and —C(=O)N($C_1$-$C_4$ alkyl)$_2$ groups;

the $C_3$-$C_{12}$ carbocyclyl, the 3- to 12-membered heterocyclyl, the $C_6$ and $C_{10}$ aryl, and the 5- to 10-membered heteroaryl of $R^3$ are each optionally substituted with 1 to 3 groups independently chosen from halogen, cyano, —OH, —NH2, —NH($C_1$-$C_4$ alkyl) (optionally substituted with —OH), —N($C_1$-$C_4$ alkyl)$_2$, $C_1$-$C_5$ alkyl (optionally substituted with —OH or —S(=O)$_2$($C_1$-$C_4$ alkyl)), $C_1$-$C_4$ alkoxy, —C(=O) $NH_2$, —C(=O)NH($C_1$-$C_4$ alkyl), —NHC(=O) ($C_1$-$C_4$ alkyl), —C(=O) ($C_1$-$C_4$ alkoxy), and —C(=O) N($C_1$-$C_4$ alkyl)$_2$ groups;

$R^4$ is chosen from halogen, $C_1$-$C_6$ alkyl, $C_1$-$C_6$ haloalkyl, —$(CH_2)_n$C(=O)$NR^nR^o$, —$NR^nR^o$, —$NR^o$C(=O)$R^p$, —$NR^n$S(=O)$_p R^p$, —$(CH_2)_n OR^p$, —S(=O)$_p R^p$, and —$(CH_2)_n$C(=O)$OR^p$ groups, wherein:

$R^n$ and $R^o$, for each occurrence, are each independently chosen from hydrogen and $C_1$-$C_4$ alkyl groups; and $R^p$, for each occurrence, is independently chosen from hydrogen, $C_1$-$C_4$ alkyl, and $C_1$-$C_4$ haloalkyl groups;

m is an integer chosen from 0, 1, 2, 3, 4, and 5;

n is an integer chosen from 0, 1, and 2;

p, for each occurrence, is an integer independently chosen from 1 and 2; and q and r, for each occurrence, are each an integer independently chosen from 1, 2, 3, and 4.

2. The compound, tautomer, deuterated derivative, or pharmaceutically acceptable salt according to claim 1, wherein $R^4$ is —OH.

3. The compound, tautomer, deuterated derivative, or pharmaceutically acceptable salt according to claim 1, wherein $R^3$ is chosen from $C_1$-$C_4$ alkyl groups.

4. The compound, tautomer, deuterated derivative, or pharmaceutically acceptable salt according to claim 1, wherein $R^3$ is —$CH_3$.

5. The compound, tautomer, deuterated derivative, or pharmaceutically acceptable salt according to claim 1, wherein $R^2$ is chosen from $C_1$-$C_4$ alkyl and

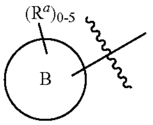

groups, wherein:

the $C_1$-$C_4$ alkyl of $R^2$ is substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_2$ alkoxy, $C_3$-$C_6$ cycloalkyl, 5- to 6-membered heterocyclyl, phenyl, and 5- to 6-membered heteroaryl groups.

6. The compound, tautomer, deuterated derivative, or pharmaceutically acceptable salt according to claim 1, wherein the compound is represented by one of the following structural formulae:

Formula Ic-4

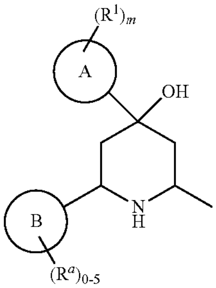

Formula II-4

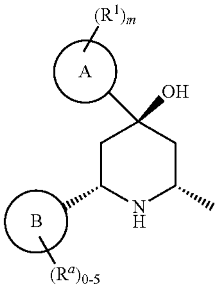

a tautomer thereof, a deuterated derivative of that compound or tautomer, or a pharmaceutically acceptable salt of any of the foregoing.

7. The compound, tautomer, deuterated derivative, or pharmaceutically acceptable salt according to claim 1, wherein Ring B is chosen from cyclopropyl, 5- to 10-membered heterocyclyl, phenyl, and 5- to 9-membered heteroaryl groups; each of which is optionally substituted with 1, 2, 3, 4, or 5 $R^a$ groups.

8. The compound, tautomer, deuterated derivative, or pharmaceutically acceptable salt according to claim 1, wherein Ring B is chosen from cyclopropyl, 5- to 10-membered heterocyclyl comprising 1 to 3 heteroatoms chosen from N and O, phenyl, and 5- to 9-membered heteroaryl comprising 1 to 3 heteroatoms chosen from N and O; each of which is optionally substituted with 1, 2, 3, 4, or 5 $R^a$ groups.

9. The compound, tautomer, deuterated derivative, or pharmaceutically acceptable salt according to claim 1, wherein Ring B is chosen from cyclopropyl, 5-membered heterocyclyl comprising 1 to 3 heteroatoms chosen from N and O, 6-membered heterocyclyl comprising 1 to 3 heteroatoms chosen from N and O, 9-membered heterocyclyl comprising 1 to 3 heteroatoms chosen from N and O, 10-membered heterocyclyl comprising 1 to 3 heteroatoms chosen from N and O, phenyl, 5-membered heteroaryl comprising 1 to 3 heteroatoms chosen from N and O, 6-membered heteroaryl comprising 1 to 3 heteroatoms chosen from N and O, and 9-membered heteroaryl comprising 1 to 3 heteroatoms chosen from N and O; each of which is optionally substituted with 1, 2, 3, 4, or 5 $R^a$ groups.

10. The compound, tautomer, deuterated derivative, or pharmaceutically acceptable salt according to claim 1, wherein Ring B is chosen from

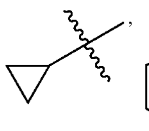 , 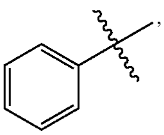 , 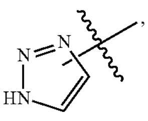 ,

-continued
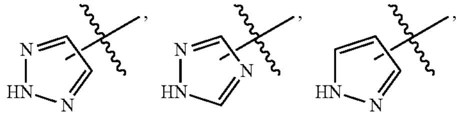
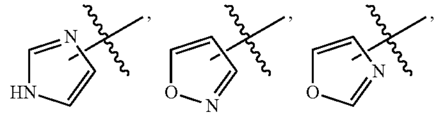
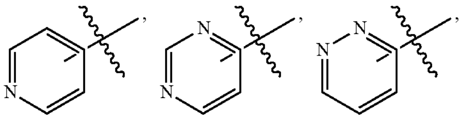
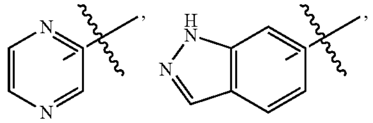
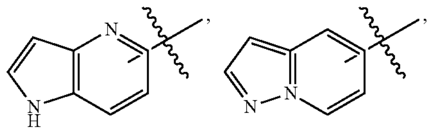
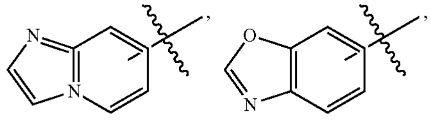
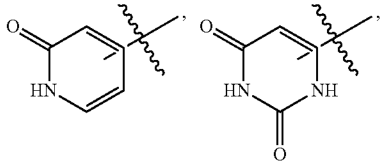
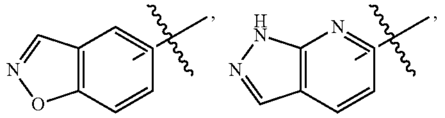
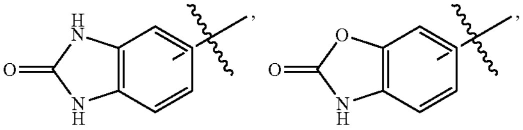
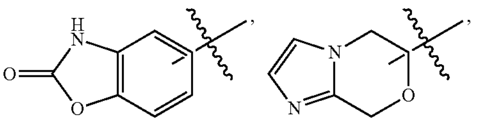
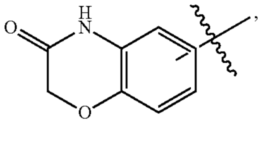
and
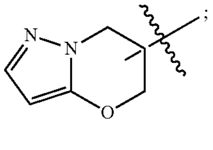
;
each of which is optionally substituted with 1, 2, 3, 4, or 5 $R^a$ groups.
11. The compound, tautomer, deuterated derivative, or pharmaceutically acceptable salt according to claim 1, wherein Ring B is chosen from
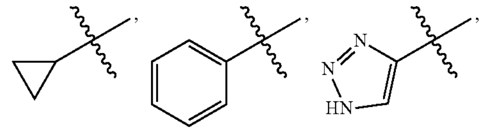
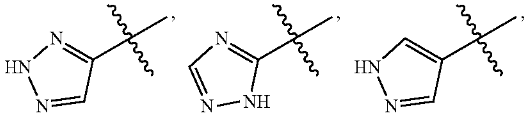
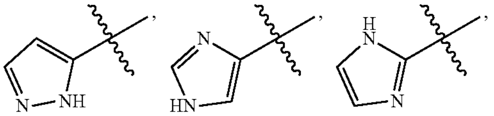
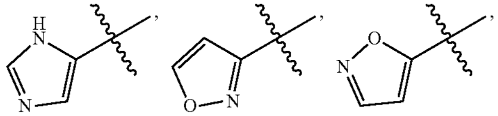
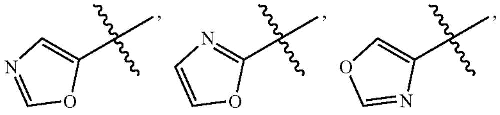
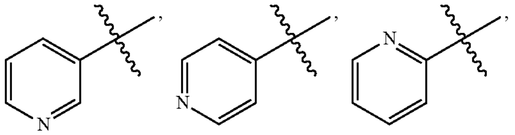
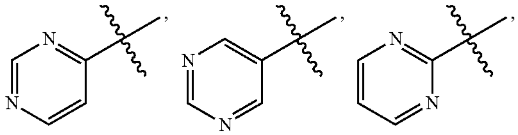
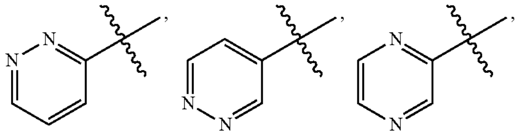
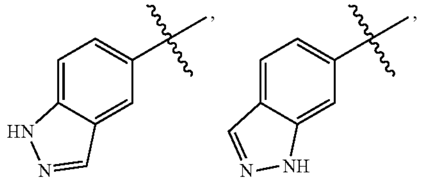
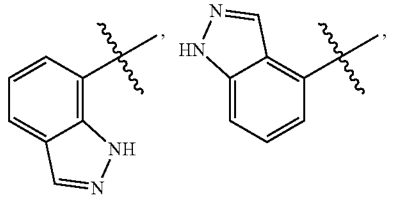
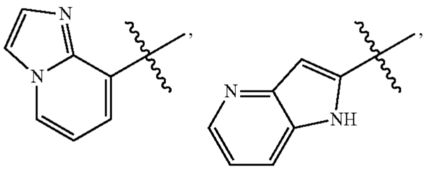

-continued

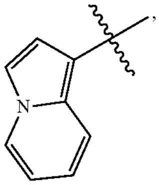, 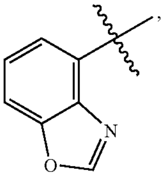, 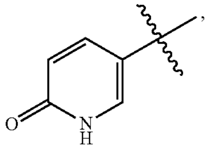,

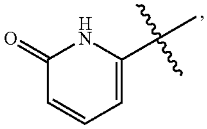, 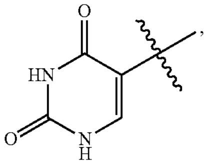,

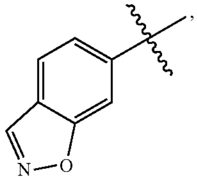, 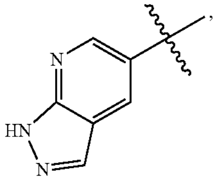,

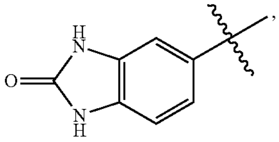, 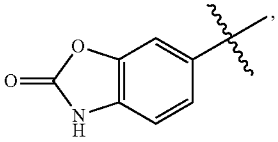,

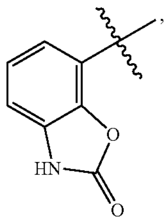, 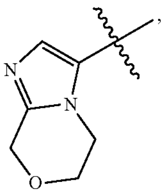, 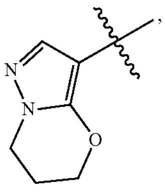,

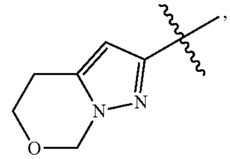, 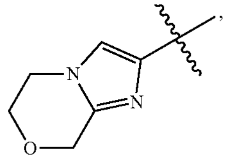,

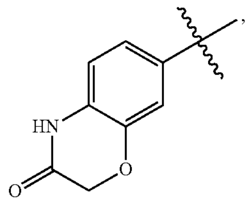, 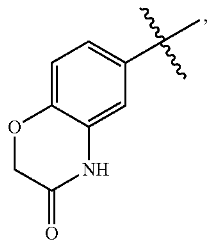,

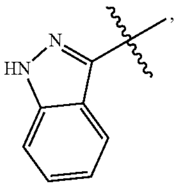, and 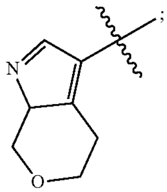;

each of which is optionally substituted with 1, 2, 3, 4, or 5 $R^a$ groups.

12. The compound, tautomer, deuterated derivative, or pharmaceutically acceptable salt according to claim 1, wherein Ring B is

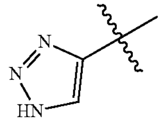 [SMILES: *c1c[nH]nn1]

which is optionally substituted with 1 $R^a$ group.

13. The compound, tautomer, deuterated derivative, or pharmaceutically acceptable salt according to claim 1, wherein $R^1$, for each occurrence, is independently chosen from hydrogen, halogen, cyano, —OH, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen, cyano, —OH, and $C_1$-$C_2$ alkoxy groups;

the $C_1$-$C_4$ alkoxy of $R^1$ is optionally substituted with 1 to 3 independently chosen from halogen groups; and the $C_3$-$C_6$ cycloalkyl of $R^1$ is optionally substituted with 1 to 3 groups independently chosen from halogen, cyano, —OH, and $C_1$-$C_2$ alkoxy groups.

14. The compound, tautomer, deuterated derivative, or pharmaceutically acceptable salt according to claim 1, wherein $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen and —OH;

the $C_1$-$C_4$ alkoxy of $R^1$ is optionally substituted with 1 to 3 independently chosen from halogen groups; and the $C_3$-$C_6$ cycloalkyl of $R^1$ is optionally substituted with 1 to 3 groups independently chosen from halogen and —OH.

15. The compound, tautomer, deuterated derivative, or pharmaceutically acceptable salt according to claim 1, wherein $R^1$, for each occurrence, is independently chosen from F, Cl, Br, $C_1$-$C_4$ alkyl, $C_1$-$C_4$ alkoxy, —C(═O)N($R^c$)$_2$, and $C_3$-$C_6$ cycloalkyl groups, wherein:

$R^c$, for each occurrence, is independently chosen from hydrogen and $C_1$-$C_2$ alkyl groups;

the $C_1$-$C_4$ alkyl of $R^1$ is optionally substituted with 1 to 3 groups independently chosen from halogen and —OH; and the $C_1$-$C_4$ alkoxy of $R^1$ is optionally substituted with 1 to 3 independently chosen from halogen groups.

16. The compound, tautomer, deuterated derivative, or pharmaceutically acceptable salt according to claim 1, wherein $R^1$, for each occurrence, is independently chosen from F, Cl, Br, —$CH_3$, —$CH(CH_3)_2$, —$CF_3$, —$OCH_3$, —$OCF_3$, —C(═O)N($CH_3$)$_2$, and cyclopropyl.

17. The compound, tautomer, deuterated derivative, or pharmaceutically acceptable salt according to claim 1, wherein $R^1$, for each occurrence, is independently chosen from —$SO_2$($R^c$) groups, wherein $R^c$ is independently chosen from $C_1$-$C_4$ alkyl groups.

18. The compound, tautomer, deuterated derivative, or pharmaceutically acceptable salt according to claim 1, wherein two $R^1$ groups taken together with the Ring A atoms connecting them form a 5- to 6-membered cycloalkyl, 5- to 8-membered heterocyclyl, 5- to 6-membered aryl, or 5- to 6-membered heteroaryl ring, wherein the 5- to 6-membered cycloalkyl, 5- to 8-membered heterocyclyl, 5- to 6-membered aryl, and 5- to 6-membered heteroaryl are each optionally substituted with 1 to 4 groups selected chosen from halogen, —OH, and $C_1$-$C_4$ alkyl.

19. The compound, tautomer, deuterated derivative, or pharmaceutically acceptable salt according to claim 1, wherein two $R^1$ groups taken together with the Ring A atoms connecting them form a group chosen from

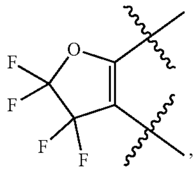,
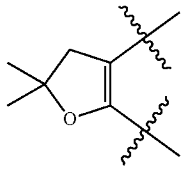,
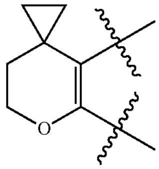, and
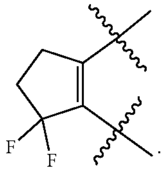.

20. The compound, tautomer, deuterated derivative, or pharmaceutically acceptable salt according to claim 1, wherein m is 1.

21. The compound, tautomer, deuterated derivative, or pharmaceutically acceptable salt according to claim 1, wherein m is 2.

22. The compound, tautomer, deuterated derivative, or pharmaceutically acceptable salt according to claim 1, wherein $R^a$, for each occurrence, is independently chosen from halogen, cyano, $C_1$-$C_6$ alkyl, $C_1$-$C_4$ alkoxy, $C_1$-$C_6$ haloalkyl, $C_1$-$C_6$ haloalkoxy, —C(═O)$NR^hR^i$, —$NR^hR^i$, —$NR^h$C(═O)$R^k$, —$OR^k$, —$[O(CH_2)_q]_r$O($C_1$-$C_6$ alkyl), —S(═O)$_2R^k$, —S(═O)$_2NR^hR^i$, $C_3$-$C_6$ cycloalkyl, 5 to 10-membered heterocyclyl, phenyl, and 5- to 8-membered heteroaryl groups, wherein:

the $C_1$-$C_6$ alkyl of $R^a$ is optionally substituted with 1 to 3 groups independently chosen from cyano, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_pR^k$, —$OR^k$, —S(═O)$_2R^k$, —S(═O)$_pNR^hR^i$, and $C_3$-$C_6$ cycloalkyl groups;

the $C_3$-$C_6$ cycloalkyl, the 5- to 10-membered heterocyclyl, the phenyl, and the 5- to 8-membered heteroaryl of $R^a$ are each optionally substituted with 1 to 3 groups independently chosen from halogen, $C_1$-$C_2$ alkyl, and —$OR^k$ groups, wherein:

$R^h$, $R^i$, and $R^j$, for each occurrence, are each independently chosen from hydrogen, $C_1$-$C_2$ alkyl, cyclopropyl, and cyclobutyl groups, wherein:

the $C_1$-$C_2$ alkyl of any one of $R^h$, $R^i$, and $R^j$ is optionally substituted with 1 to 3 groups independently chosen from halogen and —OH;

$R^k$, for each occurrence, is each independently chosen from hydrogen and $C_1$-$C_4$ alkyl groups, wherein:

the $C_1$-$C_4$ alkyl of $R^k$ is optionally substituted with 1 to 3 groups independently chosen from halogen and —OH; and q and r are each an integer chosen from 1, 2, and 3.

23. The compound, tautomer, deuterated derivative, or pharmaceutically acceptable salt according to claim 1, wherein $R^a$, for each occurrence, is independently chosen from halogen, cyano, $C_1$-$C_6$ alkyl, $C_1$-$C_4$ alkoxy, $C_1$-$C_4$ haloalkyl, $C_1$-$C_4$ haloalkoxy, —C(═O)$NR^hR^i$, —$NR^hR^i$, —$NR^h$C(═O)$R^k$, —$OR^k$, —$[O(CH_2)_q]_r$O($C_1$-$C_4$ alkyl), —S(═O)$_2R^k$, —S(═O)$_2NR^hR^i$, cyclopropyl, cyclobutyl, 5- to 6-membered heterocyclyl, phenyl, and 5- to 6-membered heteroaryl, wherein:

the $C_1$-$C_6$ alkyl of $R^a$ is optionally substituted with 1 to 3 groups independently chosen from cyano, —C(═O)$NR^hR^i$, —S(═O)$_2R^k$, —$NR^hR^i$, —$OR^k$, cyclopropyl, and cyclobutyl groups, wherein:

the cyclopropyl, the cyclobutyl, the 5- to 6-membered heterocyclyl, the phenyl, and the 5 to 6-membered heteroaryl of $R^a$ are each optionally substituted with 1 to 3 groups independently chosen from halogen, —$CH_3$, —OH, and —$OCH_3$; wherein:

$R^h$ and $R^i$, for each occurrence, are each independently chosen from hydrogen, —$CH_3$, cyclopropyl, and cyclobutyl groups, wherein:

the —$CH_3$ of any one of $R^h$ and $R^i$ is optionally substituted with 1 to 3 groups independently chosen from F, CI, and —OH;

$R^k$, for each occurrence, is each independently chosen from hydrogen and —$CH_3$, wherein:

the —$CH_3$ of $R^k$ is optionally substituted with 1 to 3 groups independently chosen from halogen and —OH.

24. The compound, tautomer, deuterated derivative, or pharmaceutically acceptable salt according to claim 1, wherein $R^a$, for each occurrence, is independently chosen from F, Cl, Br, cyano, $C_1$-$C_6$ alkyl, $C_1$-$C_2$ alkoxy, $C_1$-$C_2$ haloalkyl, —C(═O)$NR^hR^i$, —$NR^hR^i$, —$NR^h$C(═O)$R^k$, —$OR^k$, —$[O(CH_2)_q]_r$O($C_1$-$C_2$ alkyl), —S(═O)$_2R^k$, —S(═O)$_2NR^hR^i$, cyclopropyl, cyclobutyl, 5-membered heterocyclyl, phenyl, and 6-membered heteroaryl groups, wherein:

the $C_1$-$C_6$ alkyl of $R^a$ is optionally substituted with 1 to 3 groups independently chosen from cyano, —C(═O)$NR^hR^i$, —$OR^k$, —S(═O)$_2R^k$, and cyclopropyl;

the cyclopropyl, the cyclobutyl, the 5- to 6-membered heterocyclyl, the phenyl, and the 5- to 6-membered heteroaryl of $R^a$ are each optionally substituted with 1 to 3 groups independently chosen from halogen, —$CH_3$, —OH, and —$OCH_3$, wherein:

$R^h$ and $R^i$, for each occurrence, are each independently chosen from hydrogen, —$CH_3$, and cyclopropyl; wherein:

the —$CH_3$ of any one of $R^h$ and $R^i$ is optionally substituted with 1 to 3 groups independently chosen from F, CI, and —OH;

$R^k$, for each occurrence, is each independently chosen from hydrogen and —$CH_3$; and q and r are each an integer independently chosen from 1 and 2.

25. The compound, tautomer, deuterated derivative, or pharmaceutically acceptable salt according to claim 1, wherein $R^a$, for each occurrence, is independently chosen from F, cyano, —OH, —$CH_3$, —$CF_3$, —$CH(CH_3)_2$, —$(CH_2)_2OH$, —$(CH_2)_2OCH_3$, —$CH_2CH(OH)C_2H_5$, —$CH_2C(CH_3)(CH_2OH)_2$, —$OCH_3$, —$OCH_2CH_3$, —$[O(CH_2)_2]_2OCH_3$, —$CH_2$C(═O)$NHCH_3$, —$(CH_2)_2SO_2CH_3$, —$CH_2$C(═O)$N(CH_3)_2$, —$CH_2$(cyclopropyl), —C(═O)$NH_2$, —C(═O)NH(cyclopropyl), —$NH_2$, —$NHCH_3$, —$N(CH_3)_2$, —$NHC(CH_3)_2CH_2OH$, —NHC(═O) $CH_3$, —$SO_2CH_3$, —$SO_2NH_2$, cyclopropyl, 2-methoxyphenyl, N-methylpiperazinyl, tetrahydro-2H-pyranyl, methylpyrazolyl, pyridinyl, and tetrahydrothiophenyl 1,1-dioxide.

26. The compound, tautomer, deuterated derivative, or pharmaceutically acceptable salt according to claim 1, wherein $R^a$, for each occurrence, is independently chosen from —$CH_3$ and —$(CH_2)_2SO_2CH_3$.

27. The compound, tautomer, deuterated derivative, or pharmaceutically acceptable salt according to claim 1, wherein Ring A is chosen from phenyl, thiophenyl, and pyridinyl.

28. The compound, tautomer, deuterated derivative, or pharmaceutically acceptable salt according to claim 1, wherein Ring A is phenyl.

29. A compound, tautomer, deuterated derivative, or pharmaceutically acceptable salt chosen from the compounds of Table 1, Table 2, Table 3, and Table 4, tautomers thereof, deuterated derivatives of those compounds and tautomers, and pharmaceutically acceptable salts of any of the foregoing.

30. A compound represented by the formula:

Formula II-6a

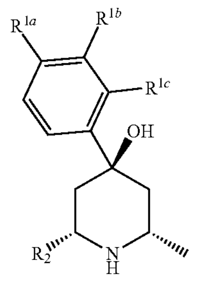

a tautomer thereof, a deuterated derivative of that compound or tautomer, or a pharmaceutically acceptable salt of any of the foregoing, wherein:

$R^{1a}$ and $R^{1b}$ are independently chosen from halogen, H, $C_1$-$C_4$ alkyl, and $C_1$-$C_4$ haloalkyl groups;

$R^{1c}$ is chosen from halogen, H, $CH_3$, —OH, and $CH_2OH$; and $R^2$ is chosen from $C_1$-$C_6$ alkyl, —C(═O)O($C_1$-$C_4$ alkyl), $C_2$-$C_6$ alkynyl, and

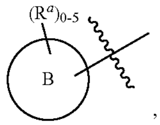

, wherein:

the $C_1$-$C_6$ alkyl of $R^2$ is substituted with 1 to 3 groups independently chosen from halogen, cyano, —OH, —$NH_2$, —NH($C_1$-$C_4$ alkyl), —N($C_1$-$C_4$ alkyl)$_2$, $C_1$-$C_4$ alkoxy, —C(═O)$NH_2$, —C(═O)NH($C_1$-$C_4$ alkyl), —C(═O)N($C_1$-$C_4$ alkyl)$_2$, $C_3$-$C_6$ carbocyclyl, 5- to 10-membered heterocyclyl, $C_6$ aryl, and 5- to 10-membered heteroaryl groups;

Ring B is chosen from $C_3$-$C_{12}$ carbocyclyl, 3- to 12-membered heterocyclyl, $C_6$ and $C_{10}$ aryl, and 5- to 10-membered heteroaryl groups, wherein Ring B is optionally substituted with 1, 2, 3, 4, or 5 $R^a$ groups; wherein:

$R^a$, for each occurrence, is independently chosen from halogen, cyano, $C_1$-$C_6$ alkyl, $C_2$-$C_6$ alkenyl, $C_1$-$C_6$ alkoxy, $C_1$-$C_6$ haloalkyl, $C_1$-$C_6$ haloalkenyl, $C_1$-$C_6$ haloalkoxy, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_pR^k$, —$OR^k$, —OC(═O)$R^k$, —OC(═O)$OR^k$, —OC(═O)$NR^hR^i$, —[O(CH$_2$)$_q$]$_r$O($C_1$-$C_6$ alkyl), —S(═O)$_pR^k$, —S(═O)$_pNR^hR^i$, —C(═O)$OR^k$, $C_3$-$C_{12}$ carbocyclyl, 3- to 12-membered heterocyclyl, $C_6$ and $C_{10}$ aryl, and 5- to 10-membered heteroaryl groups, wherein:

the $C_1$-$C_6$ alkyl, $C_1$-$C_6$ alkoxy, and the $C_2$-$C_6$ alkenyl of $R^a$ are each optionally substituted with 1 to 3 groups independently chosen from $C_6$ to $C_{10}$ aryl (optionally substituted with 1 to 3 $R^m$ groups), 5- to 10-membered heterocyclyl (optionally substituted with 1 to 3 $R^m$ groups), 5- to 10-membered heteroaryl (optionally substituted with 1 to 3 $R^m$ groups), cyano, —C(═O)$R^k$, —C(═O)$OR^k$, —C(═O)$NR^hR^i$, —$NR^hR^i$, —$NR^h$C(═O)$R^k$, —$NR^h$C(═O)$OR^k$, —$NR^h$C(═O)$NR^iR^j$, —$NR^h$S(═O)$_pR^k$, —$OR^k$, —OC(═O)$R^k$, —OC(═O)$OR^k$, —OC(═O)$NR^hR^i$, —S(═O)$_pR^k$, —S(═O)$_pNR^hR^i$, —O($C_6$ aryl) (optionally substituted with 1 to 3 $R^m$ groups), and $C_3$-$C_6$ carbocyclyl groups (optionally substituted with 1 to 3 $R^m$ groups);

the $C_3$-$C_{12}$ carbocyclyl, the 3- to 12-membered heterocyclyl, the $C_6$ and $C_{10}$ aryl, and the 5- to 10-membered heteroaryl of $R^a$ are each optionally substituted with 1 to 3 groups independently chosen from halogen, cyano, $C_1$-$C_4$ alkyl, —$NR^hR^i$, and —$OR^k$ groups, wherein:

$R^h$, $R^i$, and $R^j$, for each occurrence, are each independently chosen from hydrogen, $C_1$-$C_4$ alkyl, $C_6$-$C_{10}$ aryl, and $C_3$-$C_6$ cycloalkyl groups, wherein:

the $C_1$-$C_4$ alkyl of any one of $R^h$, $R^i$, and $R^j$ is optionally substituted with 1 to 3 groups independently chosen from halogen, cyano, and —OH groups;

$R^k$, for each occurrence, is independently chosen from hydrogen, $C_1$-$C_4$ alkyl, 5- to 10-membered heterocyclyl, and $C_3$-$C_6$ carbocyclyl groups, wherein:

the $C_1$-$C_4$ alkyl of any one of $R^k$ is optionally substituted with 1 to 3 groups independently chosen from halogen, cyano, and —OH groups;

$R^m$, for each occurrence, is independently chosen from halogen, cyano, oxo, $C_1$-$C_6$ alkyl, $C_1$-$C_6$ alkoxy, —S(═O)$_pR^k$, and —$OR^k$ groups, wherein:

the $C_1$-$C_6$ alkyl of $R^m$ is optionally substituted with 1 to 3 groups independently chosen from halogen, cyano, —OH, and —O($C_1$-$C_4$ alkyl) groups.

31. A compound represented by the formula:

Formula II-6b

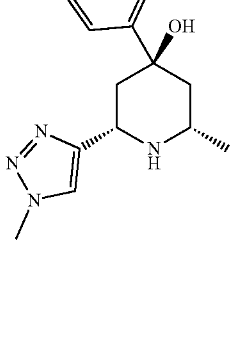

a tautomer thereof, a deuterated derivative of that compound or tautomer, or a pharmaceutically acceptable salt of any of the foregoing, wherein:

$R^{1a}$ and $R^{1b}$ are independently chosen from halogen, H, $C_1$-$C_4$ alkyl, and $C_1$-$C_4$ haloalkyl groups; and $R^{1c}$ is chosen from halogen, H, $CH_3$, —OH, and $CH_2OH$.

32. A silicon, boron, or phosphorus derivative of the at least one compound, tautomer, deuterated derivative, or pharmaceutically acceptable salt according to claim 1.

33. Compound 16 Form A.

34. A pharmaceutical composition comprising at least one compound, tautomer, deuterated derivative, or pharmaceutically acceptable salt according to claim 1 and a pharmaceutically acceptable carrier.

35. A pharmaceutical composition comprising Compound 16 Form A and a pharmaceutically acceptable carrier.

36. A method of treating focal segmental glomerulosclerosis and/or non-diabetic kidney disease comprising administering to a patient in need thereof at least one compound, tautomer, deuterated derivative, or pharmaceutically acceptable salt according to claim 1.

37. A method of treating focal segmental glomerulosclerosis and/or non-diabetic kidney disease comprising administering to a patient in need thereof Compound 16 or Compound 16 Form A, or a pharmaceutical composition comprising Compound 16 or Compound 16 Form A and a pharmaceutically acceptable carrier.

38. A compound chosen from Compound 16:

16

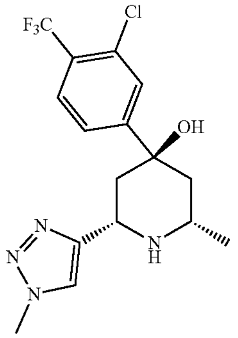

a tautomer thereof, a deuterated derivative of that compound or tautomer, and pharmaceutically acceptable salts of any of the foregoing.

39. A compound that is Compound 16:

16

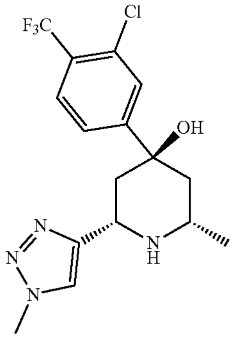

or a pharmaceutically acceptable salt thereof.

40. A compound that is Compound 16:

16

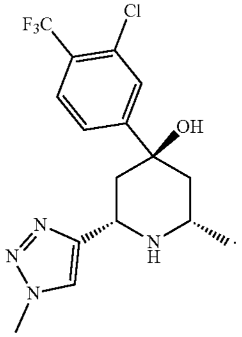

41. A method of treating an APOL1 mediated disease comprising administering to a patient in need thereof at least one compound, tautomer, deuterated derivative, or pharmaceutically acceptable salt according to claim 1.

* * * * *